US010612032B2

(12) United States Patent
Harvey et al.

(10) Patent No.: US 10,612,032 B2
(45) Date of Patent: Apr. 7, 2020

(54) INDUCIBLE PRODUCTION-PHASE PROMOTERS FOR COORDINATED HETEROLOGOUS EXPRESSION IN YEAST

(71) Applicant: The Board of Trustees of the Leland Stanford Junior University, Stanford, CA (US)

(72) Inventors: Colin Harvey, Stanford, CA (US); Ulrich Schlecht, Palo Alto, CA (US); Maureen Elizabeth Hillenmeyer, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 166 days.

(21) Appl. No.: 15/469,452

(22) Filed: Mar. 24, 2017

(65) Prior Publication Data
US 2017/0275635 A1   Sep. 28, 2017

Related U.S. Application Data

(60) Provisional application No. 62/313,108, filed on Mar. 24, 2016.

(51) Int. Cl.
| | |
|---|---|
| C12N 15/81 | (2006.01) |
| C12N 1/19 | (2006.01) |
| C12N 15/00 | (2006.01) |
| C12N 15/11 | (2006.01) |
| C12N 15/113 | (2010.01) |
| C12N 15/63 | (2006.01) |

(52) U.S. Cl.
CPC ........... *C12N 15/81* (2013.01); *C12N 15/635* (2013.01)

(58) Field of Classification Search
None
See application file for complete search history.

(56) References Cited

U.S. PATENT DOCUMENTS

| | | | |
|---|---|---|---|
| 4,876,197 A | 10/1989 | Burke et al. | |
| 5,672,491 A | 9/1997 | Khosla et al. | |
| 6,358,733 B1 | 3/2002 | Motwani et al. | |
| 7,172,886 B2 | 2/2007 | Keasling et al. | |
| 9,512,431 B2 | 12/2016 | Temme et al. | |
| 2004/0171154 A1 | 9/2004 | Storici et al. | |
| 2007/0224208 A1* | 9/2007 | Guo | A61K 39/0011 424/184.1 |
| 2010/0272698 A1* | 10/2010 | Stateva | C12N 9/2402 424/93.21 |
| 2012/0045809 A1* | 2/2012 | Buelter | C12N 15/52 435/160 |
| 2013/0237435 A1 | 9/2013 | Machida et al. | |
| 2014/0273144 A1 | 9/2014 | Hawkins | |
| 2014/0342416 A1* | 11/2014 | Jansen | C12P 7/46 435/145 |
| 2015/0275200 A1 | 10/2015 | Jayaprakash et al. | |
| 2015/0310168 A1 | 10/2015 | Machida et al. | |
| 2016/0213767 A1* | 7/2016 | King | A61K 39/04 |
| 2017/0022532 A1 | 1/2017 | Seyedsayamdost | |
| 2018/0355020 A1* | 12/2018 | Anchel | A23J 1/08 |

FOREIGN PATENT DOCUMENTS

| | | |
|---|---|---|
| WO | 1992013963 A1 | 8/1992 |
| WO | 2018094110 A2 | 5/2018 |
| WO | 2018094110 A3 | 8/2018 |

OTHER PUBLICATIONS

UniProtKB, pp. 1-3, downloaded Jan. 22, 2019.*
FBP1 / YLR377C Sequence downloaded Jul. 31, 2019.*
*S.cerevisiae* chromosome XI reading frame ORF YKR097w, downloaded Jul. 31, 2019.*
"Saccharomyces cerevisiae", American Type Culture Collection (ATCC) Product Sheet, 208288, 2017, 2 pgs.
"Saccharomyces cerevisiae", American Type Culture Collection (ATCC) Product Sheet, 4001213, 2016, 2 pgs.
Belli et al., "An activator/repressor dual system allows tight tetracycline-regulated gene expression in budding yeast", Nucleic Acids Research, vol. 26, No. 4, 1998, pp. 942-947.
Botstein et al., "Yeast as a Model Organism", Science, vol. 277, No. 5330, Aug. 29, 1997, pp. 1259-1260.
Buijs et al., "Advanced biofuel production by the yeast *Saccharomyces cerevisiae*", Current Opinion in Chemical Biology, vol. 17, No. 3, Jun. 2013, Electronic Publication: Apr. 27, 2013, pp. 480-488.
Chooi et al., "A Cytochrome P450 Serves as an Unexpected Terpene Cyclase during Fungal Meroterpenoid Biosynthesis", Journal of the American Chemical Society, vol. 135, No. 45, Nov. 13, 2013, 12 pgs.
Christianson et al., "Multifunctional yeast high-copy-number shuttle vectors", Gene, vol. 110, No. 1, Jan. 2, 1992, pp. 119-122.
Da Silva et al., "Introduction and expression of genes for metabolic engineering applications in *Saccharomyces cerevisiae*", FEMS Yeast Research, vol. 12, No. 2, Mar. 1, 2012, pp. 197-214.
Daran-Lapujade et al., "Role of Transcriptional Regulation in Controlling Fluxes in Central Carbon Metabolism of *Saccharomyces cerevisiae*", The Journal of Biological Chemistry, vol. 279, No. 10, Mar. 15, 2004, pp. 9125-9138.
De Kok et al., "Rapid and Reliable DNA Assembly via Ligase Cycling Reaction", ACS Synthetic Biology, vol. 3, No. 2, Feb. 21, 2014, Electronic Publication: Jan. 15, 2014, pp. 97-106.

(Continued)

*Primary Examiner* — Maria Marvich
(74) *Attorney, Agent, or Firm* — KPPB LLP

(57) ABSTRACT

Inducible promoters for the coordinated expression of at least one heterologous gene in yeast and methods of using them are disclosed. In particular, the invention relates to sets of inducible promoters derived from *S. cerevisiae* and related species that can be induced in the presence of nonfermentable carbon sources.

8 Claims, 16 Drawing Sheets
(13 of 16 Drawing Sheet(s) Filed in Color)
Specification includes a Sequence Listing.

(56) References Cited

OTHER PUBLICATIONS

Dimitrov et al., "Polymorphisms in multiple genes contribute to the spontaneous mitochondrial genome instability of *Saccharomyces cerevisiae* S288C strains", Genetics 183, 2009, pp. 365-383.
Galanie et al., "Complete biosynthesis of opioids in yeast", Science, vol. 349, No. 6252, Sep. 4, 2015, pp. 1095-1100.
Gibson et al., "Chemical synthesis of the mouse mitochondrial genome", Nature Methods, vol. 7, No. 11, Nov. 2010, pp. 901-903.
Gibson et al., "Enzymatic assembly of DNA molecules up to several hundred kilobases", Nature Methods, vol. 6, No. 5, May 2009, pp. 343-345.
Gietz et al., "High-efficiency yeast transformation using the LiAc/SS carrier DNA/PEG method", Nature Protocols, vol. 2, No. 1, 2007, pp. 31-34.
Guo et al., "Recent advances in genome mining of secondary metabolites in Aspergillus terreus", Frontiers in Microbiology, Dec. 23, 2014, vol. 5, Article 717, 13 pgs., doi: 10.3389/fmicb.2014.00717.
Hinnen et al., "Transformation of yeast", Proceedings of the National Academy of Sciences of the United States of America, vol. 75, No. 4, Apr. 1978, pp. 1929-1933.
Horecka et al., "The 50:50 method for PCR-based seamless genome editing in yeast", Yeast, Mar. 2014, Published Online: Nov. 29, 2013, vol. 31, No. 3, pp. 103-112, DOI:10.1002/yea.2992.
Johnston et al., "Sequences That Regulate the Divergent GAL1-GAL10 Promoter in *Saccharomyces cerevisiae*", Molecular and Cellular Biology, vol. 4, No. 8, Aug. 1984, pp. 1440-1448.
Kim et al., "Cloning large natural product gene clusters from the environment: Piecing environmental DNA gene clusters back together with TAR", Biopolymers, Sep. 2010, First Published: Jun. 23, 2010, vol. 93, No. 9, pp. 833-844, https://doi.org/10.1002/bip.21450.
Kim et al., "Screening of Yeast Diauxic Promoters for Production of Foreign Proteins", Journal of Microbiology and Biotechnology, vol. 16, No. 9, 2006, pp. 1459-1463.
Kuijpers et al., "A versatile, efficient strategy for assembly of multi-fragment expression vectors in *Saccharomyces cerevisiae* using 60 bp synthetic recombination sequences", Microbial Cell Factories, vol. 12, No. 47, May 10, 2013, 13 pgs.
Lee et al., "A Highly Characterized Yeast Toolkit for Modular, Multipart Assembly", ACS Synthetic Biology, vol. 4, No. 9, Apr. 14, 2015, pp. 975-986.
Lee et al., "Evaluation of the *Saccharomyces cerevisiae* ADH2 promoter for protein synthesis", Yeast, vol. 22, No. 6, Apr. 30, 2005, First Published: Apr. 22, 2005, pp. 431-440.
Liang et al., "Coordinated induction of multi-gene pathways in *Saccharomyces cerevisiae*", Nucleic Acids Research, vol. 41, No. 4, 2013, Published online: Dec. 22, 2012, 10 pgs.
Medema et al., "antiSMASH: rapid identification, annotation and analysis of secondary metabolite biosynthesis gene clusters in bacterial and fungal genome sequences", Nucleic Acids Research, Jul. 1, 2011, First Published: Jun. 14, 2011, vol. 39, No. suppl 2, pp. W339-W346, https://doi.org/10.1093/nar/gkr466.
Montiel et al., "Yeast homologous recombination-based promoter engineering for the activation of silent natural product biosynthetic gene clusters", Proc Natl Acad Sci U S A, Jul. 21, 2015, vol. 112, No. 29, pp. 8953-8958.
Mumberg et al., "Yeast vectors for the controlled expression of heterologous proteins in different genetic backgrounds", Gene, vol. 156, No. 1, Apr. 14, 1995, pp. 119-122.
Negritto et al., "Influence of DNA Sequence Identity on Efficiency of Targeted Gene Replacement", Molecular and Cellular Biology, vol. 17, No. 1, Jan. 1997, pp. 278-286.
Peng et al., "Controlling heterologous gene expression in yeast cell factories on different carbon substrates and across the diauxic shift: a comparison on yeast promoter activities", Microbial Cell Factories, vol. 14, No. 91, Jun. 26, 2015, 11 pgs.
Pscheidt et al., "Yeast cell factories for fine chemical and API production", Microbial Cell Factories, vol. 7, No. 25, Aug. 7, 2008, 36 pgs.

Reeves et al., "Genes for the Biosynthesis of the Fungal Polyketides Hypothemycin from Hypomyces subiculosus and Radicicol from Pochonia chlamydosporia", Applied and Environmental Microbiology, vol. 74, No. 16, Aug. 2008, pp. 5121-5129.
Ro et al., "Production of the antimalarial drug precursor artemisinic acid in engineered yeast", Nature, vol. 440, No. 7086, Apr. 13, 2006, pp. 940-943.
Scannell et al., "The Awesome Power of Yeast Evolutionary Genetics: New Genome Sequences and Strain Resources for the *Saccharomyces sensu stricto* Genus", G3: Genes, Genomes, Genetics, vol. 1, No. 1, Jun. 2011, pp. 11-25.
Shao et al., "DNA assembler, an in vivo genetic method for rapid construction of biochemical pathways", Nucleic Acids Research, vol. 37, No. 2, Feb. 2009, Published Online: Dec. 12, 2008, 10 pgs.
Smith et al., "A method for high-throughput production of sequence-verified DNA libraries and strain collections", Molecular Systems Biology, Feb. 1, 2017, vol. 13, No. 2, Article 913, 15 pgs., DOI 10.15252/msb.20167233.
Steen et al., "Metabolic engineering of *Saccharomyces cerevisiae* for the production of n-butanol", Microbial Cell Factories, vol. 7, No. 36, Dec. 3, 2008, 8 pgs.
Stinchcomb et al., "Isolation and characterisation of a yeast chromosomal replicator", Nature, vol. 282, Nov. 1, 1979, pp. 39-43.
Studier et al., "Protein production by auto-induction in high-density shaking cultures", Protein Expression and Purification, vol. 41, No. 1, May 2005, pp. 207-234.
Sun et al., "Cloning and Characterization of a Panel of Constitutive Promoters for Applications in Pathway Engineering in *Saccharomyces cerevisiae*", Biotechnology and Bioengineering, vol. 109, No. 8, Aug. 2012, Electronic Publication: Mar. 15, 2012, pp. 2082-2092.
Tang et al., "Discovery of Unclustered Fungal Indole Diterpene Biosynthetic Pathways through Combinatorial Pathway Reassembly in Engineered Yeast", Journal of the American Chemical Society, vol. 137, No. 43, Nov. 4, 2015, pp. 13724-13727.
Weber et al., "antiSMASH 3.0—a comprehensive resource for the genome mining of biosynthetic gene clusters", Nucleic Acids Research, Jul. 1, 2015, vol. 43, No. W1, pp. W237-W243.
Weinhandl et al., "Carbon source dependent promoters in yeasts", Microbial Cell Factories, vol. 13, No. 5, Jan. 9, 2014, 17 pgs.
Xu et al., "Bidirectional promoters generate pervasive transcription in yeast", Nature, vol. 457, No. 7232, Feb. 19, 2009, Published Online: Jan. 25, 2009, pp. 1033-1037.
Yu et al., "Adjacent Upstream Activation Sequence Elements Synergistically Regulate Transcription of ADH2 in *Saccharomyces cerevisiae*", Molecular and Cellular Biology, vol. 9, No. 1, Jan. 1989, pp. 34-42.
Buren et al., "Formation of Nitrogenase NifDK Tetramers in the Mitochondria of *Saccharomyces cerevisiae*", ACS Synthetic Biology, Feb. 21, 2017, vol. 6, No. 6, pp. 1043-1055, DOI: 10.1021/acssynbio.6b00371.
Deutschbauer et al., "Quantitative trait loci mapped to single-nucleotide resolution in yeast", Nature Genetics, Nov. 6, 2005, vol. 37, pp. 1333-1340, DOI: https://doi.org/10.1038/ng1674.
Jones, "Tackling the protease problem in *Saccharomyces cerevisiae*", Methods in Enzymology, 1991, vol. 194, pp. 428-453, https://doi.org/10.1016/0076-6879(91)94034-A.
Keller et al., "Translating biosynthetic gene clusters into fungal armor and weaponry", Nature Chemical Biology, Aug. 18, 2015, vol. 11, pp. 671-677, DOI: https://doi.org/10.1038/nchembio.1897.
Labbe et al., "Copper ion inducible and repressible promoter systems in yeast", Methods in Enzymology, 1999, vol. 306, pp. 145-153, https://doi.org/10.1016/S0076-6879(99)06010-3.
Lee et al., "Determination of the extent of phosphopantetheinylation of polyketide synthases expressed in *Escherichia coli* and *Saccharomyces cerevisiae*", Analytical Biochemistry, Nov. 1, 2009, vol. 394, No. 1, pp. 75-80, https://doi.org/10.1016/j.ab.2009.07.010.
Liu et al., "Rapid customised operon assembly by yeast recombinational cloning", Applied Microbiology and Biotechnology, Jun. 2017, vol. 101, No. 11, pp. 4569-4580, DOI: https://doi.org/10.1007/s00253-017-8213-9.

(56) References Cited

OTHER PUBLICATIONS

Mattoon et al., "Effects of hap mutations on heme and cytochrome formation in yeast", Current Genetics, Feb. 1990, vol. 17, No. 2, pp. 179-183, DOI: https://doi.org/10.1007/BF00312865.

Ostergaard et al., "Physiological studies in aerobic batch cultivations of *Saccharomyces cerevisiae* strains harboring the MEL1 gene", Biotechnology and Bioengineering, May 5, 2000, First Published: Mar. 31, 2000, vol. 68, No. 3, pp. 252-259, https://doi.org/10.1002/(SICI)1097-0290(20000505)68:3<252::AID-BIT3>3.0.CO;2-K.

Ronicke et al., "Use of conditional promoters for expression of heterologous proteins in *Saccharomyces cerevisiae*", Methods in Enzymology, 1997, vol. 283, pp. 313-322, https://doi.org/10.1016/S0076-6879(97)83025-X.

Rutledge et al., "Discovery of microbial natural products by activation of silent biosynthetic gene clusters", Nature Reviews Microbiology, Aug. 2015, vol. 13, No. 8, pp. 509-523, DOI: https://doi.org/10.1038/nrmicro3496.

\* cited by examiner

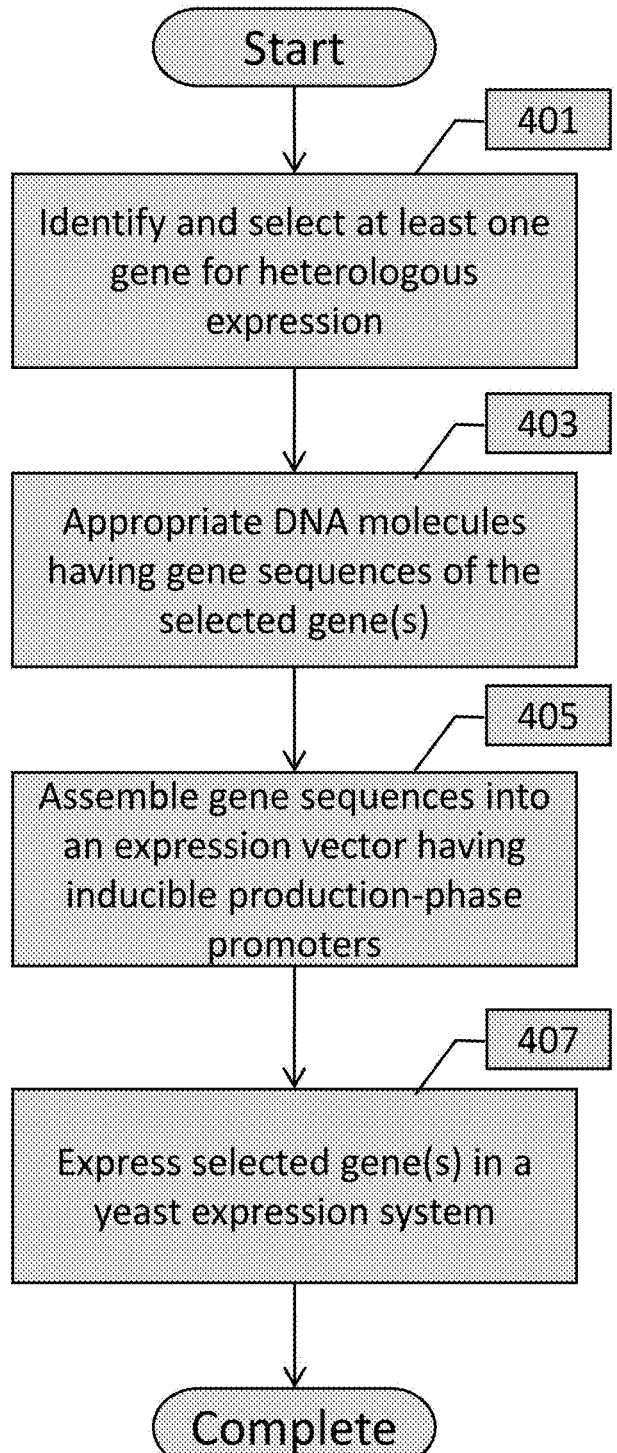

US 10,612,032 B2

INDUCIBLE PRODUCTION-PHASE PROMOTERS FOR COORDINATED HETEROLOGOUS EXPRESSION IN YEAST

CROSS REFERENCE TO RELATED APPLICATIONS

This application claims priority under 35 U.S.C. 119(e) to U.S. Provisional Application Ser. No. 62/313,108, filed Mar. 24, 2016, the disclosure of which is incorporated herein by reference in its entirety.

STATEMENT REGARDING FEDERALLY SPONSORED RESEARCH OR DEVELOPMENT

This invention was made with Government support under contract GM110706 awarded by the National Institutes of Health. The Government has certain rights in the invention.

FIELD OF THE INVENTION

The invention is generally directed to systems and constructs for heterologous expression in yeast, and more specifically to a set of inducible promoters that can be combined for coordinated expression of multiple genes and methods related to their construction and use.

BACKGROUND

Saccharomyces (S.) is a genus of fungi composed of different yeast species. The genus can be divided into two further subgenera S. sensu stricto and S. sensu lato. The former have relatively similar characteristics, including the ability to interbreed, exhibiting uniform karyotype of sixteen chromosomes, and their use in the fermentation industry. The later are more diverse and heterogeneous. Of particular importance is the S. cerevisiae species within the S. sensu stricto subgenus, which is a popular model organism used for genetic research.

The yeast S. cerevisiae is a powerful host for the heterologous expression of biosynthetic systems, including production of biofuels, commodity chemicals, and small molecule drugs. The yeast's genetic tractability, ease of culture at both small and large scale, and a suite of well-characterized genetic tools make it a desirable system for heterologous expression. Occasionally, production systems require coordinated expression of two or more heterologous genes. Coordinated expression systems in bacteria (e.g., E. coli) has long exploited the operon structure of bacterial gene clusters (e.g., lac operon), allowing a single promoter to control the expression of multiple genes. The construction of synthetic operons therefore allows a single inducible promoter to control the timing and strength of expression of an entire synthetic system. In yeast, many heterologous-expression systems do not rely on the operon system, but instead rely on a one-promoter, one-gene paradigm. Accordingly, multigene heterologous expression in most yeast strains is performed using multiple expression cassettes with a well-characterized promoter and terminator, each on a single expression vector (e.g., plasmid DNA) (See D. Mumberg, R. Muller, and M. Funk *Gene* 156:119-22, 1995, which is incorporated herein by reference). With traditional restriction-ligation cloning, it is also possible to recycle a promoter on a single plasmid by the serial cloning of multiple genes (M. C. Tang, et al., *J Am Chem Soc* 137:13724-27, 1995.

SUMMARY OF THE INVENTION

Many embodiments of the invention are directed to a DNA molecule composition comprising at least one exogenous DNA vector comprising at least two different production-phase promoters; wherein the two production-phase promoters are each capable of repressing heterologous expression of an exogenous gene in a *Saccharomyces cerevisiae* cell when the *S. cerevisiae* cell predominantly exhibits anaerobic energy metabolism; and wherein the two production-phase promoters are each also capable of inducing heterologous expression of the exogenous gene in the *S. cerevisiae* cell when the *S. cerevisiae* cell predominantly exhibits aerobic energy metabolism.

In further embodiments the at least one exogenous DNA vector further comprising a heterologous gene; wherein the heterologous gene Sequence is derived from a species other than *S. cerevisiae*; and wherein the heterologous gene is situated proximately downstream of one of the two production promoters such that the heterologous gene expression can be repressed and induced by the production promoter that is proximately upstream from the heterologous gene.

In more embodiments, the anaerobic energy metabolism is defined by the catabolism of a fermentable carbon source.

In further more embodiments, the fermentable carbon source is glucose or dextrose.

In even further more embodiments, the aerobic energy metabolism is defined by the catabolism of a nonfermetable carbon source.

In even further more embodiments, the nonfermentable carbon source is ethanol or glycerol.

In even further more embodiments, the DNA molecule compositions further comprise a *S. cerevisiae* cell, wherein the exogenous DNA vector exists within the *S. cerevisiae* cell.

In even further more embodiments, at least one of the at least two production phase promoters comprises a sequence of an endogenous production-phase promoter of *S. cerevisiae*.

In even further more embodiments, the production-phase promoter is substantially similar to a sequence selected from the group consisting of the *S. cerevisiae* ADH2 promoter (Seq. ID No. 1), *S. cerevisiae* PCK1 promoter (Seq. ID No. 2), the *S. cerevisiae* MLS1 promoter (Seq. ID No. 3), the *S. cerevisiae* ICL1 promoter (Seq. ID No. 4), the *S. cerevisiae* YLR307C-A promoter (Seq. ID No. 5), the *S. cerevisiae* YGR067C promoter (Seq. ID No. 6), the *S. cerevisiae* IDP2 promoter (Seq. ID No. 7), the *S. cerevisiae* ADY2 promoter (Seq. ID No. 8), the *S. cerevisiae* GAC1 promoter (Seq. ID No. 9), the *S. cerevisiae* ECM13 promoter (Seq. ID No. 10), the *S. cerevisiae* FAT3 promoter (Seq. ID No. 11), the *S. cerevisiae* PUT1 promoter (Seq. ID No. 12), the *S. cerevisiae* NQM1 promoter (Seq. ID No. 13), the *S. cerevisiae* SFC1 promoter (Seq. ID No. 14), the *S. cerevisiae* JEN1 promoter (Seq. ID No. 15), the *S. cerevisiae* SIP18 promoter (Seq. ID No. 16), the *S. cerevisiae* ATO2 promoter (Seq. ID No. 17), the *S. cerevisiae* YIG1 promoter (Seq. ID No. 18), and the *S. cerevisiae* FBP1 promoter (Seq. ID No. 19), In even further more embodiments, at least one of the at least two production phase promoters comprises a Sequence of an exogenous production-phase promoter of *S. cerevisiae*.

In even further more embodiments, the production-phase promoter is substantially similar to a sequence selected from the group consisting of the *S. paradoxus* ADH2 promoter (Seq. ID No. 36), the *S. kudriavzevii* ADH2 promoter (Seq. ID No. 37), *S. bayanus* ADH2 promoter (Seq. ID No.38), *S. paradoxus* PCK1 promoter (Seq. ID No. 41), the *S. kudriavzevii* PCK1 promoter (Seq. ID No. 42), *S. bayanus* PCK1 promoter (Seq. ID No. 43), *S. paradoxus* MLS1 promoter (Seq. ID No. 44), the *S. kudriavzevii* MLS1 promoter (Seq. ID No. 45), *S. bayanus* MLS1 promoter (Seq. ID No. 46), *S.*

*paradoxus* ICL1 promoter (Seq. ID No. 47), the *S. kudriavzevii* ICL1 promoter (Seq. ID No. 48), and *S. bayanus* ICL1 promoter (Seq. ID No. 49).

Many embodiments are directed to at least one exogenous DNA vector comprising a production-phase promoter, wherein the production-phase promoter is substantially similar to a sequence selected from the group consisting of the *S. cerevisiae* PCK1 promoter (Seq. ID No. 2), the *S. cerevisiae* MLS1 promoter (Seq. ID No. 3), the *S. cerevisiae* ICL1 promoter (Seq. ID No. 4), the *S. cerevisiae* YLR307C-A promoter (Seq. ID No. 5), the *S. cerevisiae* YGR067C promoter (Seq. ID No. 6), the *S. cerevisiae* IDP2 promoter (Seq. ID No. 7), the *S. cerevisiae* ADY2 promoter (Seq. ID No. 8), the *S. cerevisiae* GAC1 promoter (Seq. ID No. 9), the *S. cerevisiae* ECM13 promoter (Seq. ID No. 10), the *S. cerevisiae* FAT3 promoter (Seq. ID No. 11), the *S. cerevisiae* PUT1 promoter (Seq. ID No. 12), the *S. cerevisiae* NQM1 promoter (Seq. ID No. 13), the *S. cerevisiae* SFC1 promoter (Seq. ID No. 14), the *S. cerevisiae* JEN1 promoter (Seq. ID No. 15), the *S. cerevisiae* SIP18 promoter (Seq. ID No. 16), the *S. cerevisiae* ATO2 promoter (Seq. ID No. 17), the *S. cerevisiae* YIG1 promoter (Seq. ID No. 18), the *S. cerevisiae* FBP1 promoter (Seq. ID No. 19), the *S. paradoxus* ADH2 promoter (Seq. ID No. 36), the *S. kudriavzevii* ADH2 promoter (Seq. ID No. 37), *S. bayanus* ADH2 promoter (Seq. ID No.38), *S. paradoxus* PCK1 promoter (Seq. ID No. 41), the *S. kudriavzevii* PCK1 promoter (Seq. ID No. 42), *S. bayanus* PCK1 promoter (Seq. ID No. 43), *S. paradoxus* MLS1 promoter (Seq. ID No. 44), the *S. kudriavzevii* MLS1 promoter (Seq. ID No. 45), *S. bayanus* MLS1 promoter (Seq. ID No. 46), *S. paradoxus* ICL1 promoter (Seq. ID No. 47), the *S. kudriavzevii* ICL1 promoter (Seq. ID No. 48), and *S. bayanus* ICL1 promoter (Seq. ID No. 49).

In further embodiments, the selected production-phase promoter is substantially similar to the *S. cerevisiae* PCK1 promoter sequence (Seq. ID No. 2).

In more embodiments, the selected production-phase promoter is substantially similar to the *S. cerevisiae* MLS1 promoter sequence (Seq. ID No. 3).

In further more embodiments, the selected production-phase promoter is substantially similar to the *S. cerevisiae* ICL1 promoter sequence (Seq. ID No. 4).

In even further more embodiments, the selected production-phase promoter is substantially similar to a sequence selected from the group consisting of the *S. paradoxus* ADH2 promoter (Seq. ID No. 36), the *S. kudriavzevii* ADH2 promoter (Seq. ID No. 37), and *S. bayanus* ADH2 promoter (Seq. ID No. 38).

In even further more embodiments, the selected the production-phase promoter is substantially similar to a sequence selected from the group consisting of *S. paradoxus* PCK1 promoter (Seq. ID No. 41), the *S. kudriavzevii* PCK1 promoter (Seq. ID No. 42), *S. bayanus* PCK1 promoter (Seq. ID No. 43), *S. paradoxus* MLS1 promoter (Seq. ID No. 44), the *S. kudriavzevii* MLS1 promoter (Seq. ID No. 45), *S. bayanus* MLS1 promoter (Seq. ID No. 46), *S. paradoxus* ICL1 promoter (Seq. ID No. 47), the *S. kudriavzevii* ICL1 promoter (Seq. ID No. 48), and *S. bayanus* ICL1 promoter (Seq. ID No. 49).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The description will be more fully understood with reference to the following figures and data graphs, which are presented as exemplary embodiments of the invention and should not be construed as a complete recitation of the scope of the invention.

FIG. 4 illustrates a method to construct and utilize production-phase promoter DNA vectors in accordance with various embodiments of the invention.

BRIEF DESCRIPTION OF THE SEQUENCE LISTING

The current disclosure incorporates a sequence listing in accordance with the WIPO Standard ST.25. The Sequence listing embodies sixty-six nucleic acid sequences (Seq ID Nos. 1-66), which are referenced in Table 3 and throughout the specification.

DETAILED DESCRIPTION

Turning now to the drawings and data, embodiments of the invention are generally directed to systems and constructs of heterologous expression during the production phase of yeast. In many of these embodiments, the expression system involves coordinated expression of multiple heterologous genes. More embodiments are directed to production-phase promoter systems having promoters that are inducible upon an event in the yeast's growth or by the nutrients and supplements provided to the yeast. Specifically, a number of embodiments are directed to the promoters that are capable of being repressed in the presence of glucose and/or dextrose. In more embodiments, the promoters are capable of being induced in the presence of glycerol and/or ethanol. In additional embodiments, at least one production-phase promoter exists within an exogenous DNA vector, such as (but not limited to), for example, a shuttle vector, cloning vector, and/or expression vector. Embodiments are also directed to the use of expression vectors for the expression of heterologous genes in a yeast expression system.

Controlled gene expression is desirable in heterologous expression systems. For example, it would be desirable to express heterologous genes for production during a longer stable phase. Accordingly, decoupling the anaerobic growth and aerobic production phases of a culture allows the yeast to grow to high density prior to introducing the metabolic stress of expressing unnaturally high amounts of heterologous protein. In accordance with many embodiments, he anaerobic growth phase is defined by the yeast culture's energy metabolism in which the yeast cells predominantly catabolize fermentable carbon sources (e.g., glucose and/or dextrose), and a high growth rate (i.e., short doubling-time). In contrast, and in accordance with several embodiments, the aerobic production phase is defined by the yeast culture's energy metabolism in which the yeast cells predominantly catabolize nonfermentable carbon sources (e.g., ethanol and/or glycerol), and a steady growth rate (i.e., long doubling-time). Accordingly, each yeast cell's energy metabolism is binary and dependent on the local concentration of the carbon source.

Figure 1A:
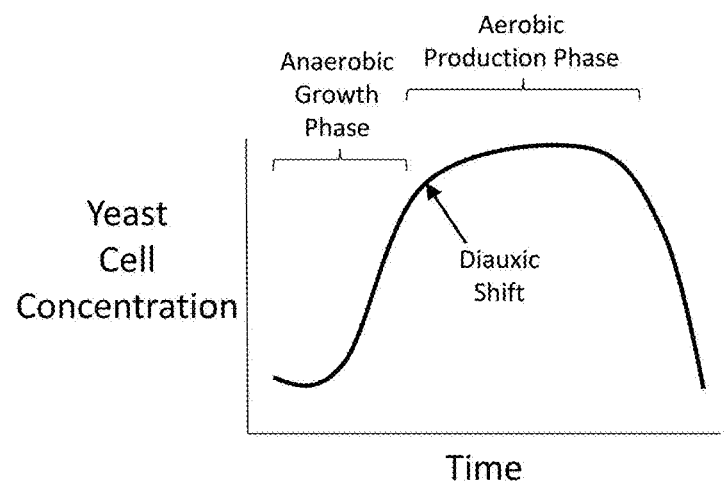
FIG. 1A illustrates a yeast phase chart displaying yeast cell concentration in relation to time to provide reference for various embodiments of the invention.

FIG. 1A depicts the phases of a yeast culture when provided a fermentable sugar, such as glucose or dextrose sugar, at a concentration of around 2-4% as its main carbon source. Initially, a yeast culture will predominantly catabolize the fermentable sugar, which correlates with an exponential growth with very high doubling rates. The growth phase typically lasts approximately 4-10 hours. During this phase, the catabolism of the fermentable sources results in the production of ethanol and glycerol.

Figure 1B:
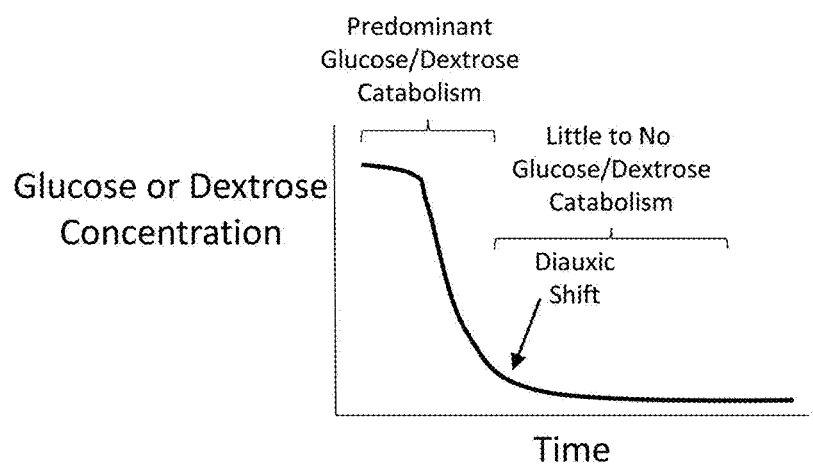
FIG. 1B illustrates a yeast phase chart displaying glucose concentration in relation to time to provide reference for various embodiments of the invention.

Once glucose becomes scarce, the growth of a yeast culture passes a diauxic shift and begins to predominantly catabolize nonfermentable carbon sources (e.g., ethanol and/or glycerol) (FIG. 1B). The predominant catabolism of nonfermentable carbon source correlates with a longer and more stable production phase that can last for several days, or even weeks in an industrial-like setting (FIG. 1A). During the production phase, yeast cultures reach and maintain a high concentration, but have a much lower doubling time (FIG. 1A). Due to the decrease in doubling rate, yeast cultures no longer expend a great amount of energy and resources on rapid growth and thus can reallocate that energy and those resources to other biological activities, including heterologous expression. Accordingly, it is hypothesized that limiting the transcription of heterologous genes to the production phase would allow a yeast culture to reach a high, healthy confluency that would in turn allow better heterologous protein expression and biosynthetic production.

In yeast, transcriptional regulation can be achieved in several ways, including inducement by chemical substrates (e.g., copper or methionine), the tetON/OFF system, and promoters engineered to bind unnatural hybrid transcription factors. Perhaps the most commonly employed inducible promoters are the promoters controlled by the endogenous GAL4 transcription factor. GAL4 promoters are strongly repressed in glucose, and upon switching to galactose as a carbon source, strong induction of transcription is observed (M. Johnston and R. W. Davis, *Mol. Cell Biol.* 4:1440-48, 1984, the disclosure of which is incorporated herein by reference). While this system leads to high-level transcription, only four galactose-responsive promoters are known, and galactose is both a more expensive and a less efficient carbon source as compared to glucose (S. Ostergaard, et al., *Biotechnol. Bioeng.* 68:252-59, 2000, the disclosure of which is incorporated herein by reference).

Other carbon-source dependent promoters have also been used for heterologous gene expression. The *S. cerevisiae* ADH2 gene exhibits significant derepression upon depletion of glucose as well as strong induction by either glycerol or ethanol (K. M. Lee & N. A. DeSilva *Yeast.* 22:431-40, 2005, the disclosure of which is incorporated herein by reference). Once induced, genes driven by the ADH2 promoter (pADH2) display expression levels equivalent to those driven by highly expressed constitutive counterparts. This induction profile was found to work in heterologous expression studies, as the system auto-induces upon glucose depletion in the late stages of fermentative growth after cells have undergone diauxic shift. The ADH2 promoter has been used extensively for yeast heterologous expression studies, resulting in high-level expression of several heterologous biosynthetic proteins (For example, see C. D. Reeves, et al., *Appl. Environ. Microbiol.* 74:5121-29, 2008, the disclosure of which is incorporated herein by reference).

Figure 1C:
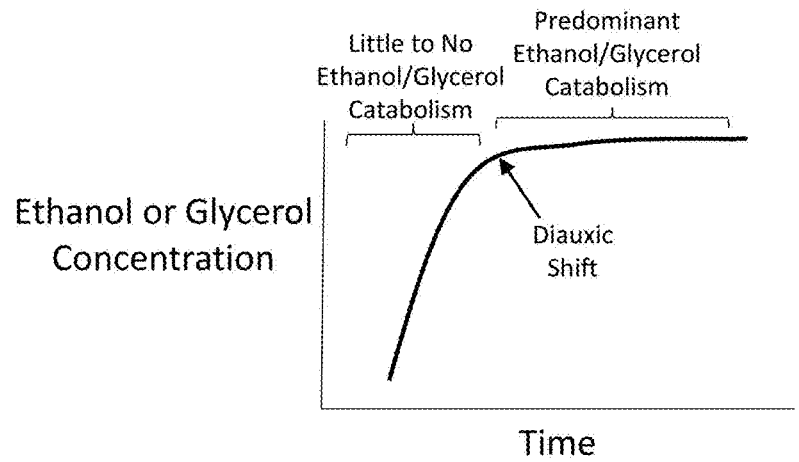
FIG. 1C illustrates a yeast phase chart displaying ethanol or glycerol concentration in relation to time to provide reference for various embodiments of the invention

As shown in FIG. 1C, the concentration of ethanol and glycerol increases as glucose and dextrose sugar decreases, due to anaerobic glycolysis (i.e., breaking down the fermentable sugar) and subsequent fermentation (i.e., converting the broken-down glucose into alcohol) and glycerol biosynthesis (i.e., converting the broken-down glucose into glycerol). Upon fermentable sugar depletion, yeast cultures undergo a diauxic shift and begin to use ethanol and glycerol as a carbon source instead of glucose. A diauxic shift, as understood in the art, is defined as a point in time when an organism switches consumption of one source for energy, to another source. This shift requires significant changes to a yeast culture's gene-expression pattern. Accordingly, it is hypothesized that higher concentrations of ethanol, (i.e., ~2-4%) and or glycerol (i.e., ~2%) could be used to stimulate promoters that either directly or indirectly respond to these concentrations (See FIGS. 1A and 1C).

Various embodiments of the invention are based on the discovery of inducible promoters that can be used for the coordinated expression of multiple genes (e.g., gene cluster pathway) in *Saccharomyces* yeast. Described below are sets of inducible promoters from *S. cerevisiae* and related species that are inactive during anaerobic growth, activating transcription only after a diauxic shift when glucose is near-depleted and the yeast cells are respiring (i.e., the production phase). As portrayed in various embodiments, various production-phase promoters are auto-inducing and allow automatic decoupling of the growth and production phases of a culture and thus initiate heterologous expression without the need for exogenous inducers. It should be noted, however, that many embodiments of the invention include production-phase promoters that are also inducible in the presence of nonfermentable carbon-sources (e.g., ethanol and/or glycerol) supplied to the yeast. As such, multiple embodiments employ recombinant production-phase promoters that act much like constitutive promoters when the host yeast cultures are constantly maintained in ethanol- and/or glycerol-containing media.

Once activated, the strength of various production-phase promoters can vary as much as 50-fold in accordance with numerous embodiments of the invention. The strongest production-phase promoters stimulate heterologous expression greater than that observed from strong constitutive promoters. The production-phase promoters could be employed in many different applications in which high expression of multiple genes is beneficial. Accordingly, the promoters can be used, for example, in multiple subunit protein production or for the production of biosynthetic compounds that are produced by multiple proteins within a pathway. Discussed in an exemplary embodiment below, embodiments of the invention are used to express multiple proteins involved in production of indole diterpene compound product. When compared to constitutive promoters, the production-phase promoters produced greater than a 2-fold increase in titer of the exemplary diterpene natural products. In other exemplary embodiments, it was found that the production-phase promoter system outperformed constitutive promoters by over 80-fold. Thus, these promoters can enable heterologous expression of biosynthetic systems in yeast.

The practice of several embodiments of the present invention will employ, unless otherwise indicated, conventional methods of chemistry, biochemistry, and molecular biology and recombinant DNA techniques within the skill of the art. Such techniques are explained fully in the literature. See, e.g., A. L. Lehninger, Biochemistry (Worth Publishers, Inc., 30 current addition); Sambrook, et al., Molecular Cloning: A Laboratory Manual (3rd Edition, 2001); Methods In Enzymology (S. Colowick and N. Kaplan eds., Academic Press, Inc.).

Inducible Production-Phase Promoters for Heterologous Expression in Yeast

In accordance with several embodiments of the invention, inducible production-phase promoters can be constructed into exogenous expression vectors for production of at least one protein in *Saccharomyces* yeast. In many embodiments, the constructed expression vectors have multiple inducible production-phase promoters in order to express multiple heterologous genes.

Several embodiments are directed to production-phase promoters and DNA vectors incorporating these promoters. Promoters, in general, are defined as a noncoding portion of DNA sequence situated proximately upstream of a gene to regulate and promote its expression. Typically, in *S. cerevisiae* and similar species, the promoter of a gene can be found within 500-bp upstream of a gene's translation start codon.

In accordance with several embodiments, production-phase promoters have two defining characteristics. First, production-phase promoters are capable of repressing heterologous expression of a gene in *S. cerevisiae* and similar species when the yeast is exhibiting anaerobic energy metabolism. As described previously, yeast exhibit anaerobic metabolism in the presence of a nontrivial concentration of fermentable carbon sources such as, for example, glucose or dextrose. In addition, production-phase promoters are also capable of inducing heterologous expression of a gene in *S. cerevisiae* and similar species when the yeast is exhibiting aerobic energy metabolism. As described previously, yeast exhibit aerobic metabolism when fermentable carbon sources are near depleted and the yeast cells switch to a catabolism of nonfermentable carbon sources such as glycerol or ethanol. These characteristics correspond to the phase charts in FIGS. 1A-1C. Tables 1 and 2 provide several examples of production-phase promoters in accordance with several embodiments. Table 3 provides sequences that correspond with the promoters and the incorporated sequence listing.

The production-phase promoters can be characterized based on their level of transgene expression relative to each other and to constitutive promoters. As described in an exemplary embodiment below, it was found that the sequence of endogenous promoters of the *S. cerevisiae* genes ADH2, PCK1, MLS1, and ICL1 exhibited high-level expression and thus can be characterized as strong production-phase promoters (Table 1). Sequences of the endogenous promoters of the *S. cerevisiae* genes YLR307C-A, ORF-YGR067C IDP2, ADY2, CAC1, ECM13, and FAT3 exhibited mid-level expression and thus can be characterized as semi-strong production phase promoters (Table 1). In addition, sequences of the endogenous promoters of the *S. cerevisiae* genes PUT1, NQM1, SFC1, JEN1, SIP18, ATO2, YIG1, and FBP1 exhibited low-level expression and thus can be characterized as weak production-phase promoters (Table 1).

TABLE 1

Production-Phase Promoters Expression Phenotype

| Gene Name | Systematic Name | Expression Phenotype | Sequence ID Number |
|---|---|---|---|
| ADH2 | YMR303C | Strong | 1 |
| PCK1 | YKR097W | Strong | 2 |
| MLS1 | YNL117W | Strong | 3 |
| ICL1 | YER065C | Strong | 4 |
| YLR307C-A | YLR307C-A | Semi-Strong | 5 |
| YGR067C | YGR067C | Semi-Strong | 6 |
| IDP2 | YLR174W | Semi-Strong | 7 |
| ADY2 | YCR010C | Semi-Strong | 8 |
| GAC1 | YOR178C | Semi-Strong | 9 |
| ECM13 | YBL043W | Semi-Strong | 10 |
| FAT3 | YKL187C | Semi-Strong | 11 |
| PUT1 | YLR142W | Weak | 12 |
| NQM1 | YGR043C | Weak | 13 |
| SFC1 | YJR095W | Weak | 14 |
| JEN1 | YKL217W | Weak | 15 |
| SIP18 | YMR175W | Weak | 16 |
| ATO2 | YNR002C | Weak | 17 |

TABLE 1-continued

Production-Phase Promoters Expression Phenotype

| Gene Name | Systematic Name | Expression Phenotype | Sequence ID Number |
|---|---|---|---|
| YIG1 | YPL201C | Weak | 18 |
| FBP1 | YLR377C | Weak | 19 |

The closely related *S. sensu stricto* species have similar genetics and growth characteristics. Accordingly, the phase charts provided in FIGS. 1A-1C apply generally to *S. sensu stricto* species. Table 2 provides a list of strong production-phase exogenous promoters of similarly related species in accordance with numerous embodiments of the invention.

TABLE 2

Strong Production-Phase Promoters of *S. sensu stricto* species

| Species | Gene Name | Sequence ID Number |
|---|---|---|
| S. paradoxus | ADH2 | 36 |
| S. kudriavzevii | ADH2 | 37 |
| S. bayanus | ADH2 | 38 |
| S. paradoxus | PCK1 | 41 |
| S. kudriavzevii | PCK1 | 42 |
| S. bayanus | PCK1 | 43 |
| S. paradoxus | MLS1 | 44 |
| S. kudriavzevii | MLS1 | 45 |
| S. bayanus | MLS1 | 46 |
| S. paradoxus | ICL1 | 47 |
| S. kudriavzevii | ICL1 | 48 |
| S. bayanus | ICL1 | 49 |

It should be noted that substantially similar sequences to the production-promoter sequences are expected to regulate heterologous expression in *S. cerevisiae* and achieve similar results. Accordingly, a substantially similar sequence of a production-phase promoter, in accordance with numerous embodiments, is any sequence with a high homology such that when regulating heterologous expression in *S. cerevisiae* that it achieves substantially similar results. For example, in an exemplary embodiment below, it was found that the ADH2 promoter of *S. bayanus* is only 61% homologous, yet achieved strong heterologous expression in *S. cerevisiae*, similar to the endogenous ADH2 promoter.

Figure 2A:
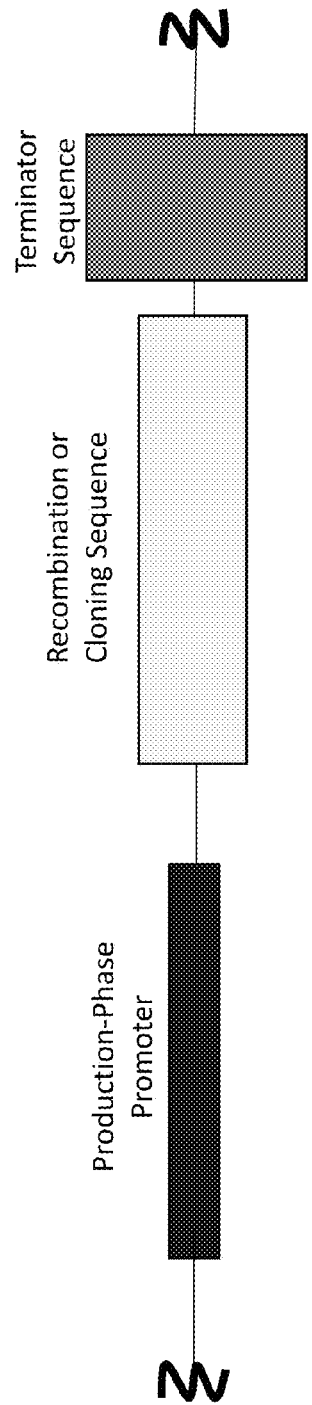
FIG. 2A illustrates a DNA vector having a production-phase promoter in accordance with an embodiment of the invention.

In FIG. 2A, an exemplary schematic of a section of an exogenous DNA vector (e.g., cloning vector, expression vector, and/or shuttle vector) having a production-phase promoter sequence embedded within. A vector is capable of transferring nucleic acid sequences to target cells (e.g., yeast). Typical DNA vectors include, but are not limited to, plasmid or viral constructs. DNA vectors are also meant to include a kit of various linear DNA fragments that are to be recombined to form a plasmid or other functional construct, as is common in yeast homologous recombination methods (See e.g., Z. Shao, H. Zhao & H. Zhao, 2009, *Nucleic Acids Research* 37:e16, 2009, the disclosure of which is incorporated herein by reference). Often, embodiments of cloning vectors will incorporate other sequences in addition to the production-phase promoter. As depicted in FIG. 2A, the exemplary cloning vector has a terminator sequence and cloning/recombination sequence in addition to the production-phase promoter, each of which can assist with expression vector construction. Furthermore, other sequences necessary for growth and amplification can be incorporated into the promoter vector. Embodiments of these sequences may include, for example, at least one appropriate origin of replication, at least one selectable marker, and/or at least one auxotrophic marker. It should be noted, however, that various embodiments of the invention are not required to contain cloning, terminator, or either sequences. For example, embodiments of a typical shuttle vector may only contain the production-phase promoter sequence along with the necessary sequences for amplification in a biological system.

For purposes of this application, an exogenous DNA vector is any DNA vector that was constructed, at least in part, exogenously. Accordingly, DNA vectors that are assembled using the yeast's own cell machinery (e.g., yeast homologous recombination) would still be considered exogenous if any of the DNA molecules transduced within yeast for recombination contain exogenous sequence or were produced by a non-host methodology, such as, for example, chemical synthesis, PCR amplification, or bacterial amplification.

Figure 2B:
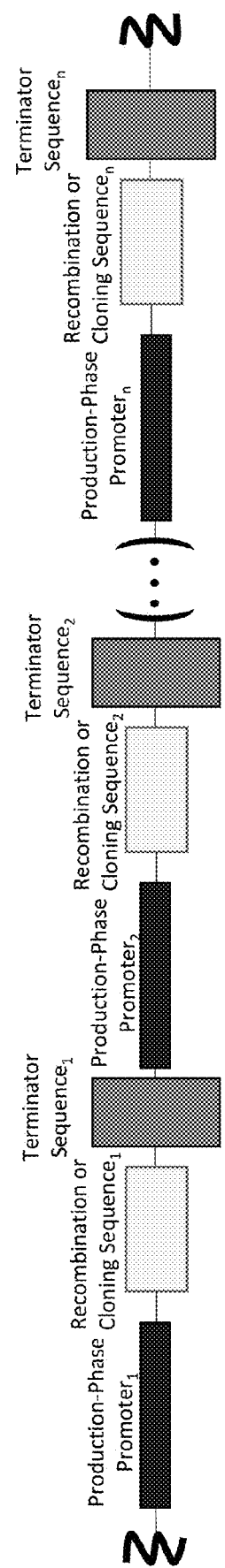
FIG. 2B illustrates a DNA vector having multiple production-phase promoters in accordance with an embodiment of the invention.

As shown in FIG. 2B, various embodiments of the invention are directed to DNA vectors having multiple production-phase promoters. In these various embodiments, multiple different production-phase promoters are incorporated, preferably each having a unique sequence and derived from a different gene and/or *S. sensu stricto* species. Having unique promoter sequences can prevent complications that can arise during product production in yeast, such as, for example, unwanted DNA recombination at sites similar to the promoter sequences that render the DNA vector constructs undesirable. In many embodiments, the DNA vector has at least two production-phase promoters and up to a number that still yields the vector useful. As the size of the DNA vector increases, the utility may decrease, as larger vectors may become unwieldly for the intended organism to handle. For example, plasmids for amplification in *E. coli* are often somewhere between 2,000 and 10,000 base pairs (bp) but can handle up to 20,000 bp or so. Likewise, plasmids for amplification and growth in yeast can vary from approximately 10,000 to 30,000 bp. Viral vectors, on the other hand, often have a limited construct size and thus may require a more precise vector size. Thus, depending on vector and intended use, the number of production-phase promoters within a DNA vector will vary.

Although FIG. 2B depicts recombination sites, cloning sites, and terminator sequences, it should be noted that these sequences may or may not be included in various embodiments of DNA vectors having multiple production-phase promoters. The incorporation of these sequences or other various sequence is often dependent on the purpose of the DNA vector. For example, cloning vectors may not include a terminator sequence if that sequence is to be incorporated into an expression construct at another stage of assembly.

Figure 3A:
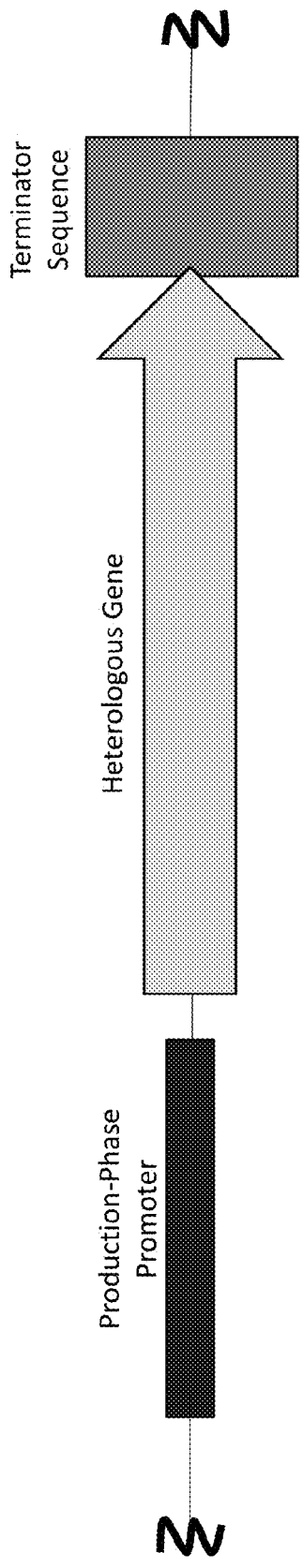
FIG. 3A illustrates a DNA expression vector having a production-phase promoter within an expression cassette in accordance with an embodiment of the invention.

FIG. 3A depicts an exemplary heterologous expression vector having a production-phase promoter for expression in yeast, in accordance with various embodiments of the invention. Expression constructs contain an expression cassette that minimally has a promoter, a heterologous gene, and a terminator sequence in order to produce an RNA molecule in an appropriate host. Expression cassette in accordance with numerous embodiments will have a production-phase promoter situated proximately upstream of a heterologous gene of which the promoter is to regulate expression. It should be understood, that the precise location of the production-phase promoter upstream of the heterologous gene may vary, but the promoter must be within a certain proximity to adequately function.

In many embodiments of the invention, a heterologous gene is any gene driven by a production-phase promoter, wherein the heterologous gene is different than the endogenous gene that the promoter regulates within its endogenous genome. Accordingly, a *S. cerevisiae* production-phase promoter could regulate another *S. cerevisiae* gene provided that the gene to be regulated is not the gene endogenously regulated. For example, the *S. cerevisiae* ADH2 promoter should not regulate the *S. cerevisiae* ADH2 gene; however, the *S. cerevisiae* ADH2 promoter can regulate any other *S. cerevisiae* gene or the ADH2 gene from any other species. Often, in accordance with many embodiments, the heterologous gene is from a different species than the species from which the production-promoter sequence was obtained.

Although not depicted, various embodiments of expression cassettes may include other sequences, such as, for example, intron sequences, Kozak-like sequences, and/or protein tag sequences (e.g., 6x-His) that may or may not improve expression, production, and/or purification. In yeast, various embodiments of expression vectors will also minimally have a yeast origin of replication (e.g., 2-micron) and an auxotrophic marker (e.g., URA3) in addition to the expression cassette. Other nonessential sequences may also be included, such as, for example, bacterial origins of replication and/or bacterial selection markers that would render the expression capable of amplification in a bacterial host in addition to a yeast host. Accordingly, various embodiments of expression vectors would include the essential sequences for heterologous expression in yeast and other various embodiments would include additional nonessential sequences.

Figure 3B:
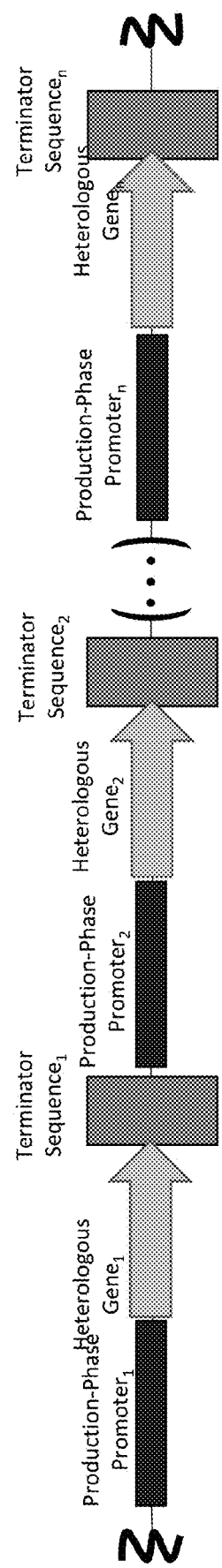
FIG. 3B illustrates a DNA expression vector having multiple production-phase promoters, each within an expression cassette in accordance with an embodiment of the invention.

In accordance with various embodiments, a DNA vector having a production-phase promoter expression cassette can be transformed into a yeast cell. Or alternatively, and in accordance with numerous embodiments, a DNA vector having a production-phase promoter expression cassette can be assembled within yeast using homologous recombination techniques. Once existing within a yeast cell, the production-phase promoter can regulate the expression of a heterologous gene in accordance with the yeast cell's energy metabolism. As described previously, and in accordance with many embodiments, production-phase promoters repress heterologous expression when the yeast cell is in an anaerobic energy metabolic state. Alternatively, and in accordance with a number of embodiments, production-phase promoters induce heterologous expression when the yeast cell is in an aerobic energy metabolic state Depicted in FIG. 3B are alternative exemplary heterologous expression vectors having multiple production-phase promoters for expression of multiple genes in yeast in accordance with numerous embodiments. In these embodiments, the expression vectors will include at least two expression cassettes, each with a unique promoter, gene, and terminator sequence in order to prevent unwanted recombination. The number of expression cassettes will vary based on vector construct design and application. For heterologous expression in *S. cerevisiae*, it has been found that plasmid expression vectors of approximately 30,000 bp are still tolerated. Thus, vectors containing up to seven production-phase promoter expression cassettes can be incorporated into an expression vector and have been found to be able to maintain adequate gene expression and protein production. Larger vectors with more expression cassettes may be tolerated.

Although FIG. 3B depicts multiple expression cassettes sequentially in the same orientation 5' to 3', it should be understood that the combination of two or more expression cassettes is not limited to sequential linear organization in the same orientation. Expression cassettes in accordance with many embodiments exist within the expression vector in any orientation and in any sequential order. Furthermore, it should be understood that other sequence elements of an expression vector (e.g., auxotrophic marker) may be among and/or between the multiple expression cassettes. Optimal vector design is likely to depend on various factors, such as, for example, optimizing the location of the auxotrophic marker to enable the final expression vector to include each expression cassette to be incorporated.

DNA heterologous expression vectors are a class of DNA vectors, and thus the description of general DNA vectors above also applies to the expression vectors. Accordingly, many embodiments of the expression vectors are formulated into a plasmid vector, a viral vector, or a kit of linear DNA fragments to be recombined into a plasmid by yeast homologous recombination. In several of these embodiments, the end-product vector contains at least one expression cassette having a production-phase promoter. It should be understood, that in addition to the at least one production-phase promoter, some vector embodiments incorporate expression cassettes that include other promoters, such as (but not limited to), constitutive promoters that maintain high expression during the growth and production phases.

The various embodiments of heterologous expression vectors having at least one production-phase promoter can be used in numerous applications. For example, high expression in the production phase can lead to better, prolonged expression, as compared to constitutive promoters. In many applications, the end product is a protein from a single gene or a protein complex of multiple genes to be purified from the culture. For these applications, high, prolonged expression using production-phase promoters can lead to better yields of proteins. Furthermore, when the heterologous protein is toxic to the host yeast cells, the use of production-phase promoters prevents the expression of the toxic protein during growth phase, allowing the yeast to reach a healthy confluency before mass protein production.

The production-phase promoter vectors can also benefit the production of a biosynthetic compound from a gene cluster. Many products derived from various natural species are produced from a cluster of genes with sequential enzymatic activity. For example, the antibiotic emindole SB is produced from a cluster of four genes that is expressed in *Aspergillus tubingensis*. To reproduce this gene cluster in a yeast production model, a production-promoter vector system with four different expression cassettes could work. This system would allow the yeast to reach a healthy confluency before the energy-draining expression of four heterologous proteins begin, leading to better overall yields of the antibiotic product. In fact, experimental results provided in an exemplary embodiment described below demonstrate that a production-phase promoter vector outperformed a constitutive promoter vector approximately 2-fold to produce the emindole SB product.

FIG. 4 depicts an exemplary process (Process 400) to implement various embodiments of production-phase promoters. To begin, Process 400 identifies and selects at least one gene for heterologous expression in yeast (401). The choice of gene(s) for expression would depend on the desired outcome. For example, to produce a biosynthetic compound, one would likely select to express all the genes within a biosynthetic gene cluster of a particular organism. Once the gene(s) have been selected, Process 400 then appropriates DNA molecules having the coding sequence of the selected genes (403). As is well known in the art, there are many ways to appropriate DNA molecules, which include chemical synthesis, extraction directly from the biological source, or amplification of a gene by polymerase chain reaction (PCR).

Process 400 then uses the appropriated DNA molecules to assemble these molecules into an expression vector having production-phase promoters (405). There are many ways to assemble DNA expression vectors that are well known in the art, which include popular methodologies such as homologous recombination and restriction digestion with subsequent ligation. After assembly, the resultant expression vectors can be expressed in *Saccharomyces* yeast to obtain the desired outcome (407).

Exemplary Embodiments

Biological data supports the systems and constructs of production-phase promoter DNA vectors and applications thereof. Provided below are several examples of incorporating production-phase promoters into DNA vectors. Many of these vectors were used to produce biosynthetic products from multi-gene clusters derived from various fungal species. Compared to a constitutive promoter system, a production-phase promoter system in accordance with various embodiments produced several fold greater product.

Production Phase Promoter Expression Analysis

Because the ADH2 promoter (Seq. ID No. 1) has properties of a production-phase promoter, a panel of promoter sequences was compared to the ADH2 promoter to identify other production-phase promoters. To begin, endogenous *S. cerevisiae* genes were identified that appeared co-regulated with ADH2 in a previous genome-wide transcription study (Z. Xu. et al., Nature 457:1033-37, 2009, the disclosure of which is incorporated herein by reference). In this study, transcription of yeast genes was quantified during mid-exponential growth in several types of growth media. Of the 5171 ORFs examined, 35 appeared co-regulated with ADH2, with co-regulation defined as a greater than two-fold increase in expression with a non-fermentable carbon source (ethanol in a yeast-peptone-ethanol (YPE) media) as compared to a fermentable carbon source (dextrose in a yeast-peptone-dextrose (YPD) media). Because these data were collected at a single time point and assessed transcription of genes in their native context, their ability to co-regulate heterologous genes in a production-phase promoter system required further validation and characterization.

A detailed characterization of the ability of 34 selected promoters to control expression of heterologous genes was performed. A promoter was defined as the shorter of (a) 500 bp upstream of the start codon, or (b) the entire 5' intergenic region. Each promoter was cloned upstream of the gene for monomeric enhanced GFP (eGFP) and integrated each of the resulting cassettes in a single copy at the ho locus of individual strains. Control strains were included in which strong constitutive FBA1 and TDH3 promoters were cloned upstream of eGFP in an identical manner. The 35 promoter sequences can be found in Table 3. (Seq. ID Nos. 2-35)

Figure 5:
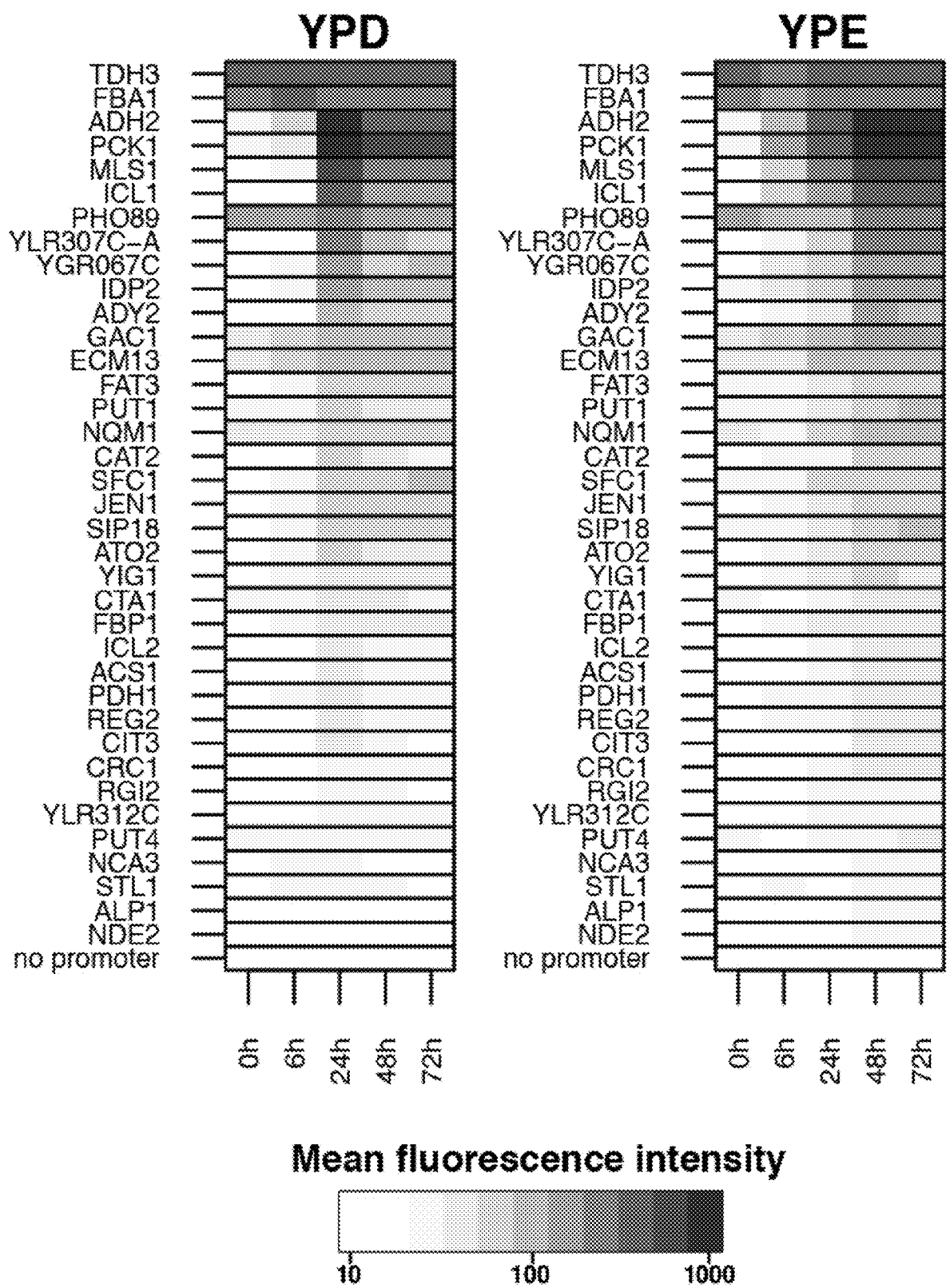
FIG. 5 is a heat map graphic generated in accordance with various embodiments of the invention with data of expression of enhanced-Green Fluorescent Protein driven by various *S. cerevisiae* promoters.
Figure 6:
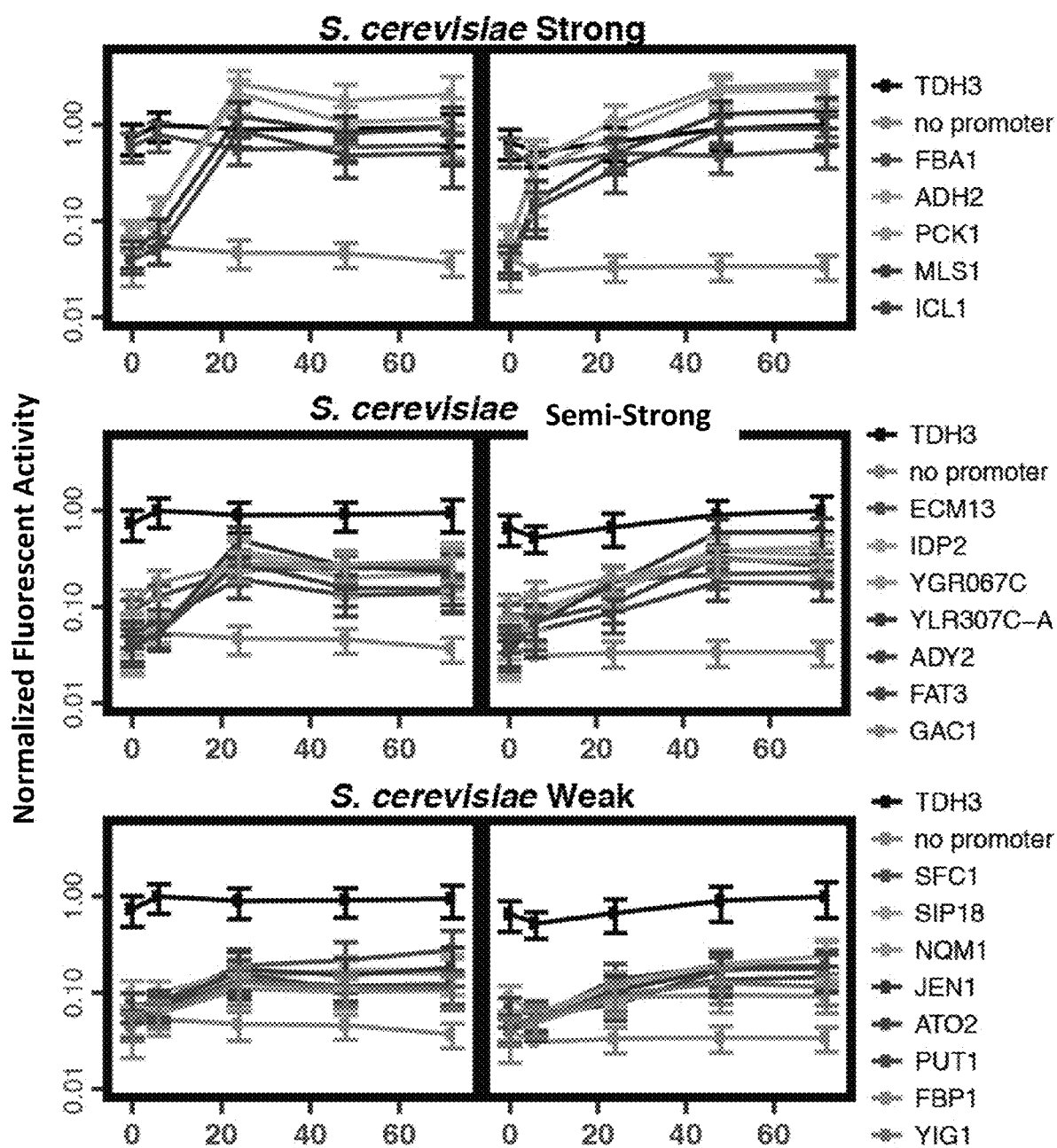
FIG. 6 is a data graph of enhanced-Green Fluorescent Protein expression driven by various *S. cerevisiae* promoters, generated in accordance with various embodiments of the invention.
Figure 7:
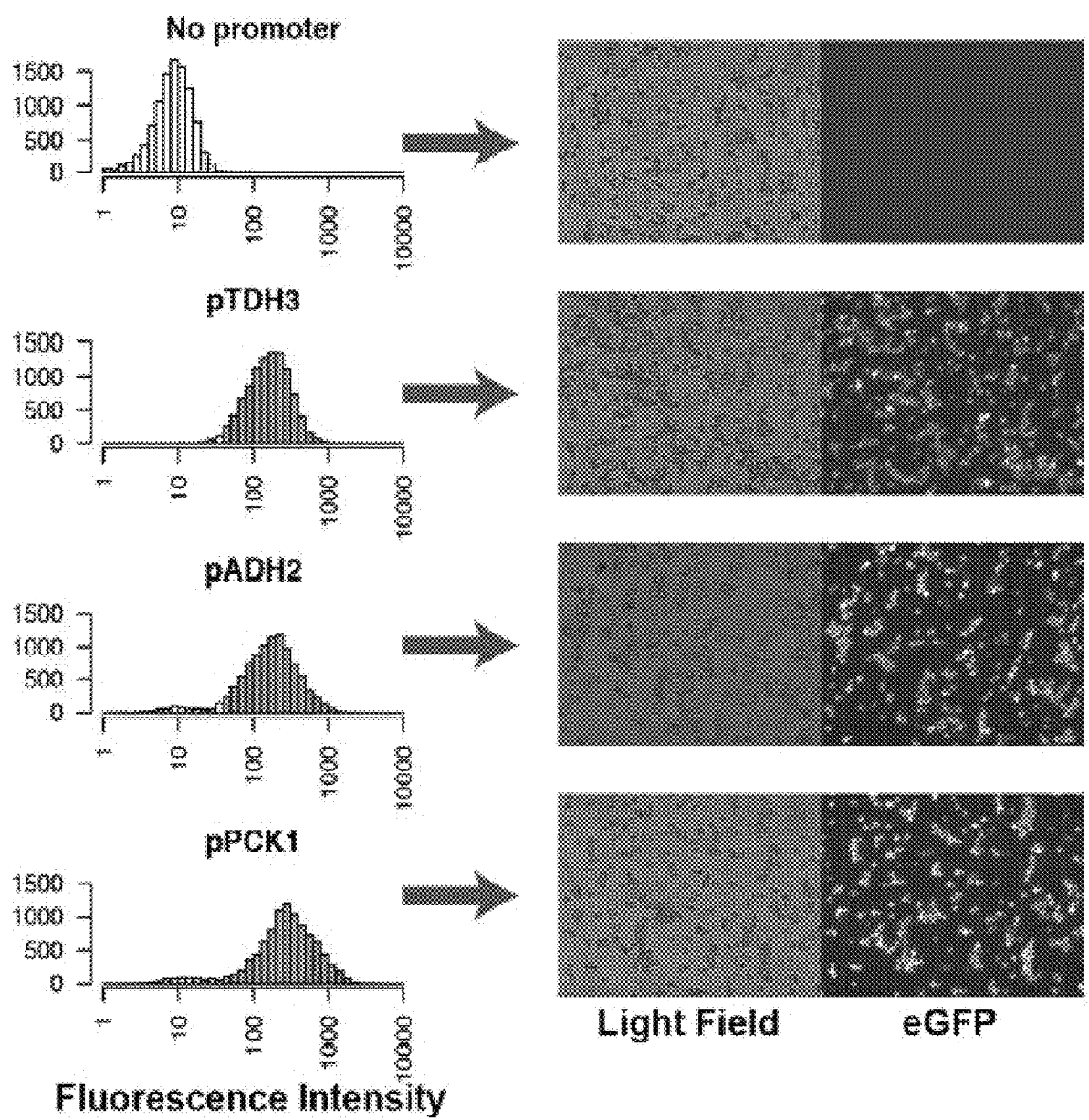
FIG. 7 illustrates fluorescence intensity of enhanced-Green Fluorescent Protein driven by various promoters, generated in accordance with various embodiments of the invention.

In order to compare the 35 putative production-phase promoters, the expression of eGFP protein was assessed over 72 hours in each strain by flow cytometry in media with both fermentable (YPD) and non-fermentable (YPE) carbon sources (FIGS. 5 and 6). All cultures were started in YPD media and analysis of eGFP expression began when cells were in the midst of exponential fermentative growth (OD600=0.4, 0 hrs). At this point, cells were either left to continue growth in YPD or spun-down and resuspended in YPE. Consistent with previous work, pADH2 was entirely repressed during exponential fermentative growth (0 hrs) unlike the constitutive promoters pTDH3 and pFBA1, which were expressed at near maximum levels regardless of phase. Moderate expression from pADH2 was observed after a further 6 hours in YPD culture or following a growth media switch to YPE. Within 24 hrs, expression reached levels exceeding those observed in the strong constitutive systems. Cytometry histograms and fluorescence microscopy demonstrated that within 48 hours, >95% of all cells with pADH2 and pPCK1 driven expression were fluorescing above background (FIG. 6). Protein expression levels spanned 50-15 fold, with most showing little or no expression until 24 hours into the culture (FIGS. 5 and 6). Transgene expression driven by the PCK1, MLS1, and ICL1 promoters (Seq. ID Nos. 2-4) not only showed the same timing of expression as pADH2, but also expressed at an equivalently high level. The promoters of genes YLR307C-A, YGR067C, IDP2, ADY2, GAC1, ECM13 and FAT3 (Seq. ID Nos. 5-11) displayed semi-strong transgene expression (FIG. 5). In addition, the promoters of genes PUT1, NQM1, SFC1, JEN1, SIP18, ATO2, YIG1, and FBP1 (Seq. ID Nos. 12-19) displayed weak of transgene expression (FIGS. 5 and 6). The promoter PHO89 (Seq. ID No. 20) did not exhibit strong repression in during the growth phase (FIG. 5, 0 and 6 hours). The results of the other sequences are also depicted in FIG. 5 (Seq. ID Nos. 22-36). The constitutive promoters pTDH3 and pFBA1 (Seq. ID Nos. 50 and 52) were used as controls (FIGS. 5 and 6).

Figure 8:
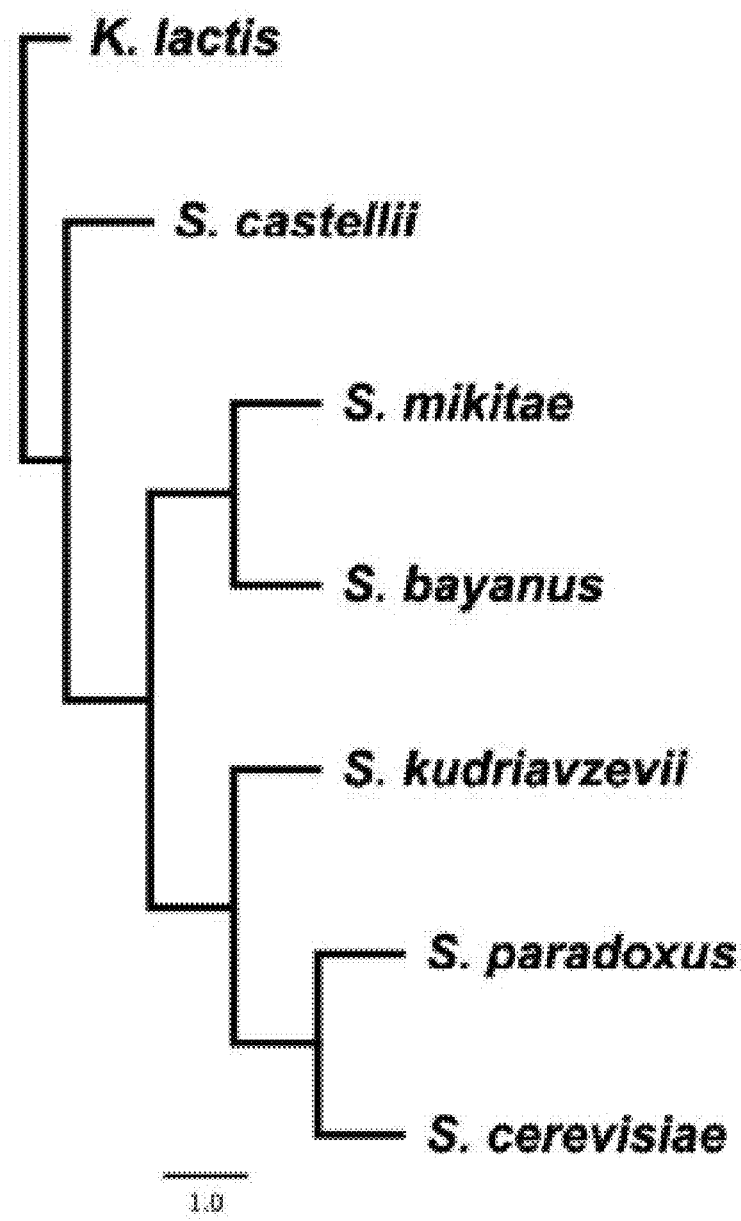
FIG. 8 illustrates a phylogenetic tree of *Saccharomyces sensu stricto* subgenus to provide reference for various embodiments of the invention.
Figure 9:
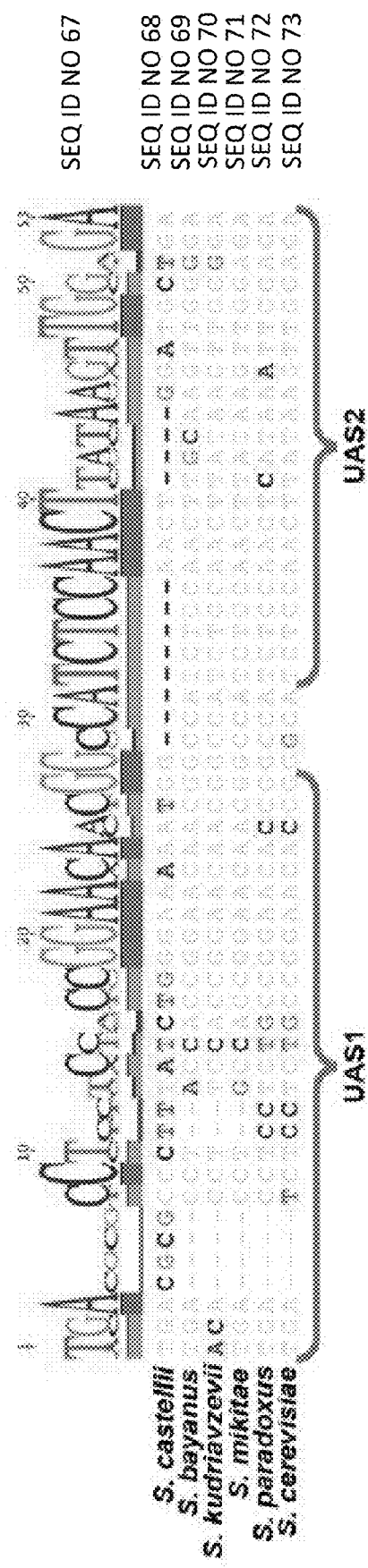
FIG. 9 illustrates a multiple sequence alignment of various *Saccharomyces sensu stricto* species' upstream activating sequences in ADH2 promoters to provide reference for various embodiments of the invention.
Figure 10:
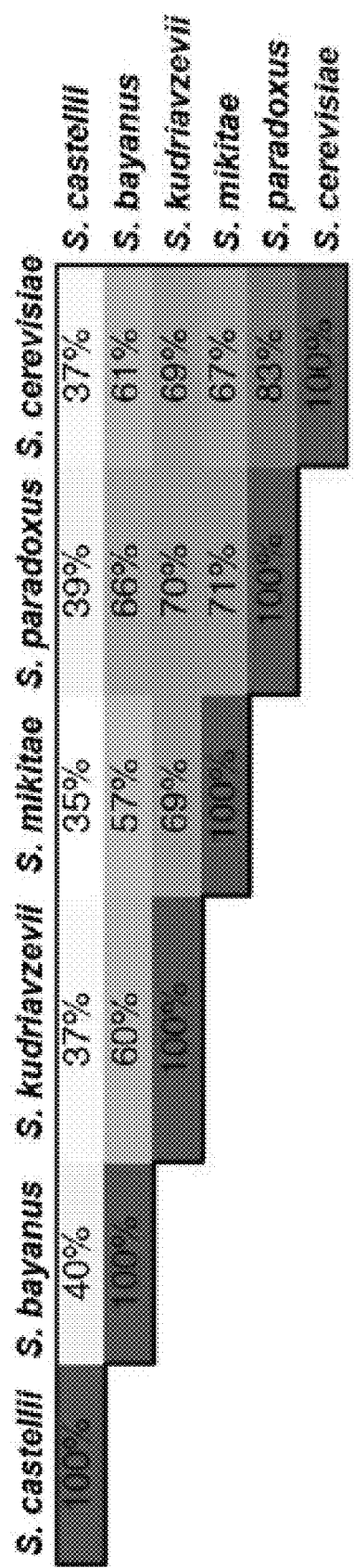
FIG. 10 illustrates homology between various *Saccharomyces sensu stricto* species' ADH2 promoters to provide reference for various embodiments of the invention.

The above analysis identified a large set of co-regulated promoters spanning a wide range of expression levels, three of which were as strong as pADH2. However, a more extensive set of strong production-phase promoters is desirable for assembly of constructs having multi-gene pathways, especially pathways having more than four genes. To identify other production-phase promoter candidates, the genomes of five closely related species within the *S. sensu stricto* complex were examined (FIG. 8). The promoter region was identified for the closest ADH2 gene homolog in the genomes of *Saccharomyces bayanus, Saccharomyces paradoxus, Saccharomyces mikitae, Saccharomyces kudriavzevii*, and *Saccharomyces castellii*. Multiple sequence alignment of the upstream activation sequences (UAS) revealed that nearly all sequences (except that from *S. castellii*) are highly conserved across this region, suggesting a potential for regulation similar to that of *S. cerevisiae* ADH2 (FIG. 9, Seq. ID Nos. 36-40). In order to be used for single-step pathway assembly, all promoter sequences must be sufficiently unique to prevent undesired recombination between each other. Therefore, the pairwise identities for each of the *Saccharomyces sensu stricto* ADH2 promoter pairs were analyzed (FIG. 10). The most similar promoter to the *S. cerevisiae* ADH2 promoter is that from *S. paradoxus*, with 83% identity, including a single 40 bp stretch located near the center of the promoter. This homology is significantly less than the 50-100 bp typically used for assembly by yeast homologous recombination, and recombination events between sequences with this level of identity occur at very low frequency, suggesting that these promoters should be compatible with a multi-gene assembly technique utilizing YHR as described above.

Figure 11:
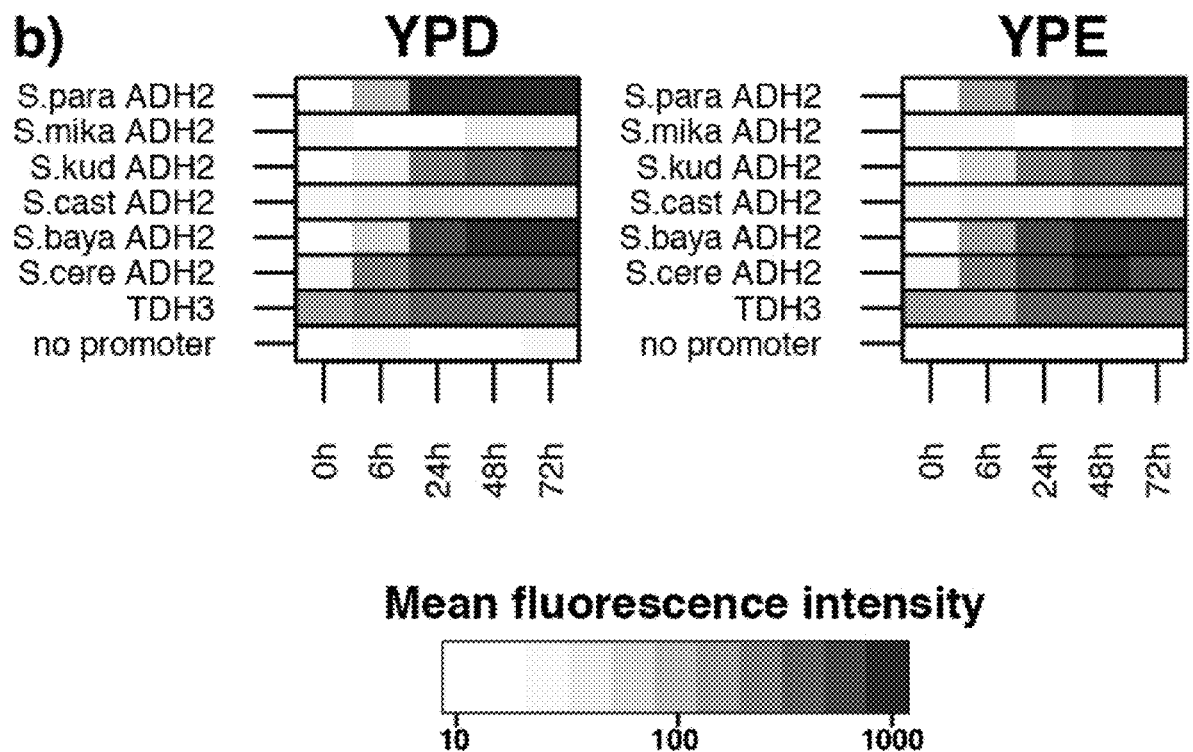
FIG. 11 is a heat map graphic generated in accordance with various embodiments of the invention with data of expression of enhanced-Green Fluorescent Protein driven by various *S. sensu stricto* ADH2 promoters.
Figure 12:
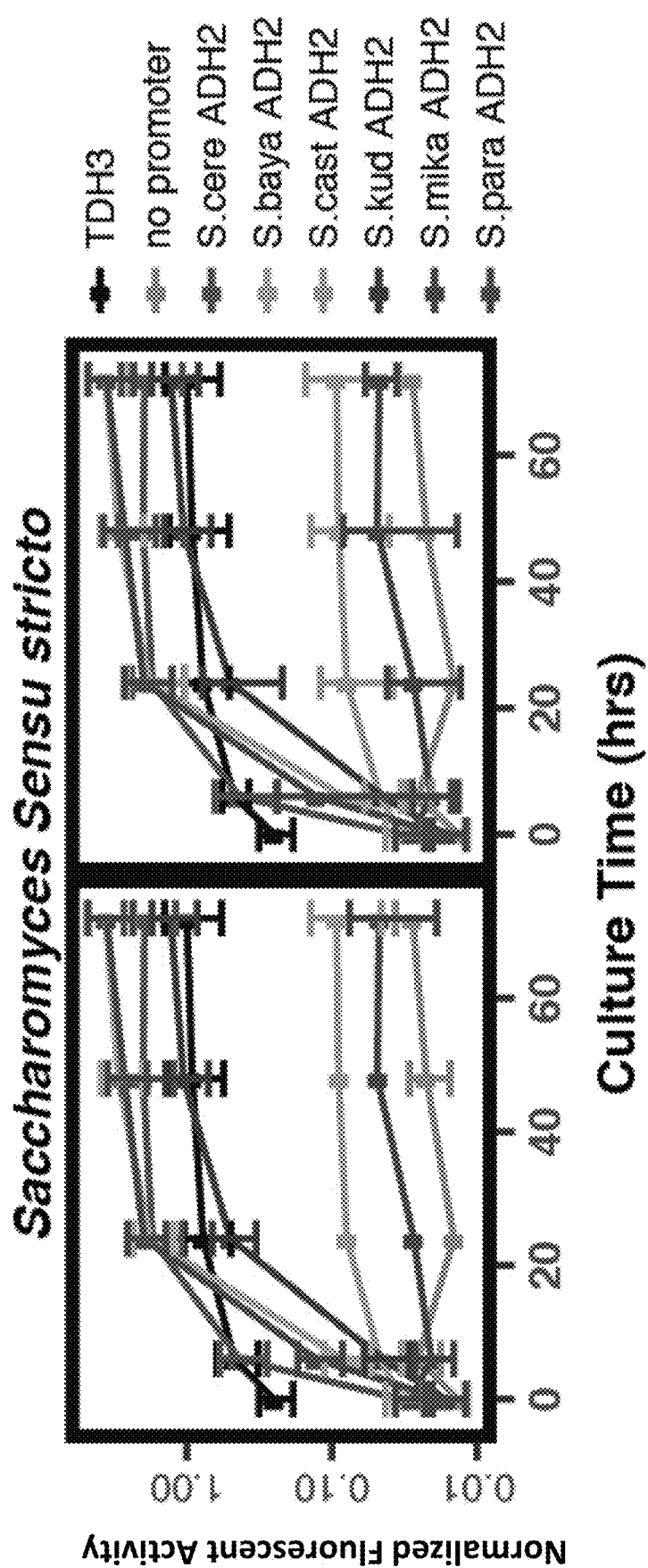
FIG. 12 is a data graph of enhanced-Green Fluorescent Protein expression driven by various *S. sensu stricto* ADH2 promoters, generated in accordance with various embodiments of the invention.

As with the endogenous yeast promoter candidates, these other putative *Saccharomyces* promoters required detailed characterization of induction profiles. DNA encoding each of these promoter sequences was obtained by commercial synthesis and characterized expression of eGFP from each promoter in the same manner as the endogenous yeast promoters (FIGS. 11 and 12). Of the five *Saccharomyces sensu stricto* pADH2s tested (Seq. ID Nos. 36-40), the promoters derived from *S. paradoxus*, *S. kudriavzevii*, and *S. bayanus* show timing and strength of expression equivalent to that of *S. cerevisiae* pADH2. In combination with the endogenous yeast promoters, these three additional *Saccharomyces* pADH2s expand the number of strong promoters with the desired induction profile.

Figure 13:
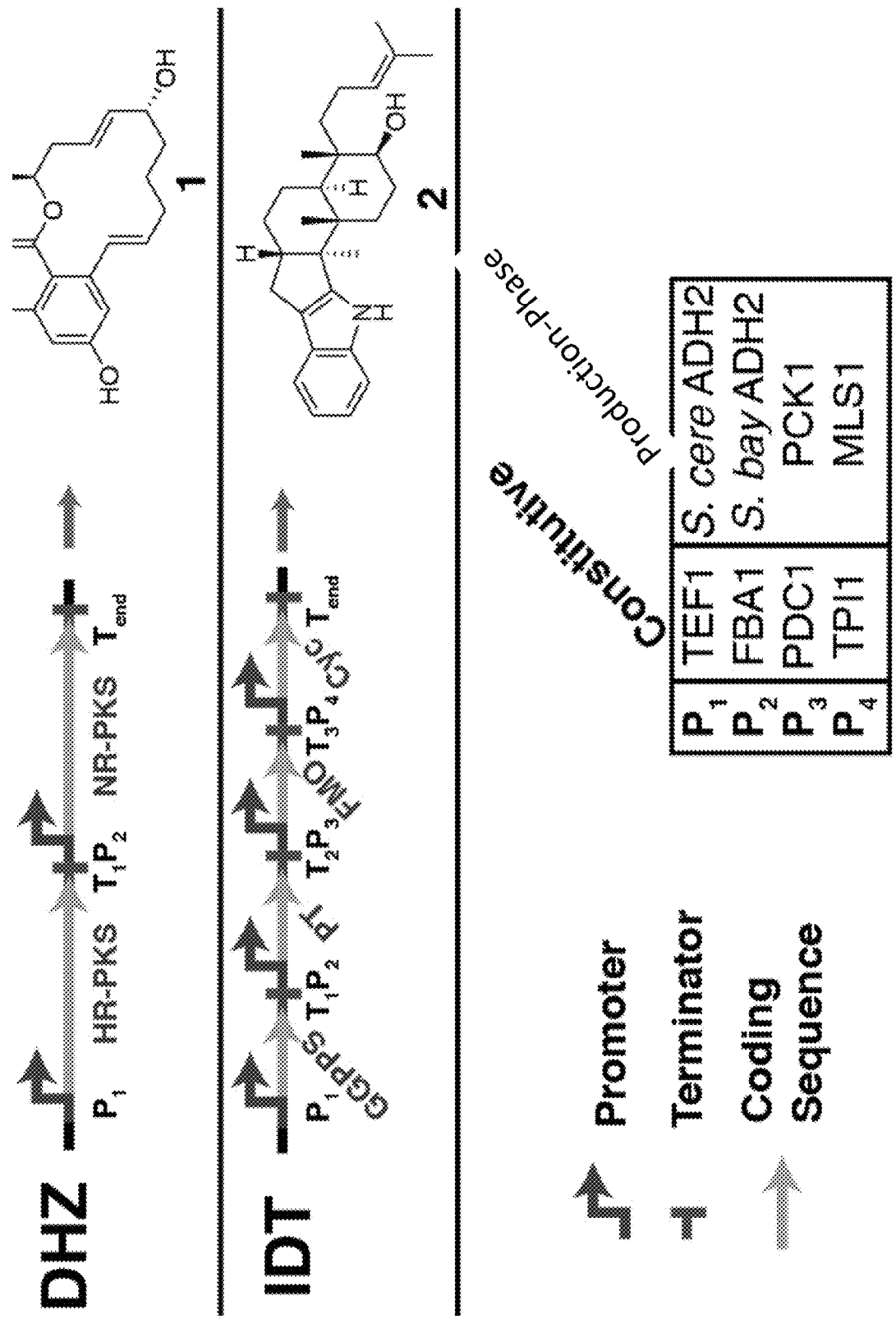
FIG. 13 illustrates four multi-gene expression vector constructs, each to generate a product compound, in accordance with an embodiment of the invention.
Figure 14:
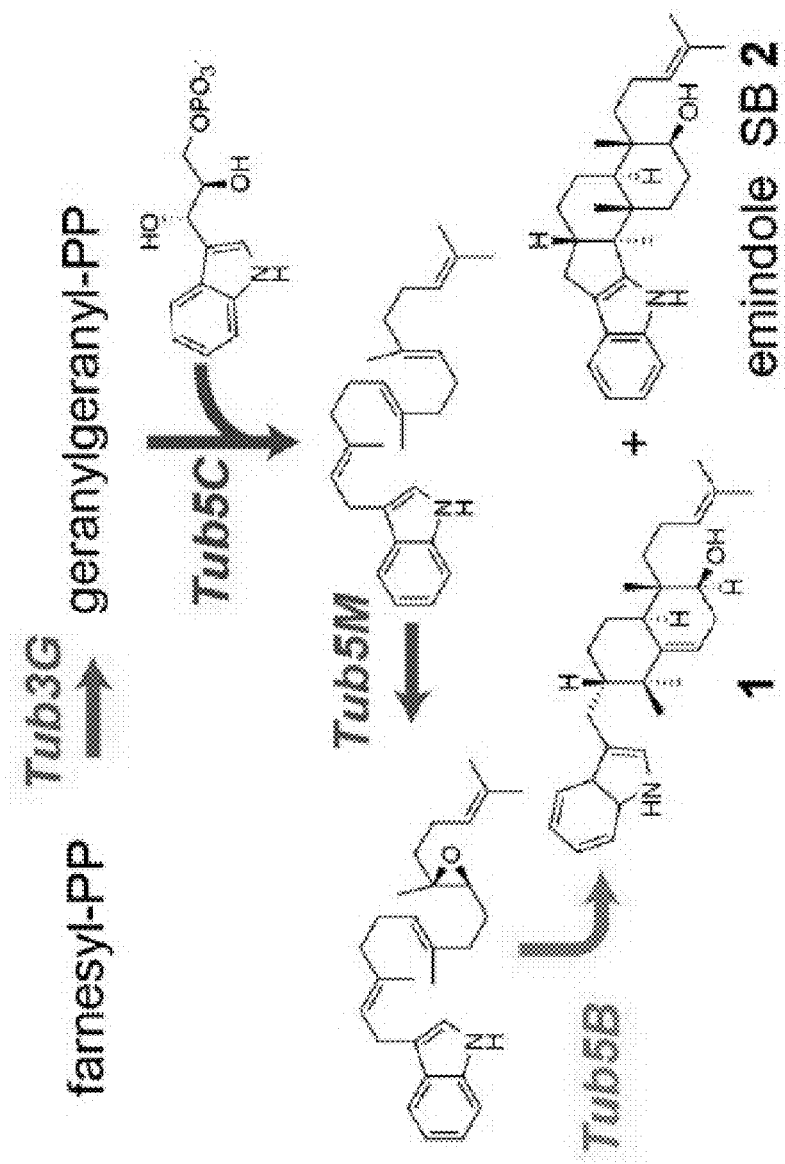
FIG. 14 illustrates a biosynthetic process that produces the compound emindole SB via a fungal four-gene cluster to provide reference for various embodiments of the invention.
Figure 15:
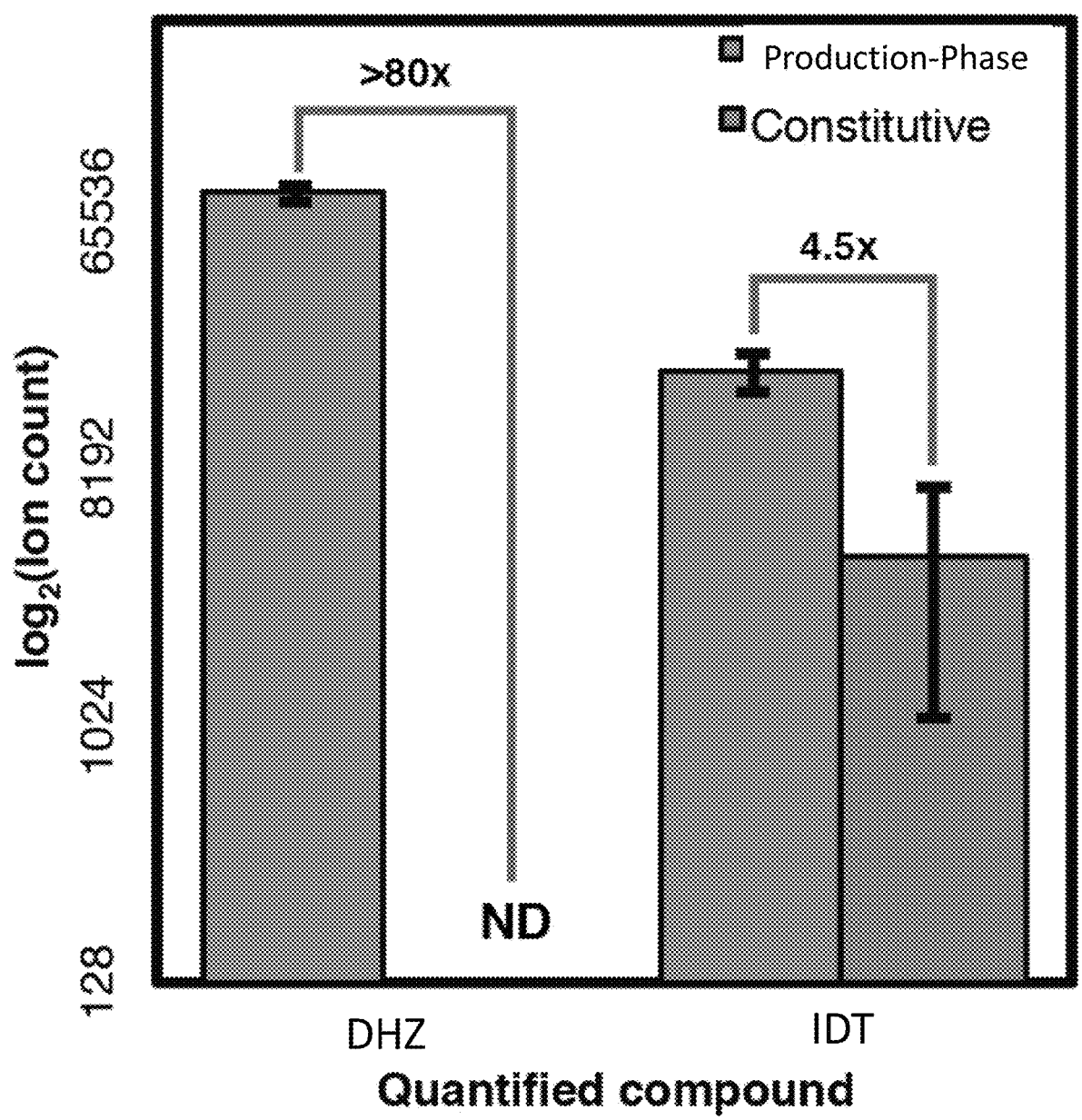
FIG. 15 is a data graph of the production results of two product compounds generated in accordance of an embodiment of the invention.

Expression of Compound Product Pathways Using the Production-Phase Promoter System To study the utility of the new promoter set for heterologous expression of a biosynthetic system, production of fungal derived deydrozearalenol (1) and indole-diterpene (2) was examined (FIG. 13, Compounds 1 & 2). The biosynthesis of the indole-diterpene compound the coordinated expression of four in *Aspergillus tubingensis* genes (FIG. 14, Seq ID Nos. 59-62). Two versions of each pathway were constructed: one having all production-phase promoters, and the other having all constitutive promoters (FIG. 14). The production-phase promoter system utilized the pADH2 from *S. cerevisiae* (Seq. ID No. 1), pADH2 from *S. bayanus* (Seq. ID No. 38), and pPCK1 (Seq. ID No. 2) and pMLS1 (Seq ID No. 3) from *S. cerevisiae*. In the constitutive system, transcription was driven by four frequently used strong constitutive promoters: pTEF1, pFBA1, pPCK1, and pTPI1 (Seq. ID Nos. 51-54). Each indole-diterpene system was constructed on a single plasmid harboring four expression cassettes: promoter::GGPPS::tADH2; promoter::PT::tPGI1; promoter::FMO::tENO2; and promoter::Cyc::tTEF1; wherein, the promoter sequences corresponded to either the production-phase or the constitutive promoters (FIG. 13). Similar constructs were built for the dehydrozearalenol compound with the two genes HR-PKS and NR-PKS (Seq. ID Nos. 63 and 64). All plasmids were constructed using yeast homologous recombination. It should be noted that pADH2 sequences from *S. cerevisiae* and *S. bayanus* (61 identity) are sufficiently unique for this type of assembly. The production of compounds 1 and 2 produced by *S. cerevisiae* BJ5464/npgA/pRS424 transformed with each of these plasmids were measured over seventy-two hours in YPD batch culture (FIG. 15). An 80-fold and 4.5-fold increase in titer of compound 1 and 2 was observed for the system using the production-phase promoters as compared to the constitutive system.

Materials and Methods Supporting the Production-Phase Promotor Experiments

General techniques, reagents, and strain information: Restriction enzymes were purchased from New England Biolabs (NEB, Ipswich, 25 MA). Cloning was performed in *E. coli* DH5α. PCR steps were performed using Q5® high-fidelity polymerase (NEB). Yeast dropout media was purchased from MP Biomedicals (Santa Ana, Calif.) and prepared according to manufacturer specifications. Promoter characterization experiments were performed in BY4741 (MATα, his3Δ1 leu2Δ0 met15Δ0 ura3Δ0) while all experiments involving the production of 1 were performed in BJ5464-npgA which is BJ5464 (MATαura3-52 his3Δ200 leu2Δ1 trp1 pep4::HIS3 prb1Δ1.6R can1 GAL) with two copies of pADH2-npgA integrated at δ elements. All Gibson assemblies were performed as previously described using 30 bp assembly overhangs.

Construction and characterization of promoter-eGFP reporter strains: All promoters were defined as the shorter of 500 base pairs upstream of a gene's start codon or the entire 5' intergenic region. All promoters from *S. cerevisiae* were amplified from genomic DNA, while ADH2 promoters from all *Saccharomyces sensu stricto* were ordered as gBlocks from Integrated DNA Technologies (IDT, Coralville, Iowa). Minimal alterations were made to promoters from *S. kudriavzevii* and *S. mikitae* in order to meet synthesis specifications. In all constructs, eGFP was cloned directly upstream of the terminator from the CYC1 gene (tCYC1). pRS415 was digested with SacI and SalI and a NotI-eGFP-tCYC1 cassette was inserted by Gibson assembly generating pCH600. Digestion of pCH600 with AccI and PmlI removed the CEN/ARS origin, which was replaced by 500 bp sequences flanking the ho locus using Gibson assembly to yield plasmid pCH600-HOint. Each of the promoters to be analyzed was amplified with appropriate assembly overhangs using primers 9-92 Table S2 and inserted into pCH600-HOint digested with NotI to generate the pCH601 plasmid series. Digestion of the pCH601 plasmid series with AscI generated linear integration cassettes which were transformed into *S. cerevisiae* BY4741 by the LiAc/PEG method. Correct integration was confirmed by PCR amplification of promoters and Sanger sequencing.

For characterization, all strains were initially grown to saturation overnight in 100 µl of YPD media. These cells were then reinoculated at an OD600 of 0.1 into 1 ml of fresh YPD and allowed to grow to OD600=0.4 to reach mid-log phase growth (approximately 6 hrs). 500 µl of each culture was pelleted by centrifugation and resuspended in YPE broth for YPE data while the remaining 500 µl was used for YPD data. The 0 hour time point was collected immediately after resuspension. For each time point, 10 µl of culture was diluted in 2 ml of DI water and sonicated for three short pulses at 35% output on a Branson Sonifier. Expression data were collected for 10000 cells using a FACSCalibur flow cytometer (BD Bioscience) with the FL1 detector. Data were analyzed in R using the flowCore package.

Figure 16:
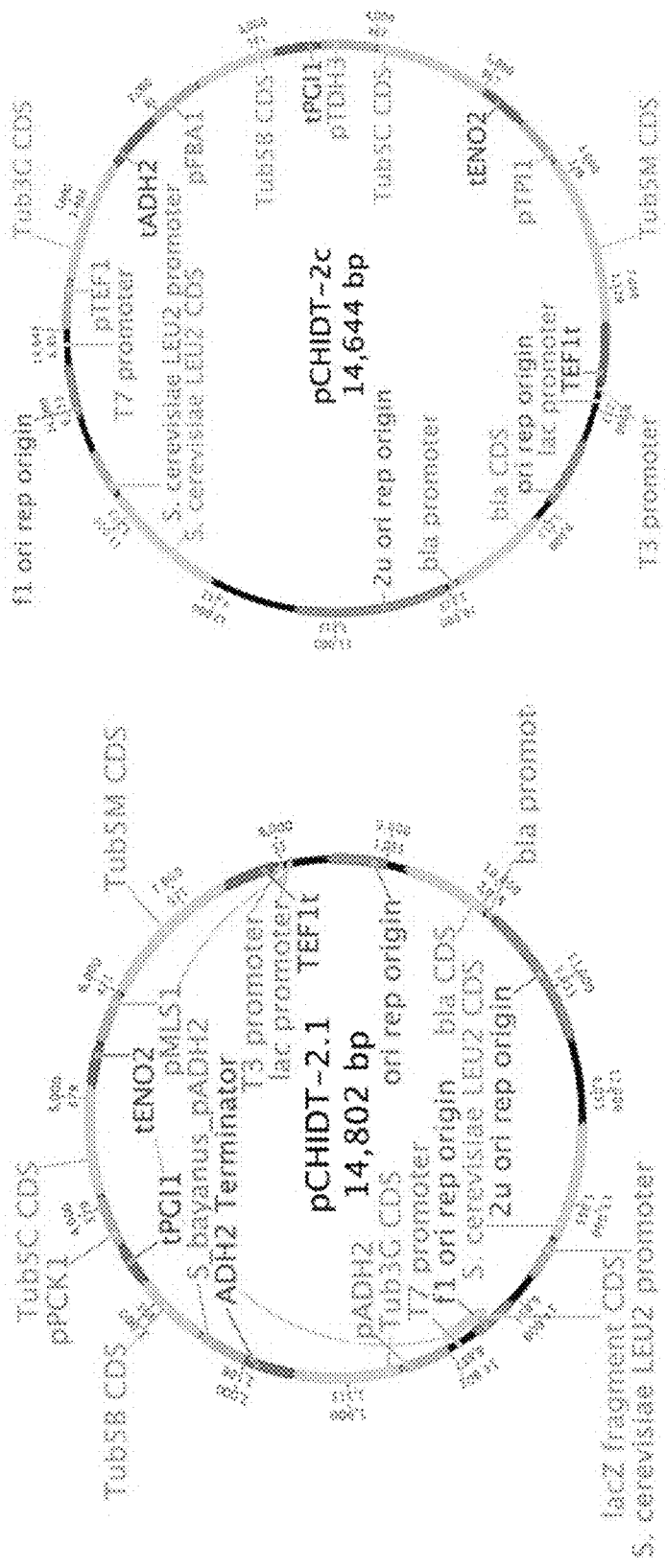
FIG. 16 illustrates two plasmid vector constructs in accordance with an embodiment of the invention.

Construction of plasmids to produce compounds in *S. cerevisiae*: The sequences for genes assembled on IDT producing plasmids are contained in the supporting information. Regulatory cassettes of promoters and terminators were fused using overlap extension PCR. All genes and regulatory cassettes were amplified by PCR, ensuring 60 bases of homology between all adjacent fragments. 500 ng of each purified fragment was combined with 100 ng of pRS425 linearized with Not1 and transformed into *S. cerevisiae* BJ5464/npgA. Sixteen clones were picked from each assembly plate and grown to saturation in 5 ml CSM-Leu medium. Plasmids were isolated, transformed into *E. coli* and purified prior to sequence confirmation using the Illumina MiSeq platform. Detailed plasmid maps for pCHIDT-2.1 and pCHIDT-2c are shown in FIG. 16 illustrates the primers used and the assembly strategy (Seq. ID Nos. 65 and 66).

Examining the productivity of indole diterpene generating systems Plasmids pCHIDT-2.1 and pCHIDT-2c were transformed into BJ5464/npgA with pRS424 as a source of tryptophan overproduction. Triplicates of each strain were inoculated into CSM-Leu/-Trp medium and grown overnight (OD$_{600}$=2.5-3.0). Each culture was used to inoculate 20 ml cultures in YPD medium at an OD$_{600}$=0.2 and incubated with shaking at 30° C. for 3 days. Every 24 hrs, 2 mls were sampled from each culture. Supernatants were clarified by centrifugation and extracted with 2 ml ethyl acetate (EtOAc). Cell pellets were extracted with 2 ml 50% EtOAc in acetone. 500 µl each of pellet and supernatant extracts were combined and dried in vacuo. Samples were resuspended in 100 µl HPLC grade methanol and LC-MS analysis was conducted on a Shimadzu LC-MS-2020 liquid chromatography mass spectrometer with a Phenomenex Kinetex C18 reverse-phase column (1.7 µm, 100 Å, 100 mm×2.1 mm) with a linear gradient of 15% to 95% acetonitrile (v/v) in water (0.1% formic acid) over 10 min followed by 95% acetonitrile for 7 min at a flow rate of 0.3 mL/min.

TABLE 3

Summary of Sequence Listing

| Sequence ID No. | Description | Sequence |
|---|---|---|
| 1 | S. cerevisiae pAHD2 | TATCTAAAAATTGCCTTATGATCCGTCTCTCCGGTTACAGCCTGTGTAACTGATTAATCCTG<br>CCTTTCTAATCACCATTCTAATGTTTTAATTAAGGGATTTTGTCTTCATTAACGGCTTTCGC<br>TCATAAAAATGTTATGACGTTTTGCCCGCAGGCGGGAAACCATCCACTTCACGAGACTGATC<br>TCCTCTGCCGGAACACCGGGCATCTCCAACTTATAAGTTGGAGAAATAAGAGAATTTCAGAT<br>TGAGAGAATGAAAAAAAAAAAAAAAAAAAAAGGCAGAGGAGAGCATAGAAATGGGGTTCACTT<br>TTTGGTAAAGCTATAGCATGCCTATCACATATAAATAGAGTGCCAGTAGCGACTTTTTTCAC<br>ACTCGAAATACTCTTACTACTGCTCTCTTGTTGTTTTTATCACTTCTTGTTTCTTCTTGGTA<br>AATAGAATATCAAGCTACAAAAAGCATACAATCAACTATCAACTATTAACTATATCGTAATA<br>CACA |
| 2 | S. cerevisiae pPCK1 | ATAGGAAAAAACCGAGCTTCCTTTCATCCGGCGCGGCTGTGTTCTACATATCACTGAAGCTC<br>CGGGTATTTTAAGTTATACAAGGGAAAGATGCCGGCTAGACTAGCAAGTTTTAGGCTGCTTA<br>ACATTATGGATAGGCGGATAAAGGGCCCAAACAGGATTGTAAAGCTTAGACGCTTCTGGTTG<br>GACAATGGTACGTTTGTGTATTAAGTAAGGCTTGGCTGGGGATAGCAACATTGGGCAGAGTA<br>TAGAAGACCACAAAAAAAGGTATATAAGGGCAGAGAAGTCTTTGTAATGTGTGTAACTTCT<br>CTTCCATGTGTAATCAGTATTTCTACTTACTTCTTAAATATACAGAAGTAAGACAGATAACC<br>AACAGCCTTTCCCAGATATACATATATATCTTTATTTCAGCTTAAACAATAATTATATTTGT<br>TTAACTCAAAAATAAAAAAAAAAAACCAAACTCACGCAACTAATTATTCCATAATAAAATAA<br>CAAC |
| 3 | S. cerevisiae pMLS1 | CCATTGGGCCGATGAAGTTAGTCGACGGATAGAAGCGGTTGTCCCCTTTCCCGGCGAGCCGG<br>CAGTCGGGCCGAGGTTCGGATAAATTTTGTATTGTGTTTTGATTCTGTCATGAGTATTACTT<br>ATGTTCTCTTTAGGTAACCCCAGGTTAATCAATCACAGTTTCATACCGGCTAGTATTCAAAT<br>TATGACTTTTCTTCTGCAGTGTCAGCCTTACGACGATTATCTATGAGCTTTGAATATAGTTT<br>GCCGTGATTCGTATCTTTAATTGGATAATAAAATGCAAGGATCGATGACCCTTATTATTAT<br>TTTTCTACACTGGCTACCGATTTAACTCATCTTCTTGAAAGTATATAAGTAACAGTAAAATA<br>TACCGTACTTCTGCTAATGTTATTTGTCCCTTATTTTTCTTTTCTTGTCTTATGCTATAGTA<br>CCTAAGAATAACGACTATTGTTTTGAACTAAACAAAGTAGTAAAAGCACATAAAAGAATTAA<br>GAAA |
| 4 | S. cerevisiae pICL1 | ATTTATTGAAAAGTAAATATCTCGTAACCCGGATGCTTTGGGCGGTCGGGTTTTGCTACTCG<br>TCATCCGATGAGAAAAACTGTTCCCTTTTGCCCCAGGTTTCCATTCATCCGAGCGATCACTT<br>ATCTGACTTCGTCACTTTTTCATTTCATCCGAAACAATCAAAACTGAAGCCAATCACCACAA<br>AATTAACACTCAACGTCATCTTTCACTACCCTTTACAGAAGAAAATATCCATAGTCCGGACT<br>AGCATCCCAGTATGTGACTCAATATTGGTGCAAAAGAGAAAAGCATAAGTCAGTCCAAAGTC<br>CGCCCTTAACCAGGCACATCGGAATTCACAAAACGTTTCTTTATTATATAAAGGAGCTGCTT<br>CACTGGCAAAATTCTTATTATTTGTCTTGGCTTGCTAATTTCATCTTATCCTTTTTTTCTTT<br>TCACACCCAAATACCTAACAATTGAGAGAAAACTCTTAGCATAACATAACAAAAAGTCAACG<br>AAAA |
| 5 | S. cerevisiae pYLR307C-A | CAAAAAAACAATGGAAGAACAAAGAAAATTTAGCGGAAGTAAAAATAACAGCCGAAAGCCAA<br>ATTCAGGCTTATCTTGCCTACTCTTTCTTTTATCGAATTCCTTTAGGCCGTTGCAATAGAAA<br>AGTAATAAAAACGCATATACGTAAGTTGTAGTCAGTGTAATTGCAATCTATTATGCGCATCA<br>GGTGCGCATACTACATCCATTGGTGCACAAAAAAAGGAACGCAGACAAGAAAATTATTCAGT<br>TTGCTGTTCGTGATGAGCCATCCCTGAATATGTAATGTTAATGTTCAATTTGGGATCTTA<br>TTTTTTTTTGTGCAGTAATAAGAATCTTTGAAAAAAAACTATATAAGCCTATATAGTTTGTA<br>AGATATAAGACAAAACACACCTGCTTTTCCACTACACATTTTCGTTATTATATAAAAAAGAC<br>AGCCAAGTATACTTGTCAACAAAATAAACTCATAGCAATTACACTATAAAAACAATAGCATC<br>AAAA |
| 6 | S. cerevisiae pYGR067C | TGGCAATCCCCTCCGATCGTCCGCGGCAAAATGGTCGTCAATCGGACAAAGGGGATGATGG<br>GATCTGGTAATAGAAGAAAATATGGACTAAAGGTAGCCGCTAAAGCGATCCAGGCATGTGTT<br>GCCAATGATGTAAGTCAAGCGAAGGAAATGGTTCAGTAATATGATAGACAGACTGCACTTCA<br>AGGGTGCGCCCCCTCCCCCGCGCATATGCTTACAACGCAAAATAATTGACGTTTAATGTGGA<br>TACTTATCGTAATCGCTGCATTATAGATTTCGAGTCATGTTCACTTAACCCCACATATTTAT<br>ATAGAACGCATCTTCAAAGTACTTATAAAGTTTAGTTTTACATTTTTCTGCTTTCTATTTCT<br>TCTTTTTCGGTTCTTCTTCATGCCAGTTGGCATGGCTTAAGAGCTTTACTTGTCGCTTTTAT<br>TTAAAACCTTCTCTCGGGAGAAGACAATTGTTGATACAGTAATTGTATTTGCATTATCAC<br>TGCT |
| 7 | S. cerevisiae pIDP2 | AACGTCTATCTATTTATTTTTATAACTCCGGGATGTCATTGCCGGTGGTCCGAAAATCGGCA<br>AATAAGGAAATAAGGGAAGAATATGCAGTAGTCAAATCATCAGTGTTCTCTTTGATACCTTT<br>CAGGGCTAGGAATAGTGGGGGTGGAGTATAATATCAAAAACCGGACTTAACATTATTGGTTC<br>GGTTGGAATTGGCTATAGGCAAACTAGTCTCCGGCATGATATATAAATGACAGCCTGCAATT<br>GTATGTTACTACACTCTTGACTTGTCGACTACAGTCGCTGCTCAGGCACGAGAATAGGAGGT<br>AAGAAGGTAACGTACGTATATATATAAATCGTA |
| 8 | S. cerevisiae pADY2 | GAGCTCCGTGGAATAGGCGAGCGGCTGAGTGGTTCTCCAAGCTACGGTTTTTACGTGTAGCC<br>CCATGTGAGCAAGCCAAACAAGGGCCCTTAAAGGCGTGACTACAAAAGGGGCGGGTTGGAA<br>GGTCATCTGCAGCGAGATACGAAAAGATTTTTTGCCAGATTTGCGGTTGGGCGGCTATTTCG<br>GTATTGTTGGGGTAACAAACGTTGGGGAAGACTGCATTTTCTTACAGCTTTTTTTCGTTATC<br>GCGGGTTGGGCGGCTATGGCGCCTTCTCCTCTGTACTCCAACCTGTCAGAGACACCAAGCTG |

TABLE 3-continued

Summary of Sequence Listing

| Sequence ID No. | Description | Sequence |
|---|---|---|
| | | TATATAAAGCACCTTGGTTGGATCGTATTTCCCTGAGATCTTGCTATAGGTTCATTTTATAT<br>ATCGTCCAATAGCAATAACAATACAACAGAAACTACTAGCATCTGTTTATAAGAAAAAGGCA<br>AATAGTCGACAGCTAACACAGATATAACTAAACAACCACAAAACAACTCATATACAAACAAA<br>TAAT |
| 9 | S. cerevisiae pGAC1 | CCCTATCTTTTTTTTTTCTCGCAATCTGGGGAAAGCTTTTCTCATGCTTATACGTGATTTG<br>TTATATAAGGGATTGCTATTTCAGGCATCATTCACCTCCTTTTGTATCCTTAGTTTCACTGC<br>ATTTGATATATATATATACGTATCTGTAGTTTCCTTCCATTACATAACGCATAATATACTAT<br>TTCCATAGTCTATCTTACATCTTTTTTCTTACTTTTGTTAAGGAACGGATAACGATAAAACA<br>AAAAGAGAGATTTAAGATTACTTCTGTAACTTTTTTGATCCATTACCAAAACTATATTTTTT<br>TTCTTTTCTCTCCTCTGGCATTAAACACAGTTATTGCTACAGCTAATCATCGATATAATAAT<br>ACATCACATTAACTGTCTATAAGAGGCTGGTACTTAGTAGATGGTGAGAATTTTTTATTTTT<br>GTATTTTAACTTCATTTTTGTAAACAAGTTGGAACTGGAACTTACTATAGAACAAGAGCTTA<br>AACC |
| 10 | S. cerevisiae pECM13 | GTTGTATCCTATTGGATCACGGGCGACGGACAAGACCCGAAGTGCGGACCGGCATGGTCAGC<br>TTGCACGGAAGCTTTAAGGGGTTTCCCTTGTTTCGGCATTAGAAGAGGCATTTCGCACGTTTT<br>ACCGGGTCAGAAACTTCGAGGAAGCTGTGACAATTGGAAAAAAAGGCAAAACTAAATGCAAT<br>GTATCCGGTTGCCCATGCATTATTTGTGATGTTTTCGGATGTAGTTCGCTGCGCTCCGCGGC<br>GATATATCCTCAGCGAGAGGCATATGTATAAATATATATATATATCTAACAAAAGCATT<br>CAAGTTTCTTTCTCTGGTGTTACGTCTTTGTTCGACTTTCTCTGCTTACAGCCCTGTATGAC<br>CAAAGAAAAATAAAAAGCAGCTACATACCAGCAGAAATTTTTTATAGTATTACACTATAC<br>ATCCAAGTTTTTTCACAATTATTTATTGTTTTTCTCACATAGAAAATTCCGCATACTGCGAT<br>TATA |
| 11 | S. cerevisiae pFAT3 | GAAAGCTTATTACTGAGTTTTGCGGAGCATCGCTCGGAGCGGCGGAATTGAATCGAACCGCC<br>GTGCTATTACCGAACAAAAAAATTCGAAAGCATAAACTCAGTAGTGAAAAACTTGAGAATTT<br>TCAGATGAGTGGCGACTTTCCAGTCCTTGCGGTTTTGTCACCTTAGTCAGCTAGTAAGGAGG<br>CCGTGTGGGTTAGAGTGGCTACAATCCTCAAAGGGCACTTCTAGAACCCACGGTGAATTTTT<br>TTTGGCATGATAAATCGGTAGAATCGGTGAAGTAATTACCCAAAAAAGGATCGGGATTGTGT<br>TTCTCGTAATTCCGTATTATTGCCGATGGCATCGACTACTTCTTTTTTCAGAAACCCCAACA<br>AGGGTCTATTGTAATTGTATATAAACCTTTTTGTAATGGATATATACATGTGGTACTATTTC<br>TCCTCATCCTGCTCCATCGAAAATCCTCATACGAAGAGTTAGGAAAGCAAAGAAAACAACAA<br>AAAC |
| 12 | S. cerevisiae pPUT1 | AGACACAATGCGAAAAATCGCGCAGGGACATAATTTTTGTTTTCATTATTCTTTCGCTTATT<br>CCCTCCGTTAGCTCCACCGCTTTTTTGATTGGAATTTCCTTTCGGCAATGGCTTTCCGGTTA<br>CCACGCCTCGGGTTTCGCATCCCGAAAAGCATATCTACACAAGAAAATGAATGATAAACAA<br>TTGATGAGTGGCGCTATTTCCCTTATCATCTCATTATTGTACTTAGTATCGTCTATTATCAG<br>GAGAAATCGCATGAACTAAGCCCATTTTCTCACCCTTCTGCCTTCTTATATAAAGCTTGCTG<br>GGAACCGAACACAAACTCCACAAGTCCGTAGCAGCTCTTCTCTTTTGTCTTTTATATATCAT<br>AAACATCGCTACATAGTAATAACACTAACGCACGCTAGAA |
| 13 | S. cerevisiae pNQM1 | AGGGGTAGCGGCTTTTTCATCAACTCGATTATTACCCTTTAGAGACCTTCCCTAAAGTGAGC<br>GGCAATTATTTCCGGATGTTAGTAGGGTAATATGGTTACGGATTTGTGACACAAAAGGGCTT<br>TTCAACAGTCGGTCTGGGTTGAAGGATTTTCAGGATGACGAAGCTTTCAATAAGAGGGACTG<br>GACTGTTAACGCGGGGAATTATAGGTTACTTTCCTTGATCTGGCTCTGGCTCTGGCTCTGAT<br>TTTGGCTCTTGTACTCCTCGGACTTCTTGACTTGTAACGAAATACGTCTTTTGTCCTTCTCT<br>TCTTCTTCCATAGTAGGGGCGAATGAGGGGAGCATAGTGGATCCTTCTAACCATCTAGAATG<br>GGGTGGACAACATATAAAGAAGAGCAATCTTGCAGCGCAGTCATATTTATGCTAAGTATAT<br>CATTATTTCTTGCTAGCGTAAGTCATAAAAAATAGGAAATAATCACATATATACAAGAAATT<br>AAAT |
| 14 | S. cerevisiae pSFC1 | AGCCTAGTCCCGGTAAACCGCAAACGGACCTTAATTGTGACGAAGGGCCCAAATTTGATGGG<br>TCGGTGTTAATGATTAGTCCTCATTGTCATAATAAAGTGTGATGATGGAGGCAATGATGATA<br>TACGGTAGTACTACTGCTCGAGGTGCTATCTTTTAACCAATCCTTTGAGATTCTTGTCGCCA<br>CGGAGTTACTACCTTTTACAAACCGTAATGTCACATTTTGCATATATCTTATGTATAAATAT<br>ATAGTTCACTTACTACTTGTTCTCGTTTTGTTAACTTTCTTGTTGTAGTTCTTCTTGTTCTT<br>GGCGTTTCCCCCTTTGTTTTCTATCTGCTTCATAAGTAAAGTGCAAAGCATTTTGGAAGATA<br>TTTATCAATTGAGTCATTGAAAGAAACTTGGCATCTTCCCTATTACTAAAACTAAGAATACTT<br>GATTCAAGAAAGAAGTTTATATTAGTTTTAGCCGTAAGATAACATAACAAAGAAGAAGAAAG<br>AAAA |
| 15 | S. cerevisiae pJEN1 | TCGATCAGCTCCAATTAAATGAAGACTATTCGCCGTACCGTTCCCAGATGGGTGCGAAAGTC<br>AGTGATCGAGGAAGTTATTGAGCGCGCGGCTTGAAACTATTTCTCCATCTCAGAGCCGCCAA<br>GCCTACCATTATTCTCCACCAGGAAGTTAGTTTGTAAGCTTCTGCACACCATCCGGACGTCC<br>ATAATTCTTCACTTAACGGTCTTTTGCCCCCCCTTCTACTATAATGCATTAGAACGTTACCT<br>GGTCATTTGGATGGAGATCTAAGTAACACTTACTATCTCCTATGGTACTATCCTTTACCAAA<br>AAAAAAAAAAAAAAAAAAAAAAAATCAGCAAAGTGAAGTACCCTCTTGATGTATAAAT<br>ACATTGCACATCATTGTTGAGAAATAGTTTTGGAAGTTGTCTAGTCCTTCTCCCTTAGATCT<br>AAAAGGAAGAAGAGTAACAGTTTCAAAAGTTTTTCCTCAAAGAGATTAAATACTGCTACTGA<br>AAAT |

TABLE 3-continued

Summary of Sequence Listing

| Sequence ID No. | Description | Sequence |
|---|---|---|
| 16 | S. cerevisiae pSIP18 | ACATAGTACTGTACGATTACTGTACGATTAATCTATCCACTTCAGATGTTCAACAATTCCTT<br>TTGGCATTACGTATTAATACTTCATAGGATCGGCACCCTCCCTTAAGCCTCCCCTAAATGCT<br>TTCGGTACCCCTTTAAGACAACTATCTCTTAACCTTCTGTATTTACTTGCATGTTACGTTGA<br>GTCTCATTGGAGGTTTGCATCATATGTTTAGGTTTTTTTGGAAACGTGGACGGCTCATAGTG<br>ATTGGTAAATGGGAGTTACGAATAAACGTATCTTAAAGGGAGCGGTATGTAAATGGATAGA<br>TGATCATGAATACAGTACGAGGTGTAAAGAATGATGGGACTGAGAGGGCAATTATCATCCCT<br>CAGAATCAACATCACAAACATATATAAAGCTCCCAATTCTGCCCCAAAGTTTTGTCCCTAGG<br>CATTTTTAATCTTTGTATCTGTGCTCTTTACTTTAGTAGAAAGGTATATAAAAAAGTATAGT<br>CAAG |
| 17 | S. cerevisiae pAT02 | AAGTTCTTGACTACCCCTATCTCACACTAGTACGTAATTCAATGTATCATTCGTATTGTAAG<br>TAGATAGAGACGCAATACAGGAAAGCTGACCTTCCTTCCAATCACCACGGCTGAAATGCTTT<br>GTTGACCAATTACGGACGCTTAAGAGCGGACGCGGCTGGAACGGCTCCATCCTAAATCGGCG<br>GAGGGAGAACTCCGATACCAGCCGACATGGCAATAATAGTGACAGTAGATGCTACCAGCCCC<br>GCAATAATTTCACAGTAGATCATCAACAGTCTCCTCATTTCTGGAAATGATCAGCAACTTCG<br>ACGGATTTAACTCTCAAGCAGTTACGCACTCCGAGAACAGCCGTGATCATCTTTGAACAAGC<br>AAAATATATAAAGCAGGAGAACTGTCCTACCTAGAGCTAGAATAGCCATAACTAACTATGTA<br>ACATTCTACAGATCAATCAAAAACAATCTTCAATCACAGAAAAAAATAAAAGGC |
| 18 | S. cerevisiae pYIG1 | TTTTCTAGTTCTTCTTCTGCAATATTGCCTTTTGGGAAGAAGGATCGAAAGTAGCCATTTGC<br>AGACACGTTTTTACTATATTTACTGTATCTTCGATTGCGCGGCTAAAGTTGCCATATTATTA<br>TTATATTGCAGCTCAACCCCGCATTTCCGGAGTTTTCTTTTTTTTATTTGGGGTAATTTGG<br>AGGTCGGCGGCTATTGGTGGGCCGGAAATGGTGACACACTTGTAATATATAAGGAGGAAATC<br>CTACATGTGTATAAGCGAAATCACAAGGATAATAATGTATTGCTAAACACCCTCAAGAAAGA<br>AAATAATCATAACGAAATC |
| 19 | S. cerevisiae pFBP1 | CGGATGGAATCGCCGCTTTTGAATTCACCTCCGGGGTATTATTATTATTCTTAGTAGTCGCG<br>GTCGTGCGGACACCCGGAGTTATGCGGGCCCGAAAGCTCATTATGTAGTAAAGCTAGGTAAT<br>GTTAAGGGCGTAAGAGCCAACGCAAGGCAGCAATAGCCTGGTATTCCCACATATCAAGAAAG<br>CTTAAAAAGTTGAGACAGGGAATTTGAAGGCGAAGATTGCCGAACTGGCCAATACCCACTAC<br>TTTTTTTTTTGGTTTGCTTGGTTTCTTCCTGTCGCTTGCCAACTTGTGGCATCTTCCCCACAC<br>TATATTATAAGGATCGTCCTATGTATAGGCAATATTATCCATTTCACTCGCTAACAAATGTA<br>CGTATATATATGGAGCAACAAGTAGTGCAATTACAGACGTGTATTTTGTCTTGATCTTGCTT<br>TTTGTATGATAGGCCTAAGAATAACAGTGCGAACATATAAGAAACATCCCTCATACTACCAC<br>ACAT |
| 20 | S. cerevisiae PHO89 | AGACCTTTTTTTCTTTTTCTGCTTTTTCGTCATCCCCACGTTGTGCCATTAATTTGTTAGT<br>GGGCCCTTAAATGTCGAAATATTGCTAAAAATTGGCCCGAGTCATTGAAAGGCTTTAAGAAT<br>ATACCGTACAAAGGAGTTTATGTAATCTTAATAAATTGCATATGACAATGCAGCACGTGGGA<br>GACAAATAGTAATAATACTAATCTATCAATACTAGATGTCACAGCCACTTTGGATCCTTCTA<br>TTATGTAAATCATTAGATTAACTCAGTCAATAGCAGATTTTTTTTACAATGTCTACTGGGTG<br>GACATCTCCAAACAATTCATGTCACTAAGCCCGGTTTTCGATATGAAGAAATTATATATAA<br>ACCTGCTGAAGATGATCTTTACATTGAGGTTATTTTACATGAATTGTCATAGAATGAGTGAC<br>ATAGATCAAAGGTGAGAATACTGGAGCGTATCTAATCGAATCAATATAAACAAAGATTAAGC<br>AAAA |
| 21 | S. cerevisiae CAT2 | TCCGAAGAGCGTGCTACCAATTCTTCATCTCGTTAACAAACTGGTTCTCCGTTAAAAATTGT<br>GCTATATGTCCTATAAGCCAACTCTATCTATATCTTTTCTTTTAGTCCTACTTTGGATACTG<br>TTACCACCATTTTAGATTGCTTTTTCTTTTGCCGCTAGCCTTACAATATTTGGCAAACTTTT<br>TTTTTTTAGCCGCCGAGACTCTTGATCTATGCCGGGCGAAAGGGCAAATGACTGCTTATCC<br>CCGCCATCACTTCCCCCCGCCCAAGGGTTTAGAATTGGGGATTAAGTAAAACGAATGACTA<br>TTCCTCTCAAAGTCATCCTTGTTCGACAAAAAGAATGGAATATAACATATTGGAACAATTTC<br>ATCCTCTTTTCCCCATTTTCGCATATAAGAGCAACTAAACGCCGGTGAGTAAAGTGCCCTTC<br>CCTACAGACTCTTTTACTCAGGTATATATATATATATATCCCTTAAAAACTAAAAAGAAAGC<br>ACTC |
| 22 | S. cerevisiae CTA1 | AGCGGTTGTTCTAACCACTATTTAAAGCCGCAATTAGTAATGCAAAAAGTTGGCCGGAATTA<br>GCCGCGCAAGTTGGTGGGGTCCCTTAATCCGAAAAAGGACGGCTTTAACAAATATAAACTCC<br>GAAAATCCCCACAGTGACAGAATTGGAGAAACAACCAGTTTTGATATCGCCATACATATAAA<br>GAGATGTAGAAAGCATTCTTCACTGTAATGTCCAAATCGTACATTTGAATTTCTTGTAGGTT<br>TATTTAAAAGGTAAGTTAAATAAATATAATAGTACTTACAAATAAATTTGGAACCCTAGAAG |
| 23 | S. cerevisiae ICL2 | AATTTTTATTTTCTCCTTCCATATGAGCGACAGCGGTTACTAGCCGCTGTCCTCAGGTTAAT<br>GATCCAAGTCCGAGATCCGGGCCGAATATGCTTGCGGGGAAAGAAATAAAGTGCATTGGAG<br>AAGAAAAGGATATGCTCTTCAATTAGAAGCGCCGAAACACTAACATCATGCTAGCGATATCA<br>TACGTACACTATATAATGTAAAAAATGGGCTTAAGAATAACTCTCTTATTTCTTAACTTTTG<br>TTGCGGTTGAAGAGCTTATAAAAGTACTAGTGGCCTAAAGAAGCTACAGCGCCGATAATAAT<br>ATCGATTTCGACTTTTCTAGTATTTCGCCG |
| 24 | S. cerevisiae ACS1 | TGTGCACATACGTCCAGAATGATATCAAGATAAATGGCACGTGTATGTACGGCTGTGTAAAT<br>ATGATAATCATCTCGGACGAACGGCGTAGCACTCTCCATCCCCTAAAAATGTTCACGTGTGA<br>CTGCTCCATTTCGCCGGATGTCGAGATGACCCCCCCCCCTCAAAAGGCACTCACCTGTTGAC<br>ATGCCCGTGGCAAATGATTGGGGTCATCCTTTTTTTCTGTTATCTCTAAGATCCAAAGAAAG<br>TAAAAAAAAAAGGTTGGGGTACGAATTGCCGCCGAGCCTCCGATGCCATTATTCAATGGGTA |

TABLE 3-continued

Summary of Sequence Listing

| Sequence ID No. | Description | Sequence |
|---|---|---|
| | | TTGCAGTTGGGGTACAGTTCCTCGGTGGCAAATAGTTCTCCCTTCATTTTGTATATAAACTG GGCGGCTATTCTAAGCATATTTCTCCCTTAGGTTATCTGGTAGTACGTTATATCTTGTTCTT ATATTTTCTATCTATAAGCAAAACCAAACATATCAAAACTACTAGAAAGACATTGCCCACTG TGCT |
| 25 | S. cerevisiae PDH1 | AATATAAATAAAATTCCATACAGCATGTCTAATCATAGCTAATTTATACATATTCATCATGA AAACATATAGGGGAAAATATGGTCGGTTAACACACCTATCAAAAAATTATTCAGCAATTCCA ATCTCGTTAGTAAAATATATTCTTATTTTTTTTTTTTCTCTGATTGTATTATTTCTGGAG TTTTGACTTATTTTTTTACCACATCGCGCTTTTCGTCCCAATCTCTCTGATATATGATGCT GTCTATAGGTAGCCACTTCCCCGATGTCGGACCTCGGGCCGTTTACAAACTTTATTGAGATG ACCTTATTTCTCCACATTCTAGTCATTCAACTTTTACCCTCATATGTTTACCTTCACTAATG TGAAAGCATGACCAAAGAAAGTGTATAAGGTATATAAATCTGCCATAATGTATGTATAACTT ATTAGGACTTTCTCAAATAGTATTTTGGTATTTTCTACTGTTCTCTGATGATCGAGAGCAAA CAGA |
| 26 | S. cerevisiae REG2 | AAGTACGATATGGTATAACTGTAACATTGAAGGACTGAAGGACTGAAGGACTGAAGGACTAT AGTCAAGGGCCAATGGGGAAGGTCCCTTCCAGGCCATTTGCCCGATAGTTTGTCCTTCTCTT GCTTTTCCGACGGCCCGATTGCATGTGGCGGGGCAGCACTGGATAAAAAAACGTGGGGGGAG TGATTAAATTTATACGCTTATTGTGTCAACACGGAAACCTTATAGTTATCATTACTAACATC GCAACAAGCTGCTTTTTTACTCGTTTTTAGCCACACCATACCCCCTTTAATTAACTAATAAT GCATAAAATAGTTATTGCTTCTTGAGTTGCAGCTTCTTCCTGGACGTACTGTTATATATGGC ATGTCTTCGCATGTCCGTCAAATTTAGCGTTGTCTCGAAACTTAGGCTGTCGTTCTTGCTGT CTGTCTTCTGATAAAATAATATATTGGAATAAGAAAAAAAAAATAGGAACAAGAAAGTGTGT GAGA |
| 27 | S. cerevisiae CIT3 | ATATTATTCAGTTGAAAGACAAAAAAACATAAATATTTCTATGAGCAAACAATTTGAACAGA AAAATAAAATTGGGGAAGTGACACACCATGGTAGCGGTTCTAAAGCGAAATCGGCAAAGCGG CTAAATAGCAGTTTTGATGACTTACTCCACACTGAAATGGATGACCTTAAATAGGAGATAA AGCTTTTTCATCCCTATGTATTTAAGATGACTGGCTTGTCAAGCATTCTAATCATAAAAAAA AGATCGTATTTGATCAAGAATTTATACATAGACGCCGCTAAATAATTGAATACAAA |
| 28 | S. cerevisiae CFRC1 | CTCGTTTGCCGTTACATTGCATTGATGGTACAATAAAGGGCATGCTTTATATCGAGATGTTT CAGTGTATATGAGGGGAAACAGAAAAGAGTCATTCCTGCCATTTTTTGGTCACTGCTTTTTC TGCTATGAGTAATGGTGAAGTTCCTTGTGGCTACACGCTTAATGTCATCGGGTTACTGCTCC TAATATCCGCATATAAGCTTTATGCAGGGATCAGTTGGGCGGCTATTTATCTACACCCAGTC ATCCGGCGTGACTGGATCTCCACTTGCCGCAATAAGTCGGTGGACAAATGGAGATTTAAGAG TAAAGATGCATGATGGTATAATTCCTTTAGTCGAAATAGATATATTTCAAGCGCATATATAG GCAGACGCTTGTACTGTAGAAATAGCCGATATTCAATTGCGCTCTATGTGTGTTTTTATTCC AGGTTTTCCTTGGATTCTACGTATTGTACGACTTTCTTATCCTCCACAAACGTCATCGTGTC AGTA |
| 29 | S. cerevisiae RGI2 | CCCAACAGATTTCAAGTCTGTCGCCTTAACCACTCGGCCATAGTGCCTAAAACAATGTAGGT TATTTAAGCAAGTATTGTAGATACTTTTCGTAATAAACTACAATGCACCCACGACTCGCGGT GTAATGATGGCATGAAATCATTGAACGAAGTTTTGCGGCTATACGGCTGAAGGACGAGACTA AAGGGACAGGAATTATTAATGCGGGGTATAATTTGAATAGTATTAACGGGCACTGCCGTTTA GCCATCAAATGCTATTGTTGGGGTATTCTCTCTACTTTTTGTTCTTGGCTTGAACCTTTTCG GCGGTTGGCAATCGTCCGTATATAAGCATCGGCTGTCCCAATCCTCTATTGCCCTTTTCCCT TGCACCTCCTTCTCAATTCTTCGTATCTTTCGCGTAAAGGTAGATCTTGATTCACCTATCTG TCGAAACACGATTAAGTGCAAACGAAACAACGTACAGTATATAACAAAGTATTTTAAATAAT AAGA |
| 30 | S. cerevisiae PUT4 | GCTATGACGTTTGGGTGGCCTAGCCGGTTCGCGTGTGCCTGTCGCTTTTGTCGCTTTTCAAC TTCTGCCCGATATTTCCTATCAAAGGAAAATGGGACGTTTTCAACCCCTCGCTATCATCGTG CCTGCACTCTGCCTATCGCCAACTACACCGGGGTTTTATCTGCTTCACCCCTCCATCCAGTG CTGATAACAAGAAGAACCTTGCAGGGTAGGGCAGGACCTACGGCCAAAATACTAATTATGTC TGTTTATGTACATGCCCCAATCTGAATATTCCATGAATGTAGGCACAGCATATCTCCATCCA TGTACTGATACAGACGCATAAACATATATGTATATACATACTTATACACTCGAATATTTGTA GACTGATGTACTTCTATATATATAGGGGGTTTGTGTTCCTCTTCCTTTCCTTTTTTTTC TCTCTTCCCTTCCAGTTTCTTTTATTCTTTGCTGTTTCGAAGAATCACACCATCAATGAATA AATC |
| 31 | S. cerevisiae NCA3 | TAGATGCGCCATCTCCGAGAAAAAATCTAGACAATAACAGCGACAATTAACCTAAAGAGGAT AGAAGATCGAGCAAAAAATTTTTTAATATGGGTCAGTGGCGATATTATACTATAGGAGT TAAAGAGTAAGTTGAGTGTAAGGTGGTAGAATTATGATTGAACTCCGAAACTAAGCGCCGAT TATGGGTGGCAAAGCGGACAGCTTTTGATATATAATCGATCGCTCTCGTAGTTGATATCCTC TCTCTTGCTTATCTTTCCTGTATATAGTATATGTGTACATACAGATACGAATATACCTCAG TTAGTTTGTTTTAACATTAAATATTCAACAGTTGCCAGTAGCAAAAGAATATATCCATTCA TTTCGAGCTTTTTCGTCTCATTACTGATATCCAACTAACAGTCTCCTCATAGACGGTACCTT ACTTTCCTTTAATATTATAATACTAGTATAGTCGCACATACTTAACTCGTCTCTCTCTAACA CATA |
| 32 | S. cerevisiae STL1 | CTACGTCGCCTGTTCGAGCGGCTCTGTTCGTTGCATGAAACTAAAATAAGCGGAAAGTGTCC AGCCATCCACTACGTCAGAAAGAAATAATGGTTGTACACTGTTTCTCGGCTATATACCGTTT TTGGTTGGTTAATCCTCGCCAGGTGCAGCTATTGCGCTTGGCTGCTTCGCGATAGTAGTAAT CTGAGAAAGTGCAGATCCCGGTAAGGGAAACACTTTTGGTTCACCTTTGATAGGGCTTTCAT |

TABLE 3-continued

Summary of Sequence Listing

| Sequence ID No. | Description | Sequence |
|---|---|---|
| | | TGGGGCATTCGTAACAAAAAGGAAGTAGATAGAGAAATTGAGAAAGCTTAAGTGAGATGTTT TAGCTTCAATTTTGTCCCCTTCAACGCTGCTTGGCCTTAGAGGGTCAGAATTGCAGTTCAGG AGTAGTCACACTCATAGTATATAAACAAGCCCTTTATTGATTTTGAATAATTATTTTGTATA CGTGTTCTAGCATACAAGTTAGAATAAATAAAAAATAGAAAAATAGAACATAGAAAGTTTTA GACC |
| 33 | S. cerevisiae ALP1 | GAGCTATAGTCTTTTGCGCTTTCAATACGTGTAGCGGTGTACCAAAAGTTGCACAAAAATGT AGTTGTCAATGAAAGCGCACTACGTATATAATGACTATTTTTTTTTTCCTGGGTTGCATGGG TAATTTGTTGTTAATATGCGATTTTCTTGGGGAAAAGGGTGTCATAGCGCCAAAAACTGCCG TGCGGCACAGTATGTATGTTTTTGAGTCGCGCGTTTAAGGGCTTGGCATAAAAAGTGGTTC AAGCGAGTGATAAGTTGGGCGAATGTCGTCTTTTTTGTAACCATGTCTTTCCTGAAAACAAC CTGTAGGCAGCTCCACTCCACATAAGGGCTTTCTCCAATGGCAATGGGAGCTCGGAACACCG GAGTAGAAATTTTTATAATGTGTATTGTATAAAACTTGCTTGTTATGCAGTTTTTGTTTTTT TTGTTACTCTTCCGTAGCACAATAGACATATATTAGCGGCAAAATTGTAGTGTTGCGATTAT TGCC |
| 34 | S. cerevisiae NDE2 | GTGTAGTATTGATCTTGTTGGTATTGCTAGAAATGCTTCAGCAATACTGTATAAAATATGGA AACGTTGCCATGGCAAGACAAAAGAAGTGATCTTGAGTGAAATAATAGAGCCCGGATGGCCG GGTAAATTCAACCGCTCGTACCGTTTATAATACGCATAAACGCCGAAAATGTCTCTATTTTA GTCATTCCCCAGAGTGCGGTATTGCGTACACCTGTCATGCGTTCCTTAGTGCCGATAGATAT ACTAATATCGATGCGTCACAGTAGCAGATCATCTCTGACACTTGTTTCCCCATTTTTTTTTT TCATTTTTTAAAGGGTTTCTCTACAGCCTACAGGCCTCCCCTAATAAGTCAGCCCCTCCCTT TGGAGTGCGCTGTTGACCTGCGTATATAAGAGGTATATCAGTGCCAGTAGGTAAACCCATCT TGCGGGGATTGTACCAGGAACATAGTAGAAAGACAAAAACAACCACCGTACTTGCCATTCGT ATAG |
| 35 | S. cerevisiae QNQ1 | CATCAATTAGGGCAAACTTGAATAGTCAGCTAGGTCATATATTTAAAATCAATTAGCCCTAT GACTACATTAGGTTTATTGTTAGGTCTTTACGGCTGCATATTTGCTTTCGCCGTTCGGCGGG GTCCTGCGACGATTTCTGCGCGGTCTTGTATGGGTGGAGTTGACAGTTAACCCTCCGGACCC CCTACCCCGGTGTGCCCCCGGTCCATCTATCCATTTTGCGGTAACCCCTTTGCGCGACAGCT GCTTATCAAGGTACCTGGATCGAGCCATAAAAATTGATCTACACAGATGAGATGGGGCATTG GGATATATTATTAGTCGGAGTATCATTATAGTTATTCAGTTTTATGCAGGTTACTGGCCAAA CGTTTTTCTTCATTTGGAATAATCGTTTAGGAGCTACTGTTCCGGTATAAAGTAACAAGCAC AGTAGCAGAGTAATACGCAGTGACGATAATAGAGACTAGTAAAACAGTCGAGTTGTCGGACC TAAA |
| 36 | S. paradoxus pADH2 | TAGTCTTATCTAAAAATTGCCTTTATAGTCCGTCTCTCCAGTCACGGCCTGTGTAACTGATT AATCCTGCCTTTCTAATCACCATTCTACTGTTTAATTAAGGGATTTTGTCTTCATCAACGGC TTCCGCCCAAAAAAAAGTATGACGTTTTGCCCGCAGGCGTGAAGCTGCCCATCTTCACGGGC CTGACCTCCTCTGCCGAACACCGGCCATCTCCAACTCATAAATTGGAGAAATAAGAGAATT TCAGATTTTCAGAGGATGAAAAAAAAAGGTAGAGAGCATAAAAATGGGGTTCACTTTTTGG CAAAGTTACAGTATGCTTATTACATATAAATAGAGTGCCGATAATGGCTTTTTTTCATCTTC GAAATACGCTTGCTACTGCTCTTCCAGCGTTTTTATTACTTCTTTCTTGTTTCTCCTTAGTA TATAAAATATCAAGCTACAACAAGCATACAATCAACTGTCAACTGTCAATTATATTATAATA CACT |
| 37 | S. kudriavzevii pADH2 | CTCTCAAATCTTTTAGCGCCAAGGACTCCAACTAATTGTATCTTGAATTTGCCTTTACGATC CGTTTGTCCAGTCACGGCATGTATATCTTATTAATCCTGCCTTTCTAATCACGTATTCTAAT GTTCAATTAAGGGATTTTATCTTCATCAACGGCTCCCACGCAAAAAATGACGTTTTGCACAC AGACACGAAATACACCTTCCACCGGAACAACGGCCATCTCCAACTTATAAGTTGGGGAAATA AGACAATTTCAGACTTCAGAGAATGAAAAAAAAAAAGGTACATCACAGATGGGGTTCAGGT TTGCTACAATTGCAGGGAGCCTGTCACATATAAATAGACCTCCAGTGATGATATCTTTCAGT CTTCAAACGTCTCTTGTCACAGTTCTGGTCGTTCTATATCACATCTCTCTTGGTTCTACTTA TTGTCTATAATATCAAGCTACAGCAAGCATACAATCAACTATCTACCATACCATAATACACA |
| 38 | S. bayanus pADH2 | GATCCAGTTCTCCAGTGACACAGCCTTTATCTGGTCAAACCTTTCTTTCTAATCACCTATGC TGATGCTTAATTAAGGGATTTTTGTCTCCATCAACGGCATGCGCCCAAAAATGACGTTTTT TTAACCCATAGACACGAAACTACCCATTTTCCACCGGCCTGACCTACCACCGGAACAACGGC CATCTCCAACTTGCAAGTTGGGGAAATTAAGAGCATCGCAGGTTTAATGGAAGAAAAAAAA AGGTACAGCACAGCGCAAATGGAGTTAGTTCCCTTATGTCACACACTCACACACAGTCGGTC AGATCAAGCATACTGGGTGCGTATAAATAGAGTGGCCATTGCCACCCTGTTTATCTCAAAAT CTGTCTTGTTAGTGGTCTTCTCCCTTTTTCAGGTTACAATTCTCTTGTTTCTACTTAGTATA TAAGTATATCAAGCTATATTAAGCATACTATCAACTGTCAACTCTATCCTCAAAATACAATA CAAA |
| 39 | S. mikitae pADH2 | TTTCCCAAAAAGTATTATTTTTAAGTGATAATTGATAAAAGGGGCAAAACGTAGACGCAAAT AAAACGGAAATAATGATTCTCAGACCTTTTAGCGTCAAGAACTGCAACTAATCTTATCTTAA AATTATCTTTATAATCCGTTTCTCCCGTCACAGTCTGTGTATCTGATTAATCCTGCCTTTCT AATCACCTATTCTAATGTTCAATTAAGGGATTTTGTCTTCACCAACGGCTTCCACCCAAAAG TAAAAAATGACGTTGTACCCACAGACATCTTCACCGGCCTGACCTGCCACCGGAACAACGGC CATCTCCAACTCATAAATTGGAGAAATAAGAGAATTTCAGATTCTGGAGGATGAAAAAAAAA AAGGTACAGCATAAATGGGGTTTTATGTGGGTACAATTACACTAGGACTATCACATATAAAT AGACGGGCAATGTAGGTTCTTTTCCACCCTTGAGACAGAGTTATTC |

TABLE 3-continued

Summary of Sequence Listing

| Sequence ID No. | Description | Sequence |
|---|---|---|
| 40 | S. castellii pADH2 | TGTCGTGGACGAAATACGCCACAATTTTGCCGAGAAGGTCATTAGTATGTCCAAGAAACCCT AGGTGTAAAGTCGGGAAATCCGAATCTCCGATTTTGGAGGGGCCCATGCCCTACTTTTTTTC GCCAGGGGTGAAATTCCAAACCCGTGCGCGTTCTTGGAATTTGACAGCGCATTGAGTATGTG CTGCGTATTCCCACTATCATGACGCGCCCTTTATCTGGGAAAAATGGAACTGGATGCTGAAA TATTTCACTCTCAGATCACATATCCCAAATCCTGTGAGTGAATTGTTTGGTCAGGCGACCAA ACAGGAATATGGAATAGATTCTATTCTCTGGATTCTACAATTATCCATTGTTAGCAAAACAA AAAAAACTGGTGGTATATATATTCAGAGCCTAAAATTTAAAGGTTGGATCTCAATTTTAAAA GTTTTCATTCTGTTTTGTTTTGTTTCTTCTTAGCTCACGAATAACCAAACAAAAAACAATC AATA |
| 41 | S. paradoxus pPCK1 | CAATAGGAAAAAACCAAGCTTCCTTTCATCCGGCACGGCTGTGTTGTACATATCACTGAAGC TCCGGGTATTTTAAGTTATACAAGAGAAATATGCGGGCTAGACTAGCAAGATTCTGGACTGT ATAACGTTGTGGATAGGCGGATAAAGGGCCCAAACAGGATTGTAAAGCTTAGACGCCTCTGG TTGGGCAATGGCATGTTTGTGTATTAAGTAAGACTTGGCTGCGGGATAGCAAAACTGAGCAG AATATGAAGGCCACAAAAAAAAGGTATATAAGGGCAGCAAAGTCTTTATATATATATGTAGA TTCTCTTCTCTGTGTAATTCATTCTTGTGCTTACCACTCAAATATACAGAAGTAAGACAGAT AACCAACAGCCTTTCCCAGATATACATATATCTCATTGTTTCAGTTTAAACAATAATCATAT TTGTTTAACTCAAAAATAAAAAAAAACTAAACTCACTCAATCAATCATTCCATAAAAAAAAA CAAT |
| 42 | S. kudriavzevii pPCK1 | CTTCCTTTCATCCGGCACGGCTGTGTCCCCACATCTCCCTAAAGCTCCGGGTATTTTAAGTT ATACAAGGGAAATATACGGGCTGGACTACAACTTGCAGGTTGCACAGCGTTATGGATAGGCG GATAAAGGGCCCAAGCAAGATCGTGAAGCTTGGACGCGTCTGGTTGGACAATGGTGACTTTT TGTGTATTAGATAATGCTTGACTGGAGAATATCAGGACTGAGCAGAGTTAGGAAGACCACAA AAAAGGTATATAAGGGCAACAAAGTCTCCGTGATATGGATAGGCTCTTCTCTCTGGTTACAA TTCATTATTTCAGTTGTTTGCTAGATATAGAGATATAATACATCTAATAAACAGTCACTTCC AGAGATATATATATATACATATATCTATCTCCTCCTCCCAGCTTAAATAATAACTATATTTG TTTAACTCGAAGAAAAAAAAAATTCAAATTTACTCTATCAATTCAATTACCTCATAAAAAAC AATA |
| 43 | S. bayanus pPCK1 | CTTCCTTTCATCCGGCACGGCTGTGTCCCCACATCTCCCTAAAGCTCCGGGTATTTTAAGTT ATACAAGGGAAATATACGGGCTGGACTACAACTTGCAGGTTGCACAGCGTTATGGATAGGCG GATAAAGGGCCCAAGCAAGATCGTGAAGCTTGGACGCGTCTGGTTGGACAATGGTGACTTTT TGTGTATTAGATAATGCTTGACTGGAGAATATCAGGACTGAGCAGAGTTAGGAAGACCACAA AAAAGGTATATAAGGGCAACAAAGTCTCCGTGATATGGATAGGCTCTTCTCTCTGGTTACAA TTCATTATTTCAGTTGTTTGCTAGATATAGAGATATAATACATCTAATAAACAGTCACTTCC AGAGATATATATATATACATATATCTATCTCCTCCTCCCAGCTTAAATAATAACTATATTTG TTTAACTCGAAGAAAAAAAAAATTCAAATTTACTCTATCAATTCAATTACCTCATAAAAAAC AATA |
| 44 | S. paradoxus pMLS1 | CGATACCACACGGTCCATTGGGCCGGTGGTGTTAGTCGACGGATATATGCATCTGTCCCCTT TCCCGGCGAGCCGGCAGTCGGGCCGAGGTTCGGATAAATTTTTGCATTGTATTAGTTTCTGT CATGAGTATTACTTATGGTTCCTTTAGAGCTAATCATTAGCTCGGTACCGGCTGTTATGCAA TTTATGACTTTTCTTCTACAGTGTCAGCCTTGTGACGATTATCTATGAACTTTGGATGTAGC GCATCGAGATTCGTATCTTTCATTGGATAGTAAATGGGAAGGATCGATGACCCTTATTACAT TCTTTCCTATACTTAATATCCATTTAATCTATCTTCTTGAAAGTATATAAGTAACGGTAAAT TTACCATACTTATGCTATTCTCATTTATCCCCTAATTTTCTTTTAACTTCTCGCCCTACAGT AACTAAGAATAACGGCTACTGTTTCGAAATTAAGCAAAGTAGTAAAGCACATAAAAGAATAA AGAA |
| 45 | S. kudriavzevii pMLS1 | AGACCGAAGCGGGTAATGGACGGAATTAAGCAATTGTCCCCTCTCCCGGGGAGCCGACAGTC GGACCGAGCTTCGGATAAATTTCTGTATTGTTTTTGTTTCCGTCATGGGTATTATTTTCGGG ATCCTTTTGCCAACCCCATAGTCAATCGTTAACATTTACCGGCCAATATGTAGGATTATGAC TATTCTCCTGCATGATCAGCGGAAGTGACGATTATCTATTAATTTTGAACTTCTACTTCGTG ATCCGGAATTTAATTGGATAATAATGTGTCCGAAGGATCGAGTGACCCTTATATTCTGTAGT TTTTTGTTACTGGCCATCCAATTCGTGTTCTTGGAAGTATATAAGTTACAGTCGATTGACCT TTCTCAAGCTATTTTCATCTTTCTCCTACATTTACGTTTCTCTTCTTCAATACAGCAGCTAG AAGTTACGATTACTCCTGTGAAGATAAACAAAGTAATAGTAGCCCACAAAAAGAGAGAAAGT AAAA |
| 46 | S. bayanus pMLS1 | GTAGCAGTCCGGAAATAAGCAAATGTCCCCTTTCCCGAGCTAACCAACGGTCGGGCCGAGCC TCGGATAAATTTTTGCTTTGTTTTTGTTTCTGTCATGGGTATTATACATCATTTATTTAGTT AACCCCTAGACTAATTAGCCGGCCATTAGTATGTAAGATTATGACTATAGTTTGTACCGGAA CCCTGGTAGCAACTACTCATGAACTTTGGGCTCAGTATTTCGCAATCCCGGTTTAATTGGA TAGCCTATCGCGAAGGATCGATGGATGACCCTTAGAATTGTCTCTTTTGTTACTACTCATTC AATGCGTGTGCTCTTGCAAGTATATAAGTCACTCTAAATTAGTTTATACTTGAGCTTTTTAC ATTTCTCCCTTGATTGTTTCTTTCTCTTTTCCCCTTGTTCTGGTTTATTGTAATAGCTAAGT GCAACGATTACCGCTGTTAAGTTAAAGAAGAGAGACAAGTAATAATAGTACACAGCAAGGAA AAAA |
| 47 | S. paradoxus pICL1 | TTACTAAATAGGCTGGCATCAGCTAACCCGGATGGTTGAATCCGGCTTTTGCTACTTGTTGT CCGATGAAAAGGAGCGGCTTCCCTTTTGCCCCAGATTTCCATTCATCCGAGAGGTCGCTTAT CAGACTTCGTCATTTCTCATTTCATCCGAGATGATCAAAATTGAAGCCAATCACCACAAAAC TAACACTTAACGTCATGTTACACTACCCTTTACAGAAGAAAATATCCATAGTCCGGACTAAC |

TABLE 3-continued

Summary of Sequence Listing

| Sequence ID No. | Description | Sequence |
|---|---|---|
| | | ATTCCAGTATGTGACTCAATATTGGTGCAAATGAGAAAATCATAGCAGTCAGCCCAAGTCCG<br>CCCTTTACCAGGGCACCGTAATTCACGAAACGTTTCTTTATTATATAAAGGAGCTACTTTAC<br>TAGCAAAATTCTTGTAATTCCTCTTCCCTTGCTAACTTCTTCTTGTTTTCTTTTCCTTTTA<br>CACACAGATATATAACAATTGAGAGAAAAACTCTAGTATAACATAACAAAAAAGTCAACGAA<br>AAAA |
| 48 | S. kudriavzevii plCL1 | GTTACGGTGCCGCGCCGGTGGCCGGTGGTCTTCCGGTAAACAAAAAAAGCTGCCTCCCTTTC<br>GCCCCAGATTTCCATTCATCCGAGGGCACCGCTTGTCAGACTTTATCGTTTTCCTCATTTCA<br>TCCGAGAAGATCAATTCAAAGGCAATGACCACAAAAGCAACTCCTAACGTTGTGTTACGCTA<br>CCCTTTACACAAAATATTCATAACCCGTAATGAATCCTAAGGTATGTGACTCAATTTTGGTG<br>TAGAAAATGAGGAAAACGTAATACTAAGTTAAAGCTCGCCCTTTAAAGTGAATATTCCTTGA<br>CCATTTGCGCAGGCACACCCGAATTCACAAACGTTTCTTTATTATATAAAGGACCAGCTCTG<br>CTAGTCAAATTTTTATAACTGCTTGTTCAGTTGCTGCTTCTTTCTTGTCAATTTATTTCTTG<br>TACTGTTCAACTACATAAAGCAAAGAGAAAACTCTCAGAATAACATAACAAAGAAGTCAACG<br>AAAA |
| 49 | S. bayanus plCL1 | ACGAGGCTCGGCGTTTACTGCTGAATTTCCGGAAAGAAAGGGAAGGTTCCCTTTACCCCAGA<br>TTTCCATTCATCCGAAGGACTGCTTATCAGAATTTGACATTTTTCTCATTTTATCCGAGAAG<br>ATCAATTTAAGGCTAGTGACCACAAAACTAACTCTCATGCTGCGCTACCGCAAGTTTCGCTC<br>ACAGAAAGAAAGCAAGCACCCATAGTCCGGACTACATCCTTGTATGTGACTCAAATTTTTGG<br>CGTTGCCAATTAAACTGAAGTGTAAAGATTACTTCAAGCTCACCCTTTAAAGTAGAATTCCT<br>TAACGGTTTTAAATAGACACACCGAAATTAATAAACACTTTCTTTATTATATAAAGGACAGA<br>GTTTATTACTGGAATTCTCTTAACGCCTTCCTCCCTTACTATTGTATCTTTTCCTTTCACAT<br>AATCGCTACATAACTACATAGAGAAAACTCTCAGATTAACACAGTAACAACGAAGAAAACAA<br>AAAA |
| 50 | S. cerevisiae pTDH3 | ACAGTTTATTCCTGGCATCCACTAAATATAATGGAGCCCGCTTTTTAAGCTGGCATCCAGAA<br>AAAAAAAAGAATCCCAGCACCAAAATATTGTTTTCTTCACCAACCATCAGTTCATAGGTCCAT<br>TCTCTTAGCGCAACTACAGAGAACAGGGGCACAAACAGGCAAAAACGGGCACAACCTCAAT<br>GGAGTGATGCAACCTGCCTGGAGTAAATGATGACACAAGGCAATTGACCCACGCATGTATCT<br>ATCTCATTTTCTTACACCTTCTATTACCTTCTGCTCTCTCTGATTTGGAAAAAGCTGAAAAA<br>AAAGGTTGAAACCAGTTCCCTGAAATTATTCCCCTACTTGACTAATAAGTATATAAAGACGG<br>TAGGTATTGATTGTAATTCTGTAAATCTATTTCTTAAACTTCTTAAATTCTACTTTTATAGT<br>TAGTCTTTTTTTTTAGTTTTAAAACACCAAGAACTTAGTTTCGAATAAACACACATAAACAAA<br>CAAA |
| 51 | S. cerevisiae pTEF1 | ATAGCTTCAAAATGTTTCTACTCCTTTTTTACTCTTCCAGATTTTCTCGGACTCCGCGCATC<br>GCCGTACCACTTCAAAACACCCAAGCACAGCATACTAAATTTCCCCTCTTTCTTCCTCTAGG<br>GTGTCGTTAATTACCCGTACTAAAGGTTTGGAAAAGAAAAAGAGACCGCCTCGTTTCTTTT<br>TCTTCGTCGAAAAAGGCAATAAAAATTTTTATCACGTTTCTTTTTCTTGAAAATTTTTTTTT<br>TTGATTTTTTTTCTCTTTCGATGACCTCCCATTGATATTTAAGTTAATAAACGGTCTTCATT<br>TCTCAAGTTTCAGTTTCATTTTCTTGTTCTATTACAACTTTTTTTTACTTCTTGCTCATTAG<br>AAAGAAAGCATAGCAATCTAATCTAAGTTTTAATTACAAA |
| 52 | S. cerevisiae pFBA1 | TGGGTCATTACGTAAATAATGATAGGAATGGGATTCTTCTATTTTTCCTTTTTCCATTCTAG<br>CAGCCGTCGGGAAAACGTGGCATCCTCTCTTTCGGGCTCAATTGGAGTCACGCTGCCGTGAG<br>CATCCTCTCTTTCCATATCTAACAACTGAGCACGTAACCAATGGAAAAGCATGAGCTTAGCG<br>TTGCTCCAAAAAAGTATTGGATGGTTAATACCATTTGTCTGTTCTCTTCTGACTTTGACTCC<br>TCAAAAAAAAAAAAATCTACAATCAACAGATCGCTTCAATTACGCCCTCACAAAACTTTTTT<br>CCTTCTTCTTCGCCCACGTTAAATTTTATCCCTCATGTTGTCTAACGGATTTCTGCACTTGA<br>TTTATTATAAAAAGACAAAGACATAATACTTCTCTATCAATTTCAGTTATTGTTCTTCCTTG<br>CGTTATTCTTCTGTTCTTCTTTTCTTTTGTCATATATAACCATAACCAAGTAATACATATT<br>CAAA |
| 53 | S. cerevisiae pPDC1 | CATGCGACTGGGTGAGCATATGTTCCGCTGATGTGATGTGCAAGATAAACAAGCAAGGCAGA<br>AACTAACTTCTTCTTCATGTAATAAACACACCCCGCGTTTATTTACCTATCTCTAAACTTCA<br>ACACCTTATATCATAACTAATATTTCTTGAGATAAGCACACTGCACCCATACCTTCCTTAAA<br>AACGTAGCTTCCAGTTTTTGGTGGTTCCGGCTTCCTTCCCGATTCCGCCCGCTAAACGCATA<br>TTTTTGTTGCCTGGTGGCATTTGCAAAATGCATAACCTATGCATTTAAAAGATTATGTATGC<br>TCTTCTGACTTTTCGTGTGATGAGGCTCGTGGAAAAAATGAATAATTTATGAATTTGAGAAC<br>AATTTGTGTTGTTACGGTATTTTACTATGGAATAATCAATCAATTGAGGATTTTATGCAAA<br>TATCGTTTGAATATTTTCCGACCCTTTGAGTACTTTTCTTCATAATTGCATAATATTGTCC<br>GCTGCCCCTTTTCTGTTAGACGGTGTCTTGATCTACTTGCTATCGTTCAACACCACCTTAT<br>TTTCTAACTATTTTTTTTTAGCTCATTTGAATCAGCTTATGGTGATGGCACATTTTTGCAT<br>AAACCTAGCTGTCCTCGTTAACATAGGAAAAAAAATATATAAACAAGGCTCTTTCACTCT<br>CCTTGCAATCAGATTTGGGTTTGTTCCCTTTATTTCATATTTCTTGTCATATTCCTTTCTC<br>AATTATTATTTTCTACTCATAACCTCACGCAAAATAACACAGTCAAATCAATCAAA |
| 54 | S. cerevisiae pTPI1 | TATATCTAGGAACCCATCAGGTTGGTGGAAGATTACCCGTTCTAAGACTTTTCAGCTTCCTC<br>TATTGATGTTACACCTGGACACCCCTTTTCTGGCATCCAGTTTTTAATCTTCAGTGGCATGT<br>GAGATTCTCCGAAATTAATTAAAGCAATCACACAATTCTCTCGGATACCACCTCGGTTGAAA<br>CTGACAGGTGGTTTGTTACGCATGCTAATGCAAAGGAGCCTATATACCTTTGGCTCGGCTGC<br>TGTAACAGGGAATATAAAGGGCAGCATAATTTAGGAGTTTAGTGAACTTGCAACATTTACTA<br>TTTTCCCTTCTTACGTAAATATTTTCTTTTTAATTCTAAATCAATCTTTTTCAATTTTTG<br>TTTGTATTCTTTTCTTGCTTAAATCTATAACTACAAAAAACACATACATAAACTAAA |

TABLE 3-continued

Summary of Sequence Listing

| Sequence ID No. | Description | Sequence |
|---|---|---|
| 55 | S. cerevisiae tADH2 | GCGGATCTCTTATGTCTTTACGATTTATAGTTTTCATTATCAAGTATGCCTATATTAGTATA TAGCATCTTTAGATGACAGTGTTCGAAGTTTCACGAATAAAAGATAATATTCTACTTTTTGC TCCCACCGCGTTTGCTAGCACGAGTGAACACCATCCCTCGCCTGTGAGTTGTACCCATTCCT CTAAACTGTAGACATGGTAGCTTCAGCAGTGTTCGTTATGTACGGCATCCTCCAACAAACAG TCGGTTATAGTTTGTCCTGCTCCTCTGAATCGTCTCCCTCGATATTTCTCATTTTCCTTCGC ATGCCAGCATTGAAATGATCGAAGTTCAATGATGAAACGGTAATTCTTCTGTCATTTACTCA TCTCATCTCATCAAGTTATATAATTCTATACGGATGTAATTTTTCACTTTTCGTCTTGACGT CCACCCTATAATTTCAATTATTGAACCCTCAC |
| 56 | S. cerevisiae tPGI1 | ACAAATCGCTCTTAAATATATACCTAAAGAACATTAAAGCTATATTATAAGCAAAGATACGT AAATTTTGCTTATATTATTATACACATATCATATTTCTATATTTTTAAGATTTGGTTATATA ATGTACGTAATGCAAAGGAAATAAATTTTATACATTATTGAACAGCGTCCAAGTAACTACAT TATGTGCACTAATAGTTTAGCGTCGTGAAGACTTTATTGTGTCGCGAAAAGTAAAAATTTTA AAAATTAGAGCACCTTGAACTTGCGAAAAAGGTTCTCATCAACTGTTTAAAAGGAGGATATC AGGTCCTATTTCTGACAAACAATATACAAATTTAGTTTCAAAGATGAATCAGTGCGCGAAGG ACATAACTCA |
| 57 | S. cerevisiae tENO2 | AGTGCTTTTAACTAAGAATTATTAGTCTTTTCTGCTTATTTTTTCATCATAGTTTAGAACAC TTTATATTAACGAATAGTTTATGAATCTATTTAGGTTTAAAAATTGATACAGTTTTATAAGT TACTTTTTCAAAGACTCGTGCTGTCTATTGCATAATGCACTGGAAGGGGAAAAAAAAGGTGC ACACGCGTGGCTTTTTCTTGAATTTGCAGTTTGAAAAATAACTACATGGATGATAAGAAAC ATGGAGTACAGTCACTTTGAGAACCTTCAATCAGCTGGTAACGTCTTCGTTAATTGGATACT CAAAAAAGATGGATAGCATGAATCACAAGATGGAAGGAAATGCGGGCCACGACCACAGTGAT ATGCATATGGGAGATGGAGATGATACCT |
| 58 | S. cerevisiae tTEF1 | GGAGATTGATAAGACTTTTCTAGTTGCATATCTTTTATATTTAAATCTTATCTATTAGTTAA TTTTTTGTAATTTATCCTTATATATAGTCTGGTTATTCTAAAATATCATTTCAGTATCTAAA AATTCCCCTCTTTTTTCAGTTATATCTTAACAGGCGACAGTCCAAATGTTGATTTATCCCAG TCCGATTCATCAGGGTTGTGAAGCATTTTGTCAATGGTCGAAATCACATCAGTAATAGTGCC TCTTACTTGCCTCATAGAATTTCTTTCTCTTAACGTCACCGTTTGGTCTTTTATAGTTTCGA AATCTATGGTGATACCAAATGGTGTTCCCAATTCATCGTTACGGGCGTATTTTTTACCAATT GAAGTATTGGAATCGTCAATTTTAAAGTATATCTCTCTTTTACGTAAAGCCTGCGAGATCCT CTTAAGTATAGCGGGGAAGCCATCGTTATTCGATATTGTCGTAACAAATACTTTGATCGGCG CTAT |
| 59 | A. tubingensis GGPPS | ATGCTGGGATTCCCAATGTTCAACCCAGCTACGCCTGATGTCTGGAAGATGAATACCCCTTA CTTTCCATTTGTTACACCGGGGTTATTTCCTGCCTCAGCACCCCCATCGCCCACCAACGTAG ATGCCGAAGCTGCCAGTTCCCAACAGTCGGAAGCAAGCTATCTGGATAAGGAGAAAATTGTT CGAGGGCCACTTGATTATCTTCTCAAATCCCCTGGAAAAGACATTCGTCGGAAATTCATTCA CGCGTTCAATGAATGGCTGCGCATTCCTGAGGACAAGTTGAATATTATCACGGAAATTGTTG GATTGCTTCACACGGCCTCCCTTCTAATCGACGATATTCAGGACAATTCCAAGCTTCGACGC GGCCTCCCAGTGGCCCATAGCATATTTGGTATTGCGCAGACAATTAACTCTGCCAATTATGC GTACTTTCTAGCCCAGGAAAGGCTCCGCGAACTGAATCATCCTGAAGCGTACGAAATATACA CAGAGGAACTGCTTCGTCTGCACCGCGGTCAAGGTATGGACTTGTACTGGCGGGACTGCCTA ACCTGTCCCACAGAGGAGGACTATATTGAGATGATCGCCAACAAGACTGGTGGCCTATTTCG ACTGGCGATTAAGCTTATGCAGTTGGAAAGCACTTTGTGCAGCAATGTCATTGAACTAGCAG ACTTGTTGGGCGTGATCTTTCAGATTCGGGATGATTACCAAAACTTACAGAGTGGACTATAC GCCAAGAACAAGGGATTTTGCGAGGATTTGACGGAGGGAAAATTTTCCTTTCTGATTATCCA CAGTATTAACAGTAACCCGAACAATCACCATCTGCTAAATATACTACGGCAGCGGAGCGAGG ACGATTCGGTGAAGAAGTATGCTGTTGATTATATCGACTCGACGGGGAGTTTTGACTACTGC CGGGAACGGCTCGCTTCCTTATTGGAAGAGGCGGATCAAATGGTTAAGAAGTTGGAAAATGA GGGGGGACAATCAAAGGGGATCTACGATATTCTGAGCTTTCTGTCGTGA |
| 60 | A. tubingensis PT | ATGGATGGGTTCGACCATTCTACTGCTCCACCAGGATATAACGAGCTAAAATGGCTCGCCGA TATCTTCGTCATCGGAATGGCTGTTGGCTGGGTTGCTCACTATATGGAGATGATTCACACGT CGTTCAAGGACCAAACATACTGCATGACCATCGGGGGCCTTTGCATCAATTTTGCCTGGGAA ATCATATTCTGCACAATGTATCCTGCCAAAGGATTTGTCGAGCGGGTTGCCTTTCTCATGGG CATTTCTCTCGACCTTGGGGTTATTTACGCGGGAATCAAGAACGCCCCAAATGAATGGCACC ACTCTGCAATGGTGAGGGACCATATGCCCCTTGTCTTCGCAGCAACGACACTTTGTTGTCTG AGCGGTCATATGGCTCTTACTGCCCAGGTTGGTCCCGCACAAGCCTATACGTGGGGGCAAT TGCATGCCAGCTCTTTATCAGCATAGGGAATGTGTTTCAATTGTTGAGTCGGGGAAACACAC GAGGGGCGTCATGGACGCTATGGACCTCCAGGTTTTTTGGATCAACATCAGCCATTGGCTTT GCTCTTGTTCGATATATTCGCTGGTGGGAGGCCTTTTCTTGGTTGAACTGCCCGCTTGTGAT ATGGTCCGTGGCCATGTTCTTTCTGTTTGAAAACACTCTATGGAGCCCTATTCTATTCTGTCA AGCGACAAGAAGGGAGATCCCAGCGTGGAATCAAGCACAAAGAGAGGTAG |
| 61 | A. tubingensis FMO | ATGGCGGCACTTCCGGACGTTGCCTCCATTCCCATCCCTCTGGTGGCAACCCTAGGCATTGC CCCTCTAATTTTCTATCTCGTCCTTGATAGAATTAGCCCCTTGTGGCCAAATTCCAAAGCTT TCCTGATTGGCAAGAAGAAACCGGAGACCGTTGATCATCGTTCGAGTGCCCATATGCCTACATC CGTCAGATCTATGGGAAGTATCACTGGGAGCCATTCGTACAGAAGCTGTCTCCGAGGCTTAA GGATGAGGATCCGGCCAAATATAAGATGGTTCTGAGAATAATGGATGCAATCCACCTGTGTC TGATGCTAGTTGACGATATAACTGACAATAGCGACTATCGAAAAGGCAAGCCAGCAGCCCAC CGGATATATGGCCCTTCAGAGACAGCAAATCGCGCTTACTACCGAGTCACCCAGATTCTAAA CAAGACCGTGCAAAAGTTCCCCAAGCTGGCCAAGTTCCTGCTTCAGAATCTGGAAGAAATTC |

TABLE 3-continued

Summary of Sequence Listing

| Sequence ID No. | Description | Sequence |
|---|---|---|
| | | TCGAAGGCCAAGACCTGTCACTAATCTGGCGACGGGATGGACTGGGTAGCCTTTCGACTGTT<br>CCTGATGAGCGAGTTGCAGCCTATCGCAAGATGGCGTCATTGAAAACTGGGGCGTTATTCCG<br>GCTGCTGGGGCAATTGGTGATGGAGGACCAATCGATGGACGGGACGATGACTACTCTTGCGT<br>GGTGCTCTCAGCTGCAGAATGACTGCAAGAATGTCTACTCATCTGAATATGCTAAGGCCAAA<br>GGGGCGCTTGCCGAAGACCTCCGAAATCGAGAGCTCTCATTTCCAATTATCCTCGCGCTGGA<br>AGCTCCTGAAGGGCATTGGGTCGCCAGTGCTTTGGAGACCAGCTCACCGCGCAACATTCGCA<br>AGGCGCTTGCTGTGATTCAGAGTGAGAGAGTGCGCAATGCTTGTTTCAAGGAGCTCAAGTCG<br>GCGAGTGCTTCGGTCCAGGACTGGTTGGCTATTTGGGGACGGAACGAGAAAATGAACTTGAA<br>GAGCCAGCAGACGTAG |
| 62 | A. tubingensis Cyc | ATGGCCAATGCCCAGCAACCCCCCTTTCGCATCCTTATTGTGGGCGGTTCTGTCGCAGGCCT<br>CATCCTTGCGCACTGTCTCGAACGCGCCAATATAGAGTACCTCATACTCGAAAAAGGAGAAG<br>ATGTTGCTCCACAAGTTGGTGCCTCGATAGGTATCATGCCAAATGGCGGACGGATCCTCGAG<br>CAACTGGGCCTATTTGGGGAGATTGAGCGTGTGATCGAGCCGTTGCATCAGGCGAATATCAG<br>CTATCCAGATGGGTTCTGCTTTAGTAACGTCTATCCTAAGGTTCTTGGCGACAGGTTCGGAT<br>ACCCGGTTGCATTCTTGGACCGGCAGAAGTTCCTGCAGATTGCATATGAGGGGCTGAGAAAG<br>AAGCAGAATGTTCTCACCGGTAAAAGGGTAGTTGGACTGCGACAGTCGGATCAAGGGACTGC<br>TGTTTCTGTGGCTGACGGGACAGAGTATGAGGCGGATCTCGTGGTTGGTGCTGATGGAGTAC<br>ATAGTCGGGTGAGAAGTGAGATTTGGAAGATGGCGGAAGAGAATCAGCCTGCATCAGTTTCG<br>ACACGTGAAAGAAGAAGCATGACTGTTGAATATGTCTGCGTTTTCGGGATTTCATCAGCCAT<br>CCCAGGGCTCGAGATAAGCGAACAGATCAACGGTATTTTCGACCATCTATCCATTCTAACAA<br>TCCATGGCAGACATGGTCGCGTGTTCTGGTTCGTGATCCAGAAGCTGGATAGGAAGTACGTC<br>TATCCTGATGTCCCGCGATTCTCAGACGAGGATGCCGTACAGCTCTTCGATCGGGTCAAACA<br>CGTGCGGTTCTGGAAAAACATCTGTGTGGGGGACTTGTGGAAGAACAGAGAGGTGTCCTCGA<br>TGACAGCGCTGGAGGAGGGAGTGTTCGAGACATGGCATCATGATAGGATGGTTTTGATTGGA<br>GATAGCGTTCACAAGATGACGCCCAACTTTGGCCAAGGAGCTAATTCAGCCATCGAGGATGC<br>TGCCGCGCTCTCTTCCCTTCTACATGATCTCGTCAACGCCCGTGGAGTTTGCAAGCCATCGA<br>ATGTCCAGATTCAGCATCTCCTCAAGCAGTATCGGGAGACCCGATACACTCGCATGGTAGGC<br>ATGTGTCGCACCGCGGCTTCAGTCTCTCGGATTCAGGCCCGAGATGGCATCCTCAACACCGT<br>CTTTGGACGATATTGGGCACCTTATGCTGGCAACCTGCCTGCTGACCTGGCATCAAAAGTGA<br>TGGCAGATGCAGAGGTTGTTACTTTTCTGCCCTTGCCAGGGCGCTCAGGACCGGGCTGGGAG<br>ATGTACAGACGAAAGGGGAAGGGAGGGCAGGTGCAATGGGTGCTTATAATCTTAAGCTTACT<br>TACGATTGGTGGATTGTGCATCTGGCTACAAAGCAATGCGTTGAGTAGATAA |
| 63 | H. subiculosis hpm8 | ATGCCTTCTACCAGCAATCCATCTCACGTCCCTGTGGCCATCATCGGCCTGGCATGCCGATT<br>CCCAGGCGAGGCCACCTCACCATCAAAATTCTGGGATCTTCTTAAGAATGGACGAGATGCCT<br>ACTCACCAAATACCGATCGATATAACGCTGATGCCTTTTACCATCCCAAGGCAAGCAACCGC<br>CAAAACGTGCTGGCAACTAAGGGCGGCCACTTCCTCAAACAGGACCCATACGTTTTTGACGC<br>CGCTTTCTTTAACATCACAGCCGCTGAGGCCATCTCCTTTGACCCCAAGCAGCGAATTGCCA<br>TGGAAGTTGTCTACGAGGCTCTAGAAAATGCCGGAAAGACACTACCCAAGGTGGCGGGCACA<br>CAAACTGCTTGCTATATCGGCTCTTCCATGAGTGATTACCGAGACGCTGTTGTCGTGACTT<br>TGGAAACAGCCCCAAGTATCATATCCTGGGAACATGCGAGGAGATGATTTCAAATCGTGTGT<br>CCCATTTCTTGGATATTCACGGCCCCAGTGCCACCATTCATACAGCCTGCTCATCAAGTCTT<br>GTTGCTACACACTTGGCTTGCCAAAGTTTGCAATCTGGAGAGTCAGAAATGGCCATCGCTGG<br>TGGTGTTGGTATGATCATCACCCCTGATGGTAATATGCATCTTAACAACTTGGGATTCTTGA<br>ACCCCGAGGGCCACTCCCGGTCATTTGATGAGAATGCTGGTGGTTACGGTCGTGGTGAGGGT<br>TGCGGTATCCTCATCCTCAAGCGGCTAGACAGAGCTCTCGAAGATGGTGATTCCATTCGCGC<br>CGTCATTCGAGCCTCTGGTGTCAACTCTGATGGCTGGACACAGGGTGTCACCATGCCCTCCA<br>GCCAAGCCCAGTCTGCCCTTATCAAATACGTATACGAATCGCATGGCCTGGATTATGGTGCG<br>ACTCAATACGTTGAGGCTCACGGTACTGGTACCAAAGCCGGTGATCCCGCAGAGATTGGCGC<br>CCTCCACCGCACAATTGGACAGGGCGCGTCCAAGTCTCGAAGGCTTTGGATTGGCAGTGTCA<br>AGCCAAACATTGGCCATCTTGAAGCCGCCGCCGGTGTGGCTGGTATCATTAAGGGCGTCCTG<br>TCCATGGAACACGGCATGATTCCTCCAAACATTTACTTCTCCAAGCCCAACCCTGCCATCCC<br>TCTTGACGAGTGGAACATGGCCGTGCCTACCAAGTTGACTCCCTGGCCCGCCAGCCAAACTG<br>GTCGCCGTATGAGTGTCAGCGGTTTCGGTATGGGTGGTACCAACGGCCACGTCGTCCTTGAG<br>GCCTACAAGCCCCAAGGAAAGCTCACCAACGGCCATACCAACGGCATCACCAATGGAATCCA<br>CAAGACTCGCCACAGCGGCAAGAGGCTTTTCGTCCTCAGCGCCCAGGATCAAGCTGGCTTCA<br>AGCGTTTGGGTAACGCCCTGGTGGAGCATCTCGATGCCCTGGGCCCTGCCGCTGCCACCCCT<br>GAGTTCCTCGCCAACCTCTCCCACACTCTTGCCGTTGGCAGATCTGGCTTGGCTTGGAGGTC<br>CAGCATCATCGCTGAGAGCGCCCCTGATCTTGGGAGAAGCTGGCAACTGATCCGGGTGAGG<br>GAGCCGCTCGTTCTTCAGGCAGCGAGCCCCGTATTGGATTCGTCTTCACGGGTCAAGGTGCT<br>CAGTGGGCCCGCATGGGCGTTGAGTTGTTGGAGCGCCCCGTCTTCAAGGCTTCCGTGATTAA<br>GTCCGCGGAGACTTTGAAGGAGCTCGGCTGTGAATGGGACCCTATCGTTGAGCTTTCCAAGC<br>CTCAAGCTGAGTCTCGACTTGGTGTTCCTGAAATCTCACAGCCCATCTGCACAGTCCTACAA<br>GTCGCCTTGGTTGATGAGTTGAAGCACTGGGGTGTATCACCTTCCAAGGTGGTCGGTCACTC<br>CAGTGGTGAAATCGGTGCCGCATACAGCATTGGCGCTCTTTCTCACCGTGACGCTGTCGCCG<br>CTGCTTACTTCAGGGGCAAGTCTTCCAACGGAGCCAAGAAGCTTGGTGGTGGTATGATGGCT<br>GTTGGGTGCTCTCGTGAGGACGCTGACAAGCTCCTCTCTGAGACCAAGCTCAAGGGCGGTGT<br>TGCTACCGTCGCATGTGTCAACTCCCCCTCCAGCGTGACCATCTCAGGCGATGCCACTGCTC<br>TCGAGGAACTCCGAGTTATTCTCGAGGAGAAGAGTGTGTTTGCTCGAAGACTCAAGGTCGAC<br>GTTGCCTACCACTCTGCCCACATGAACGCTGTCTTTGCCGAATACTCTGCTGCGATTGCCCA<br>CATTGAGCCCGCTCAGGCAGTTGAAGGTGGACCGATTATGGTCTCCAGTGTCACTGGTAGCG<br>AAGTCGACTCTGAGCTTCTCGGCCCTTACTACTGGACCCGTAACTTGATCTCTCCCGTCTTA<br>TTCGCCGACGCTGTCAAGGAATTGGTTACCCCTGCTGATGGCGACGGCCAAAACACCGTCGA<br>TCTCCCTGATTGAGATTGGTCCTCACAGCGCTCTTGGTGGCCCTGTTGAGCAGATTCTGTCCC |

TABLE 3-continued

Summary of Sequence Listing

| Sequence ID No. Description | Sequence |
|---|---|
| | ATAACGGCATCAAGAATGTTGCTTACAGATCTGCTCTTACTCGTGGCGAGAACGCTGTTGAC
TGCAGCCTCAAGCTTGCTGGCGAGCTCTTCCTTCTCGGCGTGCCCTTTGAGTTGCAAAAGGC
CAACGGTGACTCTGGTTCTCGCATGCTCACTAACCTACCTCCTTATCCTTGGAACCACTCCA
AGTCATTCCGTGCCGACTCTCGTCTCCACCGTGAGCATCTGGAGCAGAAATTCCCTACTAGG
AGTCTCATCGGTGCACCTGTCCCCATGATGGCAGAGAGCGAGTACACATGGCGCAACTTCAT
CCGTCTCGCTGACGAGCCTTGGCTCCGTGGTCACACTGTCGGTACCACCGTTCTGTTTCCTG
GTGCCGGTATCGTGAGCATCATCTTGGAAGCTGCTCAACAGCTGGTGGATACCGGCAAGACC
GTTCGGGGCTTCCGAATGCGCGATGTCAACCTCTTCGCCGCCATGGCTCTCCCCGAGGACCT
GGCTACTGAGGTTATCATCCACATCCGACCTCACCTTATCTCTACTGTTGGATCAACCGCCC
CCGGTGGATGGTGGGAGTGGACTGTTTCCTCCTGCGTCGGAACTGACCAGCTGCGAGACAAT
GCTCGCGGTCTGGTAGCCATTGACTACGAAGAGAGCCGCAGCGAGCAGATCAACGCCGAGGA
CAAAGCGTTGGTTGCTTCTCAGGTCGCGGACTACCACAAGATCCTCAGCGAATGCCCTGAGC
ATTATGCTCATGACAAGTTCTACCAGCACATGACCAAGGCCTCTTGGAGCTACGGCGAGCTC
TTCCAGGGTGTGGAGAATGTCCGTCCTGGATACGAAAGACCATCTTTGACATCAGAGTCAT
TGACATTGGTGAGACCTTTAGCAAGGGACAACTTGAGCGACCTTTCCTCATCAACGCTGCCA
CTCTCGATGCTGTATTCCAGAGCTGGCTCGGCAGTACCTACAACAACGGTGCTTTCGAGTTT
GACAAGCCCTTCGTTCCCACCTCTATTGGCGAGTTGGAAATCTCTGTCAACATTCCCGGTGA
TGGCGACTACCTCATGCCAGGCCACTGCCGCTCTGAGCGATACGGCTTCAACGAGTTGTCTG
CTGATATTGCCATCTTCGACAAGGATCTGAAGAATGTGTTCCTTTCAGTGAAGGATTTCCGA
ACTTCCGAGCTTGATATGGATTCCGGCAAGGGAGACGGAGATGCCGCTCACGTCGACCCTGC
CGATATCAACTCGGAGGTTAAGTGGAACTACGCTCTTGGCCTCCTCAAGTCCGAGGAAATCA
CCGAGCTGGTCACCAAGGTCGCCAGCAATGACAAGCTCGCCGAGCTTCTCCGTCTGACACTT
CACAACAACCCTGCTGCCACTGTCATCGAGCTTGTTTCTGATGAGAGCAAGATCTCTGGCGC
ATCTTCTGCCAAGCTGTCCAAGGGCCTTATCCTCCCCAGCCAGATCCGTTACGTAGTTGTCA
ACCCTGAGGCAGCGGACGCCGACTCTTTCTTCAAATTCTTCTCCCTTGGTGAGGATGGTGCC
CCTGTCGCTGCTGAAAGGGGCCCCGCCGAACTGTTGATCGCCTCCAGCGAAGTCACTGACGC
GGCTGTCCTTGAGCGCCTGATTACCTTGGCCAAGCCTGATGCCAGCATTCTTGTTGCTGTCA
ACAACAAGACTACCGCCGCTGCCCTCTCAGCCAAGGCGTTCCGTGTTGTCACCAGCATCCAG
GACAGCAAGTCCATTGCTCTCTACACTAGCAAGAAGGCGCCTGCCGCCGACACCTCCAAGCT
CGAGGCCATCATCCTCAAGCCAACCACTGCTCAACCTGCCGCCCAGAATTTCGCCTCCATCC
TCCAGAAGGCACTCGAGCTCCAGGGCTACTCTGTCGTTTCTCAGCCATGGGGCACCGACATC
GACGTCAACGATGCCAAGGGAAAGACCTACATTTCTCTGTTGGAGCTTGAGCAGCCTCTGCT
CGACAACCTCTCCAAGTCCGACTTCGAGAACCTCCGCGCAGTCGTTTTGAACTGCGAGCGTC
TCCTGTGGGTCACAGCAGGTGACAACCCATCTTTCGGCATGGTTGATGGTTTCGCTCGCTGC
ATCATGAGCGAAATTGCCAGCACCAAGTTCCAGGTCCTGCATTTGAGCGCTGCAACTGGTCT
GAAGTACGGATCTTCTCTCGCCACCCGCATTCTCCAGTCGGATAGCACCGACAACGAGTACC
GGGAGGTCGATGGTGCTCTCCAGGTGGCCCGTATCTTCAAGAGCTACAACGAGAACGAGAGT
CTCCGCCACCACCTCGAGGATACCACCAGCGTTGTGACTCTTGCTGACCAGGAGGATGCTCT
GCGCCTCACTATTGGCAAGCCTGGTCTTTTGGATACTTTGAAGTTTGTCCCCGATGAGCGTA
TGCTCCCACCTCTCCAGGATCACGAGGTTGAAATCCAGGTCAAGGCTACTGGTCTGAACTTC
CGAGACATCATGGCTTGCATGGGTCTTATTCCTGTTCGATCTCTGGGCCAGGAGGCCAGTGG
CATCGTCCTCAGAACCGGTGCGAAGGCTACCAACTTCAAGCCTGGCGACCGTGTTTGCACCA
TGAACGTCGGAACACATGCCACCAAGATCCGAGCCGACTACCGTGTCATGACAAAGATCCCC
GACTCCATGACCTTTGAAGAAGCTGCCTCGGTTGCTGTTGTTCACACCACCGCCTACTACGC
CTTCATCACCATCGCCAAGCTTCGCAAGGGCCAGTCCGTCTTGATCCACGCCGCCGCTGGTG
GTGTTGGCCAAGCAGCCATTCAGTTGGCCAAGCATCTCGGCCTCATCACCTATGTTACCGTA
GGTACTGAAGACAAGCGCCAGCTCATTCGGGAGCAGTATGGCATTCCCGACGAGCACATCTT
CAACTCCCGTGATGCCAGCTTCGTCAAGGGTGTCCAGCGTGTTACCAACGGTCGCGGTGTCG
ACTGCGTTCTCAACTCTCTATCCGGTGAGCTCCTGCGTGCTTCTTGGGGATGCCTTGCTACC
TTTGGTCATTTCATCGAAATTGGTCTCCGTGATATCACCAACAACATGCGTCTTGACATGCG
ACCTTTCCGCAAGAGCACCTCCTTCACATTCATCAACACCCACACTCTCTTCGAGGAAGACC
CCGCTGCGTTGGGAGATATTCTCAACGAGTCCTTCAAGCTCATGTTCGCTGGCGCCCTTACC
GCTCCTAGCCCCTTGAATGCCTATCCCATTGGCCAGGTCGAGGAGGCCTTCCGAACCATGCA
GCAGGGCAAGCACCGCGGTAAGATGGTGCTGTCCTTCTCCGATGACGCAAAGGCTCCCGTGT
TGCGCAAAGCGAAGGATTCCTTGAAACTGGACCCTGACGCCACTTACCTCTTTGTTGGTGGT
CTTGGTGGTCTGGGTCGCAGTCTTGCCAAGGAGTTTGTTGCGTCTGGCGCCCGCAACATTGC
CTTCTTATCCCGATCCGGTGACACTACCGCCCAGGCCAAGGCTATCGTGGACGAATTGGCTG
GCCAGGGTATCCAGGTCAAGGCCTATCGTGGTGATATCGCCAGCGAGGCATCCTTCCTCCAG
GCTATGGAGCAATGCTCTCAGGATCTCCCGCCCGTAAAGGGTGTGATCCAGATGGCCATGGT
TCTCCGCGATATCGTCTTTGAGAAGATGTCGTACGATGAGTGGACCGTCCCCGTTGGCCCCA
AGGTCCAAGGTTCATGGAACTTGCACAAGTACTTCAGTCATGAGCGACCTCTTGACTTCATG
GTCATCTGCTCCTCAAGCTCCGGTATCTACGGTTATCCCAGTCAGGCTCAATACGCCGCTGG
CAACACTTACCAGGATGCCTTGGCTCACTACCGTCGCTCTCAGGGCCTGAACGCCATCTCCG
TCAACTTGGGTATCATGCGAGATGTCGGTGTCCTGGCTGAGACGGGTACCACTGGTAACATC
AAGCTCTGGGAAGAGGTCTTGGGCATCCGCGAGCCTGCCTTCCACGCTCTCATGAAGAGCTT
GATCAACCATCAGCAGCGTGGGTCTGGGGACTACCCGGCGCAGGTCTGCACTGGTCTTGGTA
CTGCTGACATTATGGCTACTCACGGCCTGGCCCGGCCGAGTATTCAATGACCCCCGTTTT
GGACCCCTTGCCGTCACCACTGTCGCGACCGATGCTTCAGCTGACGGCCAGGGCTCTGCTGT
CTCGCTCGCCTCTAGGCTCTCCAAGGTTTCCACCAAGGATGAAGCTGCCGAGATCATTACCG
ATGCTCTGGTCAACAAGACGGCAGACATCCTGCAGATGCCCCCCTCTGAAGTCGACCCCGGC
CGACCTCTGTACCGTTATGGTGTTGACTCCCTTGTGGCGCTTGAGGTGCGAAACTGGATCAC
AAGGGAGATGAAGGCGAACATGGCGCTGCTGGAGATTCTGGCAGCCGTCCCCATTGAGAGCT
TCGCTGTCAAGATTGCTGAGAAGAGCAAGTTGGTTACTGTTTAA |

TABLE 3-continued

Summary of Sequence Listing

| Sequence ID No. | Description | Sequence |
|---|---|---|
| 64 | H. subiculosis hpm3 | ATGGTGACTGTACCACAGACTATCCTCTACTTTGGAGATCAGACAGACTCCTGGGTTGATTC CCTCGATCAGCTATACAGACAAGCCGCTACGATACCATGGCTACAGACGTTTCTCGACGACC TTGTAAAGGTCTTCAAGGAAGAGTCCCGGGGCATGGATCATGCGTTACAAGACAGTGTTGGT GAATACTCTACACTACTCGACTTGGCGGATAGATACCGCCATGGCACCGACGAGATTGGTAT GGTGCGTGCTGTCTTGCTACATGCCGCGAGAGGAGGCATGCTATTACAATGGGTGAAGAAAG AATCACAGCTTGTGGACCTCAATGGCTCCAAGCCTGAAGCACTCGGTATCTCTGGAGGACTC ACCAACCTCGCAGCACTGGCGATATCCACAGACTTCGAGTCTCTATATGACGCAGTCATTGA GGCTGCGAGAATATTTGTCAGATTATGCCGTTTTACTTCGGTACGATCAAGAGCTATGGAGG ACCGACCTGGCGTTTGGGGCTGGGCAGTGCTGGGAATTACACCAGAGGAACTGAGCAAAGTG CTTGAGCAGTTCCAATCCAGCATGGGGATTCCTGCCATCAAGAGAGCTAAGGTTGGCGTAAC AGGAGACCGATGGAGCACCGTTATTGGGCACCCTCAGTCTTGGACCTATTCATCCACCAGT GTCCCGCTGTGCGCAACCTCCCCAAGAATGAATTGAGCATCCACGCCCTTCAGCACACAGTC ACAGTCACAGAGGCTGACCTCGACTTCATTGTCGGGAGTGCTGAGCTTCTTAGTCACCCCAT TGTGCCAGACTTCAAAGTCTGGGGAATGGATGATCCTGTGGCATCCTACCAGAACTGGGGAG AAATGCTAAGAGCAATCGTCACTCAAGTTTTGTCCAAGCCTTTGGACATTACCAAGGTGATT GCGCAACTCAACACTCACCTCGGCCCTCGTCATGTCGACGTCCGAGTCATCGGACCTAGCAG CCACACCCCTACTTGGCGAGTTCGCTCAAAGCTGCTGGCAGCAAGGCTATTTTCCAGACCG ATAAGACTCTTGAGCAGTTACAGCCGAAGAAACTCCCCCCGGGCCGCATCGCCATTGTCGGT ATGGCTGGCCGTGGTCCTGGCTGCGAGAATGTTGATGAGTTCTGGGACGTCATTATGGCGAA GCAGGATCGTTGTGAAGAGATTCCCAAAGATCGCTTCGACATCAATGAGTTCTACTGTACCG AGCACGGGGAGGGTTGCACCACCACCACAAAATACGGCTGCTTCATGAACAAGCCTGGAAAC TTTGACTCCCGCTTCTTCCACGTGTCGCCTCGTGAGGCGCTGTTGATGGACCCCGGTCACAG GCAGTTCATGATGAGCACTTATGAAGCTCTTGAGACGGCAGGATACTCTGATGGCCAGACTA GGGACGTTGATCCTAATAGGATCGCGGCGTTCTATGGCCAGTCCAACGATGATTGGCATATG GTGAGCCATTATACCCTGGGTTGTGATGCCTACACCCTGCAGGGGGCGCAAAGAGCCTTCGG CGCTGGTCGCATCGCCTTCCACTTCAAGTGGGAGGGCCCAACATACTCGCTCGATTCTGCAT GTGCCTCCACCTCCTCTGCTATTCACCTGGCCTGCGTGAGTCTTCTATCCAAAGATGTGGAC ATGGCTGTTGTGGGTGCTGCCAACGTCGTCGGGTATCCTCACTCCTGGACAAGTCTTAGCAA GTCTGGTGTCTTGTCCGACACTGGAAACTGCAAAACCTACTGCGATGATGCTGATGGTTACT GCCGAGCAGACTTTGTCGGCTCAGTTGTGCTGAAGCGTCTCGAAGATGCTGTCGAGCAAAAC GACAACATCTTGGCTGTCGTGGCTGGTTCAGGCAGAAACCACTCCGGCAACTCTTCATCCAT CACCACGTCGGATGCCGGTGCCCAGGAGAGACTGTTTCACAAGATTATGCACAGCGCCAGAG TCTCTCCTGATGAGATCTCATATGTTGAGATGCACGGCACTGGAACTCAGATTGGCGATCCG GCCGAGATGAGTGCTGTTACCAATGTCTTCAGGAAGAGGAAGGCGAATAACCCCCTAACTGT TGGTGGAATCAAAGCGAACGTCGGGCATGCTGAAGCTTCTGCTGGCATGGCCTCCCTGCTCA AATGCATACAGATGTTCCAGAAAGATATTATGCCCCTCAGGCTCGAATGCCCCATACTCTC AACCCAAAGTATCCGAGTCTTTCTGAGCTTAACATTCATATCCCCTCCGAGCCGAAGGAGTT CAAGGCTATCGGCGAGCGGCCACGACGCATCCTCCTTAATAACTTTGACGCAGCAGGTGGCA ACGCCTCTCTCATTCTGGAAGACTTCCCCTCCACCGTCAAGGAAAATGCGGACCCCAGGCCA AGCCATGTCATCGTTTCCTCTGCCAAAACACAATCCTCATATCACGCGAATAAGCGTAACCT CCTGAAGTGGCTACGCAAGAACAAAGATGCTAAACTCGAAGATGTTGCATACACAACCACCG CCCGCAGAATGCACCACCCCCTCAGATTCTCTTGCAGTGCCTCCACAACGGAGGAGCTCATT TCCAAGCTTGAGGCAGACACGGCAGATGCAACTGCGTCTCGGGGCTCGCCCGTTGTCTTCGT ATTCACGGGACAGGGCTCTCACTACGCCGGCATGGGTGCCGAGTTGTACAAGACATGCCCTG CTTTCCGCGAGGAAGTCAACCTCTGTGCCAGCATCTCTGAGGAGCACGGGTTCCCCCCGTAC GTGGATATCATCACCAACAAAGATGTTGACATAACCACCAAGGACACCATGCAGACACAGCT CGCTGTTGTCACGCTGGAGATCGCCCTCGCCGCATTCTGGAAGGCGTCTGGTATCCAGCCGT CAGCAGTCATGGGTCACTCCCTGGGCGAGTATGTGGCTCTCCAGGTCGCAGGGGTCCTATCT CTAGCTGATCTGCTCTACCTCGTCGGCAATCGGGCCCGTCTCCTGCTGGAGCGCTGCGAAGC CGACACCTGCGCTATGTTGGCAGTATCAAGCTCTGCTGCCTCCATCCGCGAGCTCATCGACC AGCGCCCGCAGTCATCCTTCGAGATTGCATGCAAGAATAGCCCCAATGCCACGGTTATCAGC GGCAGCACTGATGAGATTTCTGAGCTCCAGTCATCCTTCACGGCATCACGAGCCAGGGCTCT GTCTGTGCCCTATGGATTTCACTCCTTCCAGATGGATCCCATGCTCGAGGATTACATCGTTC TTGCGGGTGGTGTAACCTACTCGCCACCAAAGATTCCAGTTGCTTCAACCCTGCTCGCTTCG ATTGTGGAGTCTTCAGGGGTCTTCAACGCTTCCTACCTCGGTCAGCAAACCCGCCAAGCTGT CGACTTCGTCGGTGCTCTTGGCGCCTTGAAGGAGAAGTTTGCTGACCCTCTCTGGCTGGAGA TCGGACCCAGCCAAATCTGCAGCTCCTTTGTCCGGGCGACTCTCTCACCCTCGCCGGGCAAA ATCTTGTCCACTTTGGAGGCAAATACCAACCCTGGGCATCCATTTCCAAGTGCCTCGCCGG CGCGTACAAGGATGGTGTCGCAGTTGACTGGTTGGCGGTGCATGCTCCATTCAAGGGCGGCT TGAAGCTCGTGAAGTTGCCCGCCTATGCATGGGACCTCAAGGACTTCTGGATTGTCTACTCT GAGGCCAACAAGGCTGCTCGAGCTTTGGCTCCCGCTCCCTCGTTCGAAACACAGAGGATTTC TACATGTGCTCAACAGATTGTTGAAGAATCATCATCACCCAGCCTCCATGTCTCTGCCCGAG CTGCTATCTCCGATCCTGGCTTCATGGCCTTGGTCGACGGTCATCGCATGCGCGATGTGTCC ATCTGCCCCGGAAGTGCTTCTGCGAGGCAGGCCTTGCCGTCTCCAAGTACGCACTGAAGTA CAGTGGCCGAAAGGATACCGTGGAAACAAGACTTACAATCAACAACCTGTCTCTCAAGCGCC CGCTCACAAAGTCTCTTGTAGGCACCGATGGCGAGCTTCTCACCACGGTTGTTGCAGACAAG GCCTCCAGCGATACCTTGCAGGTTTCATGGAAGGCTTCTTCCTCTCATGCATCATACGATCT TGGTAGCTGCGAGATCACCATTTGTGATGCCCAGACTCTTCAAACTAGCTGGAACAGAAGCT CATACTTCGTCAAGGCTCGTATGAACGAGTTGATCAAGAATGTCAAGACGGAAATGGTCAC CGCATGCTCCCCAGTATCCTCTACACTCTCTTCGCTAGCACAGTTGATTATGACCCTACCTT CAAGTCTGTCAAGGAGGCCTTCATCTCAAATGAGTTTGACGAAGCTGCTGCGGAGGTGGTGC TTCAGAAGAACCCGGCTGGAACTCAGTTCTTTGCGTCCCCTTACTGGGGTGAGAGCGTAGTT CATCTTGCCGGTTTCCTCGTGAACTCCAACCCTGCCCGCAAGACTGCTTCTCAGACGACCTT CATGATGCAGAGTCTTGAGAGCGTCGAGCAGACCGCTGATCTCGAGGCTGGACGCACTTACT |

TABLE 3-continued

Summary of Sequence Listing

| Sequence ID No. | Description | Sequence |
|---|---|---|
| | | ACACCTATGCTCGCGTTTTGCATGAGGAAGAAGACACAGTCAGCTGTGACTTGTTCGTCTTC<br>GACTCGGAGAAGATGGTAATGCAGTGCTCGGGACTCTCATTCCATGAGGTCAGCAACAATGT<br>TCTGGACAGACTTCTTGGAAAGGCATCACCGCCTGTGAAGCAAGTTTCCCACCAGAGAGGCGC<br>CAGTGCTTGTGCCCGCAGAGTCAAAACCGGCCCTGAAAGCTGCTGTCGAGGCGGCTCCCAAG<br>GCGCCTGAGCCTGTGAAGACAGAGGTGAAGAAGATCTCTTCGTCGGAGAGCGAATTGTTCCA<br>CACTATTCTTGAAAGCATCGCCAAGGAGACTGGCACTCAGGTCTCTGACTTCACTGATGACA<br>TGGAACTGGCTGAACTTGGCGTTGATTCCATCATGGGTATTGAGATCGCTGCCGGCGTCAGC<br>AGCAGAACCGGCCTCGATGTTCTCCTCCCCTCTTTTGTCGTAGATTATCCCACCATTGGAGA<br>TCTGCGAAACGAATTTGCGCGCTCCTCTACATCTACACCTCCCAGCAAGACCTTTTCCGAGT<br>TCTCCATCGTCGATGCCACTCCAGAGTCTACGCGCAGCTCGAGTCGAGCGCCTTCTGAGAAG<br>AAGGAGCCTGCTCCGGCTTCAGAGAAGTCTGAGGAGCTGGTGATCGTTCCGTCCGCGGTTGT<br>CGAGGATTCCTCTCCCCTCCCAGTGCCAGAATCACCTTGATCCAGGGTCGATCTTCGAGTG<br>GAAAGCAGCCTTTCTACTTGATCGCCGATGGAGCTGGTAGCATTGCTACGTATATCCACCTG<br>GCTCCCTTCAAGGACAAGAGACCGGTTTATGGCATTGATTCGCCTTTCCTCCGTTGCCCCAG<br>CAGGCTGACCACCCAGGTGGGCATTGAAGGCGTCGCAAAGATCATCTTTGAGGCGTTGATTA<br>AGTGCCAGCCTGAGGGTCCCTTTGACTTGGGAGGATTCTCTGGCGGAGCTATGCTCAGCTAT<br>GAGGTGTCTCGCCAACTCGCTGCCGCCGGTCGCGTCGTCTCCAGTCTTCTCCTCATCGATAT<br>GTGTTCTCCCCGTCCTTTGGGTGTTGAGGACACAATCGAGGTCGGCTGGAAGGTCTACGAGA<br>CCATCGCTTCCCAAGATAAGCTCTGGAACGCCTCAAGTAACACCCAGCAGCATCTCAAGGCC<br>GTCTTCGCCTGCGTCGCAGCCTACCACCCTCCTCCCATGACTCCCGCTCAACGACCCAAGCG<br>AACAGCTATCATCTGGGCTAAAAAGGGCATGGTCGACCGTTGTTCTCGCGACGAGAAGGTGA<br>TGAAGTTCCTGGCCGACAAGGGCATCCCCACCGAGTCGTACCCAGGGTTCATGGAGGACCCC<br>AAGCTGGGTGCCGTGGCGTGGGGCCTTCCGCACAAGTCCGCTGCGGACTTGGGACCCAACGG<br>ATGGGACAAGTTCCTTGGCGAGACTCTGTGCCTGTCATCGATTCGGACCACTTGGATATGC<br>CGATGCCGGGGCATGTGCACTTGCTTCAGGCGGCGATGGAGGAGTCGTTCAAATATTTCAGC<br>GAGGCAAATTAG |
| 65 | pCHIDT-2.1 | TATCTAAAAATTGCCTTATGATCCGTCTCTCCGGTTACAGCCTGTGTAACTGATTAATCCTG<br>CCTTTCTAATCACCATTCTAATGTTTTAATTAAGGGATTTTGTCTTCATTAACGGCTTTCGC<br>TCATAAAAATGTTATGACGTTTTGCCCGCAGGCGGGAAACCATCCACTTCACGAGACTGATC<br>TCCTCTGCCGGAACACCGGGCATCTCCAACTTATAAGTTGGAGAAATAAGAGAATTTCAGAT<br>TGAGAGAATGAAAAAAAAAAAAAAAAAAAGGCAGAGGGAGAGCATAGAAATGGGGTTCACTT<br>TTTGGTAAAGCTATAGCATGCCTATCACATATAAATAGAGTGCCAGTAGCGACTTTTTCAC<br>ACTCGAAATACTCTTACTACTGCTCTCTTGTTGTTTTTATCACTTCTTGTTTCTTCTTGGTA<br>AATAGAATATCAAGCTACAAAAAGCATACAATCAACTATCAACTATTAACTATATCGTAATA<br>CACAATGCTGGGATTCCCAATGTTCAACCCAGCTACGCCTGATGTCTGGAAGATGAATACCC<br>CTTACTTTCCATTTGTTACACCGGGGTTATTTCCTGCCTCAGCACCCCCATCGCCCACCAAC<br>GTAGATGCCGAAGCTGCCAGTTCCCAACAGTCGGAAGCAAGCTATCTGGATAAGGAGAAAAT<br>TGTTCGAGGGCCACTTGATTATCTTCTCAAATCCCCTGGAAAAGACATTCGTCGGAATTCA<br>TTCACGCGTTCAATGAATGGCTGCGCATTCCTGAGGACAAGTTGAATATTATCACGGAAATT<br>GTTGGATTGCTTCACACGGCCTCCCTTCTAATCGACGATATTCAGGACAATTCCAAGCTTCG<br>ACGCGGCCTCCCAGTGGCCCATAGCATATTTGGTATTGCGCAGACAATTAACTCTGCCAATT<br>ATGCGTACTTTCTAGCCCAGGAAAGGCTCCGCGAACTGAATCATCCTGAAGCGTACGAAATA<br>TACACAGAGGAACTGCTTCGTCTGCACCGCGGTCAAGGTATGGACTTGTACTGGCGGGACTG<br>CCTAACCTGTCCCACAGAGGAGGACTATATTGAGATGATCGCCAACAAGACTGGTGGCCTAT<br>TTCGACTGGCGATTAAGCTTATGCAGTTGGAAAGCACTTTGTGCAGCAATGTCATTGAACTA<br>GCAGACTTGTTGGGCGTGATCTTTCAGATTCGGGATGATTACCAAAACTTACAGAGTGGACT<br>ATACGCCAAGAACAAGGGATTTTGCGAGGATTTGACGGAGGGAAAATTTTCCTTTCTGATTA<br>TCCACAGTATTAACAGTAACCCGAACAATCACCATCTGCTAAATATACTACGGCAGCGGAGC<br>GAGGACGATTCGGTGAAGAAGTATGCTGTTGATTATATCGACTCGACGGGGAGTTTTGACTA<br>CTGCCGGGAACGGCTCGCTTCCTTATTGGAAGAGGCGGATCAAATGGTTAAGAAGTTGGAAA<br>ATGAGGGGGGACAATCAAAGGGGATCTACGATATTCTGAGCTTTCTGTCGTGAGCGGATCTC<br>TTATGTCTTTACGATTTATAGTTTTCATTATCAAGTATGCCTATATTAGTATATAGCATCTT<br>TAGATGACAGTGTTCGAAGTTTCACGAATAAAAGATAATATTCTACTTTTTGCTCCCACCGC<br>GTTTGCTAGCACGAGTGAACACCATCCCTCGCCTGTGAGTTGTACCCATTCCTCTAAACTGT<br>AGACATGGTAGCTTCAGCAGTGTTCGTTATGTACGGCATCCTCCAACAAACAGTCGGTTATA<br>GTTTGTCCTGCTCCTCTGAATCGTCTCCCTCGATATTTCTCATTTTCCTTCGCATGCCAGCA<br>TTGAAATGATCGAAGTTCAATGATGAAACGGTAATTCTTCTGTCATTTACTCATCTCATCTC<br>ATCAAGTTATATAATTCTATCGGATGTAATTTTTCACTTTTCGTCTTGACGTCCACCCTAT<br>AATTTCAATTATTGAACCCTCACGATCCAGTTCTCCAGTGACACAGCCTTTATCTGGTCAAA<br>CCTTTCTTTCTAATCACCTATGCTGATGCTTAATTAAGGGATTTTGTCTCCATCAACGGCA<br>TGCGCCCAAAAATGACGTTTTTTTAACCCATAGACACGAAACTACCCATTTTCCACCGGCC<br>TGACCTACCACCGGAACAACGGCCATCTCCAACTTGCAAGTTGGGGAAATTAAGAGCATCGC<br>AGGTTTAATGGAAGAAAAAAAAAGGTACAGCACAGCGCAAATGGAGTTAGTTCCCTTATGT<br>CACACACTCACACACAGTCGGTCAGATCAAGCATACTGGGTGCGTATAAATAGAGTGGCCAT<br>TGCCACCCTGTTTATCTCAAATCTGTCTTGTTAGTGGTCTTCTCCCTTTTTCAGGTTACAA<br>TTCTCTTGTTTCTACTTAGTATATAAGTATATCAAGCTATATTAAGCATACTATCAACTGTC<br>AACTCTATCCTCAAAATACAATACAAAATGGATGGGTTCGACCATTCTACTGCTCCACCAGG<br>ATATAACGAGCTAAAATGGCTCGCCGATATCTTCGTCATCGGAATGGCTGTTGGCTGGGTTG<br>CTCACTATATGGAGATGATTCACACGTCGTTCAAGGACCAAACCAAACTACGCATGACCATCGGG<br>GGCCTTTGCATCAATTTTGCCTGGGAAATCATATTCTGCACAATGTATCCTGCCAAAGGATT<br>TGTCGAGCGGGTTGCCTTTCTCATGGGCATTTCTCTCGACCTTGGGGTTATTTACGCGGGAA<br>TCAAGAACGCCCCAAATGAATGGCACCACTCTGCAATGGTGAGGGACCATATGCCCCTTGTC<br>TTCGCAGCAACGACACTTTGTTGTCTGAGCGGTCATATGGCTCTTACTGCCCAGGTTGGTCC<br>CGCACAAGCCTATACGTGGGGGGCAATTGCATGCCAGCTCTTTATCAGCATAGGGAATGTGT |

TABLE 3-continued

Summary of Sequence Listing

| Sequence ID No. Description | Sequence |
|---|---|
| | TTCAATTGTTGAGTCGGGGAAACACACGAGGGGCGTCATGGACGCTATGGACCTCCAGGTTT<br>TTTGGATCAACATCAGCCATTGGCTTTGCTCTTGTTCGTATATATTCGCTGGTGGGAGGCCTT<br>TTCTTGGTTGAACTGCCCGCTTGTGATATGGTCCGTGGCCATGTTCTTTCTGTTTTGAAACAC<br>TCTATGGAGCCCTATTCTATTCTGTCAAGCGACAAGAAGGGAGATCCCAGCGTGGAATCAAG<br>CACAAAGAGAGGTAGACAAATCGCTCTTAAATATATACCTAAAGAACATTAAAGCTATATTA<br>TAAGCAAAGATACGTAAATTTTGCTTATATTATTATACACATATCATATTTCTATATTTTA<br>AGATTTGGTTATATAATGTACGTAATGCAAAGGAAATAAATTTTATACATTATTGAACAGCG<br>TCCAAGTAACTACATTATGTGCACTAATAGTTTAGCGTCGTGAAGACTTTATTGTGTCGCGA<br>AAAGTAAAAATTTTAAAAATTAGAGCACCTTGAACTTGCGAAAAAGGTTCTCATCAACTGTT<br>TAAAAGGAGGATATCAGGTCCTATTTCTGACAAACAATATACAAATTTAGTTTCAAAGATGA<br>ATCAGTGCGCGAAGGACATAACTCAATAGGAAAAAACCGAGCTTCCTTTCATCCGGCGCGGC<br>TGTGTTCTACATATCACTGAAGCTCCGGGTATTTTAAGTTATACAAGGGAAAGATGCCGGCT<br>AGACTAGCAAGTTTTAGGCTGCTTAACATTATGGATAGGCGGATAAAGGGCCCAAACAGGAT<br>TGTAAAGCTTAGACGCTTCTGGTTGGACAATGGTACGTTTGTGTATTAAGTAAGGCTTGGCT<br>GGGGATAGCAACATTGGGCAGAGTATAGAAGACCACAAAAAAAGGTATATAAGGGCAGAGA<br>AGTCTTTGTAATGTGTGTAACTTCTCTTCCATGTGTAATCAGTATTTCTACTTACTTCTTAA<br>ATATACAGAAGTAAGACAGATAACCAACAGCCTTTCCCAGATATACATATATATCTTTATTT<br>CAGCTTAAACAATAATTATATTTGTTTAACTCAAAAATAAAAAAAAAAACCAAACTCACGC<br>AACTAATTATTCCATAATAAAATAACAACATGGCGGCACTTCCGGACGTTGCCTCCATTCCC<br>ATCCCTCTGGTGGCAACCCTAGGCATTGCCCCTCTAATTTTCTATCTCGTCCTTGATAGAAT<br>TAGCCCCTTGTGGCCAAATTCCAAAGCTTTCCTGATTGGCAAGAAGAAACCGGAGACCGTGA<br>CATCGTTCGAGTGCCCATATGCCTACATCCGTCAGATCTATGGGAAGTATCACTGGGAGCCA<br>TTCGTACAGAAGCTGTCTCCGAGGCTTAAGGATGAGGATCCGGCCAAATATAAGATGGTTCT<br>GGAGATAATGGATGCAATCCACCTGTGTCTGATGCTAGTTGACGATATAACTGACAATAGCG<br>ACTATCGAAAAGGCAAGCCAGCAGCCCACCGGATATATGGCCCTTCAGAGACAGCAAATCGC<br>GCTTACTACCGAGTCACCCAGATTCTAAACAAGACCGTGCAAAAGTTCCCCAAGCTGGCCAA<br>GTTCCTGCTTCAGAATCTGGAAGAAATTCTCGAAGGCCAAGACCTGTCACTAATCTGGCGAC<br>GGGATGGACTGGGTAGCCTTTCGACTGTTCCTGATGAGCGAGTTGCAGCCTATCGCAAGATG<br>GCGTCATTGAAAACTGGGGCGTTATTCCGGCTGCTGGGGCAATTGGTGATGGAGGACCAATC<br>GATGGACGGGACGATGACTACTCTTGCGTGGTGCTCTCAGCTGCAGAATGACTGCAAGAATG<br>TCTACTCATCTGAATATGCTAAGGCCAAAGGGGCGCTTGCCGAAGACCTCCGAAATCGAGAG<br>CTCTCATTTCCAATTATCCTCGCGCTGGAAGCTCCTGAAGGGCATTGGGTCGCCAGTGCTTT<br>GGAGACCAGCTCACCGCGCAACATTCGCAAGGCGCTTGCTGTGATTCAGAGTGAGAGAGTGC<br>GCAATGCTTGTTTCAAGGAGCTCAAGTCGGCGAGTGCTTCGGTCCAGGACTGGTTGGCTATT<br>TGGGGACGGAACGAGAAAATGAACTTGAAGAGCCAGCAGACGTAGAGTGCTTTTAACTAAGA<br>ATTATTAGTCTTTTCTGCTTATTTTTTCATCATAGTTTAGAACACTTTATATTAACGAATAG<br>TTTATGAATCTATTTAGGTTTAAAAATTGATACAGTTTTATAAGTTACTTTTTCAAAGACTC<br>GTGCTGTCTATTGCATAATGCACTGGAAGGGGAAAAAAAAGGTGCACACGCGTGGCTTTTTC<br>TTGAATTTGCAGTTTGAAAAATAACTACATGGATGATAAGAAAACATGGAGTACAGTCACTT<br>TGAGAACCTTCAATCAGCTGGTAACGTCTTCGTTAATTGGATACTCAAAAAAGATGGATAGC<br>ATGAATCACAAGATGGAAGGAAATGCGGGCCACGACCACAGTGATATGCATATGGGAGATGG<br>AGATGATACCTCCATTGGGCCGATGAAGTTAGTCGACGGATAGAAGCGGTTGTCCCCTTTCC<br>CGGCGAGCCGGCAGTCGGGCCGAGGTTCGGATAAATTTTGTATTGTGTTTTGATTCTGTCAT<br>GAGTATTACTTATGTTCTCTTTAGGTAACCCCAGGTTAATCAATCACAGTTTCATACCGGCT<br>AGTATTCAAATTATGACTTTTCTTCTGCAGTGTCAGCCTTACGACGTATTATCTATGAGCTT<br>GAATATAGTTTGCCGTGATTCGTATCTTTAATTGGATAATAAAATGCGAAGGATCGATGACC<br>CTTATTATTATTTTTCTACACTGGCTACCGATTTAACTCATCTTCTTGAAAGTATATAAGTA<br>ACAGTAAAATATACCGTACTTCTGCTAATGTTATTTGTCCCTTATTTTTCTTTTCTTGTCTT<br>ATGCTATAGTACCTAAGAATAACGACTATTGTTTTGAACTAAACAAAGTAGTAAAAGCACAT<br>AAAAGAATTAAGAAAATGGCCAATGCCCAGCAACCCCCCTTTCGCATCCTTATTGTGGGCGG<br>TTCTGTCGCAGGCCTCATCCTTGCGCACTGTCTCGAACGCGCCAATATAGAGTACCTCATAC<br>TCGAAAAAGGAGAAGATGTTGCTCCACAAGTTGGTGCCTCGATAGGTATCATGCCAAATGGC<br>GGACGGATCCTCGAGCAACTGGGCCTATTTGGGGAGATTGAGCGTGTGATCGAGCCGTTGCA<br>TCAGGCGAATATCAGCTATCCAGATGGGTTCTGCTTTAGTAACGTCTATCCTAAGGTTCTTG<br>GCGACAGGTTCGGATACCCGGTTGCATTCTTGGACCGGCAGAAGTTCCTGCAGATTGCATAT<br>GAGGGGCTGAGAAAGAAGCAGAATGTTCTCACCGGTAAAAGGGTAGTTGGACTGCGACAGTC<br>GGATCAAGGGACTGCTGTTTCTGTGGCTGACGGGACAGAGTATGAGGCGGATCTCGTGGTTG<br>GTGCTGATGGAGTACATAGTCGGGTGAGAAGTGAGATTTGGAAGATGGCGGAAGAGAATCAG<br>CCTGCATCAGTTTCGACACGTGAAAGAAGAAGCATGACTGTTGAATATGTCTGCGTTTTCGG<br>GATTTCATCAGCCATCCCAGGGCTCGAGATAAGCGAACAGATCAACGGTATTTTCGACCATC<br>TATCCATTCTAACAATCCATGGCAGACATGGTCGCGTGTTCTGGTTCGTGATCCAGAAGCTG<br>GATAGGAAGTACGTCTATCCTGATGTCCCGCGATTCTCAGACGAGGATGCCGTACAGCTCTT<br>CGATCGGGTCAAACACGTGCGGTTCTGGAAAAACATCTGTGTGGGGGACTTGTGGAAGAACA<br>GAGAGGTGTCCTCGATGACAGCGCTGGAGGAGGGAGTGTTCGAGACATGGCATCATGATAGG<br>ATGGTTTTGATTGGAGATAGCGTTCACAAGATGACGCCCAACTTTGGCCAAGGAGCTAATTC<br>AGCCATCGAGGATGCTGCCGCGCTCTCTTCCCTTCTACATGATCTCGTCAACGCCCGTGGAG<br>TTTGCAAGCCATCGAATGTCCAGATTCAGCATCTCCTCAAGCAGTATCGGGAGACCCGATAC<br>ACTCGCATGGTAGGCATGTGTCGCACCGCGGCTTCAGTCTCTCGGATTCAGGCCCGAGATGG<br>CATCCTCAACACCGTCTTTGGACGATATTGGGCACCTTATGCTGGCAACCTGCCTGCTGACC<br>TGGCATCAAAAGTGATGGCAGATGCAGAGGTTGTTACTTTTCTGCCCTTGCCAGGGCGCTA<br>GGACCGGGCTGGGAGATGTACAGACGAAAGGGGAAGGGAGGGCAGGTGCAATGGGTGCTTAT<br>AATCTTAAGCTTACTTACGATTGGTGGATTGTGCATCTGGCTACAAAGCAATGCGTTGAGTA<br>GATAAGGAGATTGATAAGACTTTTCTAGTTGCATATCTTTTATATTTAAATCTTATCTATTA<br>GTTAATTTTTTGTAATTTATCCTTATATATAGTCTGGTTATTCTAAAATATCATTTCAGTAT<br>CTAAAAATTCCCCTCTTTTTTCAGTTATATCTTAACAGGCGACAGTCCAAATGTTGATTTAT |

TABLE 3-continued

Summary of Sequence Listing

| Sequence ID No. Description | Sequence |
|---|---|
| | CCCAGTCCGATTCATCAGGGTTGTGAAGCATTTTGTCAATGGTCGAAATCACATCAGTAATA
GTGCCTCTTACTTGCCTCATAGAATTTCTTTCTCTTAACGTCACCGTTTGGTCTTTTATAGT
TTCGAAATCTATGGTGATACCAAATGGTGTTCCCAATTCATCGTTACGGGCGTATTTTTTAC
CAATTGAAGTATTGGAATCGTCAATTTTAAAGTATATCTCTCTTTTACGTAAAGCCTGCGAG
ATCCTCTTAAGTATAGCGGGGAAGCCATCGTTATTCGATATTGTCGTAACAAATACTTTGAT
CGGCGCTATGCGGCCGCCACCGCGGTGGAGCTCCAGCTTTTGTTCCCTTTAGTGAGGGTTAA
TTGCGCGCTTGGCGTAATCATGGTCATAGCTGTTTCCTGTGTGAAATTGTTATCCGCTCACA
ATTCCACACAACATAGGAGCCGGAAGCATAAAGTGTAAAGCCTGGGGTGCCTAATGAGTGAG
GTAACTCACATTAATTGCGTTGCGCTCACTGCCCGCTTTCCAGTCGGGAAACCTGTCGTGCC
AGCTGCATTAATGAATCGGCCAACGCGCGGGGAGAGGCGGTTTGCGTATTGGGCGCTCTTCC
GCTTCCTCGCTCACTGACTCGCTGCGCTCGGTCGTTCGGCTGCGGCGAGCGGTATCAGCTCA
CTCAAAGGCGGTAATACGGTTATCCACAGAATCAGGGGATAACGCAGGAAAGAACATGTGAG
CAAAAGGCCAGCAAAAGGCCAGGAACCGTAAAAAGGCCGCGTTGCTGGCGTTTTTCCATAGG
CTCCGCCCCCCTGACGAGCATCACAAAAATCGACGCTCAAGTCAGAGGTGGCGAAACCCGAC
AGGACTATAAAGATACCAGGCGTTTCCCCCTGGAAGCTCCCTCGTGCGCTCTCCTGTTCCGA
CCCTGCCGCTTACCGGATACCTGTCCGCCTTTCTCCCTTCGGGAAGCGTGGCGCTTTCTCAT
AGCTCACGCTGTAGGTATCTCAGTTCGGTGTAGGTCGTTCGCTCCAAGCTGGGCTGTGTGCA
CGAACCCCCCGTTCAGCCCGACCGCTGCGCCTTATCCGGTAACTATCGTCTTGAGTCCAACC
CGGTAAGACACGACTTATCGCCACTGGCAGCAGCCACTGGTAACAGGATTAGCAGAGCGAGG
TATGTAGGCGGTGCTACAGAGTTCTTGAAGTGGTGGCCTAACTACGGCTACACTAGAAGGAC
AGTATTTGGTATCTGCGCTCTGCTGAAGCCAGTTACCTTCGGAAAAAGAGTTGGTAGCTCTT
GATCCGGCAAACAAACCACCGCTGGTAGCGGTGGTTTTTTTGTTTGCAAGCAGCAGATTACG
CGCAGAAAAAAAGGATCTCAAGAAGATCCTTTGATCTTTTCTACGGGGTCTGACGCTCAGTG
GAACGAAAACTCACGTTAAGGGATTTTGGTCATGAGATTATCAAAAAGGATCTTCACCTAGA
TCCTTTTAAATTAAAAATGAAGTTTTAAATCAATCTAAAGTATATATGAGTAAACTTGGTCT
GACAGTTACCAATGCTTAATCAGTGAGGCACCTATCTCAGCGATCTGTCTATTTCGTTCATC
CATAGTTGCCTGACTCCCCGTCGTGTAGATAACTACGATACGGGAGGGCTTACCATCTGGCC
CCAGTGCTGCAATGATACCGCGAGACCCACGCTCACCGGCTCCAGATTTATCAGCAATAAAC
CAGCCAGCCGGAAGGGCCGAGCGCAGAAGTGGTCCTGCAACTTTATCCGCCTCCATCCAGTC
TATTAATTGTTGCCGGGAAGCTAGAGTAAGTAGTTCGCCAGTTAATAGTTTGCGCAACGTTG
TTGCCATTGCTACAGGCATCGTGGTGTCACGCTCGTCGTTTGGTATGGCTTCATTCAGCTCC
GGTTCCCAACGATCAAGGCGAGTTACATGATCCCCCATGTTGTGCAAAAAAGCGGTTAGCTC
CTTCGGTCCTCCGATCGTTGTCAGAAGTAAGTTGGCCGCAGTGTTATCACTCATGGTTATGG
CAGCACTGCATAATTCTCTTACTGTCATGCCATCCGTAAGATGCTTTTCTGTGACTGGTGAG
TACTCAACCAAGTCATTCTGAGAATAGTGTATGCGGCGACCGAGTTGCTCTTGCCCGGCGTC
AATACGGGATAATACCGCGCCACATAGCAGAACTTTAAAAGTGCTCATCATTGGAAAACGTT
CTTCGGGGCGAAAACTCTCAAGGATCTTACCGCTGTTGAGATCCAGTTCGATGTAACCCACT
CGTGCACCCAACTGATCTTCAGCATCTTTTACTTTCACCAGCGTTTCTGGGTGAGCAAAAAC
AGGAAGGCAAAATGCCGCAAAAAAGGGAATAAGGGCGACACGGAAATGTTGAATACTCATAC
TCTTCCTTTTTCAATATTATTGAAGCATTTATCAGGGTTATTGTCTCATGAGCGGATACATA
TTTGAATGTATTTAGAAAAATAAACAAATAGGGGTTCCGCGCACATTTCCCCGAAAAGTGCC
ACCTGAACGAAGCATCTGTGCTTCATTTTGTAGAACAAAAATGCAACGCGAGAGCGCTAATT
TTTCAAACAAAGAATCTGAGCTGCATTTTTACAGAACAGAAATGCAACGCGAAAGCGCTATT
TTACCAACGAAGAATCTGTGCTTCATTTTTGTAAACAAAAATGCAACGCGAGAGCGCTAAT
TTTTCAAACAAAGAATCTGAGCTGCATTTTTACAGAACAGAAATGCAACGCGAGAGCGCTAT
TTTACCAACAAAGAATCTATACTTCTTTTTTGTTCTACAAAAATGCATCCCGAGAGCGCTAT
TTTTCTAACAAAGCATCTTAGATTACTTTTTTTCTCCTTTGTGCGCTCTATAATGCAGTCTC
TTGATAACTTTTGCACTGTAGGTCCGTTAAGGTTAGAAGAAGGCTACTTTGGTGTCTATTT
TCTCTTCCATAAAAAAAGCCTGACTCCACTTCCCGCGTTTACTGATTACTAGCGAAGCTGCG
GGTGCATTTTTTCAAGATAAAGGCATCCCCGATTATATTCTATACCGATGTGGATTGCGCAT
ACTTTGTGAACAGAAAGTGATAGCGTTGATGATTCTTCATTGGTCAGAAAATTATGAACGGT
TTCTTCTATTTTGTCTCTATATACTACGTATAGGAAATGTTTACATTTTCGTATTGTTTTCG
ATTCACTCTATGAATAGTTCTTACTACAATTTTTTGTCTAAAGAGTAATACTAGAGATAAA
CATAAAAAATGTAGAGGTCGAGTTTAGATGCAAGTTCAAGGAGCGAAAGGTGGATGGGTAGG
TTATATAGGGATATAGCACAGAGATATATAGCAAAGAGATACTTTTGAGCAATGTTTGTGGA
AGCGGTATTCGCAATATTTTAGTAGCTCGTTACAGTCCGGTGCGTTTTTGGTTTTTTGAAAG
TGCGTCTTCAGAGCGCTTTTGGTTTTCAAAAGCGCTCTGAAGTTCCTATACTTTCTAGAGAA
TAGGAACTTCGGAATAGGAACTTCAAAGCGTTTCCGAAAACGAGCGCTTCCGAAAATGCAAC
GCGAGCTGCGCACATACAGCTCACTGTTCACGTCGCACCTATATCTGCGTGTTGCCTGTATA
TATATATACATGAGAAGAACGGCATAGTGCGTGTTTATGCTTAAATGCGTACTTATATGCGT
CTATTTATGTAGGATGAAAGGTAGTCTAGTACCTCCTGTGATATTATCCCATTCCATGCGGG
GTATCGTATGCTTCCTTCAGCACTACCCTTTAGCTGTTCTATATGCTGCCACTCCTCAATTG
GATTAGTCTCATCCTTCAATGCTATCATTTCCTTTGATATTGGATCATACTAAGAAACCATT
ATTATCATGACATTAACCTATAAAAATAGGCGTATCACGAGGCCCTTTCGTCTCGCGCGTTT
CGGTGATGACGGTGAAAACCTCTGACACATGCAGCTCCCGGAGACGGTCACAGCTTGTCTGT
AAGCGGATGCCGGGAGCAGACAAGCCCGTCAGGGCGCGTCAGCGGGTGTTGGCGGGTGTCGG
GGCTGGCTTAACTATGCGGCATCAGAGCAGATTGTACTGAGAGTGCACCATATCGACTACGT
CGTAAGGCCGTTTCTGACAGAGTAAAATTCTTGAGGGAACTTTCACCATTATGGGAAATGCT
TCAAGAAGGTATTGACTTAAACTCCATCAAATGGTCAGGTCATTGAGTGTTTTTTATTTGTT
GTATTTTTTTTTTTAGAGAAAATCCTCCAATATCAAATTAGGAATCGTAGTTTCATGATT
TTCTGTTACACCTAACTTTTTGTGTGGTGCCCTCCTCCTTGTCAATATTAATGTTAAAGTGC
AATTCTTTTCCTTATCACGTTGAGCCATTAGTATCAATTTGCTTACCTGTATTCCTTTACT
ATCCTCCTTTTTCTCCTTCTTGATAAATGTATGTAGATTGCGTATATAGTTTCGTCTACCCT
ATGAACATATTCCATTTTGTAATTTCGTGTCGTTTCTATTATGAATTTCATTTATAAAGTTT
ATGTACAAATATCATAAAAAAAGAGAATCTTTTTAAGCAAGGATTTTCTTAACTTCTTCGGC |

TABLE 3-continued

Summary of Sequence Listing

| Sequence ID No. | Description | Sequence |
|---|---|---|
| | | GACAGCATCACCGACTTCGGTGGTACTGTTGGAACCACCTAAATCACCAGTTCTGATACCTG<br>CATCCAAAACCTTTTTAACTGCATCTTCAATGGCCTTACCTTCTTCAGGCAAGTTCAATGAC<br>AATTTCAACATCATTGCAGCAGACAAGATAGTGGCGATAGGGTCAACCTTATTCTTTGGCAA<br>ATCTGGAGCAGAACCGTGGCATGGTTCGTACAAACCAAATGCGGTGTTCTTGTCTGGCAAAG<br>AGGCCAAGGACGCAGATGGCAACAAACCCAAGGAACCTGGGATAACGGAGGCTTCATCGGAG<br>ATGATATCACCCAAACATGTTGCTGGTGATTATAATACCATTTAGGTGGGTTGGGTTCTTAAC<br>TAGGATCATGGCGGCAGAATCAATCAATTGATGTTGAACCTTCAATGTAGGGAATTCGTTCT<br>TGATGGTTTCCTCCACAGTTTTTCTCCATAATCTTGAAGAGGCCAAAAGATTAGCTTTATCC<br>AAGGACCAAATAGGCAATGGTGGCTCATGTTGTAGGGCCATGAAAGCGGCCATTCTTGTGAT<br>TCTTTGCACTTCTGGAACGGTGTATTGTTCACTATCCCAAGCGACACCATCACCATCGTCTT<br>CCTTTCTCTTACCAAAGTAAATACCTCCCACTAATTCTCTGACAACAACGAAGTCAGTACCT<br>TTAGCAAATTGTGGCTTGATTGGAGATAAGTCTAAAAGAGAGTCGGATGCAAAGTTACATGG<br>TCTTAAGTTGGCGTACAATTGAAGTTCTTTACGGATTTTTAGTAAACCTTGTTCAGGTCTAA<br>CACTACCGGTACCCCATTTAGGACCAGCCACAGCACCTAACAAAACGGCATCAACCTTCTTG<br>GAGGCTTCCAGCGCCTCATCTGGAAGTGGGACACCTGTAGCATCGATAGCAGCACCACCAAT<br>TAAATGATTTTCGAAATCGAACTTGACATTGGAACGAACATCAGAAATAGCTTTAAGAACCT<br>TAATGGCTTCGGCTGTGATTTCTTGACCAACGTGGTCACCTGGCAAAACGACGATCTTCTTA<br>GGGGCAGACATAGGGGCAGACATTAGAATGGTATATCCTTGAAATATATATATATATTGCTG<br>AAATGTAAAAGGTAAGAAAAGTTAGAAAGTAAGACGATTGCTAACCACCTATTGGAAAAAAC<br>AATAGGTCCTTAAATAATATTGTCAACTTCAAGTATTGTGATGCAAGCATTTAGTCATGAAC<br>GCTTCTCTATTCTATATGAAAAGCCGGTTCCGGCCTCTCACCTTTCCTTTTTCTCCCAATTT<br>TTCAGTTGAAAAAGGTATATGCGTCAGGCGACCTCTGAAATTAACAAAAAATTTCCAGTCAT<br>CGAATTTGATTCTGTGCGATAGCGCCCCTGTGTGTTCTCGTTATGTTGAGGAAAAAAATAAT<br>GGTTGCTAAGAGATTCGAACTCTTGCATCTTACGATACCTGAGTATTCCCACAGTTAACTGC<br>GGTCAAGATATTTCTTGAATCAGGCGCCTTAGACCGCTCGGCCAAACAACCAATTACTTGTT<br>GAGAAATAGAGTATAATTATCCTATAAATATAACGTTTTTGAACACACATGAACAAGGAAGT<br>ACAGGACAATTGATTTTGAAGAGAATGTGGATTTTGATGTAATTGTTGGGATTCCATTTTTA<br>ATAAGGCAATAATATTAGGTATGTGGATATACTAGAAGTTCTCCTCGACCGTCGATATGCGG<br>TGTGAAATACCGCACAGATGCGTAAGGAGAAAATACCGCATCAGGAAATTGTAAACGTTAAT<br>ATTTTGTTAAAATTCGCGTTAAATTTTTGTTAAATCAGCTCATTTTTTAACCAATAGGCCGA<br>AATCGGCAAAATCCCTTATAAATCAAAAGAATAGACCGAGATAGGGTTGAGTGTTGTTCCAG<br>TTTGGAACAAGAGTCCACTATTAAAGAACGTGGACTCCAACGTCAAAGGGCGAAAAACCGTC<br>TATCAGGGCGATGGCCCACTACGTGAACCATCACCCTAATCAAGTTTTTTGGGGTCGAGGTG<br>CCGTAAAGCACTAAATCGGAACCCTAAAGGGAGCCCCCGATTTAGAGCTTGACGGGGAAAGC<br>CGGCGAACGTGGCGAGAAAGGAAGGGAAGAAAGCGAAAGGAGCGGGCGCTAGGGCGCTGGCA<br>AGTGTAGCGGTCACGCTGCGCGTAACCACCACACCCGCCGCGCTTAATGCGCCGCTACAGGG<br>CGCGTCGCGCCATTCGCCATTCAGGCTGCGCAACTGTTGGGAAGGGCGATCGGTGCGGGCCT<br>CTTCGCTATTACGCCAGCTGGCGAAAGGGGGATGTGCTGCAAGGCGATTAAGTTGGGTAACG<br>CCAGGGTTTTCCCAGTCACGACGTTGTAAAACGACGGCCAGTGAGCGCGCGTAATACGACTC<br>ACTATAGGGCGAATTGGGTACCGGGCCCCCCCTCGAGGTCGACGGTATCGATAAGCTTGATA<br>TCGAATTCCTGCAGCCCGGGGGATCCACTAGTTCTAGATTAATTAA |
| 66 | pCHIDT-2c | ATAGCTTCAAAATGTTTCTACTCCTTTTTTACTCTTCCAGATTTTCTCGGACTCCGCGCATC<br>GCCGTACCACTTCAAAACACCCAAGCACAGCATACTAAATTTCCCCTCTTTCTTCCTCTAGG<br>GTGTCGTTAATTACCCGTACTAAAGGTTTGGAAAAGAAAAAAGAGACCGCCTCGTTTCTTTT<br>TCTTCGTCGAAAAAGGCAATAAAAATTTTTATCACGTTTCTTTTTCTTGAAAATTTTTTTTT<br>TTGATTTTTTTCTCTTTCGATGACCTCCCATTGATATTTAAGTTAATAAACGGTCTTCAATT<br>TCTCAAGTTTCAGTTTCATTTTTCTTGTTCTATTACAACTTTTTTTACTTCTTGCTCATTAG<br>AAAGAAAGCATAGCAATCTAATCTAAGTTTTAATTACAAAATGCTGGGATTCCCAATGTTCA<br>ACCCAGCTACGCCTGATGTCTGGAAGATGAATACCCCTTACTTTCCATTTGTTACACCGGGG<br>TTATTTCCTGCCTCAGCACCCCCATCGCCCACCAACGTAGATGCCGAAGCTGCCAGTTCCCA<br>ACAGTCGGAAGCAAGCTATCTGGATAAGGAGAAAATTGTTCGAGGGCCACTTGATTATCTTC<br>TCAAATCCCCTGGAAAAGACATTCGTCGGAAATTCATTCACGCGTTCAATGAATGGCTGCGC<br>ATTCCTGAGGCAAGTTGAATATTATCACGGAAATTGTTGGATTGCTTCACACGGCCTCCCT<br>TCTAATCGACGATATTCAGGACAATTCCAAGCTTCGACGCGGCCTCCCAGTGGCCCATAGCA<br>TATTTGGTATTGCGCAGACAATTAACTCTGCCAATTATGCGTACTTTCTAGCCCAGGAAAGG<br>CTCCGCGAACTGAATCATCCTGAAGCGTACGAAATATACACAGAGGAACTGCTTCGTCTGCA<br>CCGCGGTCAAGGTATGGACTTGTACTGGCGGGACTGCCTAACCTGTCCCACAGAGGAGGACT<br>ATATTGAGATGATCGCCAACAAGACTGGTGGCCTATTTCGACTGGCGATTAAGCTTATGCAG<br>TTGGAAAGCACTTTGTGCAGCAATGTCATTGAACTAGCAGACTTGTTGGGCGTGATCTTTCA<br>GATTCGGGATGATTACCAAAACTTACAGAGTGGACTATACGCCAAGAACAAGGGATTTTGCG<br>AGGATTTGACGGAGGGAAAATTTTCCTTTCTGATTATCCACAGTATTAACAGTAACCCGAAC<br>AATCACCATCTGCTAAATATACTACGGCAGCGGAGCGAGGACGATTCGGTGAAGAAGTATGC<br>TGTTGATTATATCGACTCGACGGGGAGTTTTGACTACTGCCGGGAACGGCTCGCTTCCTTAT<br>TGGAAGAGGCGGATCAAATGGTTAAGAAGTTGGAAAATGAGGGGGGACAATCAAAGGGGATC<br>TACGATATTCTGAGCTTTCTGTCGTGAGCGGATCTCTTATGTCTTTACGATTTATAGTTTTC<br>ATTATCAAGTATGCCTATATTAGTATATAGCATCTTTAGATGACAGTGTTCGAAGTTTCACG<br>AATAAAAGATAATATTCTACTTTTTGCTCCCACCGCGTTTGCTAGCACGAGTGAACACCATC<br>CCTCGCCTGTGAGTTGTACCCATTCCTCTAAACTGTAGACATGGTAGCTTCAGCAGTGTTCG<br>TTATGTACGGCATCCTCCAACAAACAGTCGGTTATAGTTTGTCCTGCTCCTCTGAATCGTCT<br>CCCTCGATATTTCTCATTTTCCTTCGCATGCCAGCATTGAAATGATCGAAGTTCAATGATGA<br>AACGGTAATTCTTCTGTCATTTACTCATCTCATCTCATCAAGTTATATAATTCTATACGGAT<br>GTAATTTTTCACTTTTCGTCTTGACGTCCACCCTATAATTTCAATTATTGAACCCTCACTGG<br>GTCATTACGTAAATAATGATAGGAATGGGATTCTTCTATTTTTCCTTTTTTCCATTCTAGCAG<br>CCGTCGGGAAAACGTGGCATCCTCTCTTTCGGGCTCAATTGGAGTCACGCTGCCGTGAGCAT |

TABLE 3-continued

Summary of Sequence Listing

| Sequence ID No. Description | Sequence |
|---|---|
| | CCTCTCTTTCCATATCTAACAACTGAGCACGTAACCAATGGAAAAGCATGAGCTTAGCGTTG
CTCCAAAAAAGTATTGGATGGTTAATACCATTTGTCTGTTCTCTTCTGACTTTGACTCCTCA
AAAAAAAAAAATCTACAATCAACAGATCGCTTCAATTACGCCCTCACAAAAACTTTTTTCCT
TCTTCTTCGCCCACGTTAAATTTTATCCCTCATGTTGTCTAACGGATTTCTGCACTTGATTT
ATTATAAAAAGACAAAGACATAATACTTCTCTATCAATTTCAGTTATTGTTCTTCCTTGCGT
TATTCTTCTGTTCTTCTTTTTCTTTTGTCATATATAACCATAACCAAGTAATACATATTCAA
AATGGATGGGTTCGACCATTCTACTGCTCCACCAGGATATAACGAGCTAAAATGGCTCGCCG
ATATCTTCGTCATCGGAATGGCTGTTGGCTGGGTTGCTCACTATATGGAGATGATTCACACG
TCGTTCAAGGACCAAACATACTGCATGACCATCGGGGGCCTTTGCATCAATTTTGCCTGGGA
AATCATATTCTGCACAATGTATCCTGCCAAAGGATTTGTCGAGCGGGTTGCCTTTCTCATGG
GCATTTCTCTCGACCTTGGGGTTATTTACGCGGGAATCAAGAACGCCCCAAATGAATGGCAC
CACTCTGCAATGGTGAGGGACCATATGCCCCTTGTCTTCGCAGCAACGACACTTTGTTGTCT
GAGCGGTCATATGGCTCTTACTGCCCAGGTTGGTCCCGCACAAGCCTATACGTGGGGGGCAA
TTGCATGCCAGCTCTTTATCAGCATAGGGAATGTGTTTCAATTGTTGAGTCGGGGAAACACA
CGAGGGGCGTCATGGACGCTATGGACCTCCAGGTTTTTTGGATCAACATCAGCCATTGGCTT
TGCTCTTGTTCGATATATTCGCTGGTGGGAGGCCTTTTCTTGGTTGAACTGCCCGCTTGTGA
TATGGTCCGTGGCCATGTTCTTTCTGTTTGAAACACTCTATGGAGCCCTATTCTATTCTGTC
AAGCGACAAGAAGGGAGATCCCAGCGTGGAATCAAGCACAAAGAGAGGTAGACAAATCGCTC
TTAAATATATACCTAAAGAACATTAAAGCTATATTATAAGCAAAGATACGTAAATTTTGCTT
ATATTATTATACACATATCATATTTCTATATTTTTAAGATTTGGTTATATAATGTACGTAAT
GCAAAGGAAATAAATTTTATACATTATTGAACAGCGTCCAAGTAACTACATTATGTGCACTA
ATAGTTTAGCGTCGTGAAGACTTTATTGTGTCGCGAAAAGTAAAAATTTTAAAAATTAGAGC
ACCTTGAACTTGCGAAAAAGGTTCTCATCAACTGTTTAAAAGGAGGATATCAGGTCCTATTT
CTGACAAACAATATACAAATTTAGTTTCAAAGATGAATCAGTGCGCGAAGGACATAACTCAA
CAGTTTATTCCTGGCATCCACTAAATATAATGGAGCCCGCTTTTTAAGCTGGCATCCAGAAA
AAAAAAGAATCCCAGCACCAAAATATTGTTTTCTTCACCAACCATCAGTTCATAGGTCCATT
CTCTTAGCGCAACTACAGAGAACAGGGGCACAAACAGGCAAAAAACGGGCACAACCTCAATG
GAGTGATGCAACCTGCCTGGAGTAAATGATGACACAAGGCAATTGACCCACGCATGTATCTA
TCTCATTTTCTTACACCTTCTATTACCTTCTGCTCTCTCTGATTTGGAAAAAGCTGAAAAAA
AAGGTTGAAACCAGTTCCCTGAAATTATTCCCCTACTTGACTAATAAGTATATAAAGACGGT
AGGTATTGATTGTAATTCTGTAAATCTATTTCTTAAACTTCTTAAATTCTACTTTTATAGTT
AGTCTTTTTTTTAGTTTTAAAACACCAAGAACTTAGTTTCGAATAAACACACATAAACAAAC
AAAATGGCGGCACTTCCGGACGTTGCCTCATTCCCATCCCTCTGGTGGCAACCCTAGGCAT
TGCCCCTCTAATTTTCTATCTCGTCCTTGATAGAATTAGCCCCTTGTGGCCAAATTCCAAAG
CTTTCCTGATTGGCAAGAAGAAACCGGAGACCGTGACATCGTTCGAGTGCCCATATGCCTAC
ATCCGTCAGATCTATGGGAAGTATCACTGGGAGCCATTCGTACAGAAGCTGTCTCCGAGGCT
TAAGGATGAGGATCCGGCCAAATATAAGATGGTTCTGGAGATAATGGATGCAATCCACCTGT
GTCTGATGCTAGTTGACGATATAACTGACAATAGCGACTATCGAAAAGGCAAGCCAGCAGCC
CACCGGATATATGGCCCTTCAGAGACAGCAAATCGCGCTTACTACCGAGTCACCCAGATTCT
AAACAAGACCGTGCAAAAGTTCCCCAAGCTGGCCAAGTTCCTGCTTCAGAATCTGGAAGAAA
TTCTCGAAGGCCAAGACCTGTCACTAATCTGGCGACGGGATGGACTGGGTAGCCTTTCGACT
GTTCCTGATGAGCGAGTTGCAGCCTATCGCAAGATGGCGTCATTGAAAACTGGGGCGTTATT
CCGGCTGCTGGGGCAATTGGTGATGGAGGACCAATCGATGGACGGGACGATGACTACTCTTG
CGTGGTGCTCTCAGCTGCAGAATGACTGCAAGAATGTCTACTCATCTGAATATGCTAAGGCC
AAAGGGGCGCTTGCCGAAGACCTCCGAAATCGAGAGCTCTCATTTCCAATTATCCTCGCGCT
GGAAGCTCCTGAAGGGCATTGGGTCGCCAGTGCTTTGGAGACCAGCTCACCGCGCAACATTC
GCAAGGCGCTTGCTGTGATTCAGAGTGAGAGAGTGCGCAATGCTTGTTTCAAGGAGCTCAAG
TCGGCGAGTGCTTCGGTCCAGGACTGGTTGGCTATTTGGGGACGGAACGAGAAAATGAACTT
GAAGAGCCAGCAGACGTAGAGTGCTTTTAACTAAGAATTATTAGTCTTTTCTGCTTATTTT
TCATCATAGTTTAGAACACTTTATATTAACGAATAGTTTATGAATCTATTTAGGTTTAAAAA
TTGATACAGTTTTATAAGTTACTTTTTCAAAGACTCGTGCTGTCTATTGCATAATGCACTGG
AAGGGGAAAAAAAAGGTGCACACGCGTGGCTTTTTCTTGAATTTGCAGTTTGAAAAATAACT
ACATGGATGATAAGAAAACATGGAGTACAGTCACTTTGAGAACCTTCAATCAGCTGGTAACG
TCTTCGTTAATTGGATACTCAAAAAAGATGGATAGCATGAATCACAAGATGGAAGGAAATGC
GGGCCACGACCACAGTGATATGCATATGGGAGATGGAGATGATACCTTATATCTAGGAACCC
ATCAGGTTGGTGGAAGATTACCCGTTCTAAGACTTTTCAGCTTCCTCTATTGATGTTACACC
TGGACACCCCTTTTCTGGCATCCAGTTTTTAATCTTCAGTGGCATGTGAGATTCTCCGAAAT
TAATTAAAGCAATCACACAATTCTCTCGGATACCACCTCGGTTGAAACTGACAGGTGGTTTG
TTACGCATGCTAATGCAAAGGAGCCTATATACCTTTGGCTCGGCTGCTGTAACAGGGAATAT
AAAGGGCAGCATAATTTAGGAGTTTAGTGAACTTGCAACATTTACTATTTTCCCTTCTTACG
TAAATATTTTCTTTTTAATTCTAAATCAATCTTTTTCAATTTTTTGTTTGTATTCTTTTCT
TGCTTAAATCTATAACTACAAAAAACACATACATAAACTAAAAATGGCCAATGCCCAGCAAC
CCCCCTTTCGCATCCTTATTGTGGGCGGTTCTGTCGCAGGCCTCATCCTTGCGCACTGTCTC
GAACGCGCCAATATAGAGTACCTCATACTCGAAAAGGAGAAGATGTTGCTCCACAAGTTGG
TGCCTCGATAGGTATCATGCCAAATGGCGGACGGATCCTCGAGCAACTGGGCCTATTTGGGG
AGATTGAGCGTGTGATCGAGCCGTTGCATCAGGCGAATATCAGCTATCCAGATGGGTTCTGC
TTTAGTAACGTCTATCCTAAGGTTCTTGGCGACAGGTTCGGATACCCGGTTGCATTCTTGGA
CCGGCAGAAGTTCCTGCAGATTGCATATGAGGGGCTGAGAAAGAAGCAGAATGTTCTCACCG
GTAAAAGGGTAGTTGGACTGCGACAGTCGGATCAAGGGACTGCTGTTTCTGTGGCTGACGGG
ACAGAGTATGAGGCGGATCTCGTGGTTGGTGATGAGGTCAATAGTCGGGTGAGAAGTGA
GATTTGGAAGATGGCGGAAGAGAATCAGCCTGCATCAGTTTCGACACGTGAAAGAAGAAGCA
TGACTGTTGAATATGTCTCGCGTTTTCGGGATTTCATCAGCCATCCCAGGGCTCGAGATAAGC
GAACAGATCAACGGTATTTTCGACCATCTATCCATTCTAACAATCCATGGCAGACATGGTCG
CGTGTTCTGGTTCGTGATCCAGAAGCTGGATAGGAAGTACGTCTATCCTGATGTCCCGCGAT
TCTCAGACGAGGATGCCGTACAGCTCTTCGATCGGGTCAAACACGTGCGGTTCTGGAAAAAC |

TABLE 3-continued

Summary of Sequence Listing

| Sequence ID No. Description | Sequence |
|---|---|
| | ATCTGTGTGGGGGACTTGTGGAAGAACAGAGAGGTGTCCTCGATGACAGCGCTGGAGGAGGG
AGTGTTCGAGACATGGCATCATGATAGGATGGTTTTGATTGGAGATAGCGTTCACAAGATGA
CGCCCAACTTTGGCCAAGGAGCTAATTCAGCCATCGAGGATGCTGCCGCGCTCTCTTCCCTT
CTACATGATCTCGTCAACGCCCGTGGAGTTTGCAAGCCATCGAATGTCCAGATTCAGCATCT
CCTCAAGCAGTATCGGGAGACCCGATACACTCGCATGGTAGGCATGTGTCGCACCGCGGCTT
CAGTCTCTCGGATTCAGGCCCGAGATGGCATCCTCAACACCGTCTTTGGACGATATTGGGCA
CCTTATGCTGGCAACCTGCCTGCTGACCTGGCATCAAAAGTGATGGCAGATGCAGAGGTTGT
TACTTTTCTGCCCTTGCCAGGGCGCTCAGGACCGGGCTGGGAGATGTACAGACGAAAGGGGA
AGGGAGGGCAGGTGCAATGGGTGCTTATAATCTTAAGCTTACTTACGATTGGTGGATTGTGC
ATCTGGCTACAAAGCAATGCGTTGAGTAGATAAGGAGATTGATAAGACTTTTCTAGTTGCAT
ATCTTTTATATTTAAATCTTATCTATTAGTTAATTTTTTGTAATTTATCCTTATATATAGTC
TGGTTATTCTAAAATATCATTTCAGTATCTAAAAATTCCCCTCTTTTTTCAGTTATATCTTA
ACAGGCGACAGTCCAAATGTTGATTTATCCCAGTCCGATTCATCAGGGTTGTGAAGCATTTT
GTCAATGGTCGAAATCACATCAGTAATAGTGCCTCTTACTTGCCTCATAGAATTTCTTTCTC
TTAACGTCACCGTTTGGTCTTTTATAGTTTCGAAATCTATGGTGATACCAAATGGTGTTCCC
AATTCATCGTTACGGGCGTATTTTTTACCAATTGAAGTATTGGAATCGTCAATTTTAAAGTA
TATCTCTCTTTTACGTAAAGCCTGCGAGATCCTCTTAAGTATAGCGGGGAAGCCATCGTTAT
TCGATATTGTCGTAACAAATACTTTGATCGGCGCTATGCGGCCGCCACCGCGGTGGAGCTCC
AGCTTTTGTTCCCTTTAGTGAGGGTTAATTGCGCGCTTGGCGTAATCATGGTCATAGCTGTT
TCCTGTGTGAAATTGTTATCCGCTCACAATTCCACACAACATAGGAGCCGGAAGCATAAAGT
GTAAAGCCTGGGGTGCCTAATGAGTGAGGTAACTCACATTAATTGCGTTGCGCTCACTGCCC
GCTTTCCAGTCGGGAAACCTGTCGTGCCAGCTGCATTAATGAATCGGCCAACGCGCGGGGAG
AGGCGGTTTGCGTATTGGGCGCTCTTCCGCTTCCTCGCTCACTGACTCGCTGCGCTCGGTCG
TTCGGCTGCGGCGAGCGGTATCAGCTCACTCAAAGGCGGTAATACGGTTATCCACAGAATCA
GGGGATAACGCAGGAAAGAACATGTGAGCAAAAGGCCAGCAAAAGGCCAGGAACCGTAAAAA
GGCCGCGTTGCTGGCGTTTTTCCATAGGCTCCGCCCCCTGACGAGCATCACAAAAATCGAC
GCTCAAGTCAGAGGTGGCGAAACCCGACAGGACTATAAAGATACCAGGCGTTTCCCCCTGGA
AGCTCCCTCGTGCGCTCTCCTGTTCCGACCCTGCCGCTTACCGGATACCTGTCCGCCTTTCT
CCCTTCGGGAAGCGTGGCGCTTTCTCATAGCTCACGCTGTAGGTATCTCAGTTCGGTGTAGG
TCGTTCGCTCCAAGCTGGGCTGTGTGCACGAACCCCCCGTTCAGCCCGACCGCTGCGCCTTA
TCCGGTAACTATCGTCTTGAGTCCAACCCGGTAAGACACGACTTATCGCCACTGGCAGCAGC
CACTGGTAACAGGATTAGCAGAGCGAGGTATGTAGGCGGTGCTACAGAGTTCTTGAAGTGGT
GGCCTAACTACGGCTACACTAGAAGGACAGTATTTGGTATCTGCGCTCTGCTGAAGCCAGTT
ACCTTCGGAAAAAGAGTTGGTAGCTCTTGATCCGGCAAACAAACCACCGCTGGTAGCGGTGG
TTTTTTTGTTTGCAAGCAGCAGATTACGCGCAGAAAAAAAGGATCTCAAGAAGATCCTTTGA
TCTTTTCTACGGGGTCTGACGCTCAGTGGAACGAAAACTCACGTTAAGGGATTTTGGTCATG
AGATTATCAAAAGGATCTTCACCTAGATCCTTTTAAATTAAAAATGAAGTTTTAAATCAAT
CTAAAGTATATATGAGTAAACTTGGTCTGACAGTTACCAATGCTTAATCAGTGAGGCACCTA
TCTCAGCGATCTGTCTATTTCGTTCATCCATAGTTGCCTGACTCCCCGTCGTGTAGATAACT
ACGATACGGGAGGGCTTACCATCTGGCCCCAGTGCTGCAATGATACCGCGAGACCCACGCTC
ACCGGCTCCAGATTTATCAGCAATAAACCAGCCAGCCGGAAGGGCCGAGCGCAGAAGTGGTC
CTGCAACTTTATCCGCCTCCATCCAGTCTATTAATTGTTGCCGGGAAGCTAGAGTAAGTAGT
TCGCCAGTTAATAGTTTGCGCAACGTTGTTGCCATTGCTACAGGCATCGTGGTGTCACGCTC
GTCGTTTGGTATGGCTTCATTCAGCTCCGGTTCCCAACGATCAAGGCGAGTTACATGATCCC
CCATGTTGTGCAAAAAAGCGGTTAGCTCCTTCGGTCCTCCGATCGTTGTCAGAAGTAAGTTG
GCCGCAGTGTTATCACTCATGGTTATGGCAGCACTGCATAATTCTCTTACTGTCATGCCATC
CGTAAGATGCTTTTCTGTGACTGGTGAGTACTCAACCAAGTCATTCTGAGAATAGTGTATGC
GGCGACCGAGTTGCTCTTGCCCGGCGTCAATACGGGATAATACCGCGCCACATAGCAGAACT
TTAAAAGTGCTCATCATTGGAAAACGTTCTTCGGGGCGAAAACTCTCAAGGATCTTACCGCT
GTTGAGATCCAGTTCGATGTAACCCACTCGTGCACCCAACTGATCTTCAGCATCTTTTACTT
TCACCAGCGTTTCTGGGTGAGCAAAAACAGGAAGGCAAAATGCCGCAAAAAAGGGAATAAGG
GCGACACGGAAATGTTGAATACTCATACTCTTCCTTTTTCAATATTATTGAAGCATTTATCA
GGGTTATTGTCTCATGAGCGGATACATATTTGAATGTATTTAGAAAAATAAACAAATAGGGG
TTCCGCGCACATTTCCCCGAAAAGTGCCACCTGAACGAAGCATCTGTGCTTCATTTTGTAGA
ACAAAAATGCAACGCGAGAGCGCTAATTTTTCAAACAAAGAATCTGAGCTGCATTTTTACAG
AACAGAAATGCAACGCGAAAGCGCTATTTTACCAACGAAGAATCTGTGCTTCATTTTTGTAA
AACAAAAATGCAACGCGAGAGCGCTAATTTTTCAAACAAAGAATCTGAGCTGCATTTTTACA
GAACAGAAATGCAACGCGAGAGCGCTATTTTACCAACAAAGAATCTATACTTCTTTTTTGTT
CTACAAAAATGCATCCCGAGAGCGCTATTTTTCTAACAAAGCATCTTAGATTACTTTTTTTC
TCCTTTGTGCGCTCTATAATGCAGTCTCTTGATAACTTTTTGCACTGTAGGTCCGTTAAGGT
TAGAAGAAGGCTACTTTGGTGTCTATTTTCTCTTCCATAAAAAAGCCTGACTCCACTTCCC
GCGTTTACTGATTACTAGCGAAGCTGCGGGTGCATTTTTTCAAGATAAAGGCATCCCCGATT
ATATTCTATACCGATGTGGATTGCGCATACTTTGTGAACAGAAAGTGATAGCGTTGATGATT
CTTCATTGGTCAGAAAATTATGAACGGTTTCTTCTATTTTGTCTCTATATACTACGTATAGG
AAATGTTTACATTTTCGTATTGTTTTCGATTCACTCTATGAATAGTTCTTACTACAATTTTT
TTGTCTAAAGAGTAATACTAGAGATAAACATAAAAAATGTAGAGGTCGAGTTTAGATGCAAG
TTCAAGGAGCGAAAGGTGGATGGGTAGGTTATATAGGGATATAGCACAGAGATATATAGCAA
AGAGATACTTTGAGCAATGTTTGTGGAAGCGGTATTCGCAATATTTTAGTAGCTCGTTACA
GTCCGGTGCGTTTTTGGTTTTTTGAAAGTGCGTCTTCAGAGCGCTTTTGGTTTTCAAAGCG
CTCTGAAGTTCCTATACTTTCTAGAGAATAGGAACTTCGGAATAGGAACTTCAAAGCGTTTC
CGAAAACGAGCGCTTCCGAAAATGCAACGCGAGCTGCGCACATACAGCTCACTGTTCACGTC
GCACCTATATCGCGTGTTGCCTGTATATATATATACATGAGAAGAACGGCATAGTGCGTGT
TTATGCTTAAATGCGTACTTATATGCGTCTATTTATGTAGGATGAAAGGTAGTCTAGTACCT
CCTGTGATATTATCCCATTCCATGCGGGGTATCGTATGCTTCCTTCAGCACTACCCTTTAGC
TGTTCTATATGCTGCCACTCCTCAATTGGATTAGTCTCATCCTTCAATGCTATCATTTCCTT |

TABLE 3-continued

Summary of Sequence Listing

| Sequence ID No. | Description | Sequence |
|---|---|---|
| | | TGATATTGGATCATACTAAGAAACCATTATTATCATGACATTAACCTATAAAAATAGGCGTA<br>TCACGAGGCCCTTTCGTCTCGCGCGTTTCGGTGATGACGGTGAAAACCTCTGACACATGCAG<br>CTCCCGGAGACGGTCACAGCTTGTCTGTAAGCGGATGCCGGGAGCAGACAAGCCCGTCAGGG<br>CGCGTCAGCGGGTGTTGGCGGGTGTCGGGGCTGGCTTAACTATGCGGCATCAGAGCAGATTG<br>TACTGAGAGTGCACCATATCGACTACGTCGTAAGGCCGTTTCTGACAGAGTAAAATTCTTGA<br>GGGAACTTTCACCATTATGGGAAATGCTTCAAGAAGGTATTGACTTAAACTCCATCAAATGG<br>TCAGGTCATTGAGTGTTTTTTATTTGTTGTATTTTTTTTTTTTAGAGAAAATCCTCCAATA<br>TCAAATTAGGAATCGTAGTTTCATGATTTTCTGTTACACCTAACTTTTTGTGTGGTGCCCTC<br>CTCCTTGTCAATATTAATGTTAAAGTGCAATTCTTTTTCCTTATCACGTTGAGCCATTAGTA<br>TCAATTTGCTTACCTGTATTCCTTTACTATCCTCCTTTTTCTCCTTCTTGATAAATGTATGT<br>AGATTGCGTATATAGTTTCGTCTACCCTATGAACATATTCCATTTTGTAATTTCGTGTCGTT<br>TCTATTATGAATTTCATTTATAAAGTTTATGTACAAATATCATAAAAAAAGAGAATCTTTTT<br>AAGCAAGGATTTTCTTAACTTCTTCGGCGACAGCATCACCGACTTCGGTGGTACTGTTGGAA<br>CCACCTAAATCACCAGTTCTGATACCTGCATCCAAAACCTTTTTAACTGCATCTTCAATGGC<br>CTTACCTTCTTCAGGCAAGTTCAATGACAATTTCAACATCATTGCAGCAGACAAGATAGTGG<br>CGATAGGGTCAACCTTATTCTTTGGCAAATCTGGAGCAGAACCGTGGCATGGTTCGTACAAA<br>CCAAATGCGGTGTTCTTGTCTGGCAAAGAGGCCAAGGACGCAGATGGCAACAAACCCAAGGA<br>ACCTGGGATAACGGAGGCTTCATCGGAGATGATATCACCAAACATGTTGCTGGTGATTATAA<br>TACCATTTAGGTGGGTTGGGTTCTTAACTAGGATCATGGCGGCAGAATCAATCAATTGATGT<br>TGAACCTTCAATGTAGGGAATTCGTTCTTGATGGTTTCCTCCACAGTTTTTCTCCATAATCT<br>TGAAGAGGCCAAAAGATTAGCTTTATCCAAGGACCAAATAGGCAATGGTGGCTCATGTTGTA<br>GGGCCATGAAAGCGGCCATTCTTGTGATTCTTTGCACTTCTGGAACGGTGTATTGTTCACTA<br>TCCCAAGCGACACCATCACCATCGTCTTCCTTTCTCTTACCAAAGTAAATACCTCCCACTAA<br>TTCTCTGACAACAACGAAGTCAGTACCTTTAGCAAATTGTGGCTTGATTGGAGATAAGTCTA<br>AAAGAGAGTCGGATGCAAAGTTACATGGTCTTAAGTTGGCGTACAATTGAAGTTCTTTACGG<br>ATTTTTAGTAAACCTTGTTCAGGTCTAACACTACCGGTACCCCATTTAGGACCAGCCACAGC<br>ACCTAACAAAACGGCATCAACCTTCTTGGAGGCTTCCAGCGCCTCATCTGGAAGTGGGACAC<br>CTGTAGCATCGATAGCAGCACCACCAATTAAATGATTTTCGAAATCGAACTTGACATTGGAA<br>CGAACATCAGAAATAGCTTTAAGAACCTTAATGGCTTCGGCTGTGATTTCTTGACCAACGTG<br>GTCACCTGGCAAAACGACGATCTTCTTAGGGGCAGACATAGGGGCAGACATTAGAATGGTAT<br>ATCCTTGAAATATATATATATATTGCTGAAATGTAAAAGGTAAGAAAAGTTAGAAAGTAAGA<br>CGATTGCTAACCACCTATTGGAAAAAACAATAGGTCCTTAAATAATATTGTCAACTTCAAGT<br>ATTGTGATGCAAGCATTTAGTCATGAACGCTTCTCTATTCTATATGAAAAGCCGGTTCCGGC<br>CTCTCACCTTTCCTTTTTCTCCCAATTTTTCAGTTGAAAAAGGTATATGCGTCAGGCGACCT<br>CTGAAATTAACAAAAAATTTCCAGTCATCGAATTTGATTCTGTGCGATAGCGCCCCTGTGTG<br>TTCTCGTTATGTTGAGGAAAAAAATAATGGTTGCTAAGAGATTCGAACTCTTGCATCTTACG<br>ATACCTGAGTATTCCCACAGTTAACTGCGGTCAAGATATTTCTTGAATCAGGCGCCTTAGAC<br>CGCTCGGCCAAACAACCAATTACTTGTTGAGAAATAGAGTATAATTATCCTATAAATATAAC<br>GTTTTTGAACACACATGAACAAGGAAGTACAGGACAATTGATTTTGAAGAGAATGTGGATTT<br>TGATGTAATTGTTGGGATTCCATTTTTAATAAGGCAATAATATTAGGTATGTGGATATACTA<br>GAAGTTCTCCTCGACCGTCGATATGCGGTGTGAAATACCGCACAGATGCGTAAGGAGAAAAT<br>ACCGCATCAGGAAATTGTAAACGTTAATATTTTGTTAAAATTCGCGTTAAATTTTTGTTAAA<br>TCAGCTCATTTTTTAACCAATAGGCCGAAATCGGCAAAATCCCTTATAAATCAAAAGAATAG<br>ACCGAGATAGGGTTGAGTGTTGTTCCAGTTTGGAACAAGAGTCCACTATTAAAGAACGTGGA<br>CTCCAACGTCAAAGGGCGAAAAACCGTCTATCAGGGCGATGGCCCACTACGTGAACCATCAC<br>CCTAATCAAGTTTTTTGGGGTCGAGGTGCCGTAAAGCACTAAATCGGAACCCTAAAGGGAGC<br>CCCCGATTTAGAGCTTGACGGGGAAAGCCGGCGAACGTGGCGAGAAAGGAAGGGAAGAAAGC<br>GAAAGGAGCGGGCGCTAGGGCGCTGGCAAGTGTAGCGGTCACGCTGCGCGTAACCACCACAC<br>CCGCCGCGCTTAATGCGCCGCTACAGGGCGCGTCGCGCCATTCGCCATTCAGGCTGCGCAAC<br>TGTTGGGAAGGGCGATCGGTGCGGGCCTCTTCGCTATTACGCCAGCTGGCGAAAGGGGGATG<br>TGCTGCAAGGCGATTAAGTTGGGTAACGCCAGGGTTTTCCCAGTCACGACGTTGTAAAACGA<br>CGGCCAGTGAGCGCGCGTAATACGACTCACTATAGGGCGAATTGGGTACCGGGCCCCCCCTC<br>GAGGTCGACGGTATCGATAAGCTTGATATCGAATTCCTGCAGCCCGGGGATCCACTAGTTC<br>TAGATTAATTAA |

Doctrine of Equivalents

While the above description contains many specific embodiments of the invention, these should not be construed as limitations on the scope of the invention, but rather as an example of one embodiment thereof. Accordingly, the scope of the invention should be determined not by the embodiments illustrated, but by the appended claims and their equivalents.

What is claimed is:

1. A DNA vector comprising at least two different production-phase promoters and at least two different heterologous genes, wherein (1) a first production-phase promoter of the at least two different production-phase promoters is proximately upstream from a first heterologous gene of the at least two heterologous genes and (2) a second production-phase promoter of the at least two different production-phase promoters is proximately upstream from a second heterologous gene of the at least two heterologous genes:

wherein the at least two different production-phase promoters each repress heterologous expression of the proximately linked first and the proximately linked second heterologous gene in a Saccharomyces cerevisiae cell when the S. cerevisiae predominantly exhibits anaerobic energy metabolism;

wherein the at least two different production-phase promoters induce heterologous expression of the proximately linked first and the proximately linked second heterologous gene in the S. cerevisiae cell when the S. cerevisiae cell predominantly exhibits aerobic energy metabolism; and wherein each of the at least two different production-phase promoters comprise a sequence selected from the group consisting of the S. cerevisiae ADH2 promoter (SEQ ID NO: 1), the S. cerevisiae PCK1 promoter (SEQ ID NO: 2), the S. cerevisiae MLS1 promoter (SEQ ID NO: 3), the S. cerevisiae ICL1 promoter (SEQ ID NO: 4), the S. cerevisiae YLR307C-A promoter (SEQ ID NO: 5), the S. cerevisiae YGRQ67C promoter (SEQ ID NO: 6), the S. cerevisiae IDP2 promoter (SEQ ID NO:7), the S. cerevisiae ADY2 promoter (SEQ ID NO: 8), the S. cerevisiae GAC1 promoter (SEQ ID NO: 9), the S. cerevisiae ECM13 promoter (SEQ ID NO: 10), the S. cerevisiae FAT3 promoter (SEQ ID NO: 11), the S. cerevisiae PUT1 promoter (SEQ ID NO: 12), the S. cerevisiae NQM1 promoter (SEQ ID NO: 13), the S. cerevisiae SFC1 promoter (SEQ ID NO: 14), the S. cerevisiae JEN1 promoter (SEQ ID NO: 15), the S. cerevisiae SIP18 promoter (SEQ ID NO: 16), the S. cerevisiae ATO2 promoter (SEQ ID NO: 17), the S. cerevisiae YIG1 promoter (SEQ ID NO: 18), the S. cerevisiae FBP1 promoter (SEQ ID NO: 19), the S. paradoxus ADH2 promoter (SEQ ID NO: 36), the S. kudriavzevii ADFI2 promoter (SEQ ID NO: 37), the S. bavanus ADFI2 promoter (SEQ ID NO: 38), the S. paradoxus PCK1 promoter (SEQ ID NO: 41), the S. kudriavzevii PCK1 promoter (SEQ ID NO: 42), the S. bavanus PCK1 promoter (SEQ ID NO: 43), the S. paradoxus MLS1 promoter (SEQ ID NO: 44), the S. kudriavzevii MLS1 promoter (SEQ ID NO: 45), the S. bavanus MLS1 promoter (SEQ ID NO: 46), the S. paradoxus ICL1 promoter (SEQ ID NO: 47), the S. kudriavzevii ICL1 promoter (SEQ ID NO: 48), and the S. bavanus ICL1 promoter (SEQ ID NO: 49).

2. The DNA vector of claim 1, wherein the first heterologous gene sequence is from a species other than S. cerevisiae.

3. The DNA vector of claim 1, wherein the anaerobic energy metabolism is defined by the catabolism of a fermentable carbon source.

4. The DNA vector of claim 3, wherein the fermentable carbon source is glucose or dextrose.

5. The DNA vector of claim 1, wherein the aerobic energy metabolism is defined by the catabolism of a nonfermentable carbon source.

6. The DNA vector of claim 5, wherein the nonfermentable carbon source is ethanol or glycerol.

7. The DNA vector of claim 1, wherein the DNA vector is disposed within the S. cerevisiae cell.

8. The DNA vector of claim 1,
wherein each of the at least two different production-phase promoters comprise a sequence selected from the group consisting of the S. cerevisiae ADH2 promoter (SEQ ID NO: 1), the S. cerevisiae MLS1 promoter (SEQ ID NO: 3), the S. cerevisiae ICL1 promoter (SEQ ID NO: 4), the S. cerevisiae YLR307C-A promoter (SEQ ID NO: 5), the S. cerevisiae YGRO67C promoter (SEQ ID NO: 6), the S. cerevisiae IDP2 promoter (SEQ ID NO: 7), the S. cerevisiae ADY2 promoter (SEQ ID NO: 8), the S. cerevisiae GAC1 promoter (SEQ ID NO: 9), the S. cerevisiae ECM13 promoter (SEQ ID NO: 10), the S. cerevisiae FAT3 promoter (SEQ ID NO: 11), the S. cerevisiae PUT1 promoter (SEQ ID NO: 12), the S. cerevisiae NQM1 promoter (SEQ ID NO: 13), the S. cerevisiae SFC1 promoter (SEQ ID NO: 14), the S. cerevisiae JEN1 promoter (SEQ ID NO: 15), the S. cerevisiae SIP18 promoter (SEQ ID NO: 16), the S. cerevisiae ATO2 promoter (SEQ ID NO: 17), the S. cerevisiae YIG1 promoter (SEQ ID NO: 18), the S. paradoxus ADH2 promoter (SEQ ID NO: 36), the S. kudriavzevii ADH2 promoter (SEQ ID NO: 37), the S. bayanus ADH2 promoter (SEQ ID NO: 38), the S. paradoxus PCK1 promoter (SEQ ID NO: 41), the S. kudriavzevii PCK1 promoter (SEQ ID NO: 42), the S. bayanus PCK1 promoter (SEQ ID NO: 43), the S. paradoxus MLS1 promoter (SEQ ID NO: 44), the S. kudriavzevii MLS1 promoter (SEQ ID NO: 45), the S. bayanus MLS1 promoter (SEQ ID NO: 46), the S. paradoxus ICL1 promoter (SEQ ID NO: 47), the S. kudriavzevii ICL1 promoter (SEQ ID NO: 48), and the S. bayanus ICL1 promoter (SEQ ID NO: 49).

* * * * *

SEQUENCE LISTING

<160> NUMBER OF SEQ ID NOS: 73

<210> SEQ ID NO 1
<211> LENGTH: 500
<212> TYPE: DNA
<213> ORGANISM: Saccharomyces cerevisiae

<400> SEQUENCE: 1

```
tatctaaaaa ttgccttatg atccgtctct ccggttacag cctgtgtaac tgattaatcc      60
tgcctttcta atcaccattc taatgtttta attaagggat tttgtcttca ttaacggctt     120
tcgctcataa aaatgttatg acgttttgcc cgcaggcggg aaaccatcca cttcacgaga     180
ctgatctcct ctgccggaac accgggcatc tccaacttat aagttggaga ataagagaa     240 tttcagattg agagaatgaa aaaaaaaaaa aaaaaaagg cagaggagag catagaaatg     300
gggttcactt tttggtaaag ctatagcatg cctatcacat ataaatagag tgccagtagc     360 gactttttc acactcgaaa tactcttact actgctctct tgttgttttt atcacttctt     420
gtttcttctt ggtaaataga atatcaagct acaaaaagca tacaatcaac tatcaactat     480
taactatatc gtaatacaca                                                 500

<210> SEQ ID NO 2
<211> LENGTH: 500
<212> TYPE: DNA
<213> ORGANISM: Saccharomyces cerevisiae

<400> SEQUENCE: 2
ataggaaaaa accgagcttc ctttcatccg gcgcggctgt gttctacata tcactgaagc      60
tccgggtatt ttaagttata caagggaaag atgccggcta gactagcaag ttttaggctg     120
cttaacatta tggataggcg gataaagggc ccaaacagga ttgtaaagct tagacgcttc     180
tggttggaca atggtacgtt tgtgtattaa gtaaggcttg gctggggata gcaacattgg     240
gcagagtata gaagaccaca aaaaaaaggt atataagggc agagaagtct ttgtaatgtg     300
tgtaacttct cttccatgtg taatcagtat ttctacttac ttcttaaaata tacagaagta     360 agacagataa ccaacagcct ttcccagata tacatatata tctttatttc agcttaaaca     420
ataattatat ttgttaact caaaataaa aaaaaaaaac caaactcacg caactaatta     480
ttccataata aaataacaac                                                 500

<210> SEQ ID NO 3
<211> LENGTH: 500
<212> TYPE: DNA
<213> ORGANISM: Saccharomyces cerevisiae

<400> SEQUENCE: 3
ccattgggcc gatgaagtta gtcgacggat agaagcggtt gtccccttc ccggcgagcc      60 ggcagtcggg ccgaggttcg gataaatttt gtattgtgtt ttgattctgt catgagtatt     120
acttatgttc tctttaggta accccaggtt aatcaatcac agtttcatac cggctagtat     180
tcaaattatg acttttcttc tgcagtgtca gccttacgac gattatctat gagctttgaa     240
tatagtttgc cgtgattcgt atctttaatt ggataataaa atgcgaagga tcgatgaccc     300
ttattattat ttttctacac tggctaccga tttaactcat cttcttgaaa gtatataagt     360
aacagtaaaa tataccgtac ttctgctaat gttatttgtc ccttattttt cttttcttgt     420
cttatgctat agtacctaag aataacgact attgttttga actaaacaaa gtagtaaaag     480
cacataaaag aattaagaaa                                                 500

<210> SEQ ID NO 4
<211> LENGTH: 500
<212> TYPE: DNA
<213> ORGANISM: Saccharomyces cerevisiae

<400> SEQUENCE: 4
```

| atttattgaa aagtaaatat ctcgtaaccc ggatgctttg ggcggtcggg ttttgctact | 60 |
| cgtcatccga tgagaaaaac tgttcccttt tgccccaggt ttccattcat ccgagcgatc | 120 |
| acttatctga cttcgtcact ttttcatttc atccgaaaca atcaaaactg aagccaatca | 180 |
| ccacaaaatt aacactcaac gtcatctttc actaccctt acagaagaaa atatccatag | 240 |
| tccggactag catcccagta tgtgactcaa tattggtgca aaagagaaaa gcataagtca | 300 |
| gtccaaagtc cgcccttaac caggcacatc ggaattcaca aacgtttct ttattatata | 360 |
| aaggagctgc ttcactggca aaattcttat tatttgtctt ggcttgctaa tttcatctta | 420 |
| tccttttttt cttttcacac ccaaatacct aacaattgag agaaaactct tagcataaca | 480 |
| taacaaaaag tcaacgaaaa | 500 |

<210> SEQ ID NO 5
<211> LENGTH: 500
<212> TYPE: DNA
<213> ORGANISM: Saccharomyces cerevisiae

<400> SEQUENCE: 5

| caaaaaaaca atggaagaac aaagaaaatt tagcggaagt aaaataaca gccgaaagcc | 60 |
| aaattcaggc ttatcttgcc tactctttct tttatcgaat tcctttaggc cgttgcaata | 120 |
| gaaaagtaat aaaaacgcat atacgtaagt tgtagtcagt gtaattgcaa tctattatgc | 180 |
| gcatcaggtg cgcatactac atccattggt gcacaaaaaa aggaacgcag acaagaaaat | 240 |
| tattcagttt gctgttcgtg atgagccatc cctgaatatg actaatgtta atgttcaatt | 300 |
| tgggatctta ttttttttg tgcagtaata agaatctttg aaaaaaaact atataagcct | 360 |
| atatagtttg taagatataa gacaaaacac acctgctttt ccactacaca ttttcgttat | 420 |
| tatataaaaa agacagccaa gtatacttgt caacaaaata aactcatagc aattacacta | 480 |
| taaaaacaat agcatcaaaa | 500 |

<210> SEQ ID NO 6
<211> LENGTH: 500
<212> TYPE: DNA
<213> ORGANISM: Saccharomyces cerevisiae

<400> SEQUENCE: 6

| tggcaatccc ctccgatcgt ccgcggcaaa atggtcgtca atcggacaaa gggggatgat | 60 |
| gggatctggt aatagaagaa aatatggact aaaggtagcc gctaaagcga tccaggcatg | 120 |
| tgttgccaat gatgtaagtc aagcgaagga aatggttcag taatatgata gacagactgc | 180 |
| acttcaaggg tgcgcccct cccccgcgca tatgcttaca acgcaaaata attgacgttt | 240 |
| aatgtggata cttatcgtaa tcgctgcatt atagatttcg agtcatgttc acttaacccc | 300 |
| acatatttat atagaacgca tcttcaaagt acttataaag tttagtttta catttttctg | 360 |
| ctttctattt cttcttttc ggttcttctt catgccagtt ggcatggctt aagagcttta | 420 |
| cttgtcgctt ttatttaaaa ccttctctcg ggagaagaca attgttgata tacagtaatt | 480 |
| gtatttgcat tatcactgct | 500 |

<210> SEQ ID NO 7
<211> LENGTH: 344
<212> TYPE: DNA
<213> ORGANISM: Saccharomyces cerevisiae

<400> SEQUENCE: 7

| aacgtctatc tatttatttt tataactccg ggatgtcatt gccggtggtc cgaaaatcgg | 60 |

```
caaataagga aataagggaa gaatatgcag tagtcaaatc atcagtgttc tctttgatac    120 cttttcagggc taggaatagt gggggtggag tataatatca aaaaccggac ttaacattat    180
tggttcggtt ggaattggct ataggcaaac tagtctccgg catgatatat aaatgacagc    240
ctgcaattgt atgttactac actcttgact tgtcgactac agtcgctgct caggcacgag    300
aataggaggt aagaaggtaa cgtacgtata tatataaaat cgta                     344
```

<210> SEQ ID NO 8
<211> LENGTH: 500
<212> TYPE: DNA
<213> ORGANISM: Saccharomyces cerevisiae

<400> SEQUENCE: 8

```
gagctccgtg aataggcga gcggctgagt ggttctccaa gctacggttt ttacgtgtag     60
ccccatgtga gcaagccaaa caagggccct aaaggcgtg actacaaaaa ggggcgggtt    120
ggaaggtcat ctgcagcgag atacgaaaag attttttgcc agatttgcgg ttgggcggct    180
atttcggtat tgttggggta acaaacgttg gggaagactg cattttctta cagcttttt     240 tcgttatcgc gggttgggcg gctatggcgc cttctcctct gtactccaac ctgtcagaga    300
caccaagctg tatataaagc accttggttg gatcgtattt ccctgagatc ttgctatagg    360
ttcattttat atatcgtcca atagcaataa caatacaaca gaaactacta gcatctgttt    420
ataagaaaaa ggcaaatagt cgacagctaa cacagatata actaaacaac cacaaaacaa    480
ctcatataca aacaaataat                                                500
```

<210> SEQ ID NO 9
<211> LENGTH: 500
<212> TYPE: DNA
<213> ORGANISM: Saccharomyces cerevisiae

<400> SEQUENCE: 9

```
ccctatcttt ttttttttct cgcaatctgg ggaaagcttt tctcatgctt atacgtgatt     60
tgttatataa gggattgcta tttcaggcat cattcacctc cttttgtatc cttagtttca    120
ctgcatttga tatatatata tacgtatctg tagtttcctt ccattacata acgcataata    180
tactatttcc atagtctatc ttacatcttt tttcttactt tgttaaggga acggataacg    240
ataaaacaaa aagagagatt taagattact tctgtaactt ttttgatcca ttaccaaaac    300
tatatttttt ttcttttctc tcctctggca ttaaacacag ttattgctac agctaatcat    360
cgatataata atacatcaca ttaactgtct ataagaggct ggtacttagt agatggtgag    420 aatttttttat ttttgtattt taacttcatt tttgtaaaca agttggaact ggaacttact    480
atagaacaag agcttaaacc                                                500
```

<210> SEQ ID NO 10
<211> LENGTH: 499
<212> TYPE: DNA
<213> ORGANISM: Saccharomyces cerevisiae

<400> SEQUENCE: 10

```
gttgtatcct attggatcac gggcgacgga caagacccga agtgcggacc ggcatggtca     60
gcttgcacgg aagctttaag ggtttccctt gtttcggcat tagaagaggc atttcgcacg    120
ttttaccggg tcagaaactt cgaggaagct gtgacaattg aaaaaaaagg caaaactaaa    180
tgcaatgtat ccggttgccc atgcattatt tgtgatgttt tcggatgtag ttcgctgcgc    240
```

```
tccgcggcga tatatcctct agcgagaggc atatgtataa atatatatat atatatctaa    300
caaaagcatt caagtttctt tctctggtgt tacgtctttg ttcgactttc tctgcttaca    360
gccctgtatg accaaagaaa aaataaaaag acagctacat accagcagaa attttttata    420
gtattacact atacatccaa gttttttcac aattatttat tgttttctc acatagaaaa     480 ttccgcatac tgcgattat                                                 499

<210> SEQ ID NO 11
<211> LENGTH: 500
<212> TYPE: DNA
<213> ORGANISM: Saccharomyces cerevisiae

<400> SEQUENCE: 11
gaaagcttat tactgagttt tgcggagcat cgctcggagc ggcggaattg aatcgaaccg     60
ccgtgctatt accgaacaaa aaaattcgaa agcataaact cagtagtgaa aaacttgaga    120
attttcagat gagtggcgac tttccagtcc ttgcggtttt gtcaccttag tcagctagta    180
aggaggccgt gtgggttaga gtggctacaa tcctcaaagg gcacttctag aacccacggt    240 gaatttttt tggcatgata aatcggtaga atcggtgaag taattaccca aaaaaggatc     300
gggattgtgt ttctcgtaat tccgtattat tgccgatggc atcgactact tcttttttca    360
gaaaccccaa caagggtcta ttgtaattgt atataaacct ttttgtaatg gatatataca    420
tgtggtacta tttctcctca tcctgctcca tcgaaaatcc tcatacgaag agttaggaaa    480
gcaaagaaaa caacaaaaac                                                500

<210> SEQ ID NO 12
<211> LENGTH: 412
<212> TYPE: DNA
<213> ORGANISM: Saccharomyces cerevisiae

<400> SEQUENCE: 12
agacacaatg cgaaaaatcg cgcagggaca taattttgt tttcattatt ctttcgctta     60
ttccctccgt tagctccacc gcttttttga ttggaatttc ctttcggcaa tggctttccg    120
gttaccacgc ctcgggtttc gcatcccgaa aagcatatct acacaagaaa aatgaatgat    180
aaacaattga tgagtggcgc tatttccctt atcatctcat tattgtactt agtatcgtct    240
attatcagga gaaatcgcat gaactaagcc catttctca cccttctgcc ttcttatata     300
aagcttgctg ggaaccgaac acaaactcca caagtccgta gcagctcttc tcttttgtct    360
tttatatatc ataaacatcg ctacatagta ataacactaa cgcacgctag aa             412

<210> SEQ ID NO 13
<211> LENGTH: 500
<212> TYPE: DNA
<213> ORGANISM: Saccharomyces cerevisiae

<400> SEQUENCE: 13
aggggtagcg gcttttttcat caactcgatt attacccttt agagaccttc cctaaagtga    60
gcggcaatta tttccggatg ttagtagggt aatatggtta cggatttgtg acacaaaagg   120
gcttttcaac agtcggtctg ggttgaagga ttttcaggat gacgaagctt tcaataagag   180
ggactggact gttaacgcgg ggaattatag gttactttcc ttgatctggc tctggctctg   240
gctctgattt tggctcttgt actcctcgga cttcttgact tgtaacgaaa tacgtctttt   300
gtccttctct tcttcttcca tagtagggc gaatgagggg agcatagtgg atccttctaa    360
ccatctagaa tggggtggac aacatataaa agaagagcaa tcttgcagcg cagtcatatt   420
```

| tatgctaagt atatcattat ttcttgctag cgtaagtcat aaaaaatagg aaataatcac | 480 |
| atatatacaa gaaattaaat | 500 |

<210> SEQ ID NO 14
<211> LENGTH: 500
<212> TYPE: DNA
<213> ORGANISM: Saccharomyces cerevisiae

<400> SEQUENCE: 14

| agcctagtcc cggtaaaccg caaacggacc ttaattgtga cgaagggccc aaatttgatg | 60 |
| ggtcggtgtt aatgattagt cctcattgtc ataataaagt gtgatgatgg aggcaatgat | 120 |
| gatatacggt agtactactg ctcgaggtgc tatcttttaa ccaatccttt gagattcttg | 180 |
| tcgccacgga gttactacct tttacaaacc gtaatgtcac attttgcata tatcttatgt | 240 |
| ataaatatat agttcactta ctacttgttc tcgttttgtt aactttcttg ttgtagttct | 300 |
| tcttgttctt ggcgtttccc cctttgtttt ctatctgctt cataagtaaa gtgcaaagca | 360 |
| ttttggaaga tattatcaat tgagtcattg aaagaaactt ggcatcttcc ctattactaa | 420 |
| aactaagaat acttgattca agaaagaagt ttatattagt tttagccgta agataacata | 480 |
| acaaagaaga agaaagaaaa | 500 |

<210> SEQ ID NO 15
<211> LENGTH: 500
<212> TYPE: DNA
<213> ORGANISM: Saccharomyces cerevisiae

<400> SEQUENCE: 15

| tcgatcagct ccaattaaat gaagactatt cgccgtaccg ttcccagatg ggtgcgaaag | 60 |
| tcagtgatcg aggaagttat tgagcgcgcg gcttgaaact atttctccat ctcagagccg | 120 |
| ccaagcctac cattattctc caccaggaag ttagtttgta agcttctgca caccatccgg | 180 |
| acgtccataa ttcttcactt aacggtcttt tgccccccct tctactataa tgcattagaa | 240 |
| cgttacctgg tcatttggat ggagatctaa gtaacactta ctatctccta tggtactatc | 300 |
| ctttaccaaa aaaaaaaaaa aaaaaaaaa aaaaaaatc agcaaagtga agtaccctct | 360 |
| tgatgtataa atacattgca catcattgtt gagaaatagt tttggaagtt gtctagtcct | 420 |
| tctcccttag atctaaaagg aagaagagta acagtttcaa aagttttttcc tcaaagagat | 480 |
| taaatactgc tactgaaaat | 500 |

<210> SEQ ID NO 16
<211> LENGTH: 500
<212> TYPE: DNA
<213> ORGANISM: Saccharomyces cerevisiae

<400> SEQUENCE: 16

| acatagtact gtacgattac tgtacgatta atctatccac ttcagatgtt caacaattcc | 60 |
| ttttggcatt acgtattaat acttcatagg atcggcaccc tcccttaagc ctcccctaaa | 120 |
| tgctttcggt acccctttaa gacaactatc tcttaacctt ctgtatttac ttgcatgtta | 180 |
| cgttgagtct cattggaggt ttgcatcata tgtttaggtt ttttttggaaa cgtggacggc | 240 |
| tcatagtgat tggtaaatgg gagttacgaa taaacgtatc ttaaagggag cggtatgtaa | 300 |
| aatggataga tgatcatgaa tacagtacga ggtgtaaaga atgatgggac tgagagggca | 360 |
| attatcatcc ctcagaatca acatcacaaa catatataaa gctcccaatt ctgccccaaa | 420 |

```
gttttgtccc taggcatttt taatctttgt atctgtgctc tttactttag tagaaaggta    480
tataaaaaag tatagtcaag                                                 500

<210> SEQ ID NO 17
<211> LENGTH: 488
<212> TYPE: DNA
<213> ORGANISM: Saccharomyces cerevisiae

<400> SEQUENCE: 17
aagttcttga ctacccctat ctcacactag tacgtaattc aatgtatcat tcgtattgta    60
agtagataga gacgcaatac aggaaagctg accttccttc caatcaccac ggctgaaatg    120
ctttgttgac caattacgga cgcttaagag cggacgcggc tggaacggct ccatcctaaa    180
tcggcggagg gagaactccg ataccagccg acatggcaat aatagtgaca gtagatgcta    240
ccagccccgc aataatttca cagtagatca tcaacagtct cctcatttct ggaaatgatc    300
agcaacttcg acggatttaa ctctcaagca gttacgcact ccgagaacag ccgtgatcat    360
ctttgaacaa gcaaaatata taagcagga gaactgtcct acctagagct agaatagcca     420
taactaacta tgtaacattc tacagatcaa tcaaaaacaa tcttcaatca cagaaaaaaa    480
taaaaggc                                                             488

<210> SEQ ID NO 18
<211> LENGTH: 329
<212> TYPE: DNA
<213> ORGANISM: Saccharomyces cerevisiae

<400> SEQUENCE: 18
ttttctagtt cttcttctgc aatattgcct tttgggaaga aggatcgaaa gtagccattt    60
gcagacacgt ttttactata tttactgtat cttcgattgc gcggctaaag ttgccatatt    120
attattatat tgcagctcaa ccccgcattt ccggagtttt ctttttttt atttggggta     180 atttggaggt cggcggctat tggtgggccg gaaatggtga cacacttgta atatataagg    240
aggaaatcct acatgtgtat aagcgaaatc acaaggataa taatgtattg ctaaacaccc    300
tcaagaaaga aaataatcat aacgaaatc                                      329

<210> SEQ ID NO 19
<211> LENGTH: 500
<212> TYPE: DNA
<213> ORGANISM: Saccharomyces cerevisiae

<400> SEQUENCE: 19
cggatggaat cgccgctttt gaattcacct ccggggtatt attattattc ttagtagtcg    60
cggtcgtgcg gacacccgga gttatgcggg cccgaaagct cattatgtag taaagctagg    120
taatgttaag ggcgtaagag ccaacgcaag gcagcaatag cctggtattc ccacatatca    180
agaaagctta aaaagttgag acagggaatt tgaaggcgaa gattgccgaa ctggccaata    240
cccactactt ttttttttggt ttgcttggtt tcttcctgtc gcttgccaac ttgtggcatc    300
ttccccacac tatattataa ggatcgtcct atgtataggc aatattatcc atttcactcg    360
ctaacaaatg tacgtatata tatggagcaa caagtagtgc aattacagac gtgtattttg    420
tcttgatctt gcttttttgta tgataggcct aagaataaca gtgcgaacat ataagaaaca    480
tccctcatac taccacacat                                                500

<210> SEQ ID NO 20
<211> LENGTH: 442
```

<212> TYPE: DNA
<213> ORGANISM: Saccharomyces cerevisiae

<400> SEQUENCE: 20

```
agacctttt  tttctttttc  tgcttttcg   tcatccccac  gttgtgccat  taatttgtta    60
gtgggcccct  aaatgtcgaa  atattgctaa  aaattggccc  gagtcattga  aaggctttaa   120
gaatataccg  tacaaaggag  tttatgtaat  cttaataaat  tgcatatgac  aatgcagcac   180
gtgggagaca  aatagtaata  atactaatct  atcaatacta  gatgtcacag  ccactttgga   240
tccttctatt  atgtaaatca  ttagattaac  tcagtcaata  gcagattttt  tttacaatgt   300
ctactgggtg  gacatctcca  aacaattcat  gtcactaagc  ccggttttcg  atatgaagaa   360
aattatatat  aaacctgctg  aagatgatct  ttacattgag  gttatttac   atgaattgtc   420
atagaatgag  tgacatagat  ca                                               442
```

<210> SEQ ID NO 21
<211> LENGTH: 500
<212> TYPE: DNA
<213> ORGANISM: Saccharomyces cerevisiae

<400> SEQUENCE: 21

```
tccgaagagc  gtgctaccaa  ttcttcatct  cgttaacaaa  ctggttctcc  gttaaaaatt    60
gtgctatatg  tcctataagc  caactctatc  tatatctttt  cttttagtcc  tactttggat   120
actgttacca  ccattttaga  ttgcttttc   ttttgccgct  agccttacaa  tatttggcaa   180
acttttttt   tttagccgcc  gagactcttg  atctatggcc  gggcgaaagg  gcaaatgact   240
gcttatcccc  gccatcactt  ccccccgccc  aagggtttag  aattggggat  taagtaaaaa   300
cgaatgacta  ttcctctcaa  agtcatcctt  gttcgacaaa  aagaatggaa  tataacatat   360
tggaacaatt  tcatcctctt  ttccccattt  tcgcatataa  gagcaactaa  acgccggtga   420
gtaaagtgcc  cttccctaca  gactctttta  ctcaggtata  tatatatata  tatcccttaa   480
aaactaaaaa  gaaagcactc                                                   500
```

<210> SEQ ID NO 22
<211> LENGTH: 310
<212> TYPE: DNA
<213> ORGANISM: Saccharomyces cerevisiae

<400> SEQUENCE: 22

```
agcggttgtt  ctaaccacta  tttaaagccg  caattagtaa  tgcaaaaagt  tggccggaat    60
tagccgcgca  agttggtggg  gtcccttaat  ccgaaaaagg  acggctttaa  caatataaa    120
ctccgaaaat  ccccacagtg  acagaattgg  agaaacaacc  agttttgata  tcgccataca   180
tataaagaga  tgtagaaagc  attcttcact  gtaatgtcca  aatcgtacat  ttgaatttct   240
tgtaggttta  tttaaaaggt  aagttaaata  aatataatag  tacttacaaa  taaatttgga   300
accctagaag                                                               310
```

<210> SEQ ID NO 23
<211> LENGTH: 340
<212> TYPE: DNA
<213> ORGANISM: Saccharomyces cerevisiae

<400> SEQUENCE: 23

```
aatttttatt  ttctccttcc  atatgagcga  cagcggttac  tagccgctgt  cctcaggtta    60
atgatccaag  tccgagatcc  gggccgaata  tgcttgcggg  gaaagaaata  aaagtgcatt   120
```

```
ggagaagaaa aggatatgct cttcaattag aagcgccgaa acactaacat catgctagcg    180
atatcatacg tacactatat aatgtaaaaa atgggcttaa gaataactct cttatttctt    240
aacttttgtt gcggttgaag agcttataaa agtactagtg gcctaaagaa gctacagcgc    300
cgataataat atcgatttcg acttttctag tatttcgccg                          340
```

<210> SEQ ID NO 24
<211> LENGTH: 500
<212> TYPE: DNA
<213> ORGANISM: Saccharomyces cerevisiae

<400> SEQUENCE: 24

```
tgtgcacata cgtccagaat gatatcaaga taaatggcac gtgtatgtac ggctgtgtaa     60
atatgataat catctcggac gaacggcgta gcactctcca tcccctaaaa atgttcacgt    120
gtgactgctc catttcgccg gatgtcgaga tgaccccccc ccctcaaaag gcactcacct    180
gttgacatgc cgtggcaaat gattgggggtc atcctttttt tctgttatct ctaagatcca    240
aagaaaagta aaaaaaaaag gttggggtac gaattgccgc cgagcctccg atgccattat    300
tcaatgggta ttgcagttgg ggtacagttc ctcggtggca aatagttctc ccttcatttt    360
gtatataaac tgggcggcta ttctaagcat atttctccct taggttatct ggtagtacgt    420
tatatcttgt tcttatattt tctatctata agcaaaacca acatatcaa aactactaga      480 aagacattgc ccactgtgct                                                500
```

<210> SEQ ID NO 25
<211> LENGTH: 500
<212> TYPE: DNA
<213> ORGANISM: Saccharomyces cerevisiae

<400> SEQUENCE: 25

```
aatataaata aaattccata cagcatgtct aatcatagct aatttataca tattcatcat     60
gaaaacatat aggggaaaat atggtcggtt aacacaccta tcaaaaaatt attcagcaat    120
tccaatctcg ttagtaaaat atattcttat tttttttttt tttctctgat tgtattattt    180
ctggagtttt gacttatttt tttaccacat cgcgcttttc gtccccaatc tctctgatat    240
atgatgctgt ctataggtag ccacttcccc gatgtcggac ctcgggccgt ttacaaactt    300
tattgagatg accttatttc tccacattct agtcattcaa cttttaccct catatgttta    360
ccttcactaa tgtgaaagca tgaccaaaga aagtgtataa ggtatataaa tctgccataa    420
tgtatgtata acttattagg actttctcaa atagtatttt ggtattttct actgttctct    480
gatgatcgag agcaaacaga                                                500
```

<210> SEQ ID NO 26
<211> LENGTH: 500
<212> TYPE: DNA
<213> ORGANISM: Saccharomyces cerevisiae

<400> SEQUENCE: 26

```
aagtacgata tggtataact gtaacattga aggactgaag gactgaagga ctgaaggact     60
atagtcaagg gccaatgggg aaggtcccctt ccaggccatt tgcccgatag tttgtccttc    120
tcttgctttt ccgacggccc gattgcatgt ggcggggcag cactggataa aaaaacgtgg    180
ggggagtgat taaatttata cgcttattgt gtcaacacgg aaaccttata gttatcatta    240
ctaacatcgc aacaagctgc ttttttactc gttttttagcc acaccatacc cccttttaatt    300 aactaataat gcataaaata gttattgctt cttgagttgc agcttcttcc tggacgtact    360
```

```
gttatatatg gcatgtcttc gcatgtccgt caaatttagc gttgtctcga aacttaggct   420
gtcgttcttg ctgtctgtct tctgataaaa taatatattg gaataagaaa aaaaaaatag   480
gaacaagaaa gtgtgtgaga                                                500
```

<210> SEQ ID NO 27
<211> LENGTH: 304
<212> TYPE: DNA
<213> ORGANISM: Saccharomyces cerevisiae

<400> SEQUENCE: 27

```
atattattca gttgaaagac aaaaaaacat aaatatttct atgagcaaac aatttgaaca    60
gaaaataaaa attggggaag tgacacacca tggtagcggt tctaaagcga aatcggcaaa   120
gcggctaaat agcagttttg atgacttact ccacactgaa aatggatgac cttaaatagg   180
agataaagct ttttcatccc tatgtattta agatgactgg cttgtcaagc attctaatca   240
taaaaaaaag atcgtatttg atcaagaatt tatacataga cgccgctaaa taattgaata   300
caaa                                                                304
```

<210> SEQ ID NO 28
<211> LENGTH: 500
<212> TYPE: DNA
<213> ORGANISM: Saccharomyces cerevisiae

<400> SEQUENCE: 28

```
ctcgtttgcc gttacattgc attgatggta caataaaggg catgctttat atcgagatgt    60
ttcagtgtat atgaggggaa acagaaaaga gtcattcctg ccatttttttg gtcactgctt   120 tttctgctat gagtaatggt gaagttcctt gtggctacac gcttaatgtc atcgggttac   180
tgctcctaat atccgcatat aagctttatg cagggatcag ttgggcggct atttatctac   240
acccagtcat ccggcgtgac tggatctcca cttgccgcaa taagtcggtg acaaatgga    300 gatttaagag taaagatgca tgatggtata attcctttag tcgaaataga tatatttcaa   360
gcgcatatat aggcagacgc ttgtactgta gaaatagccg atattcaatt gcgctctatg   420
tgtgttttta ttccaggttt tccttggatt ctacgtattg tacgactttc ttatcctcca   480
caaacgtcat cgtgtcagta                                                500
```

<210> SEQ ID NO 29
<211> LENGTH: 500
<212> TYPE: DNA
<213> ORGANISM: Saccharomyces cerevisiae

<400> SEQUENCE: 29

```
cccaacagat ttcaagtctg tcgccttaac cactcggcca tagtgcctaa acaatgtag     60 gttatttaag caagtattgt agatactttt cgtaataaac tacaatgcac ccacgactcg   120
cggtgtaatg atggcatgaa atcattgaac gaagttttgc ggctatacgg ctgaaggacg   180
agactaaagg gacaggaatt attaatgcgg ggtataattt gaatagtatt aacgggcact   240
gccgtttagc catcaaatgc tattgttggg gtattctctc tacttttttgt tcttggcttg   300 aacctttttcg gcggttggca atcgtccgta tataagcatc ggctgtccca atcctctatt   360
gcccttttcc cttgcacctc cttctcaatt cttcgtatct ttcgcgtaaa ggtagatctt   420
gattcaccta tctgtcgaaa cacgattaag tgcaaacgaa acaacgtaca gtatataaca   480
aagtatttta aataataaga                                                500
```

<210> SEQ ID NO 30
<211> LENGTH: 500
<212> TYPE: DNA
<213> ORGANISM: Saccharomyces cerevisiae

<400> SEQUENCE: 30

| gctatgacgt | ttgggtggcc | tagccggttc | gcgtgtgcct | gtcgcttttg | tcgcttttca | 60 |
| acttctgccc | gatatttcct | atcaaaggaa | aatgggacgt | tttcaacccc | tcgctatcat | 120 |
| cgtgcctgca | ctctgcctat | cgccaactac | accggggttt | tatctgcttc | acccctccat | 180 |
| ccagtgctga | taacaagaag | aaccttgcag | ggtagggcag | gacctacggc | caaaatacta | 240 |
| attatgtctg | tttatgtaca | tgccccaatc | tgaatattcc | atgaatgtag | gcacagcata | 300 |
| tctccatcca | tgtactgata | cagacgcata | aacatatatg | tatatacata | cttatacact | 360 |
| cgaatatttg | tagactgatg | tacttctata | tatatatagg | gggtttgtgt | tcctcttcct | 420 |
| ttcctttttt | tttctctctt | cccttccagt | ttcttttatt | ctttgctgtt | tcgaagaatc | 480 |
| acaccatcaa | tgaataaatc | | | | | 500 |

<210> SEQ ID NO 31
<211> LENGTH: 500
<212> TYPE: DNA
<213> ORGANISM: Saccharomyces cerevisiae

<400> SEQUENCE: 31

| tagatgcgcc | atctccgaga | aaaaatctag | acaataacag | cgacaattaa | cctaaagagg | 60 |
| atagaagatc | gagcaaaaaa | atttttttaa | tatggggtca | gtggcgatat | tatactatag | 120 |
| gagttaaaga | gtaagttgag | tgtaaggtgg | tagaattatg | attgaactcc | gaaactaagc | 180 |
| gccgattatg | ggtggcaaag | cggacagctt | ttgatatata | atcgatcgct | ctcgtagttg | 240 |
| atatcctctc | tcttgcttat | cttttcctgt | atatagtata | tgtgtacata | cagatacgaa | 300 |
| tatacctcag | ttagtttgtt | ttaacattaa | atattcaaca | gttgccagta | gcaaaaagaa | 360 |
| tatatccatt | catttcgagc | ttttttcgtct | cattactgat | atccaactaa | cagtctcctc | 420 |
| atagacggta | ccttactttc | ctttaatatt | ataatactag | tatagtcgca | catacttaac | 480 |
| tcgtctctct | ctaacacata | | | | | 500 |

<210> SEQ ID NO 32
<211> LENGTH: 500
<212> TYPE: DNA
<213> ORGANISM: Saccharomyces cerevisiae

<400> SEQUENCE: 32

| ctacgtcgcc | tgttcgagcg | gctctgttcg | ttgcatgaaa | ctaaaataag | cggaaagtgt | 60 |
| ccagccatcc | actacgtcag | aaagaaataa | tggttgtaca | ctgtttctcg | gctatatacc | 120 |
| gtttttggtt | ggttaatcct | cgccaggtgc | agctattgcg | cttggctgct | cgcgatagt | 180 |
| agtaatctga | gaaagtgcag | atcccggtaa | gggaaacact | tttggttcac | ctttgatagg | 240 |
| gctttcattg | gggcattcgt | aacaaaaagg | aagtagatag | agaaattgag | aaagcttaag | 300 |
| tgagatgttt | tagcttcaat | tttgtcccct | tcaacgctgc | ttggccttag | agggtcagaa | 360 |
| ttgcagttca | ggagtagtca | cactcatagt | atataaacaa | gcccttttatt | gattttgaat | 420 |
| aattattttg | tatacgtgtt | ctagcataca | agttagaata | aataaaaaat | agaaaaatag | 480 |
| aacatagaaa | gttttagacc | | | | | 500 |

<210> SEQ ID NO 33
<211> LENGTH: 500
<212> TYPE: DNA
<213> ORGANISM: Saccharomyces cerevisiae

<400> SEQUENCE: 33

```
gagctatagt cttttgcgct ttcaatacgt gtagcggtgt accaaaagtt gcacaaaaat      60
gtagttgtca atgaaagcgc actacgtata taatgactat ttttttttc ctgggttgca     120
tgggtaattt gttgttaata tgcgattttc ttggggaaaa gggtgtcata gcgccaaaaa     180
ctgccgtgcg gcacagtatg tatgtttttg agtcgcggcg tttaagggct tggcataaaa     240
agtggttcaa gcgagtgata agttgggcga atgtcgtctt ttttgtaacc atgtctttcc     300
tgaaaacaac ctgtaggcag ctccactcca cataagggct ttctccaatg gcaatgggag     360
ctcggaacac cggagtagaa atttttataa tgtgtattgt ataaaacttg cttgttatgc     420
agttttgtt ttttttgtta ctcttccgta gcacaataga catatattag cggcaaaatt     480
gtagtgttgc gattattgcc                                                 500
```

<210> SEQ ID NO 34
<211> LENGTH: 500
<212> TYPE: DNA
<213> ORGANISM: Saccharomyces cerevisiae

<400> SEQUENCE: 34

```
gtgtagtatt gatcttgttg gtattgctag aaatgcttca gcaatactgt ataaaatatg      60
gaaacgttgc catggcaaga caaaagaagt gatcttgagt gaaataatag agcccggatg     120
gccgggtaaa ttcaaccgct cgtaccgttt ataatacgca taaacgccga aaatgtctct     180
attttagtca ttccccagag tgcggtattg cgtacacctg tcatgcgttc cttagtgccg     240
atagatatac taatatcgat gcgtcacagt agcagatcat ctctgacact tgtttcccca     300
tttttttttt tcatttttta aagggtttct ctacagccta caggcctccc ctaataagtc     360
agcccctccc tttggagtgc gctgttgacc tgcgtatata agaggtatat cagtgccagt     420
aggtaaaccc atcttgcggg gattgtacca ggaacatagt agaaagacaa aaacaaccac     480
cgtacttgcc attcgtatag                                                 500
```

<210> SEQ ID NO 35
<211> LENGTH: 500
<212> TYPE: DNA
<213> ORGANISM: Saccharomyces cerevisiae

<400> SEQUENCE: 35

```
catcaattag ggcaaacttg aatagtcagc taggtcatat atttaaaatc aattagccct      60
atgactacat taggtttatt gttaggtctt tacggctgca tatttgcttt cgccgttcgg     120
cggggtcctg cgacgatttc tgcgcggtct tgtatgggtg gagttgacag ttaaccctcc     180
ggacccccta ccccggtgtg ccccggtcc atctatccat tttgcggtaa cccctttgcg     240
cgacagctgc ttatcaaggt acctggatcg agccataaaa attgatctac acagatgaga     300
tggggcattg ggatatatta ttagtcggag tatcattata gttattcagt tttatgcagg     360
ttactggcca aacgttttc ttcatttgga ataatcgttt aggagctact gttccggtat     420
aaagtaacaa gcacagtagc agagtaatac gcagtgacga taatagagac tagtaaaaca     480
gtcgagttgt cggacctaaa                                                 500
```

<210> SEQ ID NO 36

```
<211> LENGTH: 500
<212> TYPE: DNA
<213> ORGANISM: Saccharomyces paradoxus

<400> SEQUENCE: 36
tagtcttatc taaaaattgc ctttatagtc cgtctctcca gtcacggcct gtgtaactga      60
ttaatcctgc ctttctaatc accattctac tgtttaatta agggattttg tcttcatcaa     120
cggcttccgc ccaaaaaaaa gtatgacgtt ttgcccgcag gcgtgaagct gcccatcttc     180
acgggcctga cctcctctgc cggaacaccg gccatctcca actcataaat tggagaaata     240
agagaatttc agattttcag aggatgaaaa aaaaaaggta gagagcataa aaatgggggtt    300
cacttttttgg caaagttaca gtatgcttat tacatataaa tagagtgccg ataatggctt    360
tttttcatct tcgaaatacg cttgctactg ctcttccagc gttttttatta ccttctttctt   420
gtttctcctt agtatataaa atatcaagct acaacaagca tacaatcaac tgtcaactgt     480
caattatatt ataatacact                                                 500

<210> SEQ ID NO 37
<211> LENGTH: 496
<212> TYPE: DNA
<213> ORGANISM: Saccharomyces kudriavzevii

<400> SEQUENCE: 37
ctctcaaatc tttttagcgcc aaggactcca actaattgta tcttgaattt gccttttacga    60
tccgtttgtc cagtcacggc atgtatatct tattaatcct gcctttctaa tcacgtattc     120
taatgttcaa ttaagggatt ttatcttcat caacggctcc cacgcaaaaa atgacgtttt     180
gcacacagac acgaaaatacca ccttccaccg gaacaacggc catctccaac ttataagttg    240
gggaaataag acaatttcag acttcagaga atgaaaaaaa aaaaaggtac atcacagatg     300
gggttcaggt ttgctacaat tgcagggagc ctgtcacata taaatagacc tccagtgatg     360
atatctttca gtcttcaaac gtctcttgtc acagttctgg tcgttctata tcacatctct    420
cttggttcta cttattgtct ataatatcaa gctacagcaa gcatacaatc aactatctac     480
cataccataa tacaca                                                    496

<210> SEQ ID NO 38
<211> LENGTH: 441
<212> TYPE: DNA
<213> ORGANISM: Saccharomyces bayanus

<400> SEQUENCE: 38
gatccagttc tccagtgaca cagcctttat ctggtcaaac ctttctttct aatcacctat      60
gctgatgctt aattaaggga ttttgtctc catcaacggc atgcgcccaa aaatgacgtt     120
tttttaacc catagacacg aaactaccca ttttccaccg gcctgaccta ccaccggaac     180
aacggccatc tccaacttgc aagttgggga aattaagagc atcgcaggtt aatggaaga     240
aaaaaaaag gtacagcaca gcgcaaatgg agttagttcc cttatgtcac acactcacac     300
acagtcggtc agatcaagca tactgggtgc gtataaatag agtggccatt gccaccctgt     360
ttatctcaaa atctgtcttg ttagtggtct tctccctttt tcaggttaca attctcttgt     420
ttctacttag tatataagta t                                              441

<210> SEQ ID NO 39
<211> LENGTH: 480
<212> TYPE: DNA
<213> ORGANISM: Saccharomyces mikitae
```

<400> SEQUENCE: 39

```
tttcccaaaa agtattattt ttaagtgata attgataaaa ggggcaaaac gtagacgcaa        60
ataaaacgga aataatgatt ctcagacctt ttagcgtcaa gaactgcaac taatcttatc       120
ttaaaattat ctttataatc cgtttctccc gtcacagtct gtgtatctga ttaatcctgc       180
cttctaatc acctattcta atgttcaatt aagggatttt gtcttcacca acggcttcca       240
cccaaaagta aaaaatgacg ttgtacccac agacatcttc accggcctga cctgccaccg       300
gaacaacggc catctccaac tcataaattg gagaaataag agaatttcag attctggagg       360
atgaaaaaaa aaaggtaca gcataaatgg ggttttatgt gggtacaatt acactaggac       420
tatcacatat aaatagacgg gcaatgtagg ttcttttcca cccttgagac agagttattc       480
```

<210> SEQ ID NO 40
<211> LENGTH: 500
<212> TYPE: DNA
<213> ORGANISM: Saccharomyces castellii

<400> SEQUENCE: 40

```
tgtcgtggac gaaatacgcc acaattttgc cgagaaggtc attagtatgt ccaagaaacc        60
ctaggtgtaa agtcgggaaa tccgaatctc cgattttgga ggggcccatg ccctactttt       120
tttcgccagg ggtgaaattc caaacccgtg cgcgttcttg gaatttgaca gcgcattgag       180
tatgtgctgc gtattcccac tatcatgacg cgccctttat ctgggaaaaa tggaactgga       240
tgctgaaata tttcactctc agatcacata tcccaaatcc tgtgagtgaa ttgtttggtc       300
aggcgaccaa acaggaatat ggaatagatt ctattctctg gattctacaa ttatccattg       360
ttagcaaaac aaaaaaaact ggtggtatat atattcagag cctaaaattt aaaggttgga       420
tctcaattttt aaaagttttc attctgtttt gttttttgttt cttcttagct cacgaataac       480
caaacaaaaa acaatcaata                                                   500
```

<210> SEQ ID NO 41
<211> LENGTH: 500
<212> TYPE: DNA
<213> ORGANISM: Saccharomyces paradoxus

<400> SEQUENCE: 41

```
caataggaaa aaaccaagct tcctttcatc cggcacggct gtgttgtaca tatcactgaa        60
gctccgggta tttaagtta tacaagagaa atatgcgggc tagactagca agattctgga       120
ctgtataacg ttgtggatag gcggataaag ggcccaaaca ggattgtaaa gcttagacgc       180
ctctggttgg gcaatggcat gtttgtgtat taagtaagac ttggctgcgg gatagcaaaa       240
ctgagcagaa tatagaaggc cacaaaaaaa aggtatataa gggcagcaaa gtctttataa       300
tatatgtaga ttctcttctc tgtgtaattc attcttgtgc ttaccactca aatatacaga       360
agtaagacag ataaccaaca gcctttccca gatatacata tatctcattg tttcagttta       420
aacaataatc atatttgttt aactcaaaaa taaaaaaaaa ctaaactcac tcaatcaatc       480
attccataaa aaaaaacaat                                                   500
```

<210> SEQ ID NO 42
<211> LENGTH: 500
<212> TYPE: DNA
<213> ORGANISM: Saccharomyces kudriavzevii

<400> SEQUENCE: 42

```
cttcctttca tccggcacgg ctgtgtcccc acatctccct aaagctccgg gtattttaag      60
ttatacaagg gaaatatacg ggctggacta caacttgcag gttgcacagc gttatggata     120
ggcggataaa gggcccaagc aagatcgtga agcttggacg cgtctggttg gacaatggtg     180
actttttgtg tattagataa tgcttgactg gagaatatca ggactgagca gagttaggaa     240
gaccacaaaa aaggtatata agggcaacaa agtctccgtg atatggatag gctcttctct     300
ctggttacaa ttcattattt cagttgtttg ctagatatag agatataata catctaataa     360
acagtcactt ccagagatat atatatatac atatatctat ctcctcctcc cagcttaaat     420
aataactata tttgtttaac tcgaagaaaa aaaaaattca aatttactct atcaattcaa     480
ttacctcata aaaacaata                                                  500
```

<210> SEQ ID NO 43
<211> LENGTH: 500
<212> TYPE: DNA
<213> ORGANISM: Saccharomyces bayanus

<400> SEQUENCE: 43

```
cttcctttca tccggcacgg ctgtgtcccc acatctccct aaagctccgg gtattttaag      60
ttatacaagg gaaatatacg ggctggacta caacttgcag gttgcacagc gttatggata     120
ggcggataaa gggcccaagc aagatcgtga agcttggacg cgtctggttg gacaatggtg     180
actttttgtg tattagataa tgcttgactg gagaatatca ggactgagca gagttaggaa     240
gaccacaaaa aaggtatata agggcaacaa agtctccgtg atatggatag gctcttctct     300
ctggttacaa ttcattattt cagttgtttg ctagatatag agatataata catctaataa     360
acagtcactt ccagagatat atatatatac atatatctat ctcctcctcc cagcttaaat     420
aataactata tttgtttaac tcgaagaaaa aaaaaattca aatttactct atcaattcaa     480
ttacctcata aaaacaata                                                  500
```

<210> SEQ ID NO 44
<211> LENGTH: 500
<212> TYPE: DNA
<213> ORGANISM: Saccharomyces paradoxus

<400> SEQUENCE: 44

```
cgataccaca cggtccattg ggccggtggt gttagtcgac ggatatatgc atctgtcccc      60
tttcccggcg agccggcagt cgggccgagg ttcggataaa ttttttgcatt gtattagttt    120 ctgtcatgag tattacttat ggttccttta gagctaatca ttagctcggt accggctgtt    180
atgcaattta tgacttttct tctacagtgt cagccttgtg acgattatct atgaactttg    240
gatgtagcgc atcgagattc gtatctttca ttggatagta atgggaagg atcgatgacc     300 cttattacat tctttcctat acttaatatc catttaatct atcttcttga agtatataa      360 gtaacggtaa atttaccata cttatgctat tctcatttat cccctaattt tcttttaact    420
tctcgcccta cagtaactaa gaataacggc tactgtttcg aaattaagca aagtagtaaa    480
gcacataaaa gaataaagaa                                                 500
```

<210> SEQ ID NO 45
<211> LENGTH: 500
<212> TYPE: DNA
<213> ORGANISM: Saccharomyces kudriavzevii

<400> SEQUENCE: 45

```
agaccgaagc gggtaatgga cggaattaag caattgtccc ctctcccggg gagccgacag      60
```

```
tcggaccgag cttcggataa atttctgtat tgttttttgtt tccgtcatgg gtattatttt    120
cgggatcctt ttgccaaccc catagtcaat cgttaacatt taccggccaa tatgtaggat    180
tatgactatt ctcctgcatg atcagcggaa gtgacgatta tctattaatt ttgaacttct    240
acttcgtgat ccggaattta attggataat aatgtgtccg aaggatcgag tgacccttat    300
attctgtagt tttttgttac tggccatcca attcgtgttc ttggaagtat ataagttaca    360
gtcgattgac ctttctcaag ctattttcat ctttctccta catttacgtt tctcttcttc    420
aatacagcag ctagaagtta cgattactcc tgtgaagata aacaaagtaa tagtagccca    480
caaaaagaga gaaagtaaaa                                                500

<210> SEQ ID NO 46
<211> LENGTH: 500
<212> TYPE: DNA
<213> ORGANISM: Saccharomyces bayanus

<400> SEQUENCE: 46
gtagcagtcc ggaaataagc aaatgtcccc tttcccgagc taaccaacgg tcgggccgag     60
cctcggataa attttttgctt tgtttttgtt tctgtcatgg gtattataca tcatttattt    120
agttaacccc tagactaatt agccggccat tagtatgtaa gattatgact atagtttgta    180
ccggaaccct ggtagcaact actcatgaac tttgggctca gtatttcgca atcccggttt    240
taattggata gcctatcgcg aaggatcgat ggatgaccct tagaattgtc tcttttgtta    300
ctactcattc aatgcgtgtg ctcttgcaag tatataagtc actctaaatt agtttatact    360
tgagcttttt acatttctcc cttgattgtt tctttctctt ttccccttgt tctggtttat    420
tgtaatagct aagtgcaacg attaccgctg ttaagttaaa gaagagagac aagtaataat    480
agtacacagc aaggaaaaaa                                                500

<210> SEQ ID NO 47
<211> LENGTH: 500
<212> TYPE: DNA
<213> ORGANISM: Saccharomyces paradoxus

<400> SEQUENCE: 47
ttactaaata ggctggcatc agctaacccg gatggttgaa tccggctttt gctacttgtt     60
gtccgatgaa aaggagcggc ttcccttttg ccccagattt ccattcatcc gagaggtcgc    120
ttatcagact tcgtcatttc tcatttcatc cgagatgatc aaaattgaag ccaatcacca    180
caaaactaac acttaacgtc atgttacact acccttaca gaagaaaata tccatagtcc     240
ggactaacat tccagtatgt gactcaatat tggtgcaaat gagaaaatca tagcagtcag    300
cccaagtccg ccctttacca gggcaccgta attcacgaaa cgtttcttta ttatataaag    360
gagctacttt actagcaaaa ttcttgtaat tcctcttccc ttgctaactt cttcttgttt    420
tcttttcctt tttacacaca gatatataac aattgagaga aaaactctag tataacataa    480
caaaaaagtc aacgaaaaaa                                                500

<210> SEQ ID NO 48
<211> LENGTH: 500
<212> TYPE: DNA
<213> ORGANISM: Saccharomyces kudriavzevii

<400> SEQUENCE: 48
gttacggtgc cgcgccggtg gccggtggtc ttccggtaaa caaaaaaagc tgcctcccctt    60
```

```
tcgccccaga tttccattca tccgagggca ccgcttgtca gactttatcg ttttcctcat    120
ttcatccgag aagatcaatt caaaggcaat gaccacaaaa gcaactccta acgttgtgtt    180
acgctaccct ttacacaaaa tattcataac ccgtaatgaa tcctaaggta tgtgactcaa    240
ttttggtgta gaaaatgagg aaaacgtaat actaagttaa agctcgccct ttaaagtgaa    300
tattccttga ccatttgcgc aggcacaccc gaattcacaa acgtttcttt attatataaa    360
ggaccagctc tgctagtcaa atttttataa ctgcttgttc agttgctgct tctttcttgt    420
caatttattt cttgtactgt tcaactacat aaagcaaaga gaaaactctc agaataacat    480
aacaaagaag tcaacgaaaa                                                500

<210> SEQ ID NO 49
<211> LENGTH: 500
<212> TYPE: DNA
<213> ORGANISM: Saccharomyces bayanus

<400> SEQUENCE: 49
acgaggctcg gcgtttactg ctgaatttcc ggaaagaaag ggaaggttcc ctttacccca     60
gatttccatt catccgaagg actgcttatc agaatttgac attttctca ttttatccga    120 gaagatcaat ttaaggctag tgaccacaaa actaactctc atgctgcgct accgcaagtt    180
tcgctcacag aaagaaagca agcacccata gtccggacta catccttgta tgtgactcaa    240 attttggcg ttgccaatta aactgaagtg taaagattac ttcaagctca ccctttaaag    300
tagaattcct taacggtttt aaatagacac accgaaatta ataaacactt tctttattat    360
ataaaggaca gagtttatta ctggaattct cttaacgcct tcctccctta ctattgtatc    420
ttttcctttc acataatcgc tacataacta catagagaaa actctcagat taacacagta    480
acaacgaaga aaacaaaaaa                                                500

<210> SEQ ID NO 50
<211> LENGTH: 500
<212> TYPE: DNA
<213> ORGANISM: Saccharomyces cerevisiae

<400> SEQUENCE: 50
acagtttatt cctggcatcc actaaatata atggagcccg cttttttaagc tggcatccag     60 aaaaaaaaag aatcccagca ccaaaatatt gttttcttca ccaaccatca gttcataggt    120
ccattctctt agcgcaacta cagagaacag gggcacaaac aggcaaaaaa cgggcacaac    180
ctcaatggag tgatgcaacc tgcctggagt aaatgatgac acaaggcaat tgacccacgc    240
atgtatctat ctcattttct tacaccttct attaccttct gctctctctg atttggaaaa    300
agctgaaaaa aaaggttgaa accagttccc tgaaattatt cccctacttg actaataagt    360
atataaagac ggtaggtatt gattgtaatt ctgtaaatct atttcttaaa cttcttaaat    420 tctacttta tagttagtct tttttttagt tttaaaacac caagaactta gtttcgaata    480
aacacacata aacaaacaaa                                                500

<210> SEQ ID NO 51
<211> LENGTH: 412
<212> TYPE: DNA
<213> ORGANISM: Saccharomyces cerevisiae

<400> SEQUENCE: 51
atagcttcaa aatgtttcta ctccttttt actcttccag attttctcgg actccgcgca     60
tcgccgtacc acttcaaaac acccaagcac agcatactaa atttcccctc tttcttcctc    120
```

```
tagggtgtcg ttaattaccc gtactaaagg tttggaaaag aaaaaagaga ccgcctcgtt    180
tcttttcctt cgtcgaaaaa ggcaataaaa attttatca cgtttctttt tcttgaaaat    240
tttttttttt gatttttttc tctttcgatg acctcccatt gatatttaag ttaataaacg    300
gtcttcaatt tctcaagttt cagtttcatt tttcttgttc tattacaact ttttttactt    360
cttgctcatt agaaagaaag catagcaatc taatctaagt tttaattaca aa            412

<210> SEQ ID NO 52
<211> LENGTH: 500
<212> TYPE: DNA
<213> ORGANISM: Saccharomyces cerevisiae

<400> SEQUENCE: 52
tgggtcatta cgtaaataat gataggaatg ggattcttct attttccctt tttccattct     60
agcagccgtc gggaaaacgt ggcatcctct ctttcgggct caattggagt cacgctgccg    120
tgagcatcct ctctttccat atctaacaac tgagcacgta accaatggaa aagcatgagc    180
ttagcgttgc tccaaaaaag tattggatgg ttaataccat ttgtctgttc tcttctgact    240
ttgactcctc aaaaaaaaaa aatctacaat caacagatcg cttcaattac gccctcacaa    300
aaactttttt ccttcttctt cgcccacgtt aaattttatc cctcatgttg tctaacggat    360
ttctgcactt gatttattat aaaaagacaa agacataata cttctctatc aatttcagtt    420
attgttcttc cttgcgttat tcttctgttc ttcttttct tttgtcatat ataaccataa    480
ccaagtaata catattcaaa                                                500

<210> SEQ ID NO 53
<211> LENGTH: 800
<212> TYPE: DNA
<213> ORGANISM: Saccharomyces cerevisiae

<400> SEQUENCE: 53
catgcgactg ggtgagcata tgttccgctg atgtgatgtg caagataaac aagcaaggca     60
gaaactaact tcttcttcat gtaataaaca cccccgcgt ttatttacct atctctaaac    120
ttcaacacct tatatcataa ctaatatttc ttgagataag cacactgcac ccataccttc    180
cttaaaaacg tagcttccag ttttttggtgg ttccggcttc cttcccgatt ccgcccgcta    240
aacgcatatt tttgttgcct ggtggcattt gcaaaatgca taacctatgc atttaaaaga    300
ttatgtatgc tcttctgact tttcgtgtga tgaggctcgt ggaaaaaatg aataatttat    360
gaatttgaga acaattttgt gttgttacgg tattttacta tggaataatc aatcaattga    420 ggatttatg caaatatcgt ttgaatattt ttccgaccct ttgagtactt ttcttcataa    480
ttgcataata ttgtccgctg ccccttttttc tgttagacgg tgtcttgatc tacttgctat    540
cgttcaacac caccttattt tctaactatt ttttttttag ctcatttgaa tcagcttatg    600
gtgatggcac attttttgcat aaacctagct gtcctcgttg aacataggaa aaaaaaatat    660
ataaacaagg ctctttcact ctccttgcaa tcagatttgg gtttgttccc tttattttca    720
tatttcttgt catattcctt tctcaattat tatttctac tcataaccctc acgcaaaata    780 acacagtcaa atcaatcaaa                                                800

<210> SEQ ID NO 54
<211> LENGTH: 430
<212> TYPE: DNA
<213> ORGANISM: Saccharomyces cerevisiae
```

<400> SEQUENCE: 54

```
tatatctagg aacccatcag gttggtggaa gattacccgt tctaagactt ttcagcttcc     60
tctattgatg ttacacctgg acaccccttt tctggcatcc agttttaat cttcagtggc    120
atgtgagatt ctccgaaatt aattaaagca atcacacaat tctctcggat accacctcgg   180
ttgaaactga caggtggttt gttacgcatg ctaatgcaaa ggagcctata tacctttggc   240
tcggctgctg taacagggaa tataaagggc agcataattt aggagtttag tgaacttgca   300
acatttacta ttttcccttc ttacgtaaat attttctttt taattctaa atcaatcttt    360
ttcaattttt tgtttgtatt cttttcttgc ttaaatctat aactacaaaa aacacataca   420
taaactaaaa                                                          430
```

<210> SEQ ID NO 55
<211> LENGTH: 466
<212> TYPE: DNA
<213> ORGANISM: Saccharomyces cerevisiae

<400> SEQUENCE: 55

```
gcggatctct tatgtcttta cgatttatag ttttcattat caagtatgcc tatattagta     60
tatagcatct ttagatgaca gtgttcgaag tttcacgaat aaaagataat attctacttt   120
ttgctcccac cgcgtttgct agcacgagtg aacaccatcc ctcgcctgtg agttgtaccc   180
attcctctaa actgtagaca tggtagcttc agcagtgttc gttatgtacg catcctcca    240
acaaacagtc ggttatagtt tgtcctgctc ctctgaatcg tctccctcga tatttctcat   300
tttccttcgc atgccagcat tgaaatgatc gaagttcaat gatgaaacgg taattcttct   360
gtcatttact catctcatct catcaagtta taattctac tacgatgta attttttcact    420
tttcgtcttg acgtccaccc tataatttca attattgaac cctcac                  466
```

<210> SEQ ID NO 56
<211> LENGTH: 382
<212> TYPE: DNA
<213> ORGANISM: Saccharomyces cerevisiae

<400> SEQUENCE: 56

```
acaaatcgct cttaaatata tacctaaaga acattaaagc tatattataa gcaaagatac     60
gtaaattttg cttatattat tatacacata tcatatttct atattttaa gatttggtta    120
tataatgtac gtaatgcaaa ggaaataaat tttatacatt attgaacagc gtccaagtaa   180
ctacattatg tgcactaata gtttagcgtc gtgaagactt tattgtgtcg cgaaaagtaa   240
aaatttaaaa aattagagca ccttgaactt gcgaaaaagg ttctcatcaa ctgtttaaaa   300
ggaggatatc aggtcctatt tctgacaaac aatatacaaa tttagtttca aagatgaatc   360
agtgcgcgaa ggacataact ca                                            382
```

<210> SEQ ID NO 57
<211> LENGTH: 400
<212> TYPE: DNA
<213> ORGANISM: Saccharomyces cerevisiae

<400> SEQUENCE: 57

```
agtgctttta actaagaatt attagtcttt tctgcttatt ttttcatcat agtttagaac     60
actttatatt aacgaatagt ttatgaatct atttaggttt aaaaattgat acagttttat   120
aagttacttt ttcaaagact cgtgctgtct attgcataat gcactggaag gggaaaaaaa   180
aggtgcacac gcgtggcttt ttcttgaatt tgcagtttga aaaataacta catggatgat   240
```

| | |
|---|---|
| aagaaaacat ggagtacagt cactttgaga accttcaatc agctggtaac gtcttcgtta | 300 |
| attggatact caaaaaagat ggatagcatg aatcacaaga tggaaggaaa tgcgggccac | 360 |
| gaccacagtg atatgcatat gggagatgga gatgatacct | 400 |

<210> SEQ ID NO 58
<211> LENGTH: 500
<212> TYPE: DNA
<213> ORGANISM: Saccharomyces cerevisiae

<400> SEQUENCE: 58

| | |
|---|---|
| ggagattgat aagacttttc tagttgcata tcttttatat ttaaatctta tctattagtt | 60 |
| aattttttgt aatttatcct tatatatagt ctggttattc taaatatca tttcagtatc | 120 |
| taaaaattcc cctctttttt cagttatatc ttaacaggcg acagtccaaa tgttgattta | 180 |
| tcccagtccg attcatcagg gttgtgaagc attttgtcaa tggtcgaaat cacatcagta | 240 |
| atagtgcctc ttacttgcct catagaattt ctttctctta acgtcaccgt ttggtctttt | 300 |
| atagtttcga aatctatggt gataccaaat ggtgttccca attcatcgtt acgggcgtat | 360 |
| ttttaccaa ttgaagtatt ggaatcgtca attttaaagt atatctctct tttacgtaaa | 420 |
| gcctgcgaga tcctcttaag tatagcgggg aagccatcgt tattcgatat tgtcgtaaca | 480 |
| aatactttga tcggcgctat | 500 |

<210> SEQ ID NO 59
<211> LENGTH: 1041
<212> TYPE: DNA
<213> ORGANISM: Aspergillus tubingensis

<400> SEQUENCE: 59

| | |
|---|---|
| atgctgggat tcccaatgtt caacccagct acgcctgatg tctggaagat gaataccect | 60 |
| tactttccat tgttacacc ggggttattt cctgcctcag cacccccatc gcccaccaac | 120 |
| gtagatgccg aagctgccag ttcccaacag tcggaagcaa gctatctgga taaggagaaa | 180 |
| attgttcgag ggccacttga ttatcttctc aaatccctg aaaagacat tcgtcggaaa | 240 |
| ttcattcacg cgttcaatga atggctgcgc attcctgagg acaagttgaa tattatcacg | 300 |
| gaaattgttg gattgcttca cacggcctcc cttctaatcg acgatattca ggacaattcc | 360 |
| aagcttcgac gcgggctccc agtggcccat agcatatttg gtattgcgca gacaattaac | 420 |
| tctgccaatt atgcgtactt tctagcccag gaaaggctcc gcgaactgaa tcatcctgaa | 480 |
| gcgtacgaaa tatacacaga ggaactgctt cgtctgcacc gcggtcaagg tatggacttg | 540 |
| tactggcggg actgcctaac ctgtcccaca gaggaggact atattgagat gatcgccaac | 600 |
| aagactggtg gctatttcg actggcgatt aagcttatgc agttggaaag cactttgtgc | 660 |
| agcaatgtca ttgaactagc agacttgttg ggcgtgatct ttcagattcg ggatgattac | 720 |
| caaaacttac agagtggact atacgccaag aacaagggat tttgcgagga tttgacggag | 780 |
| ggaaaatttt cctttctgat tatccacagt attaacagta acccgaacaa tcaccatctg | 840 |
| ctaaatatac tacggcagcg gagcgaggac gattcggtga agaagtatgc tgttgattat | 900 |
| atcgactcga cggggagttt tgactactgc cgggaacggc tcgcttcctt attggaagag | 960 |
| gcggatcaaa tggttaagaa gttggaaaat gagggggggac aatcaaaggg gatctacgat | 1020 |
| attctgagct ttctgtcgtg a | 1041 |

<210> SEQ ID NO 60

<211> LENGTH: 732
<212> TYPE: DNA
<213> ORGANISM: Aspergillus tubingensis

<400> SEQUENCE: 60

| | | | | | | |
|---|---|---|---|---|---|---|
| atggatgggt | tcgaccattc | tactgctcca | ccaggatata | acgagctaaa | atggctcgcc | 60 |
| gatatcttcg | tcatcggaat | ggctgttggc | tgggttgctc | actatatgga | gatgattcac | 120 |
| acgtcgttca | aggaccaaac | atactgcatg | accatcgggg | gcctttgcat | caattttgcc | 180 |
| tgggaaatca | tattctgcac | aatgtatcct | gccaaaggat | ttgtcgagcg | ggttgccttt | 240 |
| ctcatgggca | tttctctcga | ccttggggtt | atttacgcgg | gaatcaagaa | cgccccaaat | 300 |
| gaatggcacc | actctgcaat | ggtgagggac | catatgcccc | ttgtcttcgc | agcaacgaca | 360 |
| ctttgttgtc | tgagcggtca | tatggctctt | actgcccagg | ttggtcccgc | acaagcctat | 420 |
| acgtgggggg | caattgcatg | ccagctcttt | atcagcatag | ggaatgtgtt | tcaattgttg | 480 |
| agtcggggaa | acacacgagg | ggcgtcatgg | acgctatgga | cctccaggtt | ttttggatca | 540 |
| acatcagcca | ttggctttgc | tcttgttcga | tatattcgct | ggtgggaggc | cttttcttgg | 600 |
| ttgaactgcc | cgcttgtgat | atggtccgtg | gccatgttct | ttctgtttga | aacactctat | 660 |
| ggagccctat | tctattctgt | caagcgacaa | gaagggagat | cccagcgtgg | aatcaagcac | 720 |
| aaagagaggt | ag | | | | | 732 |

<210> SEQ ID NO 61
<211> LENGTH: 1008
<212> TYPE: DNA
<213> ORGANISM: Aspergillus tubingensis

<400> SEQUENCE: 61

| | | | | | | |
|---|---|---|---|---|---|---|
| atggcggcac | ttccggacgt | tgcctccatt | cccatccctc | tggtggcaac | cctaggcatt | 60 |
| gccctctaa | ttttctatct | cgtccttgat | agaattagcc | ccttgtggcc | aaattccaaa | 120 |
| gctttcctga | ttggcaagaa | gaaaccggag | accgtgacat | cgttcgagtg | cccatatgcc | 180 |
| tacatccgtc | agatctatgg | gaagtatcac | tgggagccat | tcgtacagaa | gctgtctccg | 240 |
| aggcttaagg | atgaggatcc | ggccaaatat | aagatggttc | tggagataat | ggatgcaatc | 300 |
| cacctgtgtc | tgatgctagt | tgacgatata | actgacaata | gcgactatcg | aaaaggcaag | 360 |
| ccagcagccc | accggatata | tggcccttca | gagacagcaa | atcgcgctta | ctaccgagtc | 420 |
| acccagattc | taaacaagac | cgtgcaaaag | ttccccaagc | tggccaagtt | cctgcttcag | 480 |
| aatctggaag | aaattctcga | aggccaagac | ctgtcactaa | tctggcgacg | ggatggactg | 540 |
| ggtagccttt | cgactgttcc | tgatgagcga | gttcagcct | atcgcaagat | ggcgtcattg | 600 |
| aaaactgggg | cgttattccg | gctgctgggg | caattggtga | tggaggacca | atcgatggac | 660 |
| gggacgatga | ctactcttgc | gtggtgctct | cagctgcaga | atgactgcaa | gaatgtctac | 720 |
| tcatctgaat | atgctaaggc | caaaggggcg | cttgccgaag | acctccgaaa | tcgagagctc | 780 |
| tcatttccaa | ttatcctcgc | gctggaagct | cctgaagggc | attgggtcgc | cagtgctttg | 840 |
| gagaccagct | caccgcgcaa | cattcgcaag | gcgcttgctg | tgattcagag | tgagagagtg | 900 |
| cgcaatgctt | gtttcaagga | gctcaagtcg | gcgagtgctt | cggtccagga | ctggttggct | 960 |
| atttggggac | ggaacgagaa | aatgaacttg | aagagccagc | agacgtag | | 1008 |

<210> SEQ ID NO 62
<211> LENGTH: 1416
<212> TYPE: DNA
<213> ORGANISM: Aspergillus tubingensis

<400> SEQUENCE: 62

```
atggccaatg cccagcaacc cccctttcgc atccttattg tgggcggttc tgtcgcaggc    60
ctcatccttg cgcactgtct cgaacgcgcc aatatagagt acctcatact cgaaaaagga   120
gaagatgttg ctccacaagt tggtgcctcg ataggtatca tgccaaatgg cggacggatc   180
ctcgagcaac tgggcctatt tggggagatt gagcgtgtga tcgagccgtt gcatcaggcg   240
aatatcagct atccagatgg gttctgcttt agtaacgtct atcctaaggt tcttggcgac   300
aggttcggat acccggttgc attcttggac cggcagaagt tcctgcagat tgcatatgag   360
gggctgagaa agaagcagaa tgttctcacc ggtaaagggg tagttggact gcgacagtcg   420
gatcaaggga ctgctgtttc tgtggctgac gggacagagt atgaggcgga tctcgtggtt   480
ggtgctgatg gagtacatag tcgggtgaga agtgagattt ggaagatggc ggaagagaat   540
cagcctgcat cagtttcgac acgtgaaaga agaagcatga ctgttgaata tgtctgcgtt   600
ttcgggattt catcagccat cccagggctc gagataagcg aacagatcaa cggtattttc   660
gaccatctat ccattctaac aatccatggc agacatggtc gcgtgttctg gttcgtgatc   720
cagaagctgg ataggaagta cgtctatcct gatgtcccgc gattctcaga cgaggatgcc   780
gtacagctct tcgatcgggt caaacacgtg cggttctgga aaaacatctg tgtggggac    840
ttgtggaaga acagagaggt gtcctcgatg acagcgctgg aggagggagt gttcgagaca   900
tggcatcatg ataggatggt tttgattgga gatagcgttc acaagatgac gcccaacttt   960
ggccaaggag ctaattcagc catcgaggat gctgccgcgc tctcttccct tctacatgat  1020
ctcgtcaacg cccgtggagt ttgcaagcca tcgaatgtcc agattcagca tctcctcaag  1080
cagtatcggg agacccgata cactcgcatg gtaggcatgt gtcgcaccgc ggcttcagtc  1140
tctcggattc aggcccgaga tggcatcctc aacaccgtct ttggacgata ttgggcacct  1200
tatgctggca acctgcctgc tgacctggca tcaaaagtga tggcagatgc agaggttgtt  1260
actttttctgc ccttgccagg gcgctcagga ccgggctggg agatgtacag acgaaagggg  1320
aagggagggc aggtgcaatg ggtgcttata atcttaagct tacttacgat tggtggattg  1380
tgcatctggc tacaaagcaa tgcgttgagt agataa                             1416
```

<210> SEQ ID NO 63
<211> LENGTH: 7050
<212> TYPE: DNA
<213> ORGANISM: Hypomyces subiculosis

<400> SEQUENCE: 63

```
atgccttcta ccagcaatcc atctcacgtc cctgtggcca tcatcggcct ggcatgccga    60
ttcccaggcg aggccacctc accatcaaaa ttctgggatc ttcttaagaa tggacgagat   120
gcctactcac caaataccga tcgatataac gctgatgcct tttaccatcc caaggcaagc   180
aaccgccaaa acgtgctggc aactaagggc ggccacttcc tcaaacagga cccatacgtt   240
tttgacgccg ctttctttaa catcacagcc gctgaggcca tctcctttga ccccaagcag   300
cgaattgcca tggaagttgt ctacgaggct ctagaaaatg ccggaaagac actacccaag   360
gtggcgggca cacaaactgc ttgctatatc ggctcttcca tgagtgatta ccgagacgct   420
gttgtgcgtg actttggaaa cagccccaag tatcatatcc tgggaacatg cgaggagatg   480
atttcaaatc gtgtgtccca tttcttggat attcacggcc ccagtgccac cattcataca   540
gcctgctcat caagtcttgt tgctacacac ttggcttgcc aaagtttgca atctggagag   600
```

```
tcagaaatgg ccatcgctgg tggtgttggt atgatcatca cccctgatgg taatatgcat    660
cttaacaact tgggattctt gaaccccgag ggccactccc ggtcatttga tgagaatgct    720
ggtggttacg gtcgtggtga gggttgcggt atcctcatcc tcaagcggct agacagagct    780
ctcgaagatg gtgattccat tcgcgccgtc attcgagcct ctggtgtcaa ctctgatggc    840
tggacacagg gtgtcaccat gccctccagc caagcccagt ctgcccttat caaatacgta    900
tacgaatcgc atggcctgga ttatggtgcg actcaatacg ttgaggctca cggtactggt    960
accaaagccg gtgatcccgc agagattggc gccctccacc gcacaattgg acagggcgcg   1020
tccaagtctc gaaggctttg gattggcagt gtcaagccaa acattggcca tcttgaagcc   1080
gccgccggtg tggctggtat cattaagggc gtcctgtcca tggaacacgg catgattcct   1140
ccaaacattt acttctccaa gcccaaccct gccatccctc ttgacgagtg gaacatggcc   1200
gtgcctacca agttgactcc ctggcccgcc agccaaactg gtcgccgtat gagtgtcagc   1260
ggtttcggta tgggtggtac caacggccac gtcgtccttg aggcctacaa gccccaagga   1320
aagctcacca acggccatac caacggcatc accaatggaa tccacaagac tcgccacagc   1380
ggcaagaggc ttttcgtcct cagcgcccag gatcaagctg gcttcaagcg tttgggtaac   1440
gccctggtgg agcatctcga tgccctgggc cctgccgctg ccacccctga gttcctcgcc   1500
aacctctccc acactcttgc cgttggcaga tctggcttgg cttggaggtc cagcatcatc   1560
gctgagagcg cccctgatct tcgggagaag ctggcaactg atccgggtga gggagccgct   1620
cgttcttcag gcagcgagcc ccgtattgga ttcgtcttca cgggtcaagg tgctcagtgg   1680
gcccgcatgg gcgttgagtt gttggagcgc cccgtcttca aggcttccgt gattaagtcc   1740
gcggagactt tgaaggagct cggctgtgaa tgggacccta tcgttgagct ttccaagcct   1800
caagctgagt ctcgacttgg tgttcctgaa atctcacagc ccatctgcac agtcctacaa   1860
gtcgccttgg ttgatgagtt gaagcactgg ggtgtatcac cttccaaggt ggtcggtcac   1920
tccagtggtg aaatcggtgc cgcatacagc attggcgctc tttctcaccg tgacgctgtc   1980
gccgctgctt acttcagggg caagtcttcc aacggagcca agaagcttgg tggtggtatg   2040
atggctgttg ggtgctctcg tgaggacgct gacaagctcc tctctgagac caagctcaag   2100
ggcggtgttg ctaccgtcgc atgtgtcaac tcccccctcca gcgtgaccat ctcaggcgat   2160
gccactgctc tcgaggaact ccgagttatt ctcgaggaga gagtgtgtt tgctcgaaga   2220 ctcaaggtcg acgttgccta ccactctgcc cacatgaacg ctgtctttgc cgaatactct   2280
gctgcgattg cccacattga gcccgctcag gcagttgaag gtggaccgat tatggtctcc   2340
agtgtcactg gtagcgaagt cgactctgag cttctcggcc cttactactg gacccgtaac   2400
ttgatctctc ccgtcttatt cgccgacgct gtcaaggaat tggttacccc tgctgatggc   2460
gacggccaaa acaccgtcga tctcctgatt gagattggtc tcacagcgc tcttggtggc   2520 cctgttgagc agattctgtc ccataacggc atcaagaatg ttgcttacag atctgctctt   2580
actcgtggcg agaacgctgt tgactgcagc ctcaagcttg ctggcgagct cttccttctc   2640
ggcgtgccct ttgagttgca aaaggccaac ggtgactctg ttctcgcat gctcactaac   2700 ctacctcctt atccttggaa ccactccaag tcattccgtg ccgactctcg tctccaccgt   2760
gagcatctgg agcagaaatt ccctactagg agtctcatcg gtgcacctgt ccccatgatg   2820
gcagagagcg agtacacatg gcgcaacttc atccgtctcg ctgacgagcc ttggctccgt   2880
ggtcacactg tcggtaccac cgttctgttt cctggtgccg gtatcgtgag catcatcttg   2940
gaagctgctc aacagctggt ggataccggc aagaccgttc ggggcttccg aatgcgcgat   3000
```

```
gtcaacctct tcgccgccat ggctctcccc gaggacctgg ctactgaggt tatcatccac   3060
atccgacctc accttatctc tactgttgga tcaaccgccc ccggtggatg gtgggagtgg   3120
actgtttcct cctgcgtcgg aactgaccag ctgcgagaca atgctcgcgg tctggtagcc   3180
attgactacg aagagagccg cagcgagcag atcaacgccg aggacaaagc gttggttgct   3240
tctcaggtcg cggactacca caagatcctc agcgaatgcc ctgagcatta tgctcatgac   3300
aagttctacc agcacatgac caaggcctct tggagctacg gcgagctctt ccagggtgtg   3360
gagaatgtcc gtcctggata cggaaagacc atctttgaca tcagagtcat tgacattggt   3420
gagacccttt gcaagggaca acttgagcga cctttcctca tcaacgctgc cactctcgat   3480
gctgtattcc agagctggct cggcagtacc tacaacaacg gtgctttcga gtttgacaag   3540
cccttcgttc ccacctctat tggcgagttg gaaatctctg tcaacattcc cggtgatggc   3600
gactacctca tgccaggcca ctgccgctct gagcgatacg gcttcaacga gttgtctgct   3660
gatattgcca tcttcgacaa ggatctgaag aatgtgttcc tttcagtgaa ggatttccga   3720
acttccgagc ttgatatgga ttccggcaag ggagacggag atgccgctca cgtcgaccct   3780
gccgatatca actcggaggt taagtggaac tacgctcttg gcctcctcaa gtccgaggaa   3840
atcaccgagc tggtcaccaa ggtcgccagc aatgacaagc tcgccgagct tctccgtctg   3900
acacttcaca caaccctgc tgccactgtc atcgagcttg tttctgatga gagcaagatc   3960
tctggcgcat cttctgccaa gctgtccaag ggccttatcc tccccagcca gatccgttac   4020
gtagttgtca accctgaggc agcggacgcc gactcttct tcaaattctt ctcccttggt    4080
gaggatggtg cccctgtcgc tgctgaaagg ggccccgccg aactgttgat cgcctccagc   4140
gaagtcactg acgcggctgt ccttgagcgc ctgattacct tggccaagcc tgatgccagc   4200
attcttgttg ctgtcaacaa caagactacc gccgctgccc tctcagccaa ggcgttccgt   4260
gttgtcacca gcatccagga cagcaagtcc attgctctct acactagcaa gaaggcgcct   4320
gccgccgaca cctccaagct cgaggccatc atcctcaagc caaccactgc tcaacctgcc   4380
gcccagaatt tcgcctccat cctccagaag gcactcgagc tccagggcta ctctgtcgtt   4440
tctcagccat ggggcaccga catcgacgtc aacgatgcca agggaaagac ctacatttct   4500
ctgttggagc ttgagcagcc tctgctcgac aacctctcca agtccgactt cgagaacctc   4560
cgcgcagtcg ttttgaactg cgagcgtctc ctgtgggtca cagcaggtga caacccatct   4620
ttcggcatgg ttgatggttt cgctcgctgc atcatgagcg aaattgccag caccaagttc   4680
caggtcctgc atttgagcgc tgcaactggt ctgaagtacg atcttctct cgccacccgc   4740 attctccagt cggatagcac cgacaacgag taccgggagg tcgatggtgc tctccaggtg   4800
gcccgtatct tcaagagcta caacgagaac gagagtctcc gccaccacct cgaggatacc   4860
accagcgttg tgactcttgc tgaccaggag gatgctctgc gcctcactat tggcaagcct   4920
ggtcttttgg atactttgaa gtttgtcccc gatgagcgta tgctcccacc tctccaggat   4980
cacgaggttg aaatccaggt caaggctact ggtctgaact tccgagacat catggcttgc   5040
atgggtctta ttcctgttcg atctctgggc caggaggcca gtggcatcgt cctcagaacc   5100
ggtgcgaagg ctaccaactt caagcctggc gaccgtgttt gcaccatgaa cgtcggaaca   5160
catgccacca agatccgagc cgactaccgt gtcatgacaa agatccccga ctccatgacc   5220
tttgaagaag ctgcctcggt tgctgttgtt cacaccaccg cctactacgc cttcatcacc   5280
atcgccaagc ttcgcaaggg ccagtccgtc ttgatccacg ccgccgctgg tggtgttggc   5340
```

| | |
|---|---|
| caagcagcca ttcagttggc caagcatctc ggcctcatca cctatgttac cgtaggtact | 5400 |
| gaagacaagc gccagctcat tcgggagcag tatggcattc ccgacgagca catcttcaac | 5460 |
| tcccgtgatg ccagcttcgt caagggtgtc cagcgtgtta ccaacggtcg cggtgtcgac | 5520 |
| tgcgttctca actctctatc cggtgagctc ctgcgtgctt cttggggatg ccttgctacc | 5580 |
| tttggtcatt tcatcgaaat tggtctccgt gatatcacca caacatgcg tcttgacatg | 5640 |
| cgacctttcc gcaagagcac ctccttcaca ttcatcaaca cccacactct cttcgaggaa | 5700 |
| gaccccgctg cgttgggaga tattctcaac gagtccttca agctcatgtt cgctggcgcc | 5760 |
| cttaccgctc ctagccccctt gaatgcctat cccattggcc aggtcgagga ggccttccga | 5820 |
| accatgcagc agggcaagca ccgcggtaag atggtgctgt ccttctccga tgacgcaaag | 5880 |
| gctcccgtgt tgcgcaaagc gaaggattcc ttgaaactgg accctgacgc cacttacctc | 5940 |
| tttgttggtg gtcttggtgg tctgggtcgc agtcttgcca aggagtttgt tgcgtctggc | 6000 |
| gcccgcaaca ttgccttctt atcccgatcc ggtgacacta ccgcccaggc caaggctatc | 6060 |
| gtggacgaat tggctggcca gggtatccag gtcaaggcct atcgtggtga tcgccagc | 6120 |
| gaggcatcct cctccaggc tatggagcaa tgctctcagg atctcccgcc cgtaaagggt | 6180 |
| gtgatccaga tggccatggt tctccgcgat atcgtctttg agaagatgtc gtacgatgag | 6240 |
| tggaccgtcc ccgttggccc caaggtccaa ggttcatgga acttgcacaa gtacttcagt | 6300 |
| catgagcgac ctcttgactt catggtcatc tgctcctcaa gctccggtat ctacggttat | 6360 |
| cccagtcagg ctcaatacgc cgctggcaac acttaccagg atgccttggc tcactaccgt | 6420 |
| cgctctcagg gcctgaacgc catctccgtc aacttgggta tcatgcgaga tgtcggtgtc | 6480 |
| ctggctgaga cgggtaccac tggtaacatc aagctctggg aagaggtctt gggcatccgc | 6540 |
| gagcctgcct tccacgctct catgaagagc ttgatcaacc atcagcagcg tgggtctggg | 6600 |
| gactacccgg cgcaggtctg cactggtctt ggtactgctg acattatggc tactcacggc | 6660 |
| ctggcccggc ccgagtattt caatgacccc cgtttggac cccttgccgt caccactgtc | 6720 |
| gcgaccgatg cttcagctga cggccagggc tctgctgtct cgctcgcctc taggctctcc | 6780 |
| aaggtttcca ccaaggatga agctgccgag atcattaccg atgctctggt caacaagacg | 6840 |
| gcagacatcc tgcagatgcc cccctctgaa gtcgaccccg gccgacctct gtaccgttat | 6900 |
| ggtgttgact cccttgtggc gcttgaggtg cgaaactgga tcacaaggga gatgaaggcg | 6960 |
| aacatggcgc tgctggagat tctggcagcc gtccccattg agagcttcgc tgtcaagatt | 7020 |
| gctgagaaga gcaagttggt tactgtttaa | 7050 |

<210> SEQ ID NO 64
<211> LENGTH: 6150
<212> TYPE: DNA
<213> ORGANISM: Hypomyces subiculosis

<400> SEQUENCE: 64

| | |
|---|---|
| atggtgactg taccacagac tatcctctac tttggagatc agacagactc ctgggttgat | 60 |
| tccctcgatc agctatacag acaagccgct acgataccat ggctacagac gtttctcgac | 120 |
| gaccttgtaa aggtcttcaa ggaagagtcc cggggcatgg atcatgcgtt acaagacagt | 180 |
| gttggtgaat actctacact actcgacttg gcggatagat accgccatgg caccgacgag | 240 |
| attggtatgg tgcgtgctgt cttgctacat gccgcgagag gaggcatgct attacaatgg | 300 |
| gtgaagaaag aatcacagct tgtggacctc aatggctcca agcctgaagc actcggtatc | 360 |
| tctggaggac tcaccaacct cgcagcactg gcgatatcca cagacttcga gtctctatat | 420 |

```
gacgcagtca ttgaggctgc gagaatattt gtcagattat gccgttttac ttcggtacga    480
tcaagagcta tggaggaccg acctggcgtt tggggctggg cagtgctggg aattacacca    540
gaggaactga gcaaagtgct tgagcagttc aatccagca tggggattcc tgccatcaag     600
agagctaagg ttggcgtaac aggagaccga tggagcaccg ttattgggcc accctcagtc    660
ttggacctat tcatccacca gtgtcccgct gtgcgcaacc tccccaagaa tgaattgagc    720
atccacgccc ttcagcacac agtcacagtc acagaggctg acctcgactt cattgtcggg    780
agtgctgagc ttcttagtca ccccattgtg ccagacttca agtctgggg aatggatgat     840 cctgtggcat cctaccagaa ctggggagaa atgctaagag caatcgtcac tcaagttttg    900
tccaagcctt tggacattac aaggtgatt gcgcaactca acactcacct cggccctcgt     960
catgtcgacg tccgagtcat cggacctagc agccacaccc cctacttggc gagttcgctc   1020
aaagctgctg gcagcaaggc tattttccag accgataaga ctcttgagca gttacagccg   1080
aagaaactcc ccccgggccg catcgccatt gtcggtatgg ctggccgtgg tcctggctgc   1140
gagaatgttg atgagttctg gacgtcatt atggcgaagc aggatcgttg tgaagagatt    1200
cccaaagatc gcttcgacat caatgagttc tactgtaccg agcacgggga gggttgcacc   1260
accaccacaa aatacggctg cttcatgaac aagcctggaa actttgactc ccgcttcttc   1320
cacgtgtcgc tcgtgaggc gctgttgatg gaccccggtc acaggcagtt catgatgagc    1380
acttatgaag ctcttgagac ggcaggatac tctgatggcc agactaggga cgttgatcct   1440
aataggatcg cggcgttcta tggccagtcc aacgatgatt ggcatatggt gagccattat   1500
accctgggtt gtgatgccta caccctgcag ggggcgcaaa gagccttcgg cgctggtcgc   1560
atcgccttcc acttcaagtg ggagggccca acatactcgc tcgattctgc atgtgcctcc   1620
acctcctctg ctattcacct ggcctgcgtg agtcttctat ccaaagatgt ggacatggct   1680
gttgtgggtg ctgccaacgt cgtcgggtat cctcactcct ggacaagtct tagcaagtct   1740
ggtgtcttgt ccgacactgg aaactgcaaa acctactgcg atgatgctga tggttactgc   1800
cgagcagact ttgtcggctc agttgtgctg aagcgtctcg aagatgctgt cgagcaaaac   1860
gacaacatct tggctgtcgt ggctggttca ggcagaaacc actccggcaa ctcttcatcc   1920
atcaccacgt cggatgccgg tgcccaggag agactgtttc acaagattat gcacagcgcc   1980
agagtctctc ctgatgagat ctcatatgtt gagatgcacg gcactggaac tcagattggc   2040
gatccggccg agatgagtgc tgttaccaat gtcttcagga agaggaaggc gaataacccc   2100
ctaactgttg gtgaatcaa agcgaacgtc gggcatgctg aagcttctgc tggcatggcc    2160
tccctgctca aatgcataca gatgttccag aaagatatta tgccccctca ggctcgaatg   2220
ccccatactc tcaacccaaa gtatccgagt ctttctgagc ttaacattca tatcccctcc   2280
gagccgaagg agttcaaggc tatcggcgag cggccacgac gcatcctcct taataacttt   2340
gacgcagcag gtggcaacgc ctctctcatt ctggaagact tccccctcca cgtcaaggaa   2400
aatgcggacc ccaggccaag ccatgtcatc gtttcctctg ccaaaacaca atcctcatat   2460
cacgcgaata agcgtaacct cctgaagtgg ctacgcaaga acaaagatgc taaactcgaa   2520
gatgttgcat acacaaccac cgcccgcaga atgcaccacc cctcagatt ctcttgcagt    2580 gcctccacaa cggaggagct catttccaag cttgaggcag acacggcaga tgcaactgcg   2640
tctcggggct cgcccgttgt cttcgtattc acgggacagg gctctcacta cgccggcatg   2700
ggtgccgagt tgtacaagac atgccctgct ttccgcgagg aagtcaacct ctgtgccagc   2760
```

```
atctctgagg agcacgggtt ccccccgtac gtggatatca tcaccaacaa agatgttgac   2820
ataaccacca aggacaccat gcagacacag ctcgctgttg tcacgctgga gatcgccctc   2880
gccgcattct ggaaggcgtc tggtatccag ccgtcagcag tcatgggtca ctccctgggc   2940
gagtatgtgg ctctccaggt cgcaggggtc ctatctctag ctgatctgct ctacctcgtc   3000
ggcaatcggg cccgtctcct gctggagcgc tgcgaagccg acacctgcgc tatgttggca   3060
gtatcaagct ctgctgcctc catccgcgag ctcatcgacc agcgcccgca gtcatccttc   3120
gagattgcat gcaagaatag ccccaatgcc acggttatca gcggcagcac tgatgagatt   3180
tctgagctcc agtcatcctt cacggcatca cgagccaggg ctctgtctgt gcccatggga   3240
tttcactcct tccagatgga tcccatgctc gaggattaca tcgttcttgc gggtggtgta   3300
acctactcgc caccaaagat tccagttgct tcaaccctgc tcgcttcgat tgtggagtct   3360
tcagggtct tcaacgcttc ctacctcggt cagcaaaccc gccaagctgt cgacttcgtc   3420
ggtgctcttg gcgccttgaa ggagaagttt gctgaccctc tctggctgga gatcggaccc   3480
agccaaatct gcagctcctt tgtccgggcg actctctcac cctcgccggg caaaatcttg   3540
tccactttgg aggcaaatac caaccctgg gcatccattt ccaagtgcct cgccggcgcg   3600
tacaaggatg gtgtcgcagt tgactggttg gcggtgcatg ctccattcaa gggcggcttg   3660
aagctcgtga agttgcccgc ctatgcatgg gacctcaagg acttctggat tgtctactct   3720
gaggccaaca aggctgctcg agctttggct cccgctccct cgttcgaaac acagaggatt   3780
tctacatgtg ctcaacagat tgttgaagaa tcatcatcac ccagcctcca tgtctctgcc   3840
cgagctgcta tctccgatcc tggcttcatg gccttggtcg acggtcatcg catgcgcgat   3900
gtgtccatct gccccggaag tgtcttctgc gaggcaggcc ttgccgtctc caagtacgca   3960
ctgaagtaca gtggccgaaa ggataccgtg gaaacaagac ttacaatcaa caacctgtct   4020
ctcaagcgcc cgctcacaaa gtctcttgta ggcaccgatg gcgagcttct caccacggtt   4080
gttgcagaca aggcctccag cgataccttg caggtttcat ggaaggcttc ttcctctcat   4140
gcatcatacg atcttggtag ctgcgagatc accatttgtg atgcccagac tcttcaaact   4200
agctggaaca gaagctcata cttcgtcaag gctcgtatga acgagttgat caagaatgtc   4260
aagagcggaa atggtcaccg catgctcccc agtatcctct acactctctt cgctagcaca   4320
gttgattatg accctacctt caagtctgtc aaggaggcct tcatctcaaa tgagtttgac   4380
gaagctgctg cggaggtggt gcttcagaag aacccggctg gaactcagtt ctttgcgtcc   4440
ccttactggg gtgagagcgt agttcatctt gccggtttcc tcgtgaactc caaccctgcc   4500
cgcaagactg cttctcagac gaccttcatg atgcagagtc ttgagagcgt cgagcagacc   4560
gctgatctcg aggctggacg cacttactac acctatgctc gcgttttgca tgaggaagaa   4620
gacacagtca gctgtgactt gttcgtcttc gactcggaga agatggtaat gcagtgctcg   4680
ggactctcat tccatgaggt cagcaacaat gttctggaca gacttcttgg aaaggcatca   4740
ccgcctgtga agcaagtttc ccaccagaag gcgccagtgc ttgtgcccgc agagtcaaaa   4800
ccggccctga agctgctgt cgaggcggct cccaaggcgc ctgagcctgt gaagacagag   4860
gtgaagaaga tctcttcgtc ggagagcgaa ttgttccaca ctattcttga agcatcgcc   4920
aaggagactg gcactcaggt ctctgacttc actgatgaca tggaactggc tgaacttggc   4980
gttgattcca tcatgggtat tgagatcgct gccggcgtca gcagcagaac cggcctcgat   5040
gttctcctcc cctcttttgt cgtagattat cccaccattg gagatctgcg aaacgaattt   5100
gcgcgctcct ctacatctac acctcccagc aagacctttt ccgagttctc catcgtcgat   5160
```

```
gccactccag agtctacgcg cagctcgagt cgagcgcctt ctgagaagaa ggagcctgct    5220
ccggcttcag agaagtctga ggagctggtg atcgttccgt ccgcggttgt cgaggattcc    5280
tctcccctcc ccagtgccag aatcaccttg atccagggtc gatcttcgag tggaaagcag    5340
cctttctact tgatcgccga tggagctggt agcattgcta cgtatatcca cctggctccc    5400
ttcaaggaca agagaccggt ttatggcatt gattcgcctt cctccgttg ccccagcagg     5460 ctgaccaccc aggtgggcat tgaaggcgtc gcaaagatca tctttgaggc gttgattaag    5520
tgccagcctg agggtcccct tgacttggga ggattctctg gcggagctat gctcagctat    5580
gaggtgtctc gccaactcgc tgccgccggt cgcgtcgtct ccagtcttct cctcatcgat    5640
atgtgttctc cccgtccttt gggtgttgag gacacaatcg aggtcggctg aaggtctac     5700 gagaccatcg cttcccaaga taagctctgg aacgcctcaa gtaaccccca gcagcatctc    5760
aaggccgtct cgcctgcgt cgcagcctac cacctcctc ccatgactcc cgctcaacga      5820
cccaagcgaa cagctatcat ctgggctaaa aagggcatgg tcgaccgttg ttctcgcgac    5880
gagaaggtga tgaagttcct ggccgacaag ggcatcccca ccgagtcgta cccagggttc    5940
atggaggacc ccaagctggg tgccgtggcg tggggccttc cgcacaagtc cgctgcggac    6000
ttgggaccca acggatggga caagttcctt ggcgagactc tgtgcctgtc tatcgattcg    6060
gaccacttgg atatgccgat gccggggcat gtgcacttgc ttcaggcggc gatggaggag    6120
tcgttcaaat atttcagcga ggcaaattag                                     6150
```

<210> SEQ ID NO 65
<211> LENGTH: 14802
<212> TYPE: DNA
<213> ORGANISM: Artificial Sequence
<220> FEATURE:
<223> OTHER INFORMATION: synthetic

<400> SEQUENCE: 65

```
tatctaaaaa ttgccttatg atccgtctct ccggttacag cctgtgtaac tgattaatcc      60
tgcctttcta atcaccattc taatgtttta attaagggat tttgtcttca ttaacggctt     120
tcgctcataa aaatgttatg acgttttgcc cgcaggcggg aaaccatcca cttcacgaga     180
ctgatctcct ctgccggaac accgggcatc tccaacttat aagttggaga ataagagaa      240 tttcagattg agagaatgaa aaaaaaaaaa aaaaaaaagg cagaggagag catagaaatg     300
gggttcactt tttggtaaag ctatagcatg cctatcacat ataaatagag tgccagtagc     360
gacttttttc acactcgaaa tactcttact actgctctct tgttgttttt atcacttctt     420
gtttcttctt ggtaaataga atatcaagct acaaaaagca tacaatcaac tatcaactat     480
taactatatc gtaatacaca atgctgggat tcccaatgtt caacccagct acgcctgatg     540
tctggaagat gaataccct tactttccat ttgttacacc ggggttattt cctgcctcag      600
cacccccatc gcccaccaac gtagatgccg aagctgccag ttcccaacag tcggaagcaa     660
gctatctgga taaggagaaa attgttcgag ggccacttga ttatcttctc aaatcccctg     720
gaaaagacat tcgtcggaaa ttcattcacg cgttcaatga atggctgcgc attcctgagg    780
acaagttgaa tattatcacg gaaattgttg gattgcttca cacggcctcc cttctaatcg    840
acgatattca ggacaattcc aagcttcgac gcggcctccc agtggcccat agcatatttg    900
gtattgcgca gacaattaac tctgccaatt atgcgtactt tctagcccag gaaaggctcc    960
gcgaactgaa tcatcctgaa gcgtacgaaa tatacacaga ggaactgctt cgtctgcacc   1020
```

```
gcggtcaagg tatggacttg tactggcggg actgcctaac ctgtcccaca gaggaggact   1080
atattgagat gatcgccaac aagactggtg gcctatttcg actggcgatt aagcttatgc   1140
agttggaaag cactttgtgc agcaatgtca ttgaactagc agacttgttg ggcgtgatct   1200
ttcagattcg ggatgattac caaaacttac agagtggact atacgccaag aacaagggat   1260
tttgcgagga tttgacggag ggaaaatttt cctttctgat tatccacagt attaacagta   1320
acccgaacaa tcaccatctg ctaaatatac tacggcagcg gagcgaggac gattcggtga   1380
agaagtatgc tgttgattat atcgactcga cggggagttt tgactactgc cgggaacggc   1440
tcgcttcctt attggaagag gcggatcaaa tggttaagaa gttggaaaat gagggggggac   1500 aatcaaaggg gatctacgat attctgagct ttctgtcgtg agcggatctc ttatgtcttt   1560
acgatttata gttttcatta tcaagtatgc ctatattagt atatagcatc tttagatgac   1620
agtgttcgaa gtttcacgaa taaagataaa tattctactt tttgctccca ccgcgtttgc   1680
tagcacgagt gaacaccatc cctcgcctgt gagttgtacc cattcctcta aactgtagac   1740
atggtagctt cagcagtgtt cgttatgtac ggcatcctcc aacaaacagt cggttatagt   1800
ttgtcctgct cctctgaatc gtctccctcg atatttctca ttttccttcg catgccagca   1860
ttgaaatgat cgaagttcaa tgatgaaacg gtaattcttc tgtcatttac tcatctcatc   1920
tcatcaagtt atataattct atacggatgt aattttcac ttttcgtctt gacgtccacc    1980
ctataatttc aattattgaa ccctcacgat ccagttctcc agtgacacag cctttatctg   2040
gtcaaacctt tctttctaat cacctatgct gatgcttaat taagggatt ttgtctccat    2100 caacggcatg cgcccaaaaa tgacgttttt tttaacccat agacacgaaa ctacccattt   2160
tccaccggcc tgacctacca ccggaacaac ggccatctcc aacttgcaag ttggggaaat   2220
taagagcatc gcaggtttaa tggaagaaaa aaaaaaggta cagcacagcg caaatggagt   2280
tagttcccct tatgtcacaca ctcacacaca gtcggtcaga tcaagcatac tgggtgcgta  2340
taaatagagt ggccattgcc accctgttta tctcaaaatc tgtcttgtta gtggtcttct   2400
ccctttttca ggttacaatt ctcttgtttc tacttagtat ataagtatat caagctatat   2460
taagcatact atcaactgtc aactctatcc tcaaaataca atacaaaatg gatgggttcg   2520
accattctac tgctccacca ggatataacg agctaaaatg gctcgccgat atcttcgtca   2580
tcggaatggc tgttggctgg gttgctcact atatggagat gattcacacg tcgttcaagg   2640
accaaacata ctgcatgacc atcgggggcc tttgcatcaa ttttgcctgg gaaatcatat   2700
tctgcacaat gtatcctgcc aaaggatttg tcgagcgggt tgcctttctc atgggcattt   2760
ctctcgacct tggggttatt tacgcgggaa tcaagaacgc cccaaatgaa tggcaccact   2820
ctgcaatggt gagggaccat atgccccttg tcttcgcagc aacgacactt tgttgtctga   2880
gcggtcatat ggctcttact gcccaggttg gtcccgcaca agcctatacg tgggggggcaa  2940 ttgcatgcca gctctttatc agcataggga atgtgtttca attgttgagt cggggaaaca   3000 cacgagggggc gtcatggacg ctatggacct ccaggttttt tggatcaaca tcagccattg   3060
gctttgctct tgttcgatat attcgctggt gggaggcctt tcttggttga aactgcccgc   3120
ttgtgatatg gtccgtggcc atgttctttc tgtttgaaac actctatgga gcccctattct  3180 attctgtcaa gcgacaagaa gggagatccc agcgtggaat caagcacaaa gagaggtaga   3240
caaatcgctc ttaaatatat acctaaagaa cattaaagct atattataag caaagatacg   3300
taaattttgc ttatattatt atacacatat catatttcta tatttttaag atttggttat   3360
ataatgtacg taatgcaaag gaaataaatt ttatacatta ttgaacagcg tccaagtaac   3420
```

| | |
|---|---|
| tacattatgt gcactaatag tttagcgtcg tgaagacttt attgtgtcgc gaaaagtaaa | 3480 |
| aatttttaaaa attagagcac cttgaacttg cgaaaaaggt tctcatcaac tgtttaaaag | 3540 |
| gaggatatca ggtcctattt ctgacaaaca atatacaaat ttagtttcaa agatgaatca | 3600 |
| gtgcgcgaag gacataactc aataggaaaa aaccgagctt cctttcatcc ggcgcggctg | 3660 |
| tgttctacat atcactgaag ctccgggtat tttaagttat acaagggaaa gatgccggct | 3720 |
| agactagcaa gttttaggct gcttaacatt atggataggc ggataaaggg cccaaacagg | 3780 |
| attgtaaagc ttagacgctt ctggttggac aatggtacgt tgtgtatta agtaaggctt | 3840 |
| ggctggggat agcaacattg ggcagagtat agaagaccac aaaaaaaagg tatataaggg | 3900 |
| cagagaagtc tttgtaatgt gtgtaacttc tcttccatgt gtaatcagta tttctactta | 3960 |
| cttcttaaat atacagaagt aagacagata accaacagcc tttcccagat atacatatat | 4020 |
| atctttattt cagcttaaac aataattata tttgtttaac tcaaaaataa aaaaaaaaaa | 4080 |
| ccaaactcac gcaactaatt attccataat aaaataacaa catggcggca cttccggacg | 4140 |
| ttgcctccat tcccatccct ctggtggcaa ccctaggcat tgcccctcta attttctatc | 4200 |
| tcgtccttga tagaattagc cccttgtggc caaattccaa agcttttcctg attggcaaga | 4260 |
| agaaaccgga gaccgtgaca tcgttcgagt gcccatatgc ctacatccgt cagatctatg | 4320 |
| ggaagtatca ctgggagcca ttcgtacaga agctgtctcc gaggcttaag gatgaggatc | 4380 |
| cggccaaata agatggtt ctggagataa tggatgcaat ccacctgtgt ctgatgctag | 4440 |
| ttgacgatat aactgacaat agcgactatc gaaaaggcaa gccagcagcc caccggatat | 4500 |
| atggcccttc agagacagca atcgcgctt actaccgagt cacccagatt ctaaacaaga | 4560 |
| ccgtgcaaaa gttccccaag ctggccaagt tcctgcttca gaatctggaa gaaattctcg | 4620 |
| aaggccaaga cctgtcacta atctggcgac gggatggact gggtagcctt tcgactgttc | 4680 |
| ctgatgagcg agttgcagcc tatcgcaaga tggcgtcatt gaaaactggg gcgttattcc | 4740 |
| ggctgctggg gcaattggtg atggaggacc aatcgatgga cgggacgatg actactcttg | 4800 |
| cgtggtgctc tcagctgcag aatgactgca agaatgtcta ctcatctgaa atgctaagg | 4860 |
| ccaaggggc gcttgccgaa gacctccgaa atcgagagct ctcatttcca attatcctcg | 4920 |
| cgctggaagc tcctgaaggg cattgggtcg ccagtgcttt ggagaccagc tcaccgcgca | 4980 |
| acattcgcaa ggcgcttgct gtgattcaga gtgagagagt gcgcaatgct tgtttcaagg | 5040 |
| agctcaagtc ggcgagtgct tcggtccagg actggttggc tatttgggga cggaacgaga | 5100 |
| aaatgaactt gaagagccag cagacgtaga gtgcttttaa ctaagaatta ttagtctttt | 5160 |
| ctgcttattt tttcatcata gtttagaaca ctttatatta acgaatagtt tatgaatcta | 5220 |
| tttaggttta aaaattgata cagttttata agttactttt tcaaagactc gtgctgtcta | 5280 |
| ttgcataatg cactggaagg ggaaaaaaaa ggtgcacacg cgtggctttt tcttgaattt | 5340 |
| gcagtttgaa aaataactac atggatgata agaaaacatg gagtacagtc actttgagaa | 5400 |
| ccttcaatca gctggtaacg tcttcgttaa ttggatactc aaaaaagatg gatagcatga | 5460 |
| atcacaagat ggaaggaaat gcgggccacg accacagtga tatgcatatg ggagatggag | 5520 |
| atgataccctc cattgggccg atgaagttag tcgacggata gaagcggttg tccccttttcc | 5580 |
| cggcgagccg gcagtcgggc cgaggttcgg ataaattttg tattgtgttt tgattctgtc | 5640 |
| atgagtatta cttatgttct ctttaggtaa ccccaggtta atcaatcaca gtttcatacc | 5700 |
| ggctagtatt caaattatga cttttcttct gcagtgtcag ccttacgacg attatctatg | 5760 |

```
agctttgaat atagtttgcc gtgattcgta tctttaattg gataataaaa tgcgaaggat   5820
cgatgaccct tattattatt tttctacact ggctaccgat ttaactcatc ttcttgaaag   5880
tatataagta acagtaaaat ataccgtact tctgctaatg ttatttgtcc cttattttc    5940
ttttcttgtc ttatgctata gtacctaaga ataacgacta ttgttttgaa ctaaacaaag   6000
tagtaaaagc acataaaaga attaagaaaa tggccaatgc ccagcaaccc cccttcgca    6060
tccttattgt gggcggttct gtcgcaggcc tcatccttgc gcactgtctc gaacgcgcca   6120
atatagagta cctcatactc gaaaaggag aagatgttgc tccacaagtt ggtgcctcga    6180
taggtatcat gccaaatggc ggacggatcc tcgagcaact gggcctattt ggggagattg   6240
agcgtgtgat cgagccgttg catcaggcga atatcagcta tccagatggg ttctgcttta   6300
gtaacgtcta tcctaaggtt cttggcgaca ggttcggata cccggttgca ttcttggacc   6360
ggcagaagtt cctgcagatt gcatatgagg ggctgagaaa aagcagaat gttctcaccg    6420
gtaaagggt agttggactg cgacagtcgg atcaagggac tgctgtttct gtggctgacg    6480
ggacagagta tgaggcggat ctcgtggttg gtgctgatgg agtacatagt cgggtgagaa   6540
gtgagatttg gaagatggcg gaagagaatc agcctgcatc agtttcgaca cgtgaaagaa   6600
gaagcatgac tgttgaatat gtctgcgttt tcgggatttc atcagccatc ccagggctcg   6660
agataagcga acagatcaac ggtattttcg accatctatc cattctaaca atccatggca   6720
gacatggtcg cgtgttctgg ttcgtgatcc agaagctgga taggaagtac gtctatcctg   6780
atgtcccgcg attctcagac gaggatgccg tacagctctt cgatcgggtc aaacacgtgc   6840
ggttctggaa aaacatctgt gtgggggact tgtggaagaa cagagaggtg tcctcgatga   6900
cagcgctgga ggagggagtg ttcgagacat ggcatcatga taggatggtt ttgattggag   6960
atagcgttca caagatgacg cccaactttg gccaaggagc taattcagcc atcgaggatg   7020
ctgccgcgct ctcttccctt ctacatgatc tcgtcaacgc ccgtggagtt tgcaagccat   7080
cgaatgtcca gattcagcat ctcctcaagc agtatcggga gacccgatac actcgcatgg   7140
taggcatgtg tcgcaccgcg gcttcagtct ctcggattca ggcccgagat ggcatcctca   7200
acaccgtctt tggacgatat tgggcacctt atgctgccaa cctgcctgct gacctggcat   7260
caaaagtgat ggcagatgca gaggttgtta cttttctgcc cttgccaggg cgctcaggac   7320
cgggctggga gatgtacaga cgaaaggga agggagggca ggtgcaatgg gtgcttataa   7380
tcttaagctt acttacgatt ggtggattgt gcatctggct acaaagcaat gcgttgagta   7440
gataaggaga ttgataagac ttttctagtt gcatatcttt tatatttaaa tcttatctat   7500
tagttaattt tttgtaattt atccttatat atagtctggt tattctaaaa tatcatttca   7560
gtatctaaaa attcccctct tttttcagtt atatcttaac aggcgacagt ccaaatgttg   7620
atttatccca gtccgattca tcagggttgt gaagcatttt gtcaatggtc gaaatcacat   7680
cagtaatagt gcctcttact tgcctcatag aatttctttc tcttaacgtc accgtttggt   7740
cttttatagt ttcgaaatct atggtgatac caaatggtgt tcccaattca tcgttacggg   7800
cgtatttttt accaattgaa gtattggaat cgtcaatttt aaagtatatc tctcttttac   7860
gtaaagcctg cgagatcctc ttaagtatag cgggaagcc atcgttattc gatattgtcg    7920
taacaaatac tttgatcggc gctatgcggc cgccaccgcg gtggagctcc agcttttgtt   7980
cccttagtg agggttaatt gcgcgcttgg cgtaatcatg gtcatagctg tttcctgtgt    8040
gaaattgtta tccgctcaca attccacaca ataggagc cggaagcata aagtgtaaag     8100
cctggggtgc ctaatgagtg agtaactca cattaattgc gttgcgctca ctgcccgctt    8160
```

```
tccagtcggg aaacctgtcg tgccagctgc attaatgaat cggccaacgc gcggggagag   8220
gcggtttgcg tattgggcgc tcttccgctt cctcgctcac tgactcgctg cgctcggtcg   8280
ttcggctgcg gcgagcggta tcagctcact caaaggcggt aatacggtta ccacagaat    8340
caggggataa cgcaggaaag aacatgtgag caaaaggcca gcaaaaggcc aggaaccgta   8400
aaaaggccgc gttgctggcg ttttccata ggctccgccc ccctgacgag catcacaaaa    8460
atcgacgctc aagtcagagg tggcgaaacc cgacaggact ataaagatac caggcgtttc   8520
ccccctggaag ctccctcgtg cgctctcctg ttccgaccct gccgcttacc ggatacctgt  8580
ccgcctttct cccttcggga agcgtggcgc tttctcatag ctcacgctgt aggtatctca   8640
gttcggtgta ggtcgttcgc tccaagctgg gctgtgtgca cgaaccccc  gttcagcccg   8700
accgctgcgc cttatccggt aactatcgtc ttgagtccaa cccggtaaga cacgacttat   8760
cgccactggc agcagccact ggtaacagga ttagcagagc gaggtatgta ggcggtgcta   8820
cagagttctt gaagtggtgg cctaactacg gctacactag aaggacagta tttggtatct   8880
gcgctctgct gaagccagtt accttcggaa aaagagttgg tagctcttga tccggcaaac   8940
aaaccaccgc tggtagcggt ggtttttttg tttgcaagca gcagattacg cgcagaaaaa   9000
aaggatctca agaagatcct ttgatctttt ctacggggtc tgacgctcag tggaacgaaa   9060
actcacgtta agggattttg gtcatgagat tatcaaaaag gatcttcacc tagatccttt   9120
taaattaaaa atgaagtttt aaatcaatct aaagtatata tgagtaaact tggtctgaca   9180
gttaccaatg cttaatcagt gaggcaccta tctcagcgat ctgtctattt cgttcatcca   9240
tagttgcctg actccccgtc gtgtagataa ctacgatacg ggagggctta ccatctggcc   9300
ccagtgctgc aatgataccg cgagacccac gctcaccggc tccagattta tcagcaataa   9360
accagccagc cggaagggcc gagcgcagaa gtggtcctgc aactttatcc gcctccatcc   9420
agtctattaa ttgttgccgg gaagctagag taagtagttc gccagttaat agtttgcgca   9480
acgttgttgc cattgctaca ggcatcgtgg tgtcacgctc gtcgtttggt atggcttcat   9540
tcagctccgg ttcccaacga tcaaggcgag ttacatgatc ccccatgttg tgcaaaaaag   9600
cggttagctc cttcggtcct ccgatcgttg tcagaagtaa gttggccgca gtgttatcac   9660
tcatggttat ggcagcactg cataattctc ttactgtcat gccatccgta agatgctttt   9720
ctgtgactgg tgagtactca accaagtcat tctgagaata gtgtatgcgg cgaccgagtt   9780
gctcttgccc ggcgtcaata cgggataata ccgcgccaca tagcagaact ttaaaagtgc   9840
tcatcattgg aaaacgttct tcggggcgaa aactctcaag gatcttaccg ctgttgagat   9900
ccagttcgat gtaacccact cgtgcaccca actgatcttc agcatctttt actttcacca   9960
gcgtttctgg gtgagcaaaa acaggaaggc aaaatgccgc aaaaaaggga ataagggcga  10020
cacggaaatg ttgaatactc atactcttcc tttttcaata ttattgaagc atttatcagg  10080
gttattgtct catgagcgga tacatatttg aatgtattta gaaaaataaa caataggggg  10140
ttccgcgcac atttccccga aaagtgccac ctgaacgaag catctgtgct tcattttgta  10200
gaacaaaaat gcaacgcgag agcgctaatt tttcaaacaa gaatctgagc tgcattttt   10260
acagaacaga aatgcaacgc gaaagcgcta ttttaccaac gaagaatctg tgcttcattt   10320
ttgtaaaaca aaaatgcaac gcgagagcgc taatttttca aacaaagaat ctgagctgca  10380
ttttacaga acagaaatgc aacgcgagag cgctatttta ccaacaaaga atctatactt  10440
cttttttgtt ctacaaaaat gcatcccgag agcgctattt tctaacaaa gcatcttaga  10500
```

```
ttactttttt tctcctttgt gcgctctata atgcagtctc ttgataactt tttgcactgt    10560
aggtccgtta aggttagaag aaggctactt tggtgtctat tttctcttcc ataaaaaaag    10620
cctgactcca cttcccgcgt ttactgatta ctagcgaagc tgcgggtgca ttttttcaag    10680
ataaaggcat ccccgattat attctatacc gatgtggatt gcgcatactt tgtgaacaga    10740
aagtgatagc gttgatgatt cttcattggt cagaaaatta tgaacggttt cttctatttt    10800
gtctctatat actacgtata ggaaatgttt acattttcgt attgttttcg attcactcta    10860
tgaatagttc ttactacaat ttttttgtct aaagagtaat actagagata aacataaaaa    10920
atgtagaggt cgagtttaga tgcaagttca aggagcgaaa ggtggatggg taggttatat    10980
agggatatag cacagagata tatagcaaag agatacttt gagcaatgtt tgtggaagcg    11040
gtattcgcaa tattttagta gctcgttaca gtccggtgcg tttttggttt tttgaaagtg    11100
cgtcttcaga gcgcttttgg ttttcaaaag cgctctgaag ttcctatact ttctagagaa    11160
taggaacttc ggaataggaa cttcaaagcg tttccgaaaa cgagcgcttc cgaaaatgca    11220
acgcgagctg cgcacataca gctcactgtt cacgtcgcac ctatatctgc gtgttgcctg    11280
tatatatata tacatgagaa gaacggcata gtgcgtgttt atgcttaaat gcgtacttat    11340
atgcgtctat ttatgtagga tgaaaggtag tctagtacct cctgtgatat tatcccattc    11400
catgcggggt atcgtatgct tccttcagca ctacccttta gctgttctat atgctgccac    11460
tcctcaattg gattagtctc atccttcaat gctatcattt cctttgatat tggatcatac    11520
taagaaacca ttattatcat gacattaacc tataaaaata ggcgtatcac gaggcccttt    11580
cgtctcgcgc gtttcggtga tgacggtgaa aacctctgac acatgcagct cccggagacg    11640
gtcacagctt gtctgtaagc ggatgccggg agcagacaag cccgtcaggg cgcgtcagcg    11700
ggtgttggcg ggtgtcgggg ctggcttaac tatgcggcat cagagcagat tgtactgaga    11760
gtgcaccata tcgactacgt cgtaaggccg tttctgacag agtaaaattc ttgagggaac    11820
tttcaccatt atgggaaatg cttcaagaag gtattgactt aaactccatc aaatggtcag    11880
gtcattgagt gttttttatt tgttgtattt tttttttttt agagaaaatc ctccaatatc    11940
aaattaggaa tcgtagtttc atgattttct gttacaccta actttttgtg tggtgccctc    12000
ctccttgtca atattaatgt taaagtgcaa ttcttttttcc ttatcacgtt gagccattag    12060
tatcaatttg cttacctgta ttcctttact atcctccttt ttctccttct tgataaatgt    12120
atgtagattg cgtatatagt ttcgtctacc ctatgaacat attccatttt gtaatttcgt    12180
gtcgtttcta ttatgaattt catttataaa gtttatgtac aaatatcata aaaaagaga    12240
atcttttta gcaaggattt tcttaacttc ttcggcgaca gcatcaccga cttcggtggt    12300
actgttggaa ccacctaaat caccagttct gatacctgca tccaaaacct ttttaactgc    12360
atcttcaatg gccttacctt cttcaggcaa gttcaatgac aatttcaaca tcattgcagc    12420
agacaagata tgtggcgatag ggtcaacctt attctttggc aaatctggag cagaaccgtg    12480
gcatggttcg tacaaaccaa atgcggtgtt cttgtctggc aaagaggcca aggacgcaga    12540
tggcaacaaa cccaaggaac ctgggataac ggaggcttca tcggagatga tatcaccaaa    12600
catgttgctg gtgattataa taccatttag gtgggttggg ttcttaacta ggatcatggc    12660
ggcagaatca atcaattgat gttgaacctt caatgtaggg aattcgttct tgatggtttc    12720
ctccacagtt tttctccata atcttgaaga ggccaaaaga ttagctttat ccaaggacca    12780
aataggcaat ggtggctcat gttgtagggc catgaaagcg gccattcctg tgattctttg    12840
cacttctgga acggtgtatt gttcactatc ccaagcgaca ccatcaccat cgtcttcctt    12900
```

```
tctcttacca aagtaaatac ctcccactaa ttctctgaca acaacgaagt cagtaccttt    12960
agcaaattgt ggcttgattg gagataagtc taaaagagag tcggatgcaa agttacatgg    13020
tcttaagttg gcgtacaatt gaagttcttt acggattttt agtaaacctt gttcaggtct    13080
aacactaccg gtaccccatt taggaccagc cacagcacct aacaaaacgg catcaacctt    13140
cttggaggct tccagcgcct catctggaag tgggacacct gtagcatcga tagcagcacc    13200
accaattaaa tgattttcga aatcgaactt gacattggaa cgaacatcag aaatagcttt    13260
aagaaccttA atggcttcgg ctgtgatttc ttgaccaacg tggtcacctg gcaaaacgac    13320
gatcttctta ggggcagaca taggggcaga cattagaatg gtatatcctt gaaatatata    13380
tatatattgc tgaaatgtaa aaggtaagaa aagttagaaa gtaagacgat tgctaaccac    13440
ctattggaaa aaacaatagg tccttaaata atattgtcaa cttcaagtat tgtgatgcaa    13500
gcatttagtc atgaacgctt ctctattcta tatgaaaagc cggttccggc ctctcacctt    13560
tccttttctc cccaattttt cagttgaaaa aggtatatgc gtcaggcgac ctctgaaatt    13620
aacaaaaaat ttccagtcat cgaatttgat tctgtgcgat agcgcccctg tgtgttctcg    13680
ttatgttgag gaaaaaaata atggttgcta agagattcga actcttgcat cttacgatac    13740
ctgagtattc ccacagttaa ctgcggtcaa gatatttctt gaatcaggcg ccttagaccg    13800
ctcggccaaa caaccaatta cttgttgaga aatagagtat aattatccta taaatataac    13860 gttttttgaac acacatgaac aaggaagtac aggacaattg atttttgaaga gaatgtggat    13920 tttgatgtaa ttgttgggat tccattttta ataaggcaat aatattaggt atgtggatat    13980
actagaagtt ctcctcgacc gtcgatatgc ggtgtgaaat accgcacaga tgcgtaagga    14040
gaaaataccg catcaggaaa ttgtaaacgt taatattttg ttaaaattcg cgttaaattt    14100
ttgttaaatc agctcatttt ttaaccaata ggccgaaatc ggcaaaatcc cttataaatc    14160
aaaagaatag accgagatag ggttgagtgt tgttccagtt tggaacaaga gtccactatt    14220
aaagaacgtg gactccaacg tcaaagggcg aaaaccgtc tatcagggcg atggcccact    14280
acgtgaacca tcaccctaat caagtttttt ggggtcgagg tgccgtaaag cactaaatcg    14340
gaaccctaaa gggagccccc gatttagagc ttgacgggga aagccggcga acgtggcgag    14400
aaaggaaggg aagaaagcga aaggagcggg cgctagggcg ctggcaagtg tagcggtcac    14460
gctgcgcgta accaccacac ccgccgcgct taatgcgccg ctacagggcg cgtcgcgcca    14520
ttcgccattc aggctgcgca actgttggga agggcgatcg gtgcgggcct cttcgctatt    14580
acgccagctg gcgaaagggg gatgtgctgc aaggcgatta agttgggtaa cgccaggggtt    14640 ttcccagtca cgacgttgta aaacgacggc cagtgagcgc gcgtaatacg actcactata    14700
gggcgaattg ggtaccgggc cccccctcga ggtcgacggt atcgataagc ttgatatcga    14760
attcctgcag cccggggggat ccactagttc tagattaatt aa                     14802
```

<210> SEQ ID NO 66
<211> LENGTH: 14644
<212> TYPE: DNA
<213> ORGANISM: Artificial Sequence
<220> FEATURE:
<223> OTHER INFORMATION: synthetic

<400> SEQUENCE: 66

```
atagcttcaa aatgtttcta ctcctttttt actcttccag attttctcgg actccgcgca      60
tcgccgtacc acttcaaaac acccaagcac agcatactaa atttcccctc tttcttcctc     120
```

```
tagggtgtcg ttaattaccc gtactaaagg tttggaaaag aaaaaagaga ccgcctcgtt    180
tcttttcttt cgtcgaaaaa ggcaataaaa atttttatca cgtttcttt tcttgaaaat    240 ttttttttt gattttttc tctttcgatg acctcccatt gatatttaag ttaataaacg    300
gtcttcaatt tctcaagttt cagtttcatt tttcttgttc tattacaact ttttttactt    360
cttgctcatt agaaagaaag catagcaatc taatctaagt tttaattaca aaatgctggg    420
attcccaatg ttcaacccag ctacgcctga tgtctggaag atgaatacccc cttactttcc    480 atttgttaca ccggggttat ttcctgcctc agcaccccca tcgcccacca acgtagatgc    540
cgaagctgcc agttcccaac agtcggaagc aagctatctg gataaggaga aaattgttcg    600
agggccactt gattatcttc tcaaatcccc tggaaaagac attcgtcgga aattcattca    660
cgcgttcaat gaatggctgc gcattcctga ggacaagttg aatattatca cggaaattgt    720
tggattgctt cacacggcct cccttctaat cgacgatatt caggacaatt ccaagcttcg    780
acgcggcctc ccagtggccc atagcatatt tggtattgcg cagacaatta actctgccaa    840
ttatgcgtac tttctagccc aggaaaggct ccgcgaacta atcatcctg aagcgtacga    900 aatatacaca gaggaactgc ttcgtctgca ccgcggtcaa ggtatggact tgtactggcg    960
ggactgccta acctgtccca cagaggagga ctatattgag atgatcgcca acaagactgg    1020 tggcctatt cgactggcga ttaagcttat gcagttggaa agcactttgt gcagcaatgt    1080
cattgaacta gcagacttgt tgggcgtgat ctttcagatt cgggatgatt accaaaactt    1140
acagagtgga ctatacgcca agaacaaggg attttgcgag gatttgacgg agggaaaatt    1200
ttcctttctg attatccaca gtattaacag taacccgaac aatcaccatc tgctaaatat    1260
actacggcag cggagcgagg acgattcggt gaagaagtat gctgttgatt atatcgactc    1320 gacgggagt tttgactact gccgggaacg gctcgcttcc ttattggaag aggcggatca    1380
aatggttaag aagttggaaa atgagggggg acaatcaaag gggatctacg atattctgag    1440
ctttctgtcg tgagcggatc tcttatgtct ttacgattta tagttttcat tatcaagtat    1500
gcctatatta gtatatagca tctttagatg acagtgttcg aagtttcacg aataaaagat    1560
aatattctac ttttgctcc caccgcgttt gctagcacga gtgaacacca tccctcgcct    1620
gtgagttgta cccattcctc taaactgtag acatggtagc ttcagcagtg ttcgttatgt    1680
acggcatcct ccaacaaaca gtcggttata gtttgtcctg ctcctctgaa tcgtctccct    1740
cgatatttct cattttcctt cgcatgccag cattgaaatg atcgaagttc aatgatgaaa    1800
cggtaattct tctgtcattt actcatctca tctcatcaag ttatataatt ctatacggat    1860 gtaattttc acttttcgtc ttgacgtcca ccctataatt tcaattattg aaccctcact    1920
gggtcattac gtaaataatg ataggaatgg gattcttcta ttttttcctt ttccattcta    1980
gcagccgtcg ggaaaacgtg gcatcctctc tttcgggctc aattggagtc acgctgccgt    2040
gagcatcctc tctttccata tctaacaact gagcacgtaa ccaatggaaa agcatgagct    2100
tagcgttgct ccaaaaaagt attggatggt taataccatt tgtctgttct cttctgactt    2160
tgactcctca aaaaaaaaaa atctacaatc aacagatcgc ttcaattacg ccctcacaaa    2220
aacttttttc cttcttcttc gcccacgtta aattttatcc ctcatgttgt ctaacggatt    2280
tctgcacttg atttattata aaaagacaaa gacataatac ttctctatca atttcagtta    2340
ttgttcttcc ttgcgttatt cttctgttct tctttttctt ttgtcatata taaccataac    2400
caagtaatac atattcaaaa tggatgggtt cgaccattct actgctccac caggatataa    2460
cgagctaaaa tggctcgccg atatcttcgt catcggaatg gctgttggct gggttgctca    2520
```

```
ctatatggag atgattcaca cgtcgttcaa ggaccaaaca tactgcatga ccatcggggg   2580
cctttgcatc aattttgcct gggaaatcat attctgcaca atgtatcctg ccaaaggatt   2640
tgtcgagcgg gttgcctttc tcatgggcat ttctctcgac cttggggtta tttacgcggg   2700
aatcaagaac gccccaaatg aatggcacca ctctgcaatg gtgagggacc atatgcccct   2760
tgtcttcgca gcaacgacac tttgttgtct gagcggtcat atggctctta ctgcccaggt   2820
tggtcccgca caagcctata cgtggggggc aattgcatgc cagctcttta tcagcatagg   2880
gaatgtgttt caattgttga gtcggggaaa cacacgaggg gcgtcatgga cgctatggac   2940
ctccaggttt tttggatcaa catcagccat tggctttgct cttgttcgat atattcgctg   3000
gtgggaggcc ttttcttggt tgaactgccc gcttgtgata tggtccgtgg ccatgttctt   3060
tctgtttgaa acactctatg gagccctatt ctattctgtc aagcgacaag aagggagatc   3120
ccagcgtgga atcaagcaca aagagaggta gacaaatcgc tcttaaatat atacctaaag   3180
aacattaaag ctatattata agcaaagata cgtaaatttt gcttatatta ttatacacat   3240
atcatatttc tatattttta agatttggtt ataataatgta cgtaatgcaa aggaaataaa   3300
ttttatacat tattgaacag cgtccaagta actacattat gtgcactaat agtttagcgt   3360
cgtgaagact ttattgtgtc gcgaaaagta aaaattttaa aaattagagc accttgaact   3420
tgcgaaaaag gttctcatca actgtttaaa aggaggatat caggtcctat ttctgacaaa   3480
caatatacaa atttagtttc aaagatgaat cagtgcgcga aggacataac tcaacagttt   3540
attcctggca tccactaaat ataatggagc ccgcttttta agctggcatc cagaaaaaaa   3600
aagaatccca gcaccaaaat attgttttct tcaccaacca tcagttcata ggtccattct   3660
cttagcgcaa ctacagagaa cagggggcaca acaggcaaaa aaacgggcac aacctcaatg   3720
gagtgatgca acctgcctgg agtaaatgat gacacaaggc aattgaccca cgcatgtatc   3780
tatctcattt tcttacacct tctattacct tctgctctct ctgatttgga aaaagctgaa   3840
aaaaaaggtt gaaaccagtt ccctgaaatt attcccctac ttgactaata agtatataaa   3900
gacggtaggt attgattgta attctgtaaa tctatttctt aaacttctta aattctactt   3960
ttatagttag tctttttttt agttttaaaa caccaagaac ttagtttcga ataaacacac   4020
ataaacaaac aaaatggcgg cacttccgga cgttgcctcc attcccatcc ctctggtggc   4080
aaccctagcc attgccccctc taattttcta tctcgtcctt gatagaatta gcccctttgtg   4140 gccaaattcc aaagctttcc tgattggcaa gaagaaaccg gagaccgtga catcgttcga   4200
gtgcccatat gcctacatcc gtcagatcta tgggaagtat cactgggagc cattcgtaca   4260
gaagctgtct ccgaggctta aggatgagga tccggccaaa tataagatgg ttctggagat   4320
aatggatgca atccacctgt gtctgatgct agttgacgat ataactgaca atagcgacta   4380
tcgaaaaggc aagccagcag cccaccggat atatggccct tcagagacag caaatcgcgc   4440
ttactaccga gtcacccaga ttctaaacaa gaccgtgcaa aagttcccca agctggccaa   4500
gttcctgctt cagaatctgg aagaaattct cgaaggccaa gacctgtcac taatctggcg   4560
acgggatgga ctgggtagcc tttcgactgt tcctgatgag cgagttgcag cctatcgcaa   4620
gatggcgtca ttgaaaactg gggcgttatt ccggctgctg gggcaattgg tgatggagga   4680
ccaatcgatg gacgggacga tgactactct tgcgtggtgc tctcagctgc agaatgactg   4740
caagaatgtc tactcatctg aatatgctaa ggccaaaggg gcgcttgccg aagacctccg   4800
aaatcgagag ctctcatttc caattatcct cgcgctggaa gctcctgaag ggcattgggt   4860
```

```
cgccagtgct ttggagacca gctcaccgcg caacattcgc aaggcgcttg ctgtgattca    4920
gagtgagaga gtgcgcaatg cttgtttcaa ggagctcaag tcggcgagtg cttcggtcca    4980
ggactggttg gctatttggg gacggaacga gaaaatgaac ttgaagagcc agcagacgta    5040
gagtgctttt aactaagaat tattagtctt ttctgcttat ttttcatca tagtttagaa    5100
cactttatat taacgaatag tttatgaatc tatttaggtt taaaaattga tacagtttta    5160
taagttactt tttcaaagac tcgtgctgtc tattgcataa tgcactggaa gggaaaaaaa    5220
aaggtgcaca cgcgtggctt tttcttgaat ttgcagtttg aaaaataact acatggatga    5280
taagaaaaca tggagtacag tcactttgag aaccttcaat cagctggtaa cgtcttcgtt    5340
aattggatac tcaaaaaaga tggatagcat gaatcacaag atggaaggaa atgcgggcca    5400
cgaccacagt gatatgcata tgggagatgg agatgatacc ttatatctag gaacccatca    5460
ggttggtgga agattacccg ttctaagact tttcagcttc ctctattgat gttacacctg    5520
gacacccctt ttctggcatc cagttttaa tcttcagtgg catgtgagat tctccgaaat    5580
taattaaagc aatcacacaa ttctctcgga taccacctcg gttgaaactg acaggtggtt    5640
tgttacgcat gctaatgcaa aggagcctat ataccttggg ctcggctgct gtaacaggga    5700
atataaaggg cagcataatt taggagttta gtgaacttgc aacatttact atttccctt    5760
cttacgtaaa tatttttctt tttaattcta aatcaatctt tttcaatttt ttgtttgtat    5820
tcttttcttg cttaaatcta taactacaaa aaacacatac ataaactaaa aatgccaat    5880
gcccagcaac ccccctttcg catccttatt gtgggcggtt ctgtcgcagg cctcatcctt    5940
gcgcactgtc tcgaacgcgc caatatagag tacctcatac tcgaaaaagg agaagatgtt    6000
gctccacaag ttggtgcctc gataggtatc atgccaaatg gcggacggat cctcgagcaa    6060
ctgggcctat ttggggagat tgagcgtgtg atcgagccgt tgcatcaggc gaatatcagc    6120
tatccagatg ggttctgctt tagtaacgtc tatcctaagg ttcttggcga caggttcgga    6180
tacccggttg cattcttgga ccggcagaag ttcctgcaga ttgcatatga ggggctgaga    6240
aagaagcaga atgttctcac cggtaaaagg gtagttggac tgcgacagtc ggatcaaggg    6300
actgctgttt ctgtggctga cgggacagag tatgaggcgg atctcgtggt tggtgctgat    6360
ggagtacata gtcgggtgag aagtgagatt tggaagatgg cggaagagaa tcagcctgca    6420
tcagtttcga cacgtgaaag aagaagcatg actgttgaat atgtctgcgt tttcgggatt    6480
tcatcagcca tcccagggct cgagataagc gaacagatca acggtatttt cgaccatcta    6540
tccattctaa caatccatgg cagacatggt cgcgtgttct ggttcgtgat ccagaagctg    6600
gataggaagt acgtctatcc tgatgtcccg cgattctcag acgaggatgc cgtacagctc    6660
ttcgatcggg tcaaacacgt gcggttctgg aaaaacatct gtgtgggga cttgtggaag    6720
aacagagagg tgtcctcgat gacagcgctg gaggagggag tgttcgagac atggcatcat    6780
gataggatgg ttttgattgg agatagcgtt cacaagatga cgcccaactt tggccaagga    6840
gctaattcag ccatcgagga tgctgccgcg ctctcttccc ttctacatga tctcgtcaac    6900
gcccgtggag tttgcaagcc atcgaatgtc cagattcagc atctcctcaa gcagtatcgg    6960
gagacccgat acactcgcat ggtaggcatg tgtcgcaccg cggcttcagt ctctcggatt    7020
caggcccgag atggcatcct caacaccgtc tttggacgat attgggcacc ttatgctggc    7080
aacctgcctg ctgacctggc atcaaaagtg atggcagatg cagaggttgt tacttttctg    7140
cccttgccag ggcgctcagg accgggctgg gagatgtaca gacgaaaggg gaagggaggg    7200
caggtgcaat gggtgcttat aatcttaagc ttacttacga ttggtggatt gtgcatctgg    7260
```

```
ctacaaagca atgcgttgag tagataagga gattgataag acttttctag ttgcatatct    7320
tttatattta aatcttatct attagttaat tttttgtaat ttatccttat atatagtctg    7380
gttattctaa aatatcattt cagtatctaa aaattcccct cttttttcag ttatatctta    7440
acaggcgaca gtccaaatgt tgatttatcc cagtccgatt catcagggtt gtgaagcatt    7500
ttgtcaatgg tcgaaatcac atcagtaata gtgcctctta cttgcctcat agaatttctt    7560
tctcttaacg tcaccgtttg gtcttttata gtttcgaaat ctatggtgat accaaatggt    7620
gttcccaatt catcgttacg ggcgtatttt ttaccaattg aagtattgga atcgtcaatt    7680
ttaaagtata tctctctttt acgtaaagcc tgcgagatcc tcttaagtat agcggggaag    7740
ccatcgttat tcgatattgt cgtaacaaat actttgatcg gcgctatgcg gccgccaccg    7800
cggtggagct ccagcttttg ttcccttag tgagggttaa ttgcgcgctt ggcgtaatca    7860
tggtcatagc tgtttcctgt gtgaaattgt tatccgctca caattccaca acatagga    7920 gccggaagca taaagtgtaa agcctggggt gcctaatgag tgaggtaact cacattaatt    7980
gcgttgcgct cactgcccgc tttccagtcg ggaaacctgt cgtgccagct gcattaatga    8040
atcggccaac gcgcggggag aggcggtttg cgtattgggc gctcttccgc ttcctcgctc    8100
actgactcgc tgcgctcggt cgttcggctg cggcgagcgg tatcagctca ctcaaaggcg    8160
gtaatacggt tatccacaga atcagggat aacgcaggaa agaacatgtg agcaaaaggc    8220
cagcaaaagg ccaggaaccg taaaaaggcc gcgttgctgg cgtttttcca taggctccgc    8280 cccccctgacg agcatcacaa aaatcgacgc tcaagtcaga ggtggcgaaa cccgacagga    8340
ctataaagat accaggcgtt tccccctgga agctccctcg tgcgctctcc tgttccgacc    8400
ctgccgctta ccggatacct gtccgccttt ctcccttcgg gaagcgtggc gctttctcat    8460
agctcacgct gtaggtatct cagttcggtg taggtcgttc gctccaagct gggctgtgtg    8520
cacgaacccc ccgttcagcc cgaccgctgc gccttatccg gtaactatcg tcttgagtcc    8580
aacccggtaa gacacgactt atcgccactg gcagcagcca ctggtaacag gattagcaga    8640
gcgaggtatg taggcggtgc tacagagttc ttgaagtggt ggcctaacta cggctacact    8700
agaaggacag tatttggtat ctgcgctctg ctgaagccag ttaccttcgg aaaaagagtt    8760
ggtagctctt gatccggcaa acaaaccacc gctggtagcg gtggtttttt tgtttgcaag    8820
cagcagatta cgcgcagaaa aaaggatctc aagaagatc ctttgatctt ttctacgggg    8880
tctgacgctc agtggaacga aaactcacgt taagggattt tggtcatgag attatcaaaa    8940
aggatcttca cctagatcct tttaaattaa aaatgaagtt ttaaatcaat ctaaagtata    9000
tatgagtaaa cttggtctga cagttaccaa tgcttaatca gtgaggcacc tatctcagcg    9060
atctgtctat ttcgttcatc catagttgcc tgactcccg tcgtgtagat aactacgata    9120
cgggagggct taccatctgg ccccagtgct gcaatgatac cgcgagaccc acgctcaccg    9180
gctccagatt tatcagcaat aaaccagcca gccggaaggg ccgagcgcag aagtggtcct    9240
gcaactttat ccgcctccat ccagtctatt aattgttgcc gggaagctag agtaagtagt    9300
tcgccagtta atagtttgcg caacgttgtt gccattgcta caggcatcgt ggtgtcacgc    9360
tcgtcgtttg gtatggcttc attcagctcc ggttcccaac gatcaaggcg agttacatga    9420
tcccccatgt tgtgcaaaaa agcggttagc tccttcggtc ctccgatcgt tgtcagaagt    9480
aagttggccg cagtgttatc actcatggtt atggcagcac tgcataattc tcttactgtc    9540
atgccatccg taagatgctt ttctgtgact ggtgagtact caaccaagtc attctgagaa    9600
```

```
tagtgtatgc ggcgaccgag ttgctcttgc ccggcgtcaa tacgggataa taccgcgcca    9660
catagcagaa ctttaaaagt gctcatcatt ggaaaacgtt cttcggggcg aaaactctca    9720
aggatcttac cgctgttgag atccagttcg atgtaaccca ctcgtgcacc caactgatct    9780
tcagcatctt ttactttcac cagcgtttct gggtgagcaa aaacaggaag gcaaaatgcc    9840
gcaaaaaagg gaataagggc gacacggaaa tgttgaatac tcatactctt ccttttttcaa   9900
tattattgaa gcatttatca gggttattgt ctcatgagcg gatacatatt tgaatgtatt    9960
tagaaaaata aacaaatagg ggttccgcgc acatttcccc gaaaagtgcc acctgaacga   10020
agcatctgtg cttcattttg tagaacaaaa atgcaacgcg agagcgctaa ttttttcaaac  10080
aaagaatctg agctgcattt ttacagaaca gaaatgcaac gcgaaagcgc tattttacca   10140
acgaagaatc tgtgcttcat ttttgtaaaa caaaaatgca acgcgagagc gctaattttt   10200
caaacaaaga atctgagctg cattttttaca gaacagaaat gcaacgcgag agcgctattt  10260
taccaacaaa gaatctatac ttctttttg ttctacaaaa atgcatcccg agagcgctat    10320
ttttctaaca aagcatctta gattactttt tttctccttt gtgcgctcta taatgcagtc   10380
tcttgataac ttttttgcact gtaggtccgt taaggttaga agaaggctac tttggtgtct  10440
attttctctt ccataaaaaa agcctgactc cacttcccgc gtttactgat tactagcgaa   10500
gctgcgggtg catttttttca agataaaggc atccccgatt atattctata ccgatgtgga  10560
ttgcgcatac tttgtgaaca gaaagtgata gcgttgatga ttcttcattg gtcagaaaat   10620
tatgaacggt ttcttctatt ttgtctctat atactacgta taggaaatgt ttacattttc   10680
gtattgttt cgattcactc tatgaatagt tcttactaca ttttttttgt ctaaagagta    10740
atactagaga taaacataaa aaatgtagag gtcgagttta gatgcaagtt caaggagcga   10800
aaggtggatg ggtaggttat atagggatat agcacagaga tatatagcaa agagatactt   10860
ttgagcaatg tttgtggaag cggtattcgc aatatttag tagctcgtta cagtccggtg   10920
cgttttggt tttttgaaag tgcgtcttca gagcgctttt ggttttcaaa agcgctctga   10980
agttcctata ctttctagag aataggaact tcggaatagg aacttcaaag cgtttccgaa   11040
aacgagcgct tccgaaaatg caacgcgagc tgcgcacata cagctcactg ttcacgtcgc   11100
acctatatct gcgtgttgcc tgtatatata tatacatgag aagaacggca tagtgcgtgt   11160
ttatgcttaa atgcgtactt atatgcgtct atttatgtag gatgaaaggt agtctagtac   11220
ctcctgtgat attatcccat tccatgcggg gtatcgtatg cttccttcag cactacccctt  11280
tagctgttct atatgctgcc actcctcaat tggattagtc tcatccttca atgctatcat   11340
ttcctttgat attggatcat actaagaaac cattattatc atgacattaa cctataaaaa   11400
taggcgtatc acgaggccct ttcgtctcgc gcgtttcggt gatgacggtg aaaacctctg   11460
acacatgcag ctcccggaga cggtcacagc ttgtctgtaa gcggatgccg ggagcagaca   11520
agcccgtcag ggcgcgtcag cgggtgttgg cgggtgtcgg ggctggctta actatgcggc   11580
atcagagcag attgtactga gagtgcacca tatcgactac gtcgtaaggc cgtttctgac   11640
agagtaaaat tcttgaggga actttcacca ttatgggaaa tgcttcaaga aggtattgac   11700
ttaaactcca tcaaatggtc aggtcattga gtgttttta tttgttgtat ttttttttt    11760
ttagagaaaa tcctccaata tcaaattagg aatcgtagtt tcatgatttt ctgttacacc   11820
taacttttg tgtggtgccc tcctccttgt caatattaat gttaaagtgc aattcttttt    11880
ccttatcacg ttgagccatt agtatcaatt tgcttacctg tattccttta ctatcctcct   11940
ttttctcctt cttgataaat gtatgtagat tgcgtatata gtttcgtcta ccctatgaac   12000
```

```
atattccatt ttgtaatttc gtgtcgtttc tattatgaat ttcatttata aagtttatgt   12060
acaaatatca taaaaaaaga gaatcttttt aagcaaggat tttcttaact tcttcggcga   12120
cagcatcacc gacttcggtg gtactgttgg aaccacctaa atcaccagtt ctgatacctg   12180
catccaaaac cttttaact gcatcttcaa tggccttacc ttcttcaggc aagttcaatg    12240
acaatttcaa catcattgca gcagacaaga tagtggcgat agggtcaacc ttattctttg   12300
gcaaatctgg agcagaaccg tggcatggtt cgtacaaacc aaatgcggtg ttcttgtctg   12360
gcaaagaggc caaggacgca gatggcaaca acccaagga acctgggata acggaggctt    12420
catcggagat gatatcacca acatgttgc tggtgattat aataccattt aggtgggttg    12480
ggttcttaac taggatcatg gcggcagaat caatcaattg atgttgaacc ttcaatgtag   12540
ggaattcgtt cttgatggtt tcctccacag tttttctcca taatcttgaa gaggccaaaa   12600
gattagcttt atccaaggac caaataggca atggtggctc atgttgtagg gccatgaaag   12660
cggccattct tgtgattctt tgcacttctg gaacggtgta ttgttcacta tcccaagcga   12720
caccatcacc atcgtcttcc tttctcttac caaagtaaat acctcccact aattctctga   12780
caacaacgaa gtcagtacct ttagcaaatt gtggcttgat tggagataag tctaaaagag   12840
agtcggatgc aaagttacat ggtcttaagt tggcgtacaa ttgaagttct ttacggattt   12900
ttagtaaacc ttgttcaggt ctaacactac cggtacccca tttaggacca gccacagcac   12960
ctaacaaaac ggcatcaacc ttcttggagg cttccagcgc ctcatctgga agtgggacac   13020
ctgtagcatc gatagcagca ccaccaatta aatgattttc gaaatcgaac ttgacattgg   13080
aacgaacatc agaaatagct ttaagaacct taatggcttc ggctgtgatt tcttgaccaa   13140
cgtggtcacc tggcaaaacg acgatcttct taggggcaga catagggca gacattagaa    13200 tggtatatcc ttgaaatata tatatatatt gctgaaatgt aaaaggtaag aaaagttaga   13260
aagtaagacg attgctaacc acctattgga aaaaacaata ggtccttaaa taatattgtc   13320
aacttcaagt attgtgatgc aagcatttag tcatgaacgc ttctctattc tatatgaaaa   13380
gccggttccg gcctctcacc tttccttttt ctcccaattt ttcagttgaa aaaggtatat   13440
gcgtcaggcg acctctgaaa ttaacaaaaa atttccagtc atcgaatttg attctgtgcg   13500
atagcgcccc tgtgtgttct cgttatgttg aggaaaaaaa taatggttgc taagagattc   13560
gaactcttgc atcttacgat acctgagtat tcccacagtt aactgcggtc aagatatttc   13620
ttgaatcagg cgccttagac cgctcggcca acaaccaat tacttgttga gaaatagagt    13680
ataattatcc tataaatata acgttttga acacacatga acaaggaagt acaggacaat    13740
tgattttgaa gagaatgtgg attttgatgt aattgttggg attccatttt taataaggca   13800
ataatattag gtatgtggat atactagaag ttctcctcga ccgtcgatat gcggtgtgaa   13860
ataccgcaca gatgcgtaag gagaaaatac cgcatcagga aattgtaaac gttaatattt   13920
tgttaaaatt cgcgttaaat ttttgttaaa tcagctcatt ttttaaccaa taggccgaaa   13980
tcggcaaaat cccttataaa tcaaaagaat agaccgagat agggttgagt gttgttccag   14040
tttggaacaa gagtccacta ttaaagaacg tggactccaa cgtcaaaggg cgaaaaaccg   14100
tctatcaggg cgatggccca ctacgtgaac catcacccta atcaagtttt ttggggtcga   14160
ggtgccgtaa agcactaaat cggaacccta aagggagccc ccgatttaga gcttgacggg   14220
gaaagccggc gaacgtggcg agaaaggaag ggaagaaagc gaaggagcg ggcgctaggg    14280 cgctggcaag tgtagcggtc acgctgcgcg taaccaccac acccgccgcg cttaatgcgc   14340
```

-continued

```
cgctacaggg cgcgtcgcgc cattcgccat tcaggctgcg caactgttgg gaagggcgat      14400
cggtgcgggc ctcttcgcta ttacgccagc tggcgaaagg gggatgtgct gcaaggcgat      14460
taagttgggt aacgccaggg ttttcccagt cacgacgttg taaaacgacg gccagtgagc      14520
gcgcgtaata cgactcacta tagggcgaat tgggtaccgg gccccccctc gaggtcgacg      14580
gtatcgataa gcttgatatc gaattcctgc agcccggggg atccactagt tctagattaa      14640
ttaa                                                                   14644
```

<210> SEQ ID NO 67
<211> LENGTH: 53
<212> TYPE: DNA
<213> ORGANISM: Saccharomyces

<400> SEQUENCE: 67

```
tgacgcgcct cctccaccgg aacaacggcc atctccaact tataagttgg aga             53
```

<210> SEQ ID NO 68
<211> LENGTH: 41
<212> TYPE: DNA
<213> ORGANISM: Saccharomyces castellii

<400> SEQUENCE: 68

```
tgacgcgccc tttatctggg aaaaatggaa ctggatgctg a                          41
```

<210> SEQ ID NO 69
<211> LENGTH: 47
<212> TYPE: DNA
<213> ORGANISM: Saccharomyces bayanus

<400> SEQUENCE: 69

```
tgacctacca ccggaacaac ggccatctcc aacttgcaag ttggga                     47
```

<210> SEQ ID NO 70
<211> LENGTH: 47
<212> TYPE: DNA
<213> ORGANISM: Saccharomyces kudriavzevii

<400> SEQUENCE: 70

```
acaccttcca ccggaacaac ggccatctcc aacttataag ttggga                     47
```

<210> SEQ ID NO 71
<211> LENGTH: 47
<212> TYPE: DNA
<213> ORGANISM: Saccharomyces mikatae

<400> SEQUENCE: 71

```
tgacctgcca ccggaacaac ggccatctcc aacttataag ttgaga                     47
```

<210> SEQ ID NO 72
<211> LENGTH: 49
<212> TYPE: DNA
<213> ORGANISM: Saccharomyces paradoxus

<400> SEQUENCE: 72

```
tgacctcctc tgccggaaca ccggccatct ccaactcata aattggaga                  49
```

<210> SEQ ID NO 73
<211> LENGTH: 49

```
<212> TYPE: DNA
<213> ORGANISM: Saccharomyces cerevisiae

<400> SEQUENCE: 73
tgatctcctc tgccggaaca ccgggcatct ccaacttata agttggaga          49
```